US011873497B2

(12) United States Patent
Caiazza et al.

(10) Patent No.: US 11,873,497 B2
(45) Date of Patent: Jan. 16, 2024

(54) REGULATORY ELEMENTS FROM LABYRINTHULOMYCETES MICROORGANISMS

(71) Applicant: Conagen Inc., Bedford, MA (US)

(72) Inventors: Nicky C. Caiazza, Rancho Santa Fe, CA (US); Maung N. Win, San Diego, CA (US); Jun Urano, Irvine, CA (US)

(73) Assignee: Conagen Inc., Bedford, MA (US)

( * ) Notice: Subject to any disclaimer, the term of this patent is extended or adjusted under 35 U.S.C. 154(b) by 648 days.

(21) Appl. No.: 16/819,518

(22) Filed: Mar. 16, 2020

(65) Prior Publication Data

US 2020/0318124 A1 Oct. 8, 2020

Related U.S. Application Data

(62) Division of application No. 15/916,171, filed on Mar. 8, 2018, now Pat. No. 10,633,665, which is a division of application No. 15/056,857, filed on Feb. 29, 2016, now Pat. No. 9,932,599.

(60) Provisional application No. 62/127,196, filed on Mar. 2, 2015.

(51) Int. Cl.

| | |
|---|---|
| ***C12N 15/00*** | (2006.01) |
| ***C12N 15/63*** | (2006.01) |
| ***C12N 15/79*** | (2006.01) |
| ***C12N 15/80*** | (2006.01) |
| ***C12N 5/00*** | (2006.01) |

(52) U.S. Cl.

CPC ............... *C12N 15/79* (2013.01); *C12N 5/00* (2013.01); *C12N 15/63* (2013.01); *C12N 15/80* (2013.01)

(58) Field of Classification Search

None

See application file for complete search history.

(56) References Cited

U.S. PATENT DOCUMENTS

| | | | |
|---|---|---|---|
| 7,001,772 | B2 | 2/2006 | Roessler et al. |
| 7,211,418 | B2 | 5/2007 | Metz et al. |
| 7,217,856 | B2 | 5/2007 | Weaver et al. |
| 7,635,472 | B2 | 12/2009 | Kufer |
| 7,759,097 | B2 | 7/2010 | Ono et al. |
| 7,851,191 | B2 | 12/2010 | Roessler et al. |
| 7,888,123 | B2 | 2/2011 | Ono et al. |
| 8,003,772 | B2 | 8/2011 | Weaver et al. |
| 8,026,083 | B2 | 9/2011 | Callewaert |
| 8,206,984 | B2 | 6/2012 | Roessler et al. |
| 8,409,825 | B2 | 4/2013 | Chiba et al. |
| 8,697,359 | B1 | 4/2014 | Zhang |
| 8,883,993 | B2 | 11/2014 | Schneider et al. |
| 9,428,784 | B2 | 8/2016 | Choi et al. |
| 9,932,599 | B2 | 4/2018 | Caiazza et al. |
| 10,457,970 | B2 | 10/2019 | Caiazza |
| 10,584,347 | B2 | 3/2020 | Caiazza et al. |
| 10,633,454 | B2 | 4/2020 | Caiazza |
| 10,633,665 | B2 | 4/2020 | Caiazza et al. |
| 2003/0166207 | A1 | 9/2003 | Roessler et al. |
| 2004/0018590 | A1 | 1/2004 | Gerngross et al. |
| 2004/0235127 | A1 | 11/2004 | Metz |
| 2006/0253928 | A1 | 11/2006 | Bakker et al. |
| 2006/0275904 | A1 | 12/2006 | Ono et al. |
| 2009/0093033 | A1 | 4/2009 | Luy |
| 2010/0016555 | A1 | 1/2010 | Bobrowicz et al. |
| 2010/0034823 | A1 | 2/2010 | Borhani et al. |
| 2010/0178298 | A1 | 7/2010 | Lindhofer |
| 2010/0221763 | A1 | 9/2010 | Matta et al. |
| 2010/0227363 | A1 | 9/2010 | Bosh et al. |
| 2010/0233760 | A1 | 9/2010 | Apt et al. |
| 2011/0118331 | A1 | 5/2011 | Behr et al. |
| 2011/0195480 | A1 | 8/2011 | Bayne et al. |
| 2011/0306075 | A1 | 12/2011 | Bosques et al. |
| 2012/0322116 | A1 | 12/2012 | Sakaguchi et al. |
| 2012/0328626 | A1 | 12/2012 | Sethuraman et al. |
| 2013/0040897 | A1 | 2/2013 | Apt et al. |
| 2013/0231255 | A1 | 9/2013 | Collins et al. |
| 2013/0323780 | A1 | 12/2013 | Schneider et al. |
| 2015/0110826 | A1 | 4/2015 | Bayne et al. |
| 2015/0132803 | A1 | 5/2015 | Apt et al. |
| 2015/0376249 | A1 | 12/2015 | Choi |

(Continued)

FOREIGN PATENT DOCUMENTS

| | | | |
|---|---|---|---|
| EP | 1414941 | B1 | 10/2002 |
| EP | 2623588 | A1 | 8/2013 |

(Continued)

OTHER PUBLICATIONS

Hong et al., GenEmbl Database, Direct submission, Accession No. JX978726, Jan. 9, 2015.*
International Search Report and Written Opinion for Application No. PCT/US2016/020114 dated Jun. 20, 2016.
International Preliminary Report on Patentability for Application No. PCT/US2016/020114 dated Sep. 5, 2017.
[No Author Listed], Approval of Humira II-adalimumab by EMEA, Jan. 1, 2004, XP055624077, Retrieved from the Internet: URL:https://www.ema.europa.eu/en/documents/scientific-discussion/humira-epar-scientific-discussion_en.pdf [retrieved on Sep. 19, 2019]. 25 pages.
[No Author Listed], Genbank 1N8Z_A, Chain A, Herceptin Fab (antibody)—Light Chain, ncbi.nlm.nih.gov/protein/28948772?sat=16&satkey=10451034. 2012. 2 pages.

(Continued)

*Primary Examiner* — Phuong T Bui

(74) *Attorney, Agent, or Firm* — Wolf, Greenfield & Sacks, P.C.

(57) ABSTRACT

The present disclosure generally relates to novel polynucleotide molecules for use in regulating gene expression in recombinant cells, such as labyrinthulomycetes cells. The disclosure further relates to nucleic acid constructs, such as vectors and expression cassettes, containing a regulatory element operably linked to a heterologous nucleotide sequence. The disclosure further relates to methods for stably transforming a host cell, such as a labyrinthulomycetes cell with transgenes. Stably transformed recombinant cells, progeny, biomaterials derived therefrom, and methods for preparing and using the same are also provided.

18 Claims, 7 Drawing Sheets

Specification includes a Sequence Listing.

(56) References Cited

U.S. PATENT DOCUMENTS

| | | | |
|---|---|---|---|
| 2016/0177255 | A1 | 6/2016 | Radakovits et al. |
| 2016/0257965 | A1 | 9/2016 | Caiazza et al. |
| 2017/0067058 | A1 | 3/2017 | Yoneyama et al. |
| 2017/0247426 | A1 | 8/2017 | Bulik et al. |
| 2017/0268015 | A1 | 9/2017 | Caiazza et al. |
| 2018/0119193 | A1 | 5/2018 | Caiazza |
| 2018/0201941 | A1 | 7/2018 | Caiazza et al. |
| 2018/0251569 | A1 | 9/2018 | Caiazza |
| 2020/0399649 | A1 | 12/2020 | Caiazza et al. |

FOREIGN PATENT DOCUMENTS

| | | |
|---|---|---|
| EP | 3265567 | 1/2018 |
| WO | WO 2006/014685 A1 | 2/2006 |
| WO | WO 2007/006570 A2 | 1/2007 |
| WO | WO 2007/084922 A2 | 7/2007 |
| WO | WO 2013/144257 A1 | 10/2013 |
| WO | WO 2014/151318 A1 | 9/2014 |
| WO | WO 2015/179844 | 11/2015 |
| WO | WO 2012/120375 A2 | 9/2016 |
| WO | WO 2016/140925 A1 | 9/2016 |
| WO | WO 2017/161005 A1 | 9/2017 |
| WO | WO 2017/194699 A1 | 11/2017 |
| WO | WO 2018/085273 A1 | 5/2018 |
| WO | WO 2019/089077 A1 | 5/2019 |
| WO | WO 2019/173226 A1 | 9/2019 |
| WO | WO 2019/213069 A1 | 11/2019 |
| WO | WO 2019/213095 A1 | 11/2019 |

OTHER PUBLICATIONS

[No Author Listed], Genbank AB557594.1, Expression vector beta-act-loxP-RFP-loxP-GFP DNA. 2010.

[No Author Listed], NCBI GenBank accession No. KC218923.1. Apr. 30, 2013.

[No Author Listed], NCBI GenBank accession No. DQ356659.1. Feb. 24, 2009.

[No Author Listed], NCBI GenBank accession No. JX978726.1. Jan. 9, 2015.

Aebi et al., Cloning and characterization of the ALG3 gene of *Saccharomyces cerevisiae*. Glycobiology. Jun. 1996;6(4):439-44.

Altschul et al., Basic local alignment search tool. J Mol Biol. Oct. 5, 1990;215(3):403-10.

Bayne et al., Vaccination against influenza with recombinant hemagglutinin expressed by sp. confers protective immunity. PLoS One. Apr. 23, 2013;8(4):e61790. doi: 10.1371/journal.pone.0061790. Print 2013.

Bayne et al., Vaccination against influenza with recombinant hemagglutinin expressed by *Schizochytrium* sp. confers protective immunity. PLoS One. Apr. 23, 2013;8(4):e61790. doi: 10.1371/journal.pone.0061790. Print 2013.

Becker et al., Isolation of the repertoire of VSG expression site containing telomeres of Trypanosoma brucei 427 using transformation-associated recombination in yeast. Genome Res. Nov. 2004;14(11):2319-29.

Bobrowicz et al., Engineering of an artificial glycosylation pathway blocked in core oligosaccharide assembly in the yeast *Pichia pastoris*: production of complex humanized glycoproteins with terminal galactose. Glycobiology. Sep. 2004;14(9):757-66. Epub Jun. 9, 2004.

Choi et al., Use of combinatorial genetic libraries to humanize N-linked glycosylation in the yeast *Pichia pastoris*. Proc Natl Acad Sci U S A. Apr. 29, 2003;100(9):5022-7. Epub Apr. 17, 2003.

Chung et al., Insertional inactivation studies of the csmA and csmC genes of the green sulfur bacterium Chlorobium vibrioforme 8327: the chlorosome protein CsmA is required for viability but CsmC is dispensable. FEMS Microbiol Lett. Jul. 15, 1998;164(2):353-61.

Ferrante et al., An optimized, chemically regulated gene expression system for Chlamydomonas. PLoS One. Sep. 12, 2008;3(9):e3200. doi: 10.1371/journal.pone.0003200.

Garcia-Vedrenne et al., Development of genomic resources for a thraustochytrid pathogen and investigation of temperature influences on gene expression. PLoS One. Sep. 17, 2013;8(9):e74196. doi: 10.1371/journal.pone.0074196.

Geijtenbeek et al., Signalling through C-type lectin receptors: shaping immune responses. Nat Rev Immunol. Jul. 2009;9(7):465-79. doi: 10.1038/nri2569.

Gerrish et al., Pancreatic beta cell-specific transcription of the pdx-1 gene. The role of conserved upstream control regions and their hepatic nuclear factor 3beta sites. J Biol Chem. Feb. 4, 2000;275(5):3485-92.

Gibson et al., Enzymatic assembly of DNA molecules up to several hundred kilobases. Nat Methods. May 2009;6(5):343-5. doi: 10.1038/nmeth.1318. Epub Apr. 12, 2009.

Gibson, Enzymatic assembly of overlapping DNA fragments. Methods Enzymol. 2011;498:349-61. doi: 10.1016/B978-0-12-385120-8.00015-2.

Hamilton et al., Glycosylation engineering in yeast: the advent of fully humanized yeast. Curr Opin Biotechnol. Oct. 2007;18(5):387-92. Epub Oct. 24, 2007.

Hellen et al., Internal ribosome entry sites in eukaryotic mRNA molecules. Genes Dev. Jul. 1, 2001;15(13):1593-612.

Henikoff et al., Amino acid substitution matrices from protein blocks. Proc Natl Acad Sci U S A. Nov. 15, 1992;89(22):10915-9.

Higo et al., Plant cis-acting regulatory DNA elements (PLACE) database: 1999. Nucleic Acids Res. Jan. 1, 1999;27(1):297-300.

Hirschmann et al., The multi-protein family of sulfotransferases in plants: composition, occurrence, substrate specificity, and functions. Front Plant Sci. Oct. 16, 2014;5:556. doi: 10.3389/fpls.2014.00556. eCollection 2014.

Isett et al., Twenty-four-well plate miniature bioreactor high-throughput system: assessment for microbial cultivations. Biotechnol Bioeng. Dec. 1, 2007;98(5):1017-28.

Ji et al., Genome Sequence of *Schizochytrium* sp. CCTCC M209059, an Effective Producer of Docosahexaenoic Acid-Rich Lipids. Genome Announc. Aug. 6, 2015;3(4). pii: e00819-15. doi: 10.1128/genomeA.00819-15.

Kai et al., Silencing of Carbohydrate Sulfotransferase 15 Hinders Murine Pulmonary Fibrosis Development. Mol Ther Nucleic Acids. Mar. 17, 2017;6:163-172. doi: 10.1016/j.omtn.2016.12.008. Epub Dec. 31, 2016.

Karlin et al., Applications and statistics for multiple high-scoring segments in molecular sequences. Proc Natl Acad Sci U S A. Jun. 15, 1993;90(12):5873-7.

Kellerman et al., Analysis of the primary structure and promoter function of a pyruvate decarboxylase gene (PDC1) from *Saccharomyces cerevisiae*. Nucleic Acids Res. Nov. 25, 1986;14(22):8963-77.

Kim et al., High cleavage efficiency of a 2A peptide derived from porcine teschovirus-1 in human cell lines, zebrafish and mice. PLoS One. 2011;6(4):e18556. doi: 10.1371/journal.pone.0018556. Epub Apr. 29, 2011.

Kindle et al., Stable nuclear transformation of Chlamydomonas using the Chlamydomonas gene for nitrate reductase. J Cell Biol. Dec. 1989; 109(6 Pt 1):2589-601.

Kindle, High-frequency nuclear transformation of Chlamydomonas reinhardtii. Proc Natl Acad Sci U S A. Feb. 1990;87(3):1228-32.

Kobayashi et al., Increase of eicosapentaenoic acid in thraustochytrids through thraustochytrid ubiquitin promoter-driven expression of a fatty acid {delta } 5 desaturase gene. Appl Environ Microbiol. Jun. 2011; 77(11):3870-6. doi: 10.1128/AEM.02664-10. Epub Apr. 8, 2011.

Komar et al., Cellular IRES-mediated translation: the war of ITAFs in pathophysiological states. Cell Cycle. Jan. 15, 2011;10(2):229-40. Epub Jan. 15, 2011.

Lescot et al., PlantCARE, a database of plant cis-acting regulatory elements and a portal to tools for in silico analysis of promoter sequences. Nucleic Acids Res. Jan. 1, 2002;30(1):325-7.

Lippmeier et al., Characterization of both polyunsaturated fatty acid biosynthetic pathways in *Schizochytrium* sp. Lipids. Jul. 2009;44(7):621-30. doi: 10.1007/s11745-009-3311-9. Epub Jun. 3, 2009.

(56) References Cited

OTHER PUBLICATIONS

Lombard. The multiple evolutionary origins of the eukaryotic N-glycosylation pathway. Biology Direct. Aug. 4, 2016;11(36):1-31.
Matsuda et al., Analysis of Δ12-fatty acid desaturase function revealed that two distinct pathways are active for the synthesis of PUFAs in T. aureum ATCC 34304. J Lipid Res. Jun. 2012;53(6):1210-22. doi: 10.1194/jlr.M024935. Epub Feb. 26, 2012. Erratum in: J Lipid Res. Dec. 2012;53(12):2806.
McCarthy et al., Differential expression analysis of multifactor RNA-Seq experiments with respect to biological variation. Nucleic Acids Res. May 2012;40(10):4288-97. doi: 10.1093/nar/gks042. Epub Jan. 28, 2012.
Mendez-Alvarez et al., Transformation of Chlorobium limicola by a plasmid that confers the ability to utilize thiosulfate. J Bacteriol. Dec. 1994;176(23):7395-7. Erratum in: J Bacteriol Feb. 1995;177(4):1121.
Mogno et al., TATA is a modular component of synthetic promoters. Genome Res. Oct. 2010;20(10):1391-7. doi: 10.1101/gr.106732.110. Epub Jul. 13, 2010.
Mortazavi et al., Mapping and quantifying mammalian transcriptomes by RNA-Seq. Nat Methods. Jul. 2008;5(7):621-8. doi: 10.1038/nmeth.1226. Epub May 30, 2008.
Needleman et al., A general method applicable to the search for similarities in the amino acid sequence of two proteins. J Mol Biol. Mar. 1970;48(3):443-53.
Ohnuma et al., Polyethylene glycol (PEG)-mediated transient gene expression in a red alga, Cyanidioschyzon merolae 10D. Plant Cell Physiol. Jan. 2008;49(1):117-20. Epub Nov. 14, 2007.
Orchard et al., Rhodanine-3-acetic acid derivatives as inhibitors of fungal protein mannosyl transferase 1 (PMT1). Bioorg Med Chem Lett. Aug. 2, 2004;14(15):3975-8.
Parsaie et al., A combined system for engineering glycosylation efficiency and glycan structure in *Saccharomyces cerevisiae*. Appl Environ Microbiol. Feb. 2013;79(3):997-1007. doi: 10.1128/AEM.02817-12. Epub Nov. 30, 2012.
Pasupathy et al., Direct plant gene delivery with a poly(amidoamine) dendrimer. Biotechnol J. Aug. 2008;3(8):1078-82. doi: 10.1002/biot.200800021.
Pearson et al., Improved tools for biological sequence comparison. Proc Natl Acad Sci U S A. Apr. 1988;85(8):2444-8.
Perrone et al., The Chlamydomonas IDA7 locus encodes a 140-kDa dynein intermediate chain required to assemble the I1 inner arm complex. Mol Biol Cell. Dec. 1998;9(12):3351-65.
Quinn et al., Copper response element and Crr1-dependent Ni(2+)-responsive promoter for induced, reversible gene expression in Chlamydomonas reinhardtii. Eukaryot Cell. Oct. 2003;2(5):995-1002.
Raghukumar, Thraustochytrid Marine Protists: production of PUFAs and Other Emerging Technologies. Mar Biotechnol (NY). Nov.-Dec. 2008;10(6):631-40. doi: 10.1007/s10126-008- 9135-4. Epub Aug. 20, 2008.
Ranasinghe et al., An improved protocol for the isolation of total genomic DNA from Labyrinthulomycetes. Biotechnol Lett. Mar. 2015;37(3):685-90. doi: 10.1007/s10529-014-1712- 1. Epub Oct. 30, 2014.
Rombauts et al., PlantCARE, a plant cis-acting regulatory element database. Nucleic Acids Res. Jan. 1, 1999;27(1):295-6.
Sakaguchi et al., Versatile transformation system that is applicable to both multiple transgene expression and gene targeting for Thraustochytrids. Appl Environ Microbiol. May 2012;78(9):3193-202. doi: 10.1128/AEM.07129-11. Epub Feb. 17, 2012.
Shagin et al., GFP-like proteins as ubiquitous metazoan superfamily: evolution of functional features and structural complexity. Mol Biol Evol. May 2004;21(5):841-50. Epub Feb. 12, 2004.
Shahmuradov et al., PlantProm: a database of plant promoter sequences. Nucleic Acids Res. Jan. 1, 2003;31(1):114-7.
Smith et al., Comparison of biosequences. Adv Appl Math. Dec. 1, 1981;2(4):482-9.
Trapnell et al., Differential gene and transcript expression analysis of RNA-seq experiments with TopHat and Cufflinks. Nat Protoc. Mar. 1, 2012;7(3):562-78. doi: 10.1038/nprot.2012.016. Erratum in: Nat Protoc. Oct. 2014;9(10):2513.
Uniprot, P38179: Dol-P_Man:Man(5)GlcNAc(2)-PP-Dol alpha-1,3-mannosyltransferase. May 4, 2016;1-9. Retrieved from www.web.archive.org/web/20160504193836/http://www.uniproLorg/uniprot/P38179.
Watt et al., urg1: a uracil-regulatable promoter system for fission yeast with short induction and repression times. PLoS One. Jan. 16, 2008;3(1):e1428. doi: 10.1371/journal.pone.0001428.
Wildt et al., The humanization of N-glycosylation pathways in yeast. Nat Rev Microbiol. Feb. 2005;3(2):119-28.
Wolk et al., Construction of shuttle vectors capable of conjugative transfer from *Escherichia coli* to nitrogen-fixing filamentous cyanobacteria. Proc Natl Acad Sci U S A. Mar. 1984;81(5):1561-5.
Yamanishi et al., A genome-wide activity assessment of terminator regions in *Saccharomyces cerevisiae* provides a "terminatome" toolbox. ACS Synth Biol. Jun. 21, 2013;2(6):337-47. doi: 10.1021/sb300116y. Epub Feb. 20, 2013.
Yokoyama et al., Taxonomic rearrangement of the genus *Schizochytrium* sensu lato based on morphology, chemotaxonomic characteristics, and 18S rRNA gene phylogeny (Thraustochytriaceae, Labyrinthulomycetes): emendation for Schizochytrium and erection of Aurantiochytrium and Oblongichytrium gen. nov. Mycoscience. Aug. 1, 2007;48(4):199-211.

* cited by examiner

REGULATORY ELEMENTS FROM LABYRINTHULOMYCETES MICROORGANISMS

CROSS-REFERENCED TO RELATED APPLICATIONS

The present application is a division of U.S. patent application Ser. No. 15/916,171, granted as U.S. Pat. No. 10,633,665, filed Mar. 8, 2018, entitled "REGULATORY ELEMENTS FROM LABYRINTHULOMYCETES MICROORGANISMS," which claims priority to U.S. patent application Ser. No. 15/056,857, granted as U.S. Pat. No. 9,932,599, filed on Feb. 29, 2016, entitled "REGULATORY ELEMENTS FROM LABYRINTHULOMYCETES MICROORGANISMS," which claims priority to U.S. Provisional Patent Application No. 62/127,196; filed on Mar. 2, 2015. The disclosures of the above-referenced applications are hereby expressly incorporated by reference in their entireties.

INCORPORATION OF THE SEQUENCE LISTING

The material in the accompanying sequence listing is hereby incorporated by reference into this application. The accompanying sequence listing text file, name C149770039US03-SEQ-ZJG, was created on Mar. 16, 2020 and is 265,951 bytes. The file can be assessed using Microsoft Word on a computer that uses Windows OS.

FIELD

The present disclosure relates to the field of molecular biology and genetic engineering, and more specifically relates to polynucleotide molecules useful for controlling expression of gene sequences in vitro and in vivo in recombinant cells, particularly labyrinthulomycetes cells.

BACKGROUND

Recent advances in biotechnology and molecular biology offer tremendous opportunities to develop biotech organisms with commercially desirable characteristics or traits. In particular, modern genetic engineering techniques have greatly accelerated the introduction of new genes and hence new traits into recombinant cells and organisms, particularly microbial organisms. The proper expression of a desirable transgene in a transgenic organism is widely considered to be a requisite requirement to achieve this goal. For example, expression of a gene in a recombinant cell that does not normally express such a gene may confer a desirable phenotypic effect. In another example, transcription of a gene or part of a gene in an antisense orientation may produce a desirable effect by preventing or inhibiting expression of an endogenous gene. Moreover, for production of recombinant cells and organisms with various desired characteristics, it would be advantageous to have a variety of promoters to provide gene expression such that a gene sequence can be transcribed efficiently in the amount necessary to produce the desired effect.

Furthermore, as the field of microbial transgenesis rapidly develops and more genes become accessible, a greater need exists for microorganisms transformed with multiple genes. In fact, the commercial development of genetically improved organisms has advanced to the stage of introducing multiple heterologous genes and traits into a single recombinant cell. These multiple heterologous genes typically need to be transcriptionally controlled by diverse regulatory sequences. For example, some transgenes need to be expressed in a constitutive manner whereas other genes should be expressed at certain developmental stages or in specific compartments of the transgenic cell. In addition, multiple regulatory sequences may be needed in order to avoid undesirable molecular interactions which can result from using the same regulatory sequence to control more than one transgene. In light of these and other considerations, it is apparent that optimal control of gene expression and regulatory element diversity are important in modern recombinant biotechnology.

However, despite the availability of many molecular tools, the genetic modification of recombinant organisms is often constrained by an insufficient expression level or temporally nonspecific expression of the engineered transgenes. In addition, while previous technological advancements have provided a number of regulatory elements that can be used to affect gene expression in transgenic organisms, there is still a great need for novel regulatory elements with beneficial expression characteristics. One example of this is the need for regulatory elements capable of driving gene expression preferentially in different microbial growth phases. On the other hand, there also exists a continuing need for regulatory elements capable of driving gene expression constitutively throughout cell life cycle and/or unaffected by growth conditions, as well as at low, moderate, high, or very high transcription levels. Thus, the identification of novel molecular tools including genes, vectors, regulatory elements that function in various types of organisms and in distinct growth phases and growth conditions will be useful in developing genetically enhanced organisms.

SUMMARY

This section provides a general summary of the disclosure, and is not comprehensive of its full scope or all of its features.

In one aspect, an isolated, synthetic, or recombinant nucleic acid molecule is provided in which the isolated, synthetic, or recombinant nucleic acid molecule includes a nucleic acid sequence hybridizing under high stringency conditions to at least 50 contiguous nucleotides of a nucleic acid sequence selected from the group consisting of any one or more of SEQ ID NOs:1-70 and 180-202, and complements thereof; or exhibiting at least 80% sequence identity to at least 50 contiguous nucleotides of a nucleic acid sequence selected from the group consisting of any one of SEQ ID NOs:1-70 and 180-202, and complements thereof. In some examples, the invention provides a nucleic acid molecule comprising a nucleic acid sequence having at least 80%, at least 85%, at least 90% or at least 95% to at least 50 contiguous nucleotides of any one of SEQ ID NOs:1-70 and 180-202 operably linked to a heterologous nucleic acid sequence, such as a heterologous nucleic acid sequence encoding a polypeptide or functional RNA. A nucleic acid sequence as provided herein having at least 80% sequence identity to at least 50 contiguous nucleotides of a nucleic acid sequence selected from the group consisting of any one or more of SEQ ID NOs:1-70 and 180-202 can have at least 80%, at least 85%, at least 90%, at least 95%, at least 96%, at least 97%, at least 98%, at least 99%, or 100% identity to at least 50, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, or at least 1000 contiguous nucleotides of any one of SEQ ID NOs:1-70 and 180-202. In some examples, a nucleic acid molecule as provided herein can comprise a nucleic acid sequence having at least 80%, at least 85%, at least 90%, at least 95%, at least 96%, at least 97%, at least 98%, or at least 99% identity to at least 50, at least 100, at least 150, at least 200, at least 250, at least 300, at least 350, at least 400, at least 450, at least 500, at least 550, at least 600, at least 650, at least 7), at least 750, at least 800, at least 850, at least 900, at least 950, or at least 1000 contiguous nucleotides extending from the 3' end of any one of SEQ ID NOs:1-70 and 180-202. A nucleic acid sequence as provided herein having at least 80%, at least 85%, at least 90%, at least 95%, at least 96%, at least 97%, at least 98%, or at least 99% identity to at least 50, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, or at least 1000 contiguous nucleotides of any one of SEQ ID NOs:1-70 and 180-202 can have promoter activity. The isolated, synthetic, or recombinant nucleic acid molecule can include a heterologous nucleic acid sequence operably linked to the nucleic acid sequence having at least 80% sequence identity to at least 50 contiguous nucleotides of any one of SEQ ID NOs:1-70 and 180-202.

In some embodiments, an isolated, synthetic, or recombinant nucleic acid molecule as provided herein includes a nucleic acid sequence hybridizing under high stringency conditions to at least 50 contiguous nucleotides of SEQ ID NO:19, SEQ ID NO:20, SEQ ID NO:23, SEQ ID NO:24, SEQ ID NO:34, SEQ ID NO:35, SEQ ID NO:49, SEQ ID NO:50, SEQ ID NO:51, SEQ ID NO:52, SEQ ID NO:53, SEQ ID NO:54, SEQ ID NO:57, SEQ ID NO:58, SEQ ID NO:181, SEQ ID NO:182, SEQ ID NO:183, SEQ ID NO:186, SEQ ID NO:190, SEQ ID NO:191, SEQ ID NO:192, SEQ ID NO:196, SEQ ID NO:197, SEQ ID NO:198, or SEQ ID NO:199, and complements thereof; or exhibiting at least 80% sequence identity to at least 50 contiguous nucleotides of SEQ ID NO:19, SEQ ID NO:20, SEQ ID NO:23, SEQ ID NO:24, SEQ ID NO:34, SEQ ID NO:35, SEQ ID NO:49, SEQ ID NO:50, SEQ ID NO:51, SEQ ID NO:52, SEQ ID NO:53, SEQ ID NO:54, SEQ ID NO:57, SEQ ID NO:58, SEQ ID NO:181, SEQ ID NO:182, SEQ ID NO:183, SEQ ID NO:186, SEQ ID NO:190, SEQ ID NO:191, SEQ ID NO:192, SEQ ID NO:196, SEQ ID NO:197, SEQ ID NO:198, or SEQ ID NO:199, and complements thereof. For example, the isolated, synthetic, or recombinant nucleic acid molecule can include a nucleic acid sequence hybridizing under high stringency conditions to at least 50 contiguous nucleotides of a nucleic acid sequence selected from the group consisting of SEQ ID NO:19, SEQ ID NO:23, SEQ ID NO:24, SEQ ID NO:34, SEQ ID NO:49, SEQ ID NO:52, SEQ ID NO:53, SEQ ID NO:58, SEQ ID NO:181, SEQ ID NO:182, SEQ ID NO:183, SEQ ID NO:186, SEQ ID NO:190, SEQ ID NO:191, SEQ ID NO:192, SEQ ID NO:196, SEQ ID NO:197, SEQ ID NO:198, or SEQ ID NO:199, and complements thereof; or exhibiting at least 80% sequence identity to at least 50 contiguous nucleotides of a nucleic acid sequence selected from the group consisting of SEQ ID NO:19, SEQ ID NO:23, SEQ ID NO:24, SEQ ID NO:34, SEQ ID NO:49, SEQ ID NO:52, SEQ ID NO:53, SEQ ID NO:58, SEQ ID NO:181, SEQ ID NO:182, SEQ ID NO:183, SEQ ID NO:186, SEQ ID NO:190, SEQ ID NO:191, SEQ ID NO:192, SEQ ID NO:196, SEQ ID NO:197, SEQ ID NO:198, or SEQ ID NO:199, and complements thereof. The nucleic acid sequence according to any of the above can have promoter activity. The isolated, synthetic, or recombinant nucleic acid molecule can include a heterologous nucleic acid sequence operably linked to the nucleic acid sequence having at least 80% sequence identity to at least 50 contiguous nucleotides of SEQ ID NO:19, SEQ ID NO:20, SEQ ID NO:23, SEQ ID NO:24, SEQ ID NO:34, SEQ ID NO:35, SEQ ID NO:49, SEQ ID NO:50, SEQ ID NO:51, SEQ ID NO:52, SEQ ID NO:53, SEQ ID NO:54, SEQ ID NO:57, SEQ ID NO:58, SEQ ID NO:181, SEQ ID NO:182, SEQ ID NO:183, SEQ ID NO:186, SEQ ID NO:190, SEQ ID NO:191, SEQ ID NO:192, SEQ ID NO:196, SEQ ID NO:197, SEQ ID NO:198, or SEQ ID NO:199. The heterologous nucleic acid sequence can be a DNA sequence encoding a polypeptide or functional RNA. Alternatively or in addition, the isolated, synthetic, or recombinant nucleic acid molecule as provided herein can be a vector.

In some examples, a nucleic acid molecule as provided herein includes a nucleic acid sequence having at least 80%, at least 85%, at least 90%, at least 95%, at least 96%, at least 97%, at least 98%, or at least 99% identity to at least 50, at least 100, at least 150, at least 200, at least 250, at least 300, at least 350, at least 400, at least 450, at least 500, at least 550, at least 600, at least 650, or at least 700 contiguous nucleotides of any one of SEQ ID NO:59, SEQ ID NO:61, SEQ ID NO:63, SEQ ID NO:66, SEQ ID NO:67, SEQ ID NO:68, SEQ ID NO:69, SEQ ID NO:70, SEQ ID NO:181, SEQ ID NO:182, SEQ ID NO:183, SEQ ID NO:186, SEQ ID NO:190, SEQ ID NO:191, SEQ ID NO:192, SEQ ID NO:196, SEQ ID NO:197, SEQ ID NO:198, or SEQ ID NO:199. The nucleic acid sequence can have promoter activity. The isolated, synthetic, or recombinant nucleic acid molecule can include a heterologous nucleic acid sequence operably linked to the nucleic acid sequence having at least 80% sequence identity to at least 50 contiguous nucleotides of any one of SEQ ID NO:59, SEQ ID NO:61, SEQ ID NO:63, SEQ ID NO:66, SEQ ID NO:67, SEQ ID NO:68, SEQ ID NO:69, SEQ ID NO:70, SEQ ID NO:181, SEQ ID NO:182, SEQ ID NO:183, SEQ ID NO:186, SEQ ID NO:190, SEQ ID NO:191, SEQ ID NO:192, SEQ ID NO:196, SEQ ID NO:197, SEQ ID NO:198, and SEQ ID NO:199. The heterologous nucleic acid sequence can be a DNA sequence encoding a polypeptide or functional RNA. Alternatively or in addition, the isolated, synthetic, or recombinant nucleic acid molecule as provided herein can be a vector.

In some embodiments, an isolated, synthetic, or recombinant nucleic acid molecule as disclosed herein includes at least 50 contiguous nucleotides of a nucleic acid sequence selected from the group consisting of any one or more of SEQ ID NOs:1-70 and 180-202, and complements thereof. In some examples, an isolated, synthetic, or recombinant nucleic acid molecule as disclosed herein can be selected from the group consisting of an isolated, synthetic, or recombinant nucleic acid molecule can comprise a nucleic acid sequence comprising at least 50 contiguous nucleotides of a sequence selected from the group consisting of SEQ ID NO:19, SEQ ID NO:20, SEQ ID NO:23, SEQ ID NO:24, SEQ ID NO:34, SEQ ID NO:35, SEQ ID NO:49, SEQ ID NO:50, SEQ ID NO:51, SEQ ID NO:52, SEQ ID NO:53, SEQ ID NO:54, SEQ ID NO:57, SEQ ID NO:58, SEQ ID NO:181, SEQ ID NO:182, SEQ ID NO:183, SEQ ID NO:186, SEQ ID NO:190, SEQ ID NO:191, SEQ ID NO:192, SEQ ID NO:196, SEQ ID NO:197, SEQ ID NO:198, and SEQ ID NO:199. In some examples, an isolated, synthetic, or recombinant nucleic acid molecule as disclosed herein can comprise a nucleic acid sequence comprising at least 50 contiguous nucleotides of a sequence selected from the group consisting of SEQ ID NO:59, SEQ ID NO:61, SEQ ID NO:63, SEQ ID NO:66, SEQ ID NO:67, SEQ ID NO:68, SEQ ID NO:69, SEQ ID NO:181, SEQ ID NO:182, SEQ ID NO:183, SEQ ID NO:186, SEQ ID NO:190, SEQ ID NO:191, SEQ ID NO:192, SEQ ID NO:196, SEQ ID NO:197, SEQ ID NO:198, and SEQ ID NO:199.

In some examples, a nucleic acid molecule can include a nucleic acid sequence having at least 80%, at least 85%, at least 90%, at least 95%, at least 96%, at least 97%, at least 98%, or at least 99% identity to at least 100, at least 200, at least 300, at least 400, at least 500, at least 650, at least 7), at least 750, at least 800, at least 850, at least 900, or at least 950 contiguous nucleotides of SEQ ID NO:20, SEQ ID NO:59, SEQ ID NO:61, SEQ ID NO:66, SEQ ID NO:68, SEQ ID NO:69, SEQ ID NO:181, SEQ ID NO:182, SEQ ID NO:183, SEQ ID NO:186, SEQ ID NO:190, SEQ ID NO:191, SEQ ID NO:192, SEQ ID NO:196, SEQ ID NO:197, SEQ ID NO:198, or SEQ ID NO:199. In some examples, a nucleic acid molecule can include a nucleic acid sequence having at least 80%, at least 85%, at least 90%, at least 95%, at least 96%, at least 97%, at least 98%, or at least 99% identity to at least 100, at least 200, at least 300, at least 400, at least 500, at least 600, at least 650, at least 700, at least 750, at least 800, at least 850, at least 900, or at least 950 contiguous nucleotides of SEQ ID NO:20, SEQ ID NO:59, SEQ ID NO:61, SEQ ID NO:66, SEQ ID NO:68, SEQ ID NO:69, SEQ ID NO:181, SEQ ID NO:182, SEQ ID NO:183, SEQ ID NO:186, SEQ ID NO:190, SEQ ID NO:191, SEQ ID NO:192, SEQ ID NO:196, SEQ ID NO:197, SEQ ID NO:198, or SEQ ID NO:199; and the nucleic acid molecule can exhibit promoter activity. A nucleic acid molecule as provided herein can include a heterologous nucleic acid sequence operably linked to a sequence having at least 80% identity to at least 100 bp of SEQ ID NO:20, SEQ ID NO:59, SEQ ID NO:61, SEQ ID NO:66, SEQ ID NO:68, SEQ ID NO:69, SEQ ID NO:181, SEQ ID NO:182, SEQ ID NO:183, SEQ ID NO:186, SEQ ID NO:190, SEQ ID NO:191, SEQ ID NO:192, SEQ ID NO:196, SEQ ID NO:197, SEQ ID NO:198, or SEQ ID NO:199. Alternatively or in addition, the nucleic acid molecule can be a vector that includes a nucleic acid sequence having at least 80%, at least 85%, at least 90%, at least 95%, at least 96%, at least 97%, at least 98%, or at least 99% identity to at least 100, at least 200, at least 300, at least 400, at least 500, at least 600, at least 650, at least 700, at least 750, at least 800, at least 850, at least 900, or at least 950 contiguous nucleotides of SEQ ID NO:20, SEQ ID NO:59, SEQ ID NO:61, SEQ ID NO:66, SEQ ID NO:68, SEQ ID NO:69, or SEQ ID NO:181, SEQ ID NO:182, SEQ ID NO:183, SEQ ID NO:186, SEQ ID NO:190, SEQ ID NO:191, SEQ ID NO:192, SEQ ID NO:196, SEQ ID NO:197, SEQ ID NO:198, and SEQ ID NO:199.

In some examples, a nucleic acid molecule as provided herein can comprise an actin promoter, for example can include a nucleic acid sequence having at least 80%, at least 85%, at least 90%, at least 95%, at least 96%, at least 97%, at least 98%, or at least 99% identity to at least 100, at least 200, at least 300, at least 400, at least 500, at least 600, at least 650, at least 700, or at least 750 contiguous nucleotides of SEQ ID NO:11, SEQ ID NO:12, SEQ ID NO:61, SEQ ID NO: 62, or SEQ ID NO:63. For example a promoter as provided herein can have at least 80%, at least 85%, at least 90%, at least 95%, at least 96%, at least 97%, at least 98%, or at least 99% identity to SEQ ID NO:11, SEQ ID NO:12, SEQ ID NO:61, SEQ ID NO: 62, or SEQ ID NO:63. In other examples, a nucleic acid molecule as provided herein can comprise an alpha tubulin promoter, for example can include a nucleic acid sequence having at least 80%, at least 85%, at least 90%, at least 95%, at least 96%, at least 97%, at least 98%, or at least 99% identity to at least 100, at least 20, at least 300, at least 400, at least 500, at least 600, at least 650, at least 700, at least 800, at least 850, at least 900, or least 950 or at least 1000 contiguous nucleotides of SEQ ID NO:19, SEQ ID NO:20, SEQ ID NO:23, or SEQ ID NO:59. For example a promoter as provided herein can have at least 80%, at least 85%, at least 90%, at least 95%, at least 96%, at least 97%, at least 98%, or at least 99% identity to SEQ ID NO:19, SEQ ID NO:20, SEQ ID NO:23, or SEQ ID NO:59.

In further examples a nucleic acid molecule as provided herein can comprise a promoter having at least 80%, at least 85%, at least 90%, at least 95%, at least 96%, at least 97%, at least 98%, or at least 99% identity to at least 100, at least 200, at least 300, at least 400, at least 500, at least 600, at least 650, at least 700, at least 800, at least 850, at least 900, or least 950 or at least 1000 contiguous nucleotides of SEQ ID NO:191, SEQ ID NO:24, SEQ ID NO:196, SEQ ID NO:198, SEQ ID NO:199, or SEQ ID NO:183. For example, a nucleic acid molecule as provided herein can comprise a promoter having at least 80%, at least 85%, at least 90%, at least 95%, at least 96%, at least 97%, at least 98%, or at least 99% identity to at least 100, at least 200, at least 300, at least 400, at least 500, at least 600, at least 650, at least 700, at least 800, at least 850, at least 900, or least 950 or at least 1000 contiguous nucleotides of SEQ ID NO:24, SEQ ID NO:196, SEQ ID NO:198, SEQ ID NO:199, or SEQ ID NO:183. In some examples, the promoter provided in a nucleic acid molecule may be confer high levels of expression to a gene to which it is operably linked under lipogenic culture conditions, and may be, for example, a promoter having at least 85%, at least 90%, at least 95%, at least 96%, at least 97%, at least 98%, or at least 99% identity to at least 100, at least 200, at least 300, at least 400, at least 500, at least 600, at least 650, at least 700, at least 800, at least 850, at least 900, or least 950 or at least 1000 contiguous nucleotides of SEQ ID 198, SEQ ID NO:183, or SEQ ID NO:191. For example, a nucleic acid molecule as provided herein can include a promoter having at least 85%, at least 90%, at least 95%, at least 96%, at least 97%, at least 98%, or at least 99% identity to SEQ ID 198 or SEQ ID NO:183.

In yet additional examples, a nucleic acid molecule as provided herein can comprise a promoter having at least 80%, at least 85%, at least 90%, at least 95%, at least 96%, at least 97%, at least 98%, or at least 99% identity to at least 100, at least 200, at least 300, at least 400, at least 500, at least 600, at least 650, at least 700, at least 800, at least 850, at least 900, or least 950 or at least 1000 contiguous nucleotides of SEQ ID NO:199 or SEQ ID NO:196. In some examples, the promoter provided in a nucleic acid molecule may be confer high levels of expression to a gene to which it is operably linked under lipogenic culture conditions as well as under nutrient replete growth conditions, and may be, for example, a promoter having at least 80%, at least 85%, at least 90%, at least 95%, at least 96%, at least 97%, at least 98%, or at least 99% identity to SEQ ID 199 or SEQ ID NO:196.

In some embodiments, an isolated, synthetic, or recombinant nucleic acid molecule as disclosed herein can find use, for example, as a sequence that, when operably linked to a nucleic acid sequence encoding a polypeptide or a functional RNA, can effect expression of the nucleic acid encoding a polypeptide or a functional RNA. In some embodiments, the isolated, synthetic, or recombinant nucleic acid molecule disclosed herein is a promoter. In some embodiments, the promoter is functional in a labyrinthulomycetes cell.

Some embodiments disclosed herein relate to a nucleic acid construct in which an isolated, synthetic, or recombinant nucleic acid molecule as provided herein is operably linked to a heterologous nucleic acid sequence. For example, a construct as provided herein can include a nucleic acid sequence as described herein, in which the nucleic acid sequence comprises a promoter that is operably linked to a heterologous nucleic acid sequence. In some embodiments, the heterologous nucleic acid sequence includes a regulatory element. In some embodiments, the heterologous regulatory element includes a 5'-untranslated (UTR) sequence. In some embodiments, a nucleic acid construct as disclosed herein includes a nucleic acid sequence as disclosed herein, for example, a nucleic acid as disclosed herein that comprises a promoter, in which the promoter is operably linked to a heterologous nucleic acid sequence encoding a polypeptide or a functional RNA. In some embodiments, the heterologous nucleic acid sequence encodes a functional RNA such as, for example, a ribosomal RNA, a tRNA, a ribozyme, a trans-activating (tr) RNA of a CRISPR system, a targeting or crispr (cr) RNA of a CRISPR system, a chimeric guide RNA of a CRISPR system, a micro RNA, an interfering RNA (RNAi) molecule, a short hairpin (sh) RNA, or an antisense RNA molecule. In some embodiments, the heterologous nucleic acid sequence is also operably linked to a terminator sequence. In some embodiments, the terminator includes a sequence having at least 90% or 95% sequence identity to a sequence selected from the group consisting of SEQ ID NOs:71-78. In some embodiments, the terminator is selected from the group consisting of *Saccharomyces cerevisiae* ADH1 terminator, *S. cerevisiae* ENO2 terminator, *S. cerevisiae* PDC1 terminator. *S. cerevisiae* PGK1 terminator, *S. cerevisiae* TDH3 terminator, *S. cerevisiae* TEF1 terminator, *S. cerevisiae* CYC1 terminator, and simian virus SV40 terminator. In some embodiments, the nucleic acid construct is functional in a labyrinthulomycetes cell. In some embodiments, the nucleic acid construct as provided herein is further defined as an expression cassette or a vector.

Some embodiments disclosed herein relate to a nucleic acid construct in which an isolated, synthetic, or recombinant nucleic acid molecule as provided herein is operably linked to heterologous nucleic acid sequence encoding a polypeptide or a functional RNA which, when expressed in a recombinant cell, directly or indirectly confers a phenotype or trait. The phenotype or trait can be selected from the group consisting of abiotic stress resistance; disease resistance; herbicide tolerance, toxin tolerance; altered carbohydrate content; altered cell wall composition, altered growth rate, altered isoprenoid content; altered amino acid content; altered biomass yield; altered fatty acid/lipid content; altered nitrogen utilization; altered photosynthetic capacity, altered activity of a polyunsaturated fatty acid-polyketide synthase (PUFA-PKS) complex; altered activity of an elongase/desaturase fatty acid synthase (FAS) pathway; and production of a biopolymer, a biofuel molecule, an enzyme, a flavor compound, a pharmaceutical compound, a pigment, an antioxidant, or a heterologous polypeptide. In some embodiments the nucleic acid molecule as provided herein comprises a promoter that is operably linked to a nucleic acid sequence encoding a polypeptide that may be, as nonlimiting examples, a transcription factor, an enzyme, or a transporter. In some embodiments, the polypeptide or the functional RNA is involved in a synthetic pathway for the production of a fatty acid or lipid.

Some embodiments disclosed herein relate to a nucleic acid construct in which an isolated, synthetic, or recombinant nucleic acid molecule as provided herein is operably linked to a heterologous nucleic acid sequence encoding a selectable marker or a reporter gene. In some embodiments, the heterologous nucleic acid sequence encoding a selectable marker can be a gene encoding a polypeptide that confers resistance to an antibiotic, a polypeptide that confers tolerance to an herbicide, a gene encoding an auxotrophic marker, or any other gene product that can allow for selection of transformants. In some embodiments, the heterologous nucleic acid sequence encoding a reporter gene can, for example, encode a fluorescent protein or an enzyme that can produce a detectable product. In some embodiments, the heterologous nucleic acid sequence encoding a selectable marker or a reporter gene selected from the group consisting of a gene conferring resistance to an antibiotic, a gene conferring resistance to an herbicide, a gene encoding acetyl CoA carboxylase (ACCase), a gene encoding acetohydroxy acid synthase (ahas), a gene encoding acetolactate synthase, a gene encoding aminoglycoside phosphotransferase, a gene encoding anthranilate synthase, a gene encoding bromoxynil nitrilase, a gene encoding cytochrome P450-NADH-cytochrome P450 oxidoreductase, a gene encoding dalapon dehalogenase, a gene encoding dihydropteroate synthase, a gene encoding a class I 5-enolpyruvylshikimate-3-phosphate synthase (EPSPS), a gene encoding a class II EPSPS (aroA), a gene encoding a non-class I II EPSPS, a gene encoding glutathione reductase, a gene encoding glyphosate acetyltransferase, a gene encoding glyphosate oxidoreductase, a gene encoding hydroxyphenylpyruvate dehydrogenase, a gene encoding hydroxy-phenylpyruvate dioxygenase, a gene encoding isoprenyl pyrophosphate isomerase, a gene encoding lycopene cyclase, a gene encoding phosphinothricin acetyl transferase, a gene encoding phytoene desaturase, a gene encoding prenyl transferase, a gene encoding protoporphyrin oxidase, a gene encoding superoxide dismutase, arg7, his3, hisD, hisG, manA, nitl, trpB, uidA, xylA, a dihydrofolate reductase gene, a mannose-6-phosphate isomerase gene, a nitrate reductase gene, an ornithine decarboxylase gene, a thymidine kinase gene, a 2-deoxyglucose resistance gene; and an R-locus gene.

In one aspect, some embodiments disclosed herein relate to a method of transforming a eukaryotic cell that includes introducing into a eukaryotic cell a nucleic acid molecule as provided herein, and selecting or screening for a transformed eukaryotic cell. In some embodiments, the nucleic acid molecule is introduced into the eukaryotic cell by a biolistic procedure or electroporation.

In a related aspect, some embodiments disclosed herein relate to a recombinant eukaryotic cell produced by a transformation method that includes introducing into a eukaryotic cell a nucleic acid molecule disclosed herein, and selecting or screening for a transformed eukaryotic cell. Some embodiments disclosed herein relate to a recombinant eukaryotic cell that includes an isolated, recombinant, or synthetic nucleic acid molecule as provided herein. In some embodiments, the nucleic acid molecule is stably integrated into the genome of the recombinant cell. As described in great detail herein, a continuing need exists for the identification of additional regulatory control elements for expression of transgenes in labyrinthulomycetes microorganisms, including regulatory control elements that are differentially expressed, for example, during different time points or under certain growth conditions, or in response to chemical or environmental stimuli. Accordingly, in some embodiments, the recombinant cell belongs to the class labyrinthulomycetes. In some embodiments, the labyrinthulomycetes microorganism is an *Aplanochytrium*, an *Aurantiochytrium*, a *Diplophrys*, a *Japonochytrium*, an *Ohlongichytrium*, a *Schizochytrium*, a *Thraustochytrium*, or an *Ulkenia* microorganism.

In a further aspect, some embodiments disclosed herein relate to an amplification reaction mixture that includes primers adapted for amplifying a nucleic acid including at least 50 contiguous nucleotides of a nucleic acid sequence selected from the group consisting of SEQ ID Nos:1-70, SEQ ID Nos:180-202, complements thereof, and nucleic acids exhibiting at least 80% sequence identity thereto.

In yet a further aspect, some embodiments disclosed herein relate to a ligation reaction mixture that includes a nucleic acid including at least 50 contiguous nucleotides of a nucleic acid sequence selected from the group consisting of SEQ ID Nos:1-70, SEQ ID Nos:180-202, complements thereof, and nucleic acids exhibiting at least 80% sequence identity thereto.

The foregoing summary is illustrative only and is not intended to be in any way limiting. In addition to the illustrative aspects, embodiments, and features described above, further aspects, embodiments, objects and features of the disclosure will become fully apparent from the drawings and the following detailed description and the claims.

Figure 1:
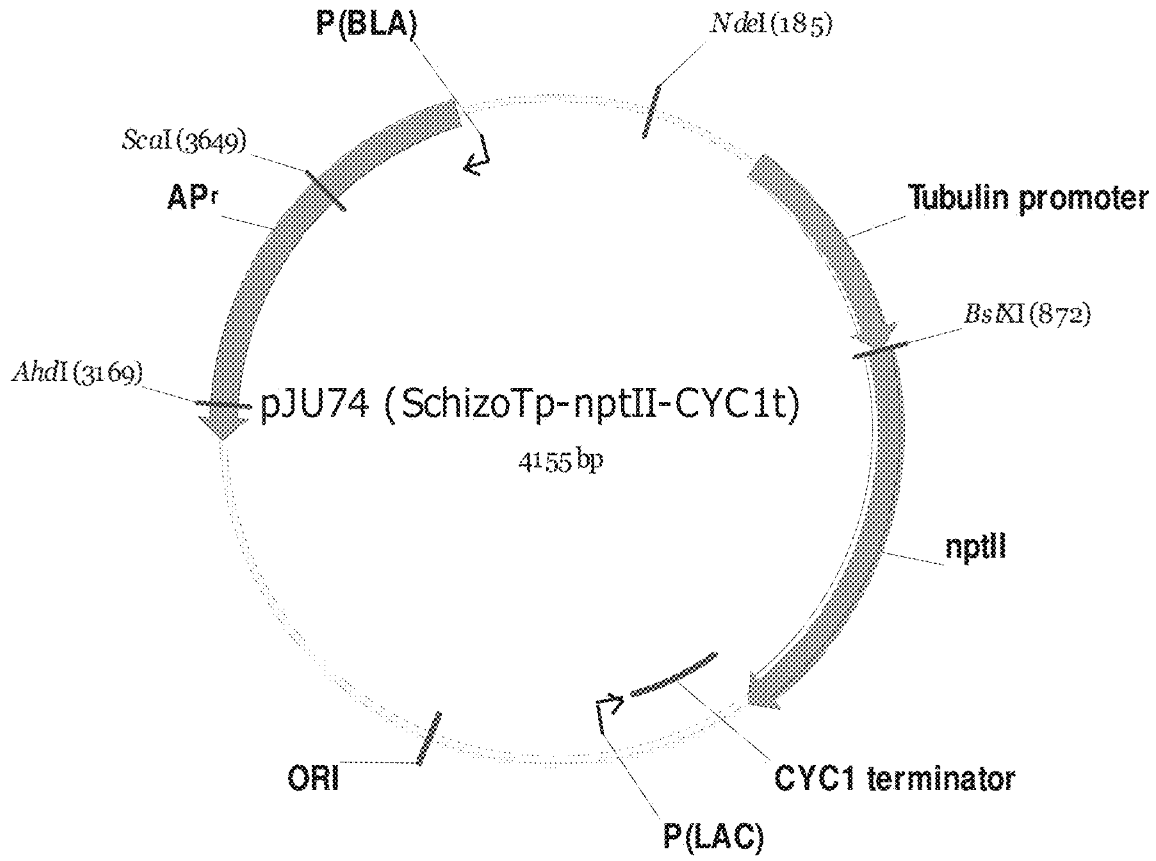
FIG. 1 is plasmid map for expression vector pSGI-JU-74 used to make promoter expression constructs described in Examples 3 and 7.

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope; the disclosure will be described with additional specificity and detail through use of the accompanying drawings.

DETAILED DESCRIPTION OF THE DISCLOSURE

The present disclosure generally relates to compositions, methods and related materials for use in genetic engineering of organisms. In particular, the disclosure provides methods and materials useful for affecting gene expression in vivo and/or in vitro. Some embodiments disclosed herein relate to isolated, recombinant, or synthetic nucleic acid molecules having transcriptional regulatory activity such as, for example, regulatory elements. Some embodiments disclosed herein relate to methods for modifying, making, and using such regulatory elements. Some embodiments disclosed herein relate to recombinant cells, methods for making and using same, and biomaterials derived therefrom.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

A. Some Definitions

Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form “a”. “an”, and “the” include plural references unless the context clearly dictates otherwise. For example, the term “a molecule” includes one or more molecules, including mixtures thereof. “A and/or B” is used herein to include all of the following alternatives: “A”. “B”, and “A and B”.

The term “about”, as used herein, means either: within plus or minus 10% of the provided value, or rounded to the nearest significant figure, in all cases inclusive of the provided value. Where ranges are provided, they are inclusive of the boundary values.

The terms, “cells”, “cell cultures”, “cell line”, “recombinant host cells”, “recipient cells” and “host cells” as used herein, include the primary subject cells and any progeny thereof, without regard to the number of transfers. It should be understood that not all progeny are exactly identical to the parental cell (due to deliberate or inadvertent mutations or differences in environment); however, such altered progeny are included in these terms, so long as the progeny retain the same functionality as that of the originally transformed cell.

As used herein, the term “construct” is intended to mean any recombinant nucleic acid molecule such as an expression cassette, plasmid, cosmid, virus, autonomously replicating polynucleotide molecule, phage, or linear or circular, single-stranded or double-stranded, DNA or RNA polynucleotide molecule, derived from any source, capable of genomic integration or autonomous replication, comprising a nucleic acid molecule where one or more nucleic acid sequences has been linked in a functionally operative manner. e.g. operably linked.

A “control organism”, “control microorganism”, or “control cell” as used herein, refers to an organism, microorganism, or cell that is substantially identical to the subject organism, microorganism, or cell, except for the engineered genetic manipulation disclosed for the subject organism, microorganism, or cell, and can provide a reference point for measuring changes in phenotype of the subject organism or cell. “Substantially identical” thus includes, for example, small random variations in genome sequence (“SNPs”) that are not relevant to the genotype, phenotype, parameter, or gene expression level that is of interest in the subject microorganism. Depending on specific purposes of their use, a control organism or cell may comprise, for example, (a) a progenitor strain or species, cell or microorganism population, or organism, with respect to the subject organism, microorganism, or cell, where the progenitor lacks the genetically engineered constructs or alterations that were introduced into the progenitor strain, species, organism, or cell or microorganism population to generate the subject organism, microorganism, or cell; b) a wild-type organism or cell, e.g., of the same genotype as the starting material for the genetic alteration which resulted in the subject organism or cell; (c) an organism or cell of the same genotype as the starting material but which has been transformed with a null construct (e.g. a construct which has no known effect on the trait of interest, such as a construct comprising a reporter gene); (d) an organism or cell which is a non-transformed segregant among progeny of a subject organism, microorganism, or cell; or (e) the subject organism or cell itself, under conditions in which the gene of interest is not expressed. In some instances, “control organism” may refer to an organism that does not contain the exogenous nucleic acid present in the transgenic organism of interest, but otherwise has the same or very similar genetic background as such a transgenic organism.

As used herein, “exogenous” with respect to a nucleic acid or gene indicates that the nucleic or gene has been introduced (“transformed”) into an organism, microorganism, or cell by human intervention. Typically, such an exogenous nucleic acid is introduced into a cell or organism via a recombinant nucleic acid construct. An exogenous nucleic acid can be a sequence from one species introduced into another species. e.g., a heterologous nucleic acid. An exogenous nucleic acid can also be a sequence that is homologous to an organism (e.g., the nucleic acid sequence occurs naturally in that species or encodes a polypeptide that occurs naturally in the host species) that has been isolated and subsequently reintroduced into cells of that organism. An exogenous nucleic acid that includes a homologous sequence can often be distinguished from the naturally-occurring sequence by the presence of non-natural sequences linked to the exogenous nucleic acid, e.g., non-native regulatory sequences flanking the homologous gene sequence in a recombinant nucleic acid construct. Alternatively or in addition, a stably transformed exogenous nucleic acid can be detected and/or distinguished from a native gene by its juxtaposition to sequences in the genome where it has integrated. Further, a nucleic acid is considered exogenous if it has been introduced into a progenitor of the cell, organism, or strain under consideration.

As used herein. “expression” refers to the process of converting genetic information of a polynucleotide into RNA through transcription, which is typically catalyzed by an enzyme, RNA polymerase, and, where the RNA encodes a polypeptide, into protein, through translation of mRNA on ribosomes to produce the encoded protein.

The term “expression cassette” as used herein, refers to a nucleic acid construct that encodes a protein or functional RNA operably linked to expression control elements, such as a promoter, and optionally, any or a combination of other nucleic acid sequences that affect the transcription or translation of the gene, such as, but not limited to, a transcriptional terminator, a ribosome binding site, a splice site or splicing recognition sequence, an intron, an enhancer, a polyadenylation signal, an internal ribosome entry site, etc.

A “functional RNA molecule” is an RNA molecule that can interact with one or more proteins or nucleic acid molecules to perform or participate in a structural, catalytic, or regulatory function that affects the expression or activity of a gene or gene product other than the gene that produced the functional RNA. A functional RNA can be, for example, a transfer RNA (tRNA), ribosomal RNA (rRNA), anti-sense RNA (asRNA), microRNA (miRNA), short-hairpin RNA (shRNA), small interfering RNA (siRNA), small nucleolar RNAs (snoRNAs), piwi-interacting RNA (piRNA), or a ribozyme.

The term “gene” is used broadly to refer to any segment of nucleic acid molecule that encodes a protein or that can be transcribed into a functional RNA. Genes may include sequences that are transcribed but are not part of a final, mature, and/or functional RNA transcript, and genes that encode proteins may further comprise sequences that are transcribed but not translated, for example, 5' untranslated regions, 3' untranslated regions, introns, etc. Further, genes may optionally further comprise regulatory sequences required for their expression, and such sequences may be, for example, sequences that are not transcribed or translated. Genes can be obtained from a variety of sources, including cloning from a source of interest or synthesizing from known or predicted sequence information, and may include sequences designed to have desired parameters.

The term "heterologous" when used in reference to a polynucleotide, a gene, a nucleic acid, a polypeptide, or an enzyme, refers to a polynucleotide, gene, a nucleic acid, polypeptide, or an enzyme that is not derived from the host species. For example, "heterologous gene" or "heterologous nucleic acid sequence" as used herein, refers to a gene or nucleic acid sequence from a different species than the species of the host organism it is introduced into. When referring to a gene regulatory sequence or to an auxiliary nucleic acid sequence used for manipulating expression of a gene sequence (e.g. a 5' untranslated region, 3' untranslated region, poly A addition sequence, intron sequence, splice site, ribosome binding site, internal ribosome entry sequence, genome homology region, recombination site, etc.) or to a nucleic acid sequence encoding a protein domain or protein localization sequence. "heterologous" means that the regulatory or auxiliary sequence or sequence encoding a protein domain or localization sequence is from a different source than the gene with which the regulatory or auxiliary nucleic acid sequence or nucleic acid sequence encoding a protein domain or localization sequence is juxtaposed in a genome, chromosome or episome. Thus, a promoter operably linked to a gene to which it is not operably linked to in its natural state (for example, in the genome of a non-genetically engineered organism) is referred to herein as a "heterologous promoter." even though the promoter may be derived from the same species (or, in some cases, the same organism) as the gene to which it is linked. Similarly, when referring to a protein localization sequence or protein domain of an engineered protein, "heterologous" means that the localization sequence or protein domain is derived from a protein different from that into which it is incorporated by genetic engineering.

The term "hybridization", as used herein, refers generally to the ability of nucleic acid molecules to join via complementary base strand pairing. Such hybridization may occur when nucleic acid molecules are contacted under appropriate conditions and/or circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, nucleic acid molecules are said to exhibit "complete complementarity" when every nucleotide of one of the molecules is complementary to its base pairing partner nucleotide of the other. Two molecules are said to be "minimally complementary" if they can hybridize to one another with sufficient stability to permit them to remain annealed to one another under at least conventional "low-stringency" conditions. In some instances, the molecules are said to be "complementary" if they can hybridize to one another with sufficient stability to permit them to remain annealed to one another under conventional "high-stringency" conditions. Nucleic acid molecules that hybridize to other nucleic acid molecules, e.g., at least under low stringency conditions are said to be "hybridizable cognates" of the other nucleic acid molecules. Conventional stringency conditions are described by Sambrook et al., *Molecular Cloning, A Laboratory Handbook*, Cold Spring Harbor Laboratory Press, 1989), and by Haymes et al. In: *Nucleic Acid Hybridization, A Practical Approach*, IRL Press, Washington. D.C. (1985). Departures from complete complementarity are therefore permissible, as long as such departures do not completely preclude the capacity of the molecules to form a double-stranded structure. Thus, in order for a nucleic acid molecule or fragment thereof of the present disclosure to serve as a primer or probe it needs only be sufficiently complementary in sequence to be able to form a stable double-stranded structure under the particular solvent and salt concentrations employed.

Appropriate stringency conditions which promote DNA hybridization include, for example, 6.0×sodium chloride/sodium citrate (SSC) at about 45° C., followed by a wash of 2.0×SSC at about 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. These conditions are known to those skilled in the art, or can be found in *Current Protocols in Molecular Biology*, John Wiley & Sons. N.Y. (1989), 6.3.1-6.3.6. For example, low stringency conditions may be used to select nucleic acid sequences with lower sequence identities to a target nucleic acid sequence. One may wish to employ conditions such as about 0.15 M to about 0.9 M sodium chloride, at temperatures ranging from about 20° C. to about 55° C. High stringency conditions may be used to select for nucleic acid sequences with higher degrees of identity to the disclosed nucleic acid sequences (Sambrook et al., 1989, supra). In one embodiment of the present disclosure, high stringency conditions involve nucleic acid hybridization in about 2×SSC to about 10×SSC (diluted from a 20×SSC stock solution containing 3 M sodium chloride and 0.3 M sodium citrate, pH 7.0 in distilled water), about 2.5× to about 5×Denhardt's solution (diluted from a 50×stock solution containing 1% (w/v) bovine serum albumin, 1% (w/v) ficoll, and 1% (w/v) polyvinylpyrrolidone in distilled water), about 10 mg/mL to about 100 mg/mL fish sperm DNA, and about 0.02% (w/v) to about 0.1% (w/v) SDS, with an incubation at about 50° C. to about 70° C. for several hours to overnight. High stringency conditions are preferably provided by 6×SSC, 5×Denhardt's solution, 100 mg/mL sheared and denatured salmon sperm DNA, and 0.1% (w/v) SDS, with incubation at 55×C for several hours. Hybridization is generally followed by several wash steps. The wash compositions generally comprise 0.5×SSC to about 10×SSC, and 0.01% (w/v) to about 0.5% (w/v) SDS with a 15-min incubation at about 20° C. to about 70° C. Preferably, the nucleic acid segments remain hybridized after washing at least one time in 0.1×SSC at 65° C. In some instances, very high stringency conditions may be used to select for nucleic acid sequences with much higher degrees of identity to the disclosed nucleic acid sequences. Very high stringency conditions are defined as prehybridization and hybridization at 42° C. in 5×SSPE, 0.3% SDS, 200 μg/mL sheared and denatured salmon sperm DNA, and 50% formamide and washing three times each for 15 minutes using 2×SSC, 0.2% SDS at 70° C.

The terms, "identical" or percent "identity", in the context of two or more nucleic acids or polypeptide sequences, refer to two or more sequences or subsequences that are the same or have a specified percentage of amino acid residues or nucleotides that are the same, when compared and aligned for maximum correspondence over a comparison window. Unless otherwise specified, the comparison window for a selected sequence, e.g., "SEQ ID NO:X" is the entire length of SEQ ID NO:X. and, e.g., the comparison window for "100 bp of SEQ ID NO:X" is the stated 100 bp. The degree of amino acid or nucleic acid sequence identity can be determined by various computer programs for aligning the sequences to be compared based on designated program parameters. For example, sequences can be aligned and compared using the local homology algorithm of Smith & Waterman *Adv. Appl. Math.* 2:482-89, 1981, the homology alignment algorithm of Needleman & Wunsch *J. Mol. Biol.* 48:443-53, 1970, or the search for similarity method of Pearson & Lipman *Proc. Nat'l. Acad. Sci. USA* 85:2444-48, 1988, and can be aligned and compared based on visual inspection or can use computer programs for the analysis (for example, GAP, BESTFIT, FASTA, and TFASTA in the Wisconsin Genetics Software Package, Genetics Computer Group, 575 Science Dr., Madison, WI).

The BLAST algorithm, described in Altschul et al., *J. Mol. Biol.* 215:403-10, 1990, is publicly available through software provided by the National Center for Biotechnology Information (available at ncbi.nlm.nih.gov). This algorithm identifies high scoring sequence pairs (HSPS) by identifying short words of length W in the query sequence, which either match or satisfy some positive-valued threshold score T when aligned with a word of the same length in a database sequence. T is referred to as the neighborhood word score threshold (Altschul et al., 1990, supra). Initial neighborhood word hits act as seeds for initiating searches to find longer HSPs containing them. The word hits are then extended in both directions along each sequence for as far as the cumulative alignment score can be increased. Cumulative scores are calculated for nucleotides sequences using the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below due to the accumulation of one or more negative-scoring residue alignments; or the end of either sequence is reached. For determining the percent identity of an amino acid sequence or nucleic acid sequence, the default parameters of the BLAST programs can be used. For analysis of amino acid sequences, the BLASTP defaults are: word length (W), 3; expectation (E), 10; and the BLOSUM62 scoring matrix. For analysis of nucleic acid sequences, the BLASTN program defaults are word length (W), 11; expectation (E), 10; M=5; N=−4; and a comparison of both strands. The TBLASTN program (using a protein sequence to query nucleotide sequence databases) uses as defaults a word length (W) of 3, an expectation (E) of 10, and a BLOSUM 62 scoring matrix. See, Henikoff& Henikoff, *Proc. Nat'l. Acad. Sci. USA* 89: 10915-19, 1989.

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-87, 1993). The smallest sum probability (P(N)), provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, preferably less than about 0.01, and more preferably less than about 0.001.

The term "isolated" molecule, such as an isolated nucleic acid or protein, as used herein, refers to a biomolecule removed from the context in which the biomolecule exists in nature. An isolated biomolecule can be, in some instances, partially or substantially purified. The term "substantially purified", as used herein, refers to a biomolecule separated from substantially all other molecules normally associated with it in its native state. More preferably a substantially purified molecule is the predominant species present in a preparation that is, or results, however indirect, from human manipulation of a polynucleotide or polypeptide. A substantially purified molecule may be greater than 60% free, preferably 75% free, preferably 80% free, more preferably 85% free, more preferably 90% free, and most preferably 95% free from the other molecules (exclusive of solvent) present in the natural mixture. Thus, an "isolated" nucleic acid preferably is free of sequences that naturally flank the nucleic acid (that is, the sequences naturally located at the 5' and 3' ends of the nucleic acid) in the cell of the organism from which the nucleic acid is derived. Thus, "isolated nucleic acid" as used herein includes a naturally-occurring nucleic acid, provided one or both of the sequences immediately flanking that nucleic acid in its naturally-occurring genome is removed or absent. Thus, an isolated nucleic acid includes a nucleic acid that exists as a purified molecule or a nucleic acid molecule that is incorporated into a vector or an expression cassette. A nucleic acid existing among hundreds to millions of other nucleic acids within, for example, cDNA libraries, genomic libraries, or gel slices containing a genomic DNA restriction digest, is not to be considered an isolated nucleic acid. For example, in various embodiments, the isolated regulatory polynucleotide molecule can contain less than about 5 kb, 4 kb, 3 kb, 2 kb, 1 kb, 0.5 kb, or 0.1 kb of nucleotide sequences that naturally flank the nucleic acid molecule in the cell from which the nucleic acid is derived.

The term "native" is used herein to refer to nucleic acid sequences or amino acid sequences as they naturally occur in the host. The term "non-native" is used herein to refer to nucleic acid sequences or amino acid sequences that do not occur naturally in the host, or are not configured as they are naturally configured in the host. A nucleic acid sequence or amino acid sequence that has been removed from a host cell, subjected to laboratory manipulation, and introduced or reintroduced into a host cell is considered "non-native." Synthetic or partially synthetic genes introduced into a host cell are "non-native." Non-native genes further include genes endogenous to the host microorganism operably linked to one or more heterologous regulatory sequences that have been recombined into the host genome, or genes endogenous to the host organism that are in a locus of the genome other than that where they naturally occur.

The terms "naturally-occurring" and "wild-type", as used herein, refer to a form found in nature. For example, a naturally occurring or wild-type nucleic acid molecule, nucleotide sequence or protein may be present in and isolated from a natural source, and is not intentionally modified by human manipulation. As described in detail below, the nucleic acid molecules according to some embodiments of the present disclosure are non-naturally occurring nucleic acid molecules.

The terms "nucleic acid molecule" and "polynucleotide" are used interchangeably herein, and refer to both RNA and DNA molecules, including nucleic acid molecules comprising cDNA, genomic DNA, synthetic DNA, and DNA or RNA molecules containing nucleic acid analogs. Nucleic acid molecules can have any three-dimensional structure. A nucleic acid molecule can be double-stranded or single-stranded (e.g., a sense strand or an antisense strand). Non-limiting examples of nucleic acid molecules include genes, gene fragments, exons, introns, messenger RNA (mRNA), transfer RNA, ribosomal RNA, siRNA, micro-RNA, tracrR- NAs, crRNAs, guide RNAs, ribozymes, cDNA, recombinant polynucleotides, branched polynucleotides, nucleic acid probes and nucleic acid primers. A nucleic acid molecule may contain unconventional or modified nucleotides. The terms "polynucleotide sequence" and "nucleic acid sequence" as used herein interchangeably refer to the sequence of a polynucleotide molecule. The nomenclature for nucleotide bases as set forth in 37 CFR § 1.822 is used herein.

The nucleic acid molecules of the present disclosure will preferably be "biologically active" with respect to either a structural attribute, such as the capacity of a nucleic acid molecule to hybridize to another nucleic acid molecule, or the ability of a nucleic acid sequence to be recognized and bound by a transcription factor (or to compete with another nucleic acid molecule for such binding).

Nucleic acid molecules of the present disclosure will include nucleic acid sequences of any length, including nucleic acid molecules that are preferably between about 0.05 Kb and about 300 Kb, for example between about 0.05 Kb and about 250 Kb, between about 0.05 Kb and about 150 Kb, or between about 0.1 Kb and about 150 Kb, for example between about 0.2 Kb and about 150 Kb, about 0.5 Kb and about 150 Kb, or about 1 Kb and about 150 Kb.

The term "operably linked", as used herein, denotes a functional linkage between two or more sequences. For example, an operably linkage between a polynucleotide of interest and a regulatory sequence (for example, a promoter) is functional link that allows for expression of the polynucleotide of interest. In this sense, the term "operably linked" refers to the positioning of a regulatory region and a coding sequence to be transcribed so that the regulatory region is effective for regulating transcription or translation of the coding sequence of interest. In some embodiments disclosed herein, the term "operably linked" denotes a configuration in which a regulatory sequence is placed at an appropriate position relative to a sequence that encodes a polypeptide or functional RNA such that the control sequence directs or regulates the expression or cellular localization of the mRNA encoding the polypeptide, the polypeptide, and/or the functional RNA. Thus, a promoter is in operable linkage with a nucleic acid sequence if it can mediate transcription of the nucleic acid sequence. Operably linked elements may be contiguous or non-contiguous. Further, when used to refer to the joining of two protein coding regions, by "operably linked" is intended that the coding regions are in the same reading frame.

The terms "promoter". "promoter region", or "promoter sequence", as used interchangeably herein, refer to a nucleic acid sequence capable of binding RNA polymerase to initiate transcription of a gene in a 5' to 3' ("downstream") direction. The specific sequence of the promoter typically determines the strength of the promoter. For example, a strong promoter leads to a high rate of transcription initiation. A gene is "under the control of" or "regulated by" a promoter when the binding of RNA polymerase to the promoter is the proximate cause of said gene's transcription. The promoter or promoter region typically provides a recognition site for RNA polymerase and other factors necessary for proper initiation of transcription. A promoter may be isolated from the 5' untranslated region (5' UTR) of a genomic copy of a gene. Alternatively, a promoter may be synthetically produced or designed by altering known DNA elements. Also considered are chimeric promoters that combine sequences of one promoter with sequences of another promoter. Promoters may be defined by their expression pattern based on, for example, metabolic, environmental, or developmental conditions. Some embodiments relate to promoters capable of driving gene expression preferentially in different microbial growth phases. The term "lipogenic promoter", as used herein, refers to a promoter of a gene that is preferentially expressed at high levels during lipid production phase of a chytrid cell culture. The lipid production phase, in which the rate of lipid biosynthesis increases significantly with respect to lipid production during the nutrient replete growth phase of a culture, can be induced by nutrient limitation, particularly nitrogen limitation. Some embodiments of the present disclosure relate to promoters capable of driving gene expression constitutively throughout cell life cycle and/or unaffected by growth conditions, as well as at low, moderate, high, or very high transcription levels. A promoter can be used as a regulatory element for modulating expression of an operably linked polynucleotide molecule such as, for example, a coding sequence of a polypeptide or a functional RNA sequence. Promoters may contain, in addition to sequences recognized by RNA polymerase and, preferably, other transcription factors, regulatory sequence elements such as cis-elements or enhancer domains that affect the transcription of operably linked genes. A "labyrinthulomycetes promoter" as used herein refers to a native or non-native promoter that is functional in labyrinthulomycetes cells.

The term "recombinant" or "engineered" nucleic acid molecule as used herein, refers to a nucleic acid molecule that has been altered through human intervention. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant nucleic acid molecule: 1) has been synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination)) of nucleic acid molecules; 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

When applied to organisms, the terms "transgenic" "transformed" or "recombinant" or "engineered" or "genetically engineered" refer to organisms that have been manipulated by introduction of an exogenous or recombinant nucleic acid sequence into the organism. Non-limiting examples of such manipulations include gene knockouts, targeted mutations and gene replacement, promoter replacement, deletion, or insertion, as well as introduction of transgenes into the organism. For example, a transgenic microorganism can include an introduced exogenous regulatory sequence operably linked to an endogenous gene of the transgenic microorganism. Recombinant or genetically engineered organisms can also be organisms into which constructs for gene "knock down" have been introduced. Such constructs include, but are not limited to, RNAi, microRNA, shRNA, antisense, and ribozyme constructs. Also included are organisms whose genomes have been altered by the activity of meganucleases or zinc finger nucleases. A heterologous or recombinant nucleic acid molecule can be integrated into a genetically engineered/recombinant organism's genome or, in other instances, not integrated into a recombinant/genetically engineered organism's genome. As used herein, "recombinant microorganism" or "recombinant host cell" includes progeny or derivatives of the recombinant microorganisms of the disclosure. Because certain modifications may occur in succeeding generations from either mutation or environmental influences, such progeny or derivatives may not, in fact, be identical to the parent cell, but are still included within the scope of the term as used herein.

"Regulatory sequence", "regulatory element", or "regulatory element sequence" refers to a nucleotide sequence located upstream (5'), within, or downstream (3') of a polypeptide-encoding sequence or functional RNA-encoding sequence. Transcription of the polypeptide-encoding sequence or functional RNA-encoding sequence and/or translation of an RNA molecule resulting from transcription of the coding sequence are typically affected by the presence or absence of the regulatory sequence. These regulatory element sequences may comprise promoters, cis-elements, enhancers, terminators, or introns. Regulatory elements may be isolated or identified from untranslated regions (UTRs) from a particular polynucleotide sequence. Any of the regulatory elements described herein may be present in a chimeric or hybrid regulatory expression element. Any of the regulatory elements described herein may be present in a recombinant construct of the present disclosure.

A "reporter gene", as used herein, is a gene encoding a protein that is detectable or has an activity that produces a detectable product. A reporter gene can encode a visual marker or enzyme that produces a detectable signal, such as cat, lacZ, uidA, xylE, an alkaline phosphatase gene, an α-amylase gene, an α-galactosidase gene, a p-glucuronidase gene, a β-lactamase gene, a horseradish peroxidase gene, a luciferin/luciferase gene, an R-locus gene, a tyrosinase gene, or a gene encoding a fluorescent protein, including but not limited to a blue, cyan, green, red, or yellow fluorescent protein, a photoconvertible, photoswitchable, or optical highlighter fluorescent protein, or any of variant thereof, including, without limitation, codon-optimized, rapidly folding, monomeric, increased stability, and enhanced fluorescence variants.

The term "selectable marker" or "selectable marker gene" as used herein includes any gene that confers a phenotype on a cell in which it is expressed to facilitate the selection of cells that are transfected or transformed with a nucleic acid construct of the disclosure. The term may also be used to refer to gene products that effectuate said phenotypes. Examples of selectable markers include:

- genes conferring resistance to antibiotics such as amikacin (aphA6), ampicillin (amp), blasticidin (bis, bsr, bsd), bleomicin or phleomycin (ZEOCIN™) (ble), chloramphenicol (cat), emetine (RBS 14p or cry 1-1), erythromycin (ermE), G418 (GENETICIN™) (neo), gentamycin (aac3 or aacC4), hygromycin B (aphlV, hph, hpt), kanamycin (nptII), methotrexate (DHFR mtxR), penicillin and other β-lactams (β-lactamases), streptomycin or spectinomycin (aadA, spec/strep), and tetracycline (tetA, tetM, tetQ);
- genes conferring tolerance to herbicides such as aminotriazole, amitrole, andrimid, aryloxyphenoxy propionates, atrazines, bipyridyliums, bromoxynil, cyclohexandione oximes dalapon, dicamba, diclfop, dichlorophenyl dimethyl urea (DCMU), difunone, diketonitriles, diuron, fluridone, glufosinate, glyphosate, halogenated hydrobenzonitriles, haloxyfop, 4-hydroxypyridines, imidazolinones, isoxasflutole, isoxazoles, isoxazolidinones, miroamide B, p-nitrodiphenylethers, norflurazon, oxadiazoles, m-phenoxybenzamides, N-phenyl imides, pinoxadin, protoporphyrionogen oxidase inhibitors, pyridazinones, pyrazolinates, sulfonylureas, 1,2,4-triazol pyrimidine, triketones, or urea; acetyl Co A carboxylase (ACCase); acetohydroxy acid synthase (ahas); acetolactate synthase (als, csrl-1, csrl-2, imrl, imr2), aminoglycoside phosphotransferase (apt), anthranilate synthase, bromoxynil nitrilase (bxn), cytochrome P450-NADH-cytochrome P450 oxidoreductase, dalapon dehalogenase (dehal), dihydropteroate synthase (sul), class I 5-enolpyruvylshikimate-3-phosphate synthase (EPSPS), class II EPSPS (aroA), non-class VII EPSPS, glutathione reductase, glyphosate acetyltransferase (gat), glyphosate oxidoreductase (gox), hydroxyphenylpyruvate dehydrogenase, hydroxy-phenylpyruvate dioxygenase (hppd), isoprenyl pyrophosphate isomerase, lycopene cyclase, phosphinothricin acetyl transferase (pat, bar), phytoene desaturase (crtJ), prenyl transferase, protoporphyrin oxidase, the psbA photosystem II polypeptide (psbA), and SMM esterase (SulE) superoxide dismutase (sod);
- genes that may be used in auxotrophic strains or to confer other metabolic effects, such as arg7, his3, hisD, hisG, lysA, manA, metE, nitl, trpB, ura3, xylA, a dihydrofolate reductase gene, a mannose-6-phosphate isomerase gene, a nitrate reductase gene, or an ornithine decarboxylase gene; a negative selection factor such as thymidine kinase; or toxin resistance factors such as a 2-deoxyglucose resistance gene.

The term "terminator" or "terminator sequence" or "transcription terminator", as used herein, refers to a regulatory section of genetic sequence that causes RNA polymerase to cease transcription.

The term "transformation", "transfection", and "transduction", as used interchangeably herein, refers to the introduction of one or more exogenous nucleic acid sequences into a host cell or organism by using one or more physical, chemical, or biological methods. Physical and chemical methods of transformation include, by way of non-limiting example, electroporation and liposome delivery. Biological methods of transformation include transfer of DNA using engineered viruses or microbes (for example, *Agrobacterium*).

As used herein, the term "vector" refers to a recombinant polynucleotide construct designed for transfer between host cells, and that may be used for the purpose of transformation, e.g. the introduction of heterologous DNA into a host cell. As such, the term "vector" as used herein sometimes refers to a replicon, such as a plasmid, phage, or cosmid, into which another DNA segment may be inserted so as to bring about the replication of the inserted segment. A vector typically includes one or both of 1) an origin of replication, and 2) a selectable marker. A vector can additionally include sequence for mediating recombination of a sequence on the vector into a target genome, cloning sites, and/or regulatory sequences such as promoters and/or terminators. Generally, a vector is capable of replication when associated with the proper control elements. The term "vector" includes cloning vectors and expression vectors, as well as viral vectors and integrating vectors. An "expression vector" is a vector that includes a regulatory region, thereby capable of expressing DNA sequences and fragments in vitro and/or in vivo.

B. Molecules of the Disclosure

Some embodiments disclosed herein relate to promoter sequences that were identified from genomic sequences of the labyrinthulomycetes strains isolated from marine environments designated SGI-i886 of the genus *Aurantiochytrium*, which was described previously as WH-5628 strain in U.S. application Ser. No. 14/720,679 and PCT Pub. No. WO2015/179844, and SGI-i94 of the genus *Schizochytrium* and can find use in the expression of genes, such as but not limited to transgenes, in eukaryotic microorganisms. The method by which these new promoter sequences were discovered is described more fully in the examples herein. SEQ ID NOs: 1-70 and 180-202 were identified as comprising promoters, many of which were subsequently demonstrated to mediate expression of transgenes in a labyrinthulomycetes strain. In addition. SEQ ID NOs:71-78 were identified as comprising terminators derived from *Saccharomyces cerevisiae* or simian virus 40 that were demonstrated to be functional in a labyrinthulomycetes strain.

Based on the demonstration that these sequences mediate expression heterologous genes, one aspect of the present disclosure provides isolated, synthetic, and recombinant DNA (nucleic acid) molecules that correspond to SEQ ID NOs: 1-70 and 180-202 and to nucleic acid molecules comprising nucleotide sequences having about 80% identity to at least 50 contiguous nucleotides to any one of SEQ ID NOs: 1-70 and 180-202. Additionally provided herein are isolated, synthetic, or recombinant nucleic acid molecules hybridizing under high stringency conditions to at least 50 contiguous nucleotides to any one of SEQ ID NOs: 1-70 and 180-202.

A nucleic acid molecule as provided herein can comprise, for example, a nucleic acid sequence having at least 80%, at least 85%, at least 90%, at least 95%, at least 96%, at least 97%, at least 98%, or at least 99% identity to at least 50, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, or at least 1000 contiguous nucleotides of any one of SEQ ID NOs:1-70 and 180-202. In some examples, a nucleic acid molecule as provided herein can comprise a nucleic acid sequence having at least 80%, at least 85%, at least 90%, at least 95%, at least 96%, at least 97%, at least 98%, at least 99% or 100% identity to at least 50, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, or at least 1000 contiguous nucleotides from the 3'-most end and extending in the 5' direction of any one of SEQ ID NOs:1-70 and 180-202. The nucleic acid sequence can have promoter activity, as demonstrated by any of the assays herein or any assays for promoter activity known in the art. The nucleic acid molecule can comprise a nucleic acid sequence having homology to at least a portion of one or more of SEQ ID NO: 1-70 and 180-202 in a vector and/or operably linked to a heterologous nucleic acid sequence. The heterologous nucleic acid sequence can be, for example, a heterologous nucleic acid sequence encoding a polypeptide or a functional RNA. A nucleic acid sequence having at least 80% identity to at least 50 nucleotides of SEQ ID NOs:1-70 and 180-202 can have promoter activity in a microorganism, such as but not limited to a fungus, a heterokont, or an alga. For example, a nucleic acid sequence as provided herein can have promoter activity in a heterokont species such as a labyrinthulomycetes species.

In some embodiments, an isolated, synthetic, or recombinant nucleic acid molecule as provided herein can include a nucleotide sequence having at least 80% identity to at least 50 contiguous nucleotides of SEQ ID NO:20, SEQ ID NO:34, SEQ ID NO:35, SEQ ID NO:49, SEQ ID NO:50, SEQ ID NO:53, SEQ ID NO:54, SEQ ID NO:182, SEQ ID NO:183, SEQ ID NO:186, SEQ ID NO:190, SEQ ID NO:191, SEQ ID NO:196, SEQ ID NO:198, or SEQ ID NO:199. In some examples, a nucleic acid molecule as provided herein can comprise a nucleic acid sequence having at least 80%, at least 85%, at least 90%, at least 95%, at least 96%, at least 97%, at least 98%, or at least 99% identity to at least 50, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, or at least 1000 contiguous nucleotides of SEQ ID NO:20, SEQ ID NO:34, SEQ ID NO:35, SEQ ID NO:49, SEQ ID NO:50, SEQ ID NO:53, SEQ ID NO:54, SEQ ID NO:182, SEQ ID NO:183, SEQ ID NO:186, SEQ ID NO:190, SEQ ID NO:191, SEQ ID NO:196, SEQ ID NO:198, or SEQ ID NO:199, where the contiguous nucleotides extend from the 3'-most end of SEQ ID NO:20, SEQ ID NO:34, SEQ ID NO:35, SEQ ID NO:49, SEQ ID NO:50, SEQ ID NO:53, SEQ ID NO:54, SEQ ID NO:182, SEQ ID NO:183, SEQ ID NO:186, SEQ ID NO:190, SEQ ID NO:191, SEQ ID NO:196, SEQ ID NO:198, or SEQ ID NO:199. For example, the isolated, synthetic, or recombinant nucleic acid molecule can include a nucleic acid sequence exhibiting at least 80% sequence identity to at least 50 contiguous nucleotides of a nucleic acid sequence selected from the group consisting of SEQ ID NO:20, SEQ ID NO:34, SEQ ID NO:35, SEQ ID NO:49, SEQ ID NO:50, SEQ ID NO:53, SEQ ID NO:54, SEQ ID NO:182, SEQ ID NO:183, SEQ ID NO:186, SEQ ID NO:190, SEQ ID NO:191, SEQ ID NO:196, SEQ ID NO:198, and SEQ ID NO:199. In some examples, a nucleic acid molecule as provided herein can include a nucleic acid sequence having at least 80%, at least 85%, at least 90%, at least 95%, at least 96%, at least 97%, at least 98%, or at least 99% identity to SEQ ID NO:59, SEQ ID NO:61, SEQ ID NO:63, SEQ ID NO:66, SEQ ID NO:67, SEQ ID NO:68, SEQ ID NO:69, SEQ ID NO:70, SEQ ID NO:181, SEQ ID NO:182, SEQ ID NO:183, SEQ ID NO:186, SEQ ID NO:190, SEQ ID NO:191, SEQ ID NO:196, SEQ ID NO:198, or SEQ ID NO:199 or at least 50 contiguous nucleotides of any thereof. In some embodiments, the isolated, synthetic, or recombinant nucleic acid molecule as provided herein is functional and can direct expression of a gene to which it is operably linked (e.g., a gene encoding a polypeptide or functional RNA) in a eukaryotic cell, such as but not limited to an algal, fungal, heterokont, or labyrinthulomycetes cell. For example, the isolated, synthetic, or recombinant nucleic acid molecule as provided herein can include a heterologous nucleic acid sequence, such as protein-encoding DNA sequence or a DNA sequence encoding a functional RNA, operably linked to the nucleic acid sequence having homology to at least a portion of SEQ ID NO:19, SEQ ID NO:20, SEQ ID NO:23, SEQ ID NO:24, SEQ ID NO:34, SEQ ID NO:35, SEQ ID NO:49, SEQ ID NO:50, SEQ ID NO:51, SEQ ID NO:52, SEQ ID NO:53, SEQ ID NO:54, SEQ ID NO:57, SEQ ID NO:58, SEQ ID NO:181, SEQ ID NO:182, SEQ ID NO:183, SEQ ID NO:186, SEQ ID NO:190, SEQ ID NO:191, SEQ ID NO:192, SEQ ID NO:196, SEQ ID NO:197, SEQ ID NO:198, or SEQ ID NO:199. For example, the nucleic acid sequence having at least 80% identity to at least 50 contiguous nucleotides of SEQ ID NO:19, SEQ ID NO:20, SEQ ID NO:23, SEQ ID NO:24, SEQ ID NO:34, SEQ ID NO:35, SEQ ID NO:49, SEQ ID NO:50, SEQ ID NO:51, SEQ ID NO:52, SEQ ID NO:53, SEQ ID NO:54, SEQ ID NO:57, SEQ ID NO:58, SEQ ID NO:181, SEQ ID NO:182, SEQ ID NO:183, SEQ ID NO:186, SEQ ID NO:190, SEQ ID NO:191, SEQ ID NO:192, SEQ ID NO:196, SEQ ID NO:197, SEQ ID NO:198, or SEQ ID NO:199, which can be, in some examples, a nucleic acid sequence having at least 80% identity to SEQ ID NO:59, SEQ ID NO:61, SEQ ID NO:63, SEQ ID NO:66, SEQ ID NO:67, SEQ ID NO:68, SEQ ID NO:69, SEQ ID NO:70, SEQ ID NO:181, SEQ ID NO:182, SEQ ID NO:183, SEQ ID NO:186, SEQ ID NO:190, SEQ ID NO:191, SEQ ID NO:196, SEQ ID NO:198, or SEQ ID NO:199, or at least 50 contiguous nucleotides of any thereof, can direct transcription of the heterologous nucleic acid sequence.

For example, an isolated, synthetic, or recombinant nucleic acid molecule as provided herein can include a nucleotide sequence having at least 80%, at least 85%, at least 90%, at least 95%, at least 96%, at least 97%, at least 98%, or at least 99% identity to SEQ ID NO:59, SEQ ID NO:61, SEQ ID NO:63, SEQ ID NO:66, SEQ ID NO:67, SEQ ID NO:68, SEQ ID NO:69, SEQ ID NO:70, SEQ ID NO:181, SEQ ID NO:182, SEQ ID NO:183, SEQ ID NO:186, SEQ ID NO:190, SEQ ID NO:191, SEQ ID NO:196, SEQ ID NO:198, or SEQ ID NO:199. In some embodiments, the isolated, synthetic, or recombinant nucleic acid molecule as provided herein is functional and can direct expression of a gene to which it is operably linked (e.g., a gene encoding a polypeptide or functional RNA) in a eukaryotic cell, such as but not limited to an algal, fungal, heterokont, or labyrinthulomycetes cell. For example, the isolated, synthetic, or recombinant nucleic acid molecule as provided herein can include a heterologous nucleic acid sequence, such as protein-encoding DNA sequence or a DNA sequence encoding a functional RNA, operably linked to the nucleic acid sequence having at least 80% identity to SEQ ID NO:59, SEQ ID NO:61, SEQ ID NO:63, SEQ ID NO:66, SEQ ID NO:67, SEQ ID NO:68, SEQ ID NO:69, SEQ ID NO:70, SEQ ID NO:181, SEQ ID NO:182, SEQ ID NO:183, SEQ ID NO:186, SEQ ID NO:190, SEQ ID NO:191, SEQ ID NO:196, SEQ ID NO:198, or SEQ ID NO:199 can direct transcription of the heterologous nucleic acid sequence.

Further alternatively or in addition, an isolated, synthetic, or recombinant nucleic acid molecule as provided herein can include a nucleotide sequence having at least 80%, at least 85%, at least 90%, at least 95%, at least 96%, at least 97%, at least 98%, or at least 99% identity to SEQ ID NO:20, SEQ ID NO:59, SEQ ID NO:68, SEQ ID NO:69, SEQ ID NO:181, SEQ ID NO:182, SEQ ID NO:183, SEQ ID NO:186, SEQ ID NO:190, SEQ ID NO:191, SEQ ID NO:196, SEQ ID NO:198, or SEQ ID NO:199. In some embodiments, the isolated, synthetic, or recombinant nucleic acid molecule as provided herein is functional and can direct expression of a gene to which it is operably linked (e.g., a gene encoding a polypeptide or functional RNA) in a eukaryotic cell, such as but not limited to an algal, fungal, heterokont, or labyrinthulomycetes cell. For example, the isolated, synthetic, or recombinant nucleic acid molecule as provided herein can include a heterologous nucleic acid sequence, such as protein-encoding DNA sequence or a DNA sequence encoding a functional RNA, operably linked to the nucleic acid sequence having homology to SEQ ID NO:20, SEQ ID NO:59, SEQ ID NO:68, SEQ ID NO:69, SEQ ID NO:181, SEQ ID NO:182, SEQ ID NO:183, SEQ ID NO:186, SEQ ID NO:190, SEQ ID NO:191, SEQ ID NO:196, SEQ ID NO:198, or SEQ ID NO:199. For example, the nucleic acid sequence having at least 80% identity to at least 50 contiguous nucleotides of SEQ ID NO:20, SEQ ID NO:59, SEQ ID NO:68, SEQ ID NO:69, SEQ ID NO:181, SEQ ID NO:182, SEQ ID NO:183, SEQ ID NO:186, SEQ ID NO:190, SEQ ID NO:191, SEQ ID NO:196, SEQ ID NO:198, o SEQ ID NO:199 can direct transcription of the heterologous nucleic acid sequence.

The isolated, synthetic or recombinant nucleic acid molecules as provided herein can find use, for example, as a sequence that, when operably linked to a heterologous nucleic acid sequence, can affect expression of the heterologous nucleic acid sequence. In some embodiments, the heterologous nucleic acid sequence comprises, for example, a sequence encoding a polypeptide or functional RNA. For example, an isolated, synthetic or recombinant nucleic acid molecule as provided herein can, as a promoter, increase or decrease expression of a nucleic acid sequence (or a portion thereof) to which it is operably linked, or may mediate transcription of the operably-linked nucleic acid sequence (or a portion thereof). Methods for assessing the functionality of nucleotide sequences for promoter activity, as well as for enhancing or decreasing the activity of proximal promoters, are well-known in the art. For example, promoter function can be validated by confirming the ability of the putative promoter or promoter variant or fragment to drive expression of a selectable marker gene to which the putative promoter or promoter fragment or variant is operably linked by detecting and, optionally, analyzing, resistant colonies after plating of cells transformed with the promoter construct on selective media.

Additionally or alternatively, promoter activity may be assessed by measuring the levels of RNA transcripts produced from a promoter construct, for example, using reverse transcription-polymerase chain reaction (RT-PCR; see. e.g., Watt et al., PLoS ONE 1:e1428, 2008), by detection of the expressed protein, or by in vivo assays that rely on an activity of the protein encoded by the transcribed sequence. For example, promoter activity can be assessed using chloramphenicol acetyltransferase (CAT) assays (where the heterologous sequence operably linked to the isolated nucleic acid molecule that comprises a putative promoter encodes chloramphenicol acetyltransferase, see, for example, Gerrish et al. (*J. Biol. Chem.* 275:3485-92, 2000), luciferase assays, where the heterologous nucleic acid is a lux or luc gene, for example (see, for example, Ferrante et al., PLoS ONE 3:e3200, 2008), or in vivo assays using a fluorescent protein gene to determine the functionality of any of the sequences disclosed herein, including sequences of reduced size or having one or more nucleotide changes with respect to any of SEQ ID NOs: 1-70 and 180-202 (see, for example. Akamura et al., *Anal. Biochem.* 4/2: 159-64, 2011).

Testing of sequence modifications, including deletions (e.g., promoter truncations) and base substitutions of the promoter-containing sequences using reporter constructs such as but not limited to those provided herein are well-known in the art (see, for example. Quinn et al., *Eukaryotic Cell* 2:995-1002, 2003; Ranjan et al., *J. Biotechnol.* 152:58-62, 2011; Gerrish et al., 2000, supra).

In other embodiments, an isolated, synthetic, or recombinant nucleic acid molecule as provided herein having a promoter having homology to at least a portion of any one of SEQ ID NO:1-70 and SEQ ID NO:180-202, operably linked to a heterologous sequence encoding a polypeptide or functional RNA according to any of the above examples, can further include a nucleotide sequence having at least 80% identity to at least 50 contiguous nucleotides of SEQ ID NO:71, a nucleotide sequence having at least 80% identity to at least 50 contiguous nucleotides of SEQ ID NO:72, a nucleotide sequence having at least 80% identity to at least 50 contiguous nucleotides of SEQ ID NO:73, a nucleotide sequence having at least 80% identity to at least 50 contiguous nucleotides of SEQ ID NO:74, a nucleotide sequence having at least 80% identity to at least 50 contiguous nucleotides of SEQ ID NO:75, a nucleotide sequence having at least 80% identity to at least 50 contiguous nucleotides of SEQ ID NO:76, a nucleotide sequence having at least 80% identity to at least 50 contiguous nucleotides of SEQ ID NO:77, a nucleotide sequence having at least 80% identity to at least 50 contiguous nucleotides of SEQ ID NO:78. The nucleic acid sequence having homology to at least a portion of any of SEQ ID NO:71-SEQ ID NO:78 can be operably linked at the 3' end of the heterologous sequence encoding a polypeptide or functional RNA. The isolated, synthetic, or recombinant nucleic acid molecule can mediate transcriptional termination of a gene to which it is operably linked. The nucleic acid sequence having homology to at least a portion of any of SEQ ID NO:71-SEQ ID NO:78 can have at least 95%, 96%, 97%, 98%, or 99% percent identity to at least 50 contiguous nucleotides to any one of SEQ ID NOs:71-78, for example, can have at least 95%, 96%, 97%, 98%, or 99% percent identity to any one of SEQ ID NOs:71-78.

Cis-Acting Elements

As used herein, the term "cis-acting element" refers to a cis-acting transcriptional regulatory element which confers an aspect of the overall control of gene expression. In general, cis-acting elements are believed to affect DNA topology, producing local conformations that selectively allow or restrict access of RNA polymerase to the DNA template or that facilitate selective opening of the double helix at the site of transcriptional initiation. Many cis-acting elements may function to interact with transcription factors.

Cis-acting elements occur within the 5' genomic region associated with a particular coding sequence, and are often found within, but are not limited to promoters, and promoter-modulating sequences (inducible elements). Examples of cis-acting elements in the 5' genomic region associated with a polynucleotide coding sequence include, but are not limited to, promoters, repressors, and enhancers.

Cis-acting element can be identified by a number of techniques, including deletion analysis, e.g., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays well known to the skilled artisan; or by DNA sequence similarity analysis with known cis-acting element motifs by conventional DNA sequence comparison methods such as, for example, those described herein. The fine structure of a cis-acting element can be further studied by mutagenesis (or substitution) of one or more nucleotides or by other conventional methods well known in molecular genetics and molecular biology. Cis-acting elements can be obtained by chemical synthesis or by isolation from promoters that include such elements, and they can be synthesized with additional flanking nucleotides that contain useful restriction enzyme sites to facilitate subsequence manipulation. Furthermore, cis-acting elements can be identified using known cis-acting elements as a target sequence or target motif in various BLAST-based computer programs.

In some embodiments, the nucleic acid molecules of the present disclosure may comprise multiple cis-acting elements each of which confers a different aspect to the overall control of gene expression. In a preferred embodiment, cis-acting elements from the polynucleotide molecules of SEQ ID NOs: 1-70 and 180-202, are identified using computer programs designed specifically to identify cis-acting elements, domains, or motifs within sequences. Cis-elements may either positively or negatively regulate gene expression, depending on the conditions. The present disclosure therefore encompasses cis-acting elements of the nucleic acid molecules disclosed herein.

In some embodiments, promoters of the present disclosure may include homologs of cis-acting elements known to effect gene regulation and that show sequence homology with the promoter sequences of the present disclosure. In one embodiment, a regulatory region according to the present disclosure can contain conserved regulatory motifs. Such a regulatory region can be any one of the sequences set forth in SEQ ID NOs:1-70 and 180-202, or a regulatory region having a nucleotide sequence that deviates from any one of the sequences set forth in SEQ ID NOs:1-70 and 180-202, while retaining the ability to direct expression of an operably linked nucleic acid. For example, a regulatory region can contain a CAAT box or a TATA box. A CAAT box is a conserved nucleotide sequence involved in modulation of gene transcription, and can function as a recognition and binding site for a family of regulatory proteins, or transcription factors. A TATA box is another conserved nucleotide sequence found in the promoter region of a large number of genes, and is widely believed to be involved in transcription initiation. Indeed. TATA box has been reported to be important in determining accurately the position at which transcription is initiated. In addition, a particular promoter may contain multiple TATA-boxes, in which case each of the TATA boxes may have different strengths; and stronger TATA boxes are reported to increase expression in a more predictable fashion. It has also reported that the sequence and spacing of TATA box elements are important for accurate initiation of transcription (see, e.g., Mogno et al., *Genome Res.* 20: 1391-1397, 2010).

Other conserved regulatory motifs can be identified using a variety of techniques and methods known in the art. For example, those skilled in the art will recognize that conserved regulatory regions and regulatory motifs can be identified using the PlantCARE web resource, which is a database of plant promoters and their cis-acting regulatory elements, including enhancers and repressors (Lescot et al., *Nucleic Acids Res.,* 30: 325 327, 2002). In PlantCARE database, regulatory elements are represented by positional matrices, consensus sequences and individual sites on particular promoter sequences.

One skilled in the art will further appreciate that conserved regulatory regions and regulatory motifs can be also identified using the PlantProm plant promoter database, which is an annotated, non-redundant collection of proximal promoter sequences for RNA polymerase II with experimentally determined transcription start site(s) (TSS), from various plant species (Shahmuradov et al., *Nucleic Acids Res.,* 31:114 117, 2003). It provides DNA sequence of the promoter regions with TSS, taxonomic/promoter type classification of promoters and Nucleotide Frequency Matrices (NFM) for promoter elements: TATA-box, CCAAT-box and TSS-motif.

Additionally, it will be further appreciated by the skilled artisan that conserved regulatory regions and regulatory motifs can also be identified and/or analyzed using the PLACE (PLAnt Cis-acting regulatory DNA Elements) database, which is a database of nucleotide sequence motifs found in plant cis-acting regulatory DNA elements. See, e.g., Higo et al., *Nucleic Acids Res.,* 27(1):297-300, 1999; and Prestridge, CABIOS, 7:203-206, 1991. Approximately 1,340 conserved regulatory motifs can be found in the PLACE database. Depending upon the need for using a specific cis-acting element, the regulatory database can be searched using a web signal scan program that can be found on the World Wide Web at dna.affrc.go.jp/PLACE/signalscan.html. Documents for each motif in the PLACE database contain a motif sequence, a brief definition and description of each motif, and relevant literature with PubMed ID numbers and GenBank accession numbers (Higo et al., 1999, supra). The listed cis-acting regulatory elements in the PLACE database and the cis-acting regulatory elements that are provided in Raumbauts et al., *Nucleic Acids Res.* 27:295-296 1999) and Higo et al. (1999, supra) can be used with various embodiments of the disclosure.

Promoters

Also provided herein are promoters comprising a nucleic acid sequence such as any described herein, for example, a nucleic acid sequence having at least 80%, at least 85%, at least 90%, or at least 95% identity to at least 50 contiguous nucleotides of any one of SEQ ID NOs: 1-70 and 180-202. For example, a promoter as provided herein may include a nucleotide sequence that has at least 85%, at least 90%, at least 95%, at least 96%, at least 97%, at least 98%, or at least 99% sequence identity to at least 50, at least 100, at least 150, at least 200, least 250, at least 300, at least 350, at least 400, at least 450, at least 500, at least 550, at least 600, at least 550, at least 600, at least 650, at least 700, or at least 750, contiguous nucleotides of any of SEQ ID NOs: 1-70 and 180-202.

For example, a promoter as provided herein may include a nucleotide sequence that has at least 80%, at least 85%, at least 90%, or at least 95% sequence identity to at least 50, 100, 200, 300, 400, 500, 600, or 700 contiguous nucleotides of SEQ ID NO:19, SEQ ID NO:20, SEQ ID NO:23, SEQ ID NO:24, SEQ ID NO:34, SEQ ID NO:35, SEQ ID NO:49, SEQ ID NO:50, SEQ ID NO:51, SEQ ID NO:52, SEQ ID NO:53, SEQ ID NO:54, SEQ ID NO:57, SEQ ID NO:58, SEQ ID NO:181, SEQ ID NO:182, SEQ ID NO:183, SEQ ID NO:186, SEQ ID NO:190, SEQ ID NO:191, SEQ ID NO:192, SEQ ID NO:196, SEQ ID NO:197, SEQ ID NO:198, or SEQ ID NO:199, and can be for example, a nucleotide sequence having at least 80%, at least 85%, at least 90%, or at least 95% sequence identity to SEQ ID NO:59, SEQ ID NO:61, SEQ ID NO:63, SEQ ID NO:66, SEQ ID NO:67, SEQ ID NO:68, SEQ ID NO:69, SEQ ID NO:70, SEQ ID NO:181, SEQ ID NO:182, SEQ ID NO:183, SEQ ID NO:186, SEQ ID NO:190, SEQ ID NO:191, SEQ ID NO:196, SEQ ID NO:198, or SEQ ID NO:199. A promoter as provided herein can include a nucleotide sequence that has at least 96%, at least 97%, at least 98%, or at least 99% sequence identity to at least 50, 100, 200, 300, 400, 500, 600, or 700 contiguous nucleotides of SEQ ID NO:19, SEQ ID NO:20, SEQ ID NO:23, SEQ ID NO:24, SEQ ID NO:34, SEQ ID NO:35, SEQ ID NO:49, SEQ ID NO:50, SEQ ID NO:51, SEQ ID NO:52, SEQ ID NO:53, SEQ ID NO:54, SEQ ID NO:57, SEQ ID NO:58, SEQ ID NO:181, SEQ ID NO:182, SEQ ID NO:183, SEQ ID NO:186, SEQ ID NO:190, SEQ ID NO:191, SEQ ID NO:192, SEQ ID NO:196, SEQ ID NO:197, SEQ ID NO:198, or SEQ ID NO:199.

In some embodiments, a promoter as provided herein can include a nucleotide sequence that has at least 80%, at least 85%, at least 90%, or at least 95% sequence identity to at least 50, 100, 200, 300, 400, 500, 550, 600, 650, or 700 contiguous nucleotides of any one of SEQ ID NO:20, SEQ ID NO:59, SEQ ID NO:66, SEQ ID NO:68, SEQ ID NO:69, SEQ ID NO:181, SEQ ID NO:182, SEQ ID NO:183, SEQ ID NO:186, SEQ ID NO:190, SEQ ID NO:191, SEQ ID NO:196, SEQ ID NO:198, or SEQ ID NO:199. A promoter as provided herein can include a nucleotide sequence that has at least 96%, at least 97%, at least 98%, or at least 99% sequence identity to at least 50, 100, 200, 300, 400, 500, 600, or 700 contiguous nucleotides of SEQ ID NO:20, SEQ ID NO:59, SEQ ID NO:66, SEQ ID NO:68, SEQ ID NO:69, SEQ ID NO:181, SEQ ID NO:182, SEQ ID NO:183, SEQ ID NO:186, SEQ ID NO:190, SEQ ID NO:191, SEQ ID NO:196, SEQ ID NO:198, or SEQ ID NO:199.

A promoter as provided herein can be a constitutive promoter, and may be active in a host cell cultured under conditions in which one or more nutrients are deficient as well as in culture conditions in which nutrients are sufficient for proliferation and/or growth of the culture. For example, a promoter as provided herein may direct expression of an operably linked nucleic acid sequence under conditions in which a host cell that includes the promoter construct is limited in oxygen availability (oxygen depletion/deficiency) as well as under conditions in which a host cell that includes the promoter construct is not limited in oxygen availability (oxygen replete conditions).

Some embodiments described herein relate to promoters that are capable of driving gene expression constitutively throughout cell life cycle and/or unaffected by growth conditions. Some embodiments described herein relate to promoters capable of driving gene expression at low, moderate, high, or very high transcription levels (e.g., strong promoters).

Some embodiments described herein relate to promoters that are capable of driving gene expression preferentially in different microbial growth phases. For example, in the case of EPA production, it is beneficial to express pathway genes using a promoter that is expressed highly during one, two, and/or more culture phases (for example, a growth phase and a lipid production phase). In particular, high expression during growth phase allows for sufficient EPA production that is required for growth without PUFA supplementation. Furthermore, high expression during lipogenesis, e.g. lipid production phase, allows for the engineered strains to produce and accumulate EPA.

Without being bound by theory, promoters generally allow RNA polymerase to attach to DNA near a coding sequence in order for transcription to take place. Promoters contain specific DNA sequences that provide transcription factors to an initial binding site from which they can recruit RNA polymerase binding. These transcription factors have specific protein motifs that enable them to interact with specific corresponding nucleotide sequences to regulate gene expressions. The minimal portion of the promoter required for proper transcription initiation typically include: (1) the Transcription Start Site ("TSS") and elements directly upstream; (2) an RNA polymerase binding site; and (3) general transcription factor binding sites such as, for example, a TATA box.

A proximal promoter sequence may be approximately 250 base pairs (bp) upstream of the translational start site of the open reading frame of the gene and may contain, in addition to sequences for binding RNA polymerase, specific transcription factor binding sites. The term "promoter" as used herein can therefore refer to a sequence that optionally includes at least a portion of the 5' untranslated region ("5' UTR") of a gene that is upstream of the translational start site of the open reading frame of the gene. Some promoters also include a distal sequence upstream of the gene that may contain additional regulatory elements, often with a weaker influence than the proximal promoter. Eukaryotic transcriptional complexes can bend the DNA back on itself, thus allowing for potential placement of additional regulatory sequences as far as several kilobases (kb) from the transcription start site (TSS). Many eukaryotic promoters contain a TATA box. The TATA box binds the TATA binding protein, which assists in the formation of the RNA polymerase transcriptional complex. TATA boxes usually lie within approximately 50 bp of the TSS. A promoter may be constitutive or expressed conditionally. Some promoters are inducible, and may activate or increase transcription in response to an inducing agent. In contrast, the rate of transcription of a gene under control of a constitutive promoter is not dependent on an inducing agent. A constitutive promoter can be made a conditional or inducible promoter by the addition of sequences that confer responsiveness to particular conditions or to an inducing agent. Thus, promoters provided herein may be constitutive or may be inducible or conditional. Further, promoters or portions of promoters may be combined in series to achieve a stronger level of expression or a more complex pattern of regulation.

In various examples, a promoter as provided herein, such as but not limited to a promoter that comprises a nucleotide sequence having at least 80%, at least 85%, at least 90%, at least 95%, at least 96%, at least 97%, at least 98%, at least 99%, or about 100% identity to at least 50, at least 100, at least 200, at least 300, at least 400, or at least 500 contiguous nucleotides of any one of SEQ ID NOs: 1-70 and 180-202, can mediate transcription of an operably linked nucleic acid sequence in a eukaryotic cell, such as, for example, a labyrinthulomycetes cell. In some instances, a promoter as provided herein can mediate transcription of an operably linked nucleic acid sequence in a eukaryotic cell, such as but not limited to a labyrinthulomycetes cell, during culturing of the cell under conditions of nutrient depletion as well as during culturing of the cell under nutrient replete conditions. For example, a promoter as described herein can preferably mediate transcription of an operably linked nucleic acid sequence in labyrinthulomycetes cells cultured under conditions of nutrient depletion or cultured under nutrient replete conditions.

Additionally, as contemplated herein, a promoter or promoter region can include variants of the promoters disclosed herein derived by deleting sequences, duplicating sequences, or adding sequences from other promoters or as designed, for example, by bioinformatics, or by subjecting the promoter to random or site-directed mutagenesis, etc.

Any of the nucleic acid molecules described herein may comprise nucleic acid sequences comprising promoters. For example, nucleic acid molecules of the present disclosure can comprise promoters including nucleic acid sequences having at least 80%, at least 85%, at least 90%, at least 95%, or between 95% and 100% identity to the sequences located between about 0 bp, 10 bp, 20 bp, 50 bp, 100 bp, 200 bp or 300 bp to about 500 bp, 600 bp, 700 bp, 800 bp, 900 bp, or 1 kb upstream of the trinucleotide ATG sequence at the start site of a protein coding region of a native labyrinthulomycetes gene, such as, for example, a 40s ribosomal protein S3a (RPS3a) gene, a 60s ribososomal protein 11 (RPL11) gene, a 60S ribosomal protein L26 (RPL26) gene, a 60S ribosomal protein L6 (RPL6) gene, a 60S ribosomal protein L9 (RPL9) gene, an acetyl-coenzyme A synthetase 2 (ACS2) gene, an actin (Act) gene, an actin depolymerase (Adp) gene, an adenosylhomocysteinase (AHC) gene, an alternative oxidase (AOX) gene, a Catalase (cat) gene, a cytochrome C oxidase (cox) gene, an Eft2p GTPase and translation elongation factor 2 (EF-2) gene, an elongation factor 1-alpha 1 (EF1alpha) gene, an elongation factor 1-beta (EF1beta) gene, a eukaryotic translation initiation factor 5A isoform IV (IF-5a) gene, a Fa ATP synthase (FAAS) gene, a heat shock protein 70 (hsp70) gene, a heavy metal associated domain (HMA) gene, a hexose transporter 1 (HXT1) gene, a mitochondrial chaperonin 60 (hsp60) gene, a neighbor of BRCA1 gene 1 (NBR1) gene, a phosphoglycerate kinase (PGK) gene, a phosphotidylinositol 3-kinase (PL3K) gene, a small nuclear ribonucleoprotein (snRNP) gene, a superoxide dismutase (SOD) gene, a Tetraspanin (Tsp) gene, a transcription elongation factor 3 (EF-3) gene, a transcriptionally-controlled tumor protein homolog (TCTP) gene, a translation elongation factor 1-alpha (EF-1a) gene, a tubulin alpha chain gene, or a tubulin alpha chain gene.

Additionally or alternatively, promoters of the present disclosure can include nucleic acid sequences having at least 80%, at least 85%, at least 90%, at least 95%, or between 95% and 100% identity to the reverse complement of sequences between about 0 bp, 20 bp, 50 bp, 100 bp, 200 bp or 300 bp to about 500 bp, 600 bp, 700 bp, 800 bp, 900 bp, or 1 kb upstream of the trinucleotide ATG sequence, that is at the start site of a protein coding region of a native labyrinthulomycetes gene, such as, a mitochondrial chaperonin 60 (hsp60) gene, a phosphotidylinositol 3-kinase (PI3K) gene, or a 60s ribososomal protein 11 (RPL11) gene.

The activity or strength of a promoter may be measured in terms of the amount of RNA it produces, or the amount of protein accumulation in a cell or tissue, which can optionally be measured by an activity of the expressed protein such as, for example, fluorescence, luminescence, acyltransferase activity, etc., relative to a promoter whose transcriptional activity has been previously assessed, relative to a promoter-less construct, or relative to non-transformed cells. For example, the activity or strength of a promoter may be measured in terms of the amount of mRNA accumulated that corresponds to a nucleic acid sequence to which it is operably linked in a cell, relative to the total amount of mRNA or protein produced by the cell. The promoter preferably expresses an operably linked nucleic acid sequence at a level greater than 0.01%, preferably in a range of about 0.5% to about 20% (w/w) of the total cellular RNA. The promoter activity can also be measured by quantifying fluorescence, luminescence, or absorbance of the cells or a product made by the cells or an extract thereof, depending on the activity of a reporter protein that may be expressed from the promoter, as described in further detail in the Examples. The activity or strength of a promoter may be expressed relative to a well-characterized promoter (for which transcriptional activity was previously assessed). For example, a less-characterized promoter may be operably linked to a reporter sequence (for example, a fluorescent protein) and introduced into a specific cell type. A well-characterized promoter is similarly prepared and introduced into the same cellular context. Transcriptional activity of the less-characterized promoter is determined by comparing the amount of reporter expression, relative to the well characterized promoter.

A promoter described herein can have promoter activity in a eukaryotic cell, preferably in a labyrinthulomycetes cell. In a particular example, a promoter as provided herein is active in a labyrinthulomycetes cell in nutrient replete and nutrient-depleted culture conditions. An labyrinthulomycetes promoter as provided herein can be used as a 5' regulatory element for modulating expression of an operably linked gene or genes in labyrinthulomycetes species as well as other organisms, including fungi, heterokonts, and plants.

Using promoter assay methods, such as but not limited to the method described in Examples 3-7 of the present disclosure, the promoter sequences as provided herein can be further modified. e.g. truncated or mutated, and screened to refine the active promoter regions.

Terminators

In another embodiment of the present disclosure, terminators are provided in which the terminators comprise a nucleotide sequence having at least 80%, at least 85%, at least 90%, at least 95%, at least 96%, at least 97%, at least 98%, at least 99%, or about 100% identity to at least 50, at least 100 or at least 150 contiguous nucleotides of any one of SEQ ID NOs: 71-78.

Terminators are genetic sequences that mark the end of a gene for transcription. Without being bound by theory, the terminators of the present disclosure may improve expression improve expression of the nucleic acid sequence (amount of encoded RNA or protein produced), and may mediate polyadenylation or enhance RNA transcript stability. Most terminator sequences in eukaryotes consist of at least two DNA sequences: (1) a binding site for terminator proteins and (2) an upstream element located among the last twelve nucleotides of the transcript. The protein binding sites are usually orientation-sensitive and essential to termination. Termination usually occurs between twelve and twenty nucleotides upstream of the binding site. The upstream element's functionality usually depends more on its overall base composition (T-rich) than on the specific sequence (see, for example. Reeder and Lang, *Trends Biochem Sci.* 22:473-477, 1997).

Expression Cassettes

Expression cassettes are also provided in the present disclosure, in which the expression cassettes comprise one or more promoters or regulatory elements as provided herein to drive the expression of transgenes. An expression cassette can comprise any of the nucleic acid sequences as described herein or any combination thereof that comprise promoters, operably linked to a gene of interest, with the gene of interest positioned downstream of the promoter sequence. For example, any of the promoters listed in TABLE 2, or any subfragments thereof having promoter activity can be used in an expression cassette. Expression cassettes can include, for example, a promoter that comprises a nucleic acid sequence having at least 80%, at least 85%, at least 90%, at least 95%, at least 96%, at least 97%, at least 98%, at least 99%, or about 100% identity to at least 50, at least 100, at least 150, at least 200, at least 250, or at least 300 contiguous nucleotides of any one of SEQ ID NOs: 1-70 and 180-202 operably linked to a gene of interest.

The gene of interest can be operably linked at its 5' end to a terminator. A terminator used in an expression cassette can be any terminator that functions in a host cell. As demonstrated herein, terminator sequences can function in hosts unrelated to the host species from which the terminator is derived. Thus, as non-limiting examples, terminator sequences from fungi, plants, heterokonts, and algae are considered for use in an expression cassette that includes a promoter comprising a sequence having at least 80% identity to at least 50 contiguous nucleotides of any one of SEQ ID NOs: 1-70 and 180-202, including terminators disclosed in U.S. Pat. No. 8,883,993, US2013/0323780, and those disclosed herein as SEQ ID NOs:71-78.

For example, an expression cassette as provided herein can include a promoter positioned upstream of and operably linked to the gene to be expressed, where the promoter comprises a nucleic acid sequence having at least 80% identity to at least 50 contiguous nucleotides of any one of SEQ ID NOs: 1-70 and 180-202, and where the gene of interest is also operably linked to any terminator listed in TABLE 7, where the terminator is positioned downstream of the gene. Non-limiting examples of the expression cassettes provided herein include any of those described in Examples 2-7 of the disclosure.

The basic techniques for operably linking two or more sequences of DNA together are familiar to the skilled worker, and such methods have been described in a number of texts for standard molecular biological manipulation (see, for example, Maniatis et al., "*Molecular Cloning: A Laboratory Manual*" $2^{nd}$ ed. Cold Spring Harbor Laboratory Press, Cold Spring Harbor. N.Y.; and Gibson et al., *Nature Methods* 6:343-45, 2009).

The promoters of the disclosure can be used with any heterologous or homologous gene(s). A heterologous or homologous gene according to the present disclosure may encode a protein or polypeptide. Any known or later-discovered heterologous or homologous gene which encodes a desired gene product can be operably linked to a promoter sequence of the present disclosure using known methods. Non-limiting examples of genes that may be in expression constructs with the promoters of the present disclosure include genes encoding proteins associated with genome editing (e.g., a cas nuclease, TALEN, or meganuclease), abiotic stress resistance; disease resistance; herbicide tolerance, toxin tolerance; carbohydrate metabolism; cell wall composition, growth rate, isoprenoid metabolism; amino acid metabolism; biomass metabolism; fatty acid/lipid metabolism; nitrogen utilization metabolism; photosynthetic capacity; or production of a biopolymer, a biofuel molecule, an enzyme, a flavor compound, a pharmaceutical compound, a pigment, an antioxidant, or a heterologous polypeptide.

For example, in some embodiments, an expression cassette can comprise a promoter as described herein (for example, a promoter comprising a nucleotide sequence having at least 80% identity to at least 50 contiguous nucleotides of any one of SEQ ID NOs: 1-70 and 180-202) operably linked to a gene encoding a polypeptide, where the polypeptide can be any polypeptide of interest, and in illustrative and non-limiting examples, can be a protein associated with biosynthetic pathway of interest.

For example, a promoter as described herein can be operably linked to a gene encoding a polypeptide such as a transcription factor. DNA binding protein, splicing factor, nuclease (including, without limitation, an RNA-guided endonuclease such as a cas protein of a CRISPR system), a recombinase (e.g., a cre or flp recombinase), a G protein, a nucleotide cyclase, a phosphodiesterase, a kinase, a polypeptide of that participates in protein secretion or protein trafficking, a structural protein, a hormone, a cytokine, an antibody, a transporter, or an enzyme, such as but not limited to an enzyme having lipolytic activity, a thioesterase, an amidase, a lipase, a fatty acid synthase or a component of a fatty acid synthase complex, a pfaA, pfaB, pfaC, pfaD, or pfaE polypeptide, an acyl-CoA synthetase, an acyl-ACP synthetase, an acyl carrier protein, an acyl-CoA carboxylase, an acyl transferase, an enzyme that participates in glycolysis, a dehydrogenase, an enzyme of the TCA cycle, a fatty acid desaturase, or a fatty acid elongase.

In further examples, an expression cassette can comprise a promoter as described herein (for example, a promoter comprising a nucleotide sequence having at least 80% identity to at least 50 contiguous nucleotides of any one of SEQ ID NOs: 1-70 and 180-202) operably linked to a gene encoding a functional RNA, optionally wherein the functional RNA is a tRNA, a rRNA, a small nucleolar RNA (snoRNA), a ribozyme, an antisense RNA (asRNA), a micro RNA (miRNA), a short hairpin RNA (shRNA), a small interfering RNA (siRNA), a piwi-interacting RNA (piRNA), a transactivating (tr) RNA of a CRISPR system, a crispr (cr) RNA of a CRISPR system, or a chimeric guide RNA of a CRISPR system.

In some embodiments, a nucleic acid construct as provided herein can include a heterologous nucleic acid sequence that encodes a polypeptide or functional RNA that is operably linked at its 5' end to a promoter as provided herein that mediates gene expression in a labyrinthulomycetes species, and to a terminator as provided herein (e.g., a terminator having at least 80%, at least 85%, at least 90%, at least 95%, at least 96%, at least 97%, at least 98%, at least 99%, or about 100% identity to at least 50, at least 100 or at least 150 contiguous nucleotides of any one of SEQ ID NOs: 71-78) at its 3' end. The construct can be functional in a labyrinthulomycetes species. In some embodiments, the terminator is selected from the group consisting of *S. cerevisiae* ADH1 terminator, *S. cerevisiae* ENO2 terminator. *S. cerevisiae* PDC1 terminator. *S. cerevisiae* PGK1 terminator. *S. cerevisiae* TDH3 terminator. *S. cerevisiae* TEF1 terminator. *S. cerevisiae* CYC1 terminator, and simian virus SV40 terminator. In some embodiments, the terminator includes a sequence having at least 90% or at least 95% sequence identity to a sequence selected from the group consisting of SEQ ID NOs:71-78 set forth in the Sequence Listing.

Vectors

The present disclosure also provides vectors that can comprise one or more of the regulatory elements and/or expression cassettes described herein. The vectors can comprise the expression cassettes described herein and further include at least one origin of replication ("ORI") sequence for replication in a cell. The vectors may further optionally comprise one or more selectable markers under the control of one or more eukaryotic promoters, one or more selectable markers under the control of one or more prokaryotic promoters, and/or one or more sequences that mediate recombination of an exogenous nucleic acid sequence into the target cell's genome.

An ORI is the sequence in a DNA molecule at which replication begins. The ORI serves as a base of assembly for the pre-replication complex. Depending on the ORI, such replication can proceed unidirectionally or bidirectionally. An expression vector as provided herein can include an ORI for replication of the expression vector in a cloning host, such as *E. coli* or *Saccharomyces*, and/or can include an ORI for replication of the expression vector in a target cell, which can be, for example, a Labyrinthulomycetes cell. The structural biology of ORIs is widely conserved among prokaryotes, eukaryotes, and viruses. Most ORIs possess simple tri-, tetra-, or higher nucleotide repetition patterns. Most are AT-rich and contain inverted repeats. Those skilled in the art will be familiar with the more common ORIs, such as P15A and the pUC's ORI.

A vector may also carry a selectable marker. By way of example, a vector that includes an expression cassette may include, as a selectable marker, a gene conferring resistance to a poisonous substance, such as an antibiotic, a herbicide, or some other toxin, so that transformants can be selected by exposing the cells to the poison and selecting those cells which survive the encounter. Non-limiting examples of selectable markers include genes conferring resistance to antibiotics such as amikacin (aphA6), ampicillin (ampR), blasticidin (bls, bsr, bsd), bleomicin or phleomycin (ZEOCIN™) (ble), chloramphenicol (cat), emetine (RBS 14p or cry1-1), erythromycin (ermE). G418 (GENETICIN™) (neo), gentamycin (aac3 or aacC4), hygromycin B (aphIV, hph, hpt), kanamycin (ntpII), methotrexate (DHFR mtxR), penicillin and other β-lactams (p-lactamases), streptomycin or spectinomycin (aadA, spec/strep), and tetracycline (tetA, tetM, tetQ); genes conferring resistance to herbicides such as aminotriazole, amitrole, andrimid, aryloxyphenoxy propionates, atrazines (psbA), bipyridyliums, bromoxynil, cyclohexandione oximes dalapon, dicamba, diclfop, dichlorophenyl dimethyl urea (DCMU), difunone, diketonitriles, diuron, fluridone, glufosinate, glyphosate, halogenated hydrobenzonitriles, haloxyfop, 4-hydroxypyridines, imidazolinones, isoxasflutole, isoxazoles, isoxazolidinones, miroamide B, p-nitrodiphenylethers, norflurazon, oxadiazoles, m-phenoxybenzamides. N-phenyl imides, pinoxadin, protoporphyrionogen oxidase inhibitors, pyridazinones, pyrazolinates, sulfonylureas, 1,2,4-triazol pyrimidine, triketones, or urea compounds; including genes encoding enzymes that provide resistance or tolerance to herbicides as acetyl CoA carboxylase (ACCase), acetohydroxy acid synthase (ahas), acetolactate synthase (als, csrl-1, csrl-2, imrl, imr2), aminoglycoside phosphotransferase (apt), anthranilate synthase, bromoxynil nitrilase (bxn), cytochrome P450-NADH-cytochrome P450 oxidoreductase, dalapon dehalogenase (dehal), dihydropteroate synthase (sul), class I 5-enolpyruvylshikimate-3-phosphate synthase (EPSPS), class II EPSPS (aroA), non-class I/II EPSPS, glutathione reductase, glyphosate acetyltransferase (gat), glyphosate oxidoreductase (gox), hydroxyphenylpyruvate dehydrogenase, hydroxyphenylpyruvate dioxygenase (hppd), isoprenyl pyrophosphate isomerase, lycopene cyclase, phosphinothricin acetyl transferase (pat, bar), phytoene desaturase (crtI), prenyl transferase, protoporphyrin oxidase, psbA of photosystem II (psbA). SMM esterase (SulE) superoxide dismutase (sod); genes that may be used in auxotrophic strains or to confer autotrophic growth or other metabolic effects, such as arg7, his3, hisD, hisG, lysA, manA, metE, nit1, trpB, ura3, xylA, a dihydrofolate reductase gene, a mannose-6-phosphate isomerase gene, a nitrate reductase gene, or an ornithine decarboxylase gene; a negative selection factor such as thymidine kinase; or toxin resistance factors such as a 2-deoxyglucose resistance gene; and an R-locus gene. The selectable marker gene can be operably linked to a promoter as provided herein.

In some embodiments, the selectable marker may be under the control of a promoter including but not limited to a promoter as provided herein. In some embodiments, the promoter regulating expression of the selectable marker may be conditional or inducible. In some embodiments, the promoter regulating expression of the selectable marker may be preferably constitutive, and can be, for example, any promoter disclosed herein or another promoter. Alternatively, the selectable marker may be placed under the control of the expression cassette promoter. If a selectable marker is placed under the control of the expression cassette promoter, the selectable marker and the expression cassette may be operably linked with an internal ribosome entry site ("IRES") element between the expression cassette and the selectable marker (Komar & Hatzoglou, *Cell Cycle* 10:229-240, 2011; and Hellen & Sarnow, *Genes & Dev.* 15:1593-1612, 2001) or a “2A” sequence (Kim et al. PLoS One 6(4):e18556, 2011).

Further provided herein is a vector for transformation of a eukaryotic cell, such as but not limited to a labyrinthulomycetes cell, in which the vector includes a selectable marker gene operably linked to a promoter as provided herein, for example, a promoter that includes a nucleotide sequence having at least 80%, at least 85%, at least 90%, at least 95%, at least 96%, at least 97%, at least 98%, at least 99%, or about 100% identity to at least 50, at least 100, at least 200, at least 300, at least 400, at least 500, at least 600, at least 700, or at least 800 contiguous nucleotides of any one of SEQ ID NOs: 1-70 and 180-202, or a promoter that comprises any one of SEQ ID NOs: 1-70 and 180-202. The transformation can further include one or more additional genes or constructs for transfer into the host cell, such as a gene encoding a polypeptide such as but not limited to any disclosed hereinabove or a construct encoding a functional RNA, where the gene encoding a polypeptide or functional RNA can optionally be operably linked to a promoter as described herein, or can optionally be operably linked to another promoter.

In an alternative transformation strategy, a selectable marker operably linked to a promoter such as a promoter described herein can be provided on a separate construct, where both the gene-of-interest construct and the selectable marker construct are used together in transformation protocols. Selected transformants are then analyzed for co-transformation of the construct that includes the gene-of-interest (see, for example, Kindle *Proc. Natl. Acad. Sci. USA* 87:1228-1232, 1990).

If a vector as provided herein that includes an expression cassette lacks a selectable marker gene, transformants may be selected by routine methods familiar to those skilled in the art, such as, by way of a non-limiting example, extracting nucleic acid from the putative transformants and screening by PCR. Alternatively or in addition, transformants may be screened by detecting expression of a reporter gene, such as but not limited to a chloramphenicol acyltransferase gene (cat) lacZ, uidA, xylE, an alkaline phosphatase gene, an α-amylase gene, an α-galactosidase gene, a β-lactamase gene, a β-glucuronidase gene, a horseradish peroxidase gene, a luciferin/luciferase gene, an R-locus gene, a tyrosinase gene, or a gene encoding a fluorescent protein, such as any of the green, yellow, red, blue, cyan, photo-convertable, or photo-switchable fluorescent proteins or any of their variants, including codon-optimized, rapidly folding, monomeric, increased stability, and enhanced fluorescence variants. In some embodiments, a reporter gene used in a vector may optionally be regulated by a promoter as provided herein. In some embodiments, a transformation vector may include a gene encoding a reporter, such as, for example, a fluorescent protein, operably linked to a promoter as provided herein.

In some embodiments, the vector is designed for integration of one or more genes (such as the expression cassette) into the host genome. For example, the expression vectors may include *Agrobacterium* flanking sequences designed for integrating transgenes into the genome of a target plant cell. In other embodiments, vectors can be targeted for integration into a labyrinthulomycetes' chromosome by including flanking sequences that enable homologous recombination into the chromosome or targeted for integration into endogenous host plasmids by including flanking sequences that enable homologous recombination into the endogenous plasmids. Further, a transformation vector can include sequences for site-specific recombination such as but not limited to lox sites that are acted on by the “cre” recombinase.

In addition to the promoters provided herein, one skilled in the art would know various promoters, introns, enhancers, transit peptides, targeting signal sequences, 5' and 3' untranslated regions (UTRs), IRES, 2A sequences, and terminator sequences, as well as other molecules involved in the regulation of gene expression that are useful in the design of effective expression vectors. In some embodiments, the expression vector will contain one or more enhancer elements. Enhancers are short regions of DNA that can bind trans-acting factors to enhance transcription levels. Although enhancers usually act in cis, an enhancer need not be particularly close to its target gene, and may sometimes not be located on the same chromosome (e.g. acting in trans). Enhancers can sometimes be located in introns.

In some embodiments, a gene or genes encoding enzymes that participate in the synthesis of a fatty acid product (e.g., a fatty acid, a fatty acid derivative, or a glycerolipid) is cloned into the vector as an expression cassette that includes a promoter as disclosed herein. The expression cassette may optionally include a transit peptide-encoding sequence for directing the expressed enzyme to the endoplasmic reticulum of transformed eukaryotic cells, an intron sequence, a sequence having a poly-adenylation signal, etc.

In a further embodiment, a vector is provided comprising an expression cassette as described herein, wherein the vector further comprises one or more of: a selectable marker gene, an origin of replication, and one or more sequences for promoting integration of the expression cassette into the host genome.

In a further embodiment, a vector is provided comprising an isolated, synthetic or recombinant nucleic acid molecule as described herein, wherein the nucleic acid molecule is operably linked to a nucleic acid sequence encoding a selectable marker or a reporter protein, such as, for example, any reporter protein described herein. In a particular embodiment, the vector further comprises one or more of: an origin of replication, one or more sequences for promoting integration of the expression cassette into the host genome, a sequence as reported herein that comprises a terminator, or an additional gene, wherein the additional gene encodes a ribosomal RNA, a tRNA, a ribozyme, a transactivating (tr) RNA of a CRISPR system, a crispr (cr) RNA of a CRISPR system, a chimeric guide RNA of a CRISPR system, a micro RNA, an interfering RNA (RNAi) molecule, a short hairpin (sh) RNA, an antisense RNA molecule, a structural protein, an enzyme, a transcription factor, or a transporter.

C. Transformation Methods

The present disclosure provides transformation methods in which a eukaryotic cell is transformed with an expression vector as described herein. The transformation methods comprise introducing an expression vector as provided herein that includes a promoter as disclosed herein operably linked to a selectable marker gene into a host cell and then selecting for a transformant. General procedures, systems, and methods of transforming prokaryotic and eukaryotic host cells are well known in the art. Sec. e.g., Maniatis et al., 2009, supra, 2$^{nd}$ NY, 2009; and Sambrook et al., 1989, supra. The expression cassettes and vectors as provided herein may be introduced into a host cell by many methods familiar to those skilled in the art including, as non-limiting examples: natural DNA uptake (Chung et al., *FEMS Microbiol. Lett.* 164:353-361, 1988); conjugation (Wolk et al., *Proc. Natl. Acad. Sci. USA* 81, 1561-1565, 1984); transduction: glass bead transformation (Kindle et al., *J. Cell Biol.* 109:2589-601, 1989); silicon carbide whisker transformation (Dunahay et al., Methods Mol. Biol. 62:503-9, 1997); biolistics (Dawson et al., *Curr. Microbiol.* 35:356-62, 1997); electroporation (Kjaerulff et al., *Photosynth. Res.* 41:277-283, 1994); laser-mediated transformation; or incubation with DNA in the presence of or after pre-treatment with any of poly(amidoamine) dendrimers (Pasupathy et al., *Biotechnol. J.* 3:1078-82, 2008), polyethylene glycol (Ohnuma et al., *Plant Cell Physiol.* 49:117-120, 2008), cationic lipids (Muradawa et al., *J. Biosci. Bioeng.* 105:77-80, 2008), dextran, calcium phosphate, or calcium chloride (Mendez-Alvarez et al., *J. Bacteriol.* 176:7395-7397, 1994), optionally after treatment of the cells with cell wall-degrading enzymes (Perrone et al., *Mol. Biol. Cell* 9:3351-3365, 1998.

In principle, the methods and molecules according to the present disclosure can be deployed for genetically engineering any prokaryotic or eukaryotic species, including, but not limited to, bacteria, chytrids, microfungi, and microalgae. Host cells to be transformed can be either untransformed cells or cells that are already transformed with at least one nucleic acid molecule. The methods and compositions are preferably used with microorganisms that are important or interesting for aquaculture, agriculture, for the production of biomass used in production of fatty acid molecules and other chemicals. In particular, a cell used in any of the methods herein can be, in some embodiments, of a heterokont strain of the labyrinthulomycetes class. While the classification of the Thraustochytrids and Labyrinthulids has evolved over the years, for the purposes of the present application, "labyrinthulomycetes" is a comprehensive term that includes microorganisms of the orders Thraustochytrids and Labyrinthulids, and includes the genera *Althornia, Aplanochytrium, Aurantiochytrium, Corallochytrium, Diplophryids, Diplophrys, Elina, Japonochytrium, Labyrinthula, Labryinthuloides, Oblongichytrium, Pyrrhosorus, Schizochytrium, Thraustochytrium, and Ulkenia.*

Non-limiting examples of preferred species include, for instance, microorganisms from the genera including, but not limited to *Aplanochytrium, Aurantiochytrium, Thraustochytrium, Labyrinthuloides, Japonochytrium, Ulkenia*, and *Schizochytrium*. Particularly suitable species are within the genera including, but are not limited to: any *Aurantiochytrium* species, including but not limited to any disclosed herein, such as, for example, WH-06267 and WH-05628; any Schizochytrium species, including *Schizochytrium aggregatum, Schizochytrium limacinum, Schizochytrium minutum*; any *Thraustochytrium* species (including former *Ulkenia* species such as *U. visurgensis, U. anoeboida, U. sarkariana, U. profunda, U. radiata, U. minuta* and *Ulkenia* sp. BP-5601), and including *Thraustochytrium striatum, Thraustochytrium aureum, Thraustochytrium roseum*; and any *Japonochytrium* species. Strains of *Thraustochytriales* particularly suitable for the present disclosure include, but are not limited to: *Schizochytrium* sp. S31)(ATCC 20888); *Schizochytrium* sp. S8 (ATCC 20889); *Schizochytrium* sp. LC-RM (ATCC 18915); *Schizochytrium* sp. SR21; *Schizochytrium aggregatum* ATCC 28209; *Schizochytrium limacinum* IFO 32693; *Thraustochytrium* sp. 23B ATCC 20891; *Thraustochytrium striatum* ATCC 24473; *Thraustochytrium aureum* ATCC 34304; *Thraustochytrium roseum* ATCC 28210; and *Japonochytrium* sp. Ll ATCC 28207.

Eukaryotic host cells, such as any of the cells disclosed hereinabove transformed with a molecule or construct of the present disclosure are also provided herein. Therefore, in one embodiment, a recombinant eukaryotic cell is provided comprising an isolated or recombinant nucleic acid molecule as described herein or an expression cassette as described herein, or a vector as described herein. In some embodiments, transformed cell cultures can be diluted, plated on agar, and allowed to grow until isolated colonies can be selected for further propagation as clonal strain.

D. Bioproducts

In one aspect, some embodiments disclosed herein relate to methods for producing a bioproduct. Such methods involve culturing a recombinant cell harboring an isolated, synthetic, or recombinant nucleic acid molecule according to any one of the preceding aspects and embodiments, and producing the bioproduct therefrom. In some embodiments, such methods further include recovering the bioproduct from the cultured cells.

Thus, also provided herein is a bioproduct produced by a method according to this aspect of the disclosure. In some embodiments, the bioproduct can be a lipid product. In some embodiments, the lipid product disclosed herein includes one or more PUFAs. In some embodiments, the one or more PUFAs include an omega-3 PUFA or an omega-6 PUFA. In some embodiments, the one or more PUFAs include arachidonic acid (ARA), docosahexaenoic acid (DHA), docosapentaenoic acid (DPA), or eicosapentaenoic acid (EPA), or a combination of any thereof.

Bioproducts of the disclosure include, but are not limited to, food products, feed products, medicinal and pharmaceutical compositions, cosmetics, and industrial products.

A food product that may include labyrinthulomycetes oil derived from an engineered labyrinthulomycetes microorganism as provided herein includes both solid and liquid bioproduct. A food product can be an additive to animal or human foods. Foods include, but are not limited to, common foods; liquid products, including milks, beverages, therapeutic drinks, and nutritional drinks; functional foods; supplements; nutraceuticals; infant formulas, including formulas for pre-mature infants; foods for pregnant or nursing women; foods for adults; geriatric foods; and animal foods.

A labyrinthulomycetes biomass or microbial oil derived from an engineered labyrinthulomycetes microorganism as described herein can be used directly as or included as an additive within one or more of: an oil, shortening, spread, other fatty ingredient, beverage, sauce, dairy-based or soy-based food (such as milk, yogurt, cheese and ice-cream), a baked good, a nutritional product. e.g., as a nutritional supplement (in capsule or tablet form), a vitamin supplement, a diet supplement, a powdered drink, a finished or semi-finished powdered food product, and combinations thereof.

In some embodiments, the bioproduct is an animal feed, including without limitation, feed for aquatic animals and terrestrial animals. In some embodiments, the bioproduct is a feed or feed supplement for any animal whose meat or products are consumed by humans, such as any animal from which meat, eggs, or milk is derived for human consumption. When fed to such animals, nutrients such as LC-PUFAs can be incorporated into the flesh, milk, eggs or other products of such animals to increase their content of these nutrients.

In some embodiments, the bioproduct is a pharmaceutical composition. Suitable pharmaceutical compositions include, but are not limited to, an anti-inflammatory composition, a drug for treatment of coronary heart disease, a drug for treatment of arteriosclerosis, a chemotherapeutic agent, an active excipient, an osteoporosis drug, an anti-depressant, an anti-convulsant, an anti-*Helicobacter pylori* drug, a drug for treatment of neurodegenerative disease, a drug for treatment of degenerative liver disease, an antibiotic, a cholesterol lowering composition, and a triglyceride lowering composition. In some embodiments, the bioproduct is a medical food. A medical food includes a food that is in a composition to be consumed or administered externally under the supervision of a physician and that is intended for the specific dietary management of a condition, for which distinctive nutritional requirements, based on recognized scientific principles, are established by medical evaluation.

The labyrinthulomycetes oil or microbial oil derived from an engineered labyrinthulomycetes microorganism as described herein can be formulated in a dosage form. Dosage forms can include, but are not limited to, tablets, capsules, cachets, pellets, pills, powders and granules, and parenteral dosage forms, which include, but are not limited to, solutions, suspensions, emulsions, and dry powders comprising an effective amount of the microbial oil. It is also known in the art that such formulations can also contain pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. Administration forms can include, but are not limited to, tablets, dragees, capsules, caplets, and pills, which contain the microbial oil and one or more suitable pharmaceutically acceptable carriers.

For oral administration, the labyrinthulomycetes oil or microbial oil derived from an engineered labyrinthulomycetes microorganism as described herein can be combined with pharmaceutically acceptable carriers well known in the art. Such carriers enable the microbial oils of the invention to be formulated as tablets, pills, dragees, capsules, liquids, gels, syrups, slurries, suspensions and the like, for oral ingestion by a subject to be treated. In some embodiments, the dosage form is a tablet, pill or caplet. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl cellulose, sodium carboxymethyl cellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate. Pharmaceutical preparations that can be used orally include, but are not limited to, push-fit capsules made of gelatin, as well as soft, sealed capsules made of gelatin and a plasticizer, such as glycerol or sorbitol.

In further embodiments, the bioproduct is a cosmetic. Cosmetics include, but are not limited to, emulsions, creams, lotions, masks, soaps, shampoos, washes, facial creams, conditioners, make-ups, bath agents, and dispersion liquids. Cosmetic agents can be medicinal or non-medicinal.

All publications and patent applications mentioned in this specification are herein incorporated by reference to the same extent as if each individual publication or patent application was specifically and individually indicated to be incorporated by reference.

No admission is made that any reference cited herein constitutes prior art. The discussion of the references states what their authors assert, and the applicants reserve the right to challenge the accuracy and pertinence of the cited documents. It will be clearly understood that, although a number of information sources, including scientific journal articles, patent documents, and textbooks, are referred to herein, this reference does not constitute an admission that any of these documents forms part of the common general knowledge in the art.

The discussion of the general methods given herein is intended for illustrative purposes only. It is not intended to be exhaustive or to limit the disclosure. Individual aspects or features of a particular embodiment are generally not limited to that particular embodiment, but, where applicable, are interchangeable and can be used in a selected embodiment, even if not specifically shown or described. It is expressly contemplated that any aspect or feature of the present disclosure can be combined with any other aspect, features, or combination of aspects and features disclosed herein. Other alternative methods and embodiments will be apparent to those of skill in the art upon review of this disclosure, and are to be included within the spirit and purview of this application.

EXAMPLES

Additional embodiments are disclosed in further detail in the following examples, which are not in any way intended to limit the scope of the claims.

Example 1

Labyrinthulomycetes Strains and Culture Media

Labyrinthulomycetes strains used in the present disclosure were *Aurantiochytrium* sp. SGI-i886, which was described previously as WH-5628 strain in U.S. application Ser. No. 14/720,679 (Publication No. US2016-0177255, abandoned) and PCT Pub. No. WO2015/179844, and *Schizochytrium* sp. SGI-i94.

Compositions of media used in the experiments described below study are the following.

1) FM002 growth medium contained 17 g/L Instant Ocean salts (Aquatic Eco Systems, Apopka, FL), 10 g/L yeast extract, 10 g/L Peptone, and 10 g/L Dextrose.
2) FM005 growth medium contained 17 g/L Instant Ocean salts (Aquatic Eco Systems. Apopka, FL), 1 g/L mono-Potassium Phosphate ($KH_2PO_4$), 6 g/L ammonium sulfate [$(NH_4)_2SO_4$]; 0.5 g/L potassium chloride (KCl), 250 ml/L of MES Hydrate solution (800 mM, pH 5.8), 80 ml/L of 50% Dextrose solution, 5 ml/L of $MgSO_4 \cdot 7H_2O$ stock solution (in 34 g/L in Instant Ocean), 5 g/L of DG Trace Metals solution, and 1 g/L of DG Vitamin solution. The growth medium was adjusted with NaOH pellets to pH 5.8. The DG Trace Metals solution contained 6 g/L EDTA di-sodium salt ($Na_2EDTA \cdot 2H_2O$); 0.29 g/L iron chloride ($FeCl_3 \cdot 6H_2O$); 6.84 g/L boric acid ($H_2BO_3$); 1 ml/L sodium molybdenate stock solution ($Na_2MoO_4 \cdot 2H_2O$, 5 g/L); 0.86 g/L manganese chloride ($MnCl_2 \cdot 4H_2O$); 1 ml/L zinc chloride stock solution (($ZnCl_2$, 60 g/L); 1 ml/L cobalt chloride stock solution ($CoCl_2 \cdot 6H_2O$, 26 g/L); 1 ml/L copper sulfate stock solution ($CuSO_4 \cdot 5H_2O$, 2 g/L); and 1 ml/L nickel sulfate stock solution ($NiSO_4 \cdot 6H_2O$, 60 g/L). The DG Vitamins solution contained 200 mg/L thiamine, 10 ml/L biotin stock solution (0.1 g/L); and 1 ml/L stock solution of Vitamin $B_{12}$ cyanocobalamin (1 g/L).

3) FM006 growth medium contained 17 g/L Instant Ocean salts (Aquatic Eco Systems, Apopka, FL), 1 g/L mono potassium phosphate $KH_2PO_4$, 1.65 g/L ammonium sulfate $[(NH_4)_2SO_4]$, 0.5 g/L potassium chloride (KCl), 250 ml/L of MES Hydrate solution (800 mM, pH 5.8), 80 ml/L of 50% Dextrose solution, 5 ml/L of $MgSO_4 \cdot 7H_2O$ stock solution (34 g/L in Instant Ocean), 5 g/L of DG Trace Metals solution, and 1 g/L of DG Vitamin solution. The growth medium was adjusted with NaOH pellets to pH 5.8.

Example 2

Evaluation of *Aurantiochytrium* sp. SGI-i886 Gene Expression by Transcriptomics Study This Example describes the experimental characterization and evaluation of several promoter sequences derived from strain SGI-i886 based on average coverage of the cDNA in next-generation sequencing (NGS) data of the transcriptomes of the strain SGI-i886 during mid- to late-log phase of growth.

Replicate flasks (n=2) of strain SGI-i886 were grown in nitrogen-deplete and control (that is, nitrogen-replete) media, respectively. Each flask was sampled for transcriptomics analysis at 0, 2, and 24 hours. A total of 12 polyA-selected mRNA samples were prepared for next-generation RNA sequencing. The transcript abundance was evaluated during the growth phase, i.e. at the 2-hour time point in nitrogen-replete growth conditions in the transcriptomics experiments.

RNA was isolated by pelleting approximately $10^7$ cells and lysing by pipetting up and down in 1 mL Trizol reagent. Insoluble material was removed from the lysate by centrifugation at 12,000×g for 10 min. at 4° C. The cleared supernatant was removed to a fresh tube and incubated at room temperature (RT) for 5 min before extracting with chloroform by adding 0.2 mL chloroform to mL of the cleared Trizol lysate. The tubes were capped securely and vigorously shaken for 15 seconds, then incubated at RT for 2-3 min. The samples were then centrifuged at no more than 12,000×g for 15 minutes at 4° C. Following centrifugation the mixture was separated into a lower (red) phenol-chloroform phase, an interface, and a colorless upper aqueous phase. The aqueous phase containing the RNA was transferred to a fresh tube and precipitate by adding 0.5 ml of isopropanol per 1 ml of aqueous phase, incubating the samples at RT for 10 minutes, and centrifuging at no more than 12,000×g for 15 minutes at 4° C. The RNA precipitate, often invisible before centrifugation, formed a gel-like pellet on the whole wall. The supernatant was removed completely, then the pellet was washed twice with 1.5 mL 75% ethanol. The sample was mixed by flicking the tube, and centrifugations were at no more than 7500×g for 5 minutes at 4° C. The twice-washed RNA pellets were allowed to air dry for 7 min, then dissolved in 50 to 100 L of DEPC-treated water for 10 min at 55° C. Samples were stored at −80° C.

Next-generation sequencing libraries were prepared from the isolated RNA and sequenced using sequencing-by-synthesis (Illumina) to generate 100 bp paired-end reads using the mRNA-Seq procedure described in Mortazavi et al. (*Nature Methods* 5:621-628, 2008). Mappable reads were aligned to the *Aurantiochytrium* sp. SGI-i886 reference genome sequence using tophat (tophat.cbeb.umd.edu/). Expression levels were computed for every annotated gene using the Cuffdiff component of the Cufflinks software (cufflinks.cbcb.umd.edu). Tophat and Cufflinks are described in Trapnell et al. (*Nature Protocols* 7: 562-578, 2012). Differential expression analysis was performed using the R package edger (McCarthy et al., *Nucl. Acids Res.* May; 40(10):4288-97, 2012). Expression levels in units of "fragments per kilobase per million" (FPKM) were reported for every gene in each sample using standard parameters. In this experiment. FPKM was a measure of relative transcriptional levels that normalizes for differences in transcript length.

The average sequencing coverage, shown for eight different genes in Table 1, measured in terms of FPKM according to a procedure described in Mortazavi et al. (*Nature Methods* 5:621-28, 2008), corresponds to the transcript abundance of each gene. In RNA sequencing experiments, the relative expression of a transcript was predicted to be proportional to the number of cDNA fragments that originated from it.

TABLE 1

Transcript abundance of genes associated with promoter sequences identified as strong constitutive promoters.

| Gene Description | Avg Coverage (FPKM) |
|---|---|
| Neighbor of BRCA1 gene 1 (NBR1), transcript variant 1 | 4581 |
| Eft2p GTPasel translation elongation factor 2 (EF-2) | 3907 |
| 40S ribosomal protein S3a | 3744 |
| Eukaryotic translation initiation factor 5A isoform IV | 2967 |
| 60S ribosomal protein L9; Conserved predicted protein | 2839 |
| Actin A | 2500 |
| Heat shock rotein 70 | 2422 |
| Translation elongation factor 1-alpha | 2382 |
| 60S ribosomal protein L26 | 1664 |
| Tubulin alpha chain | 1164 |

Example 3

Construction of Expression Cassettes and Transformation Vectors

Promoter regions were identified in the sequenced genomes of two labyrinthulomycetes strains isolated from marine environments, *Aurantiochytrium* sp. strain SGI-i886 and *Schizochytrium* sp. strain SGI-i94. The genomes of these strains were sequenced and regions of between approximately 500 bp and approximately 2 kb extending upstream (5') of the initiating methionine codon of bioinformatically identified genes were selected as comprising promoters, as listed in Table 2 (*Aurantiochytrium* promoter sequences) and Table 3 (*Schizochytrium* promoter sequences). To evaluate their ability to regulate expression of operably linked heterologous genes, these promoters were cloned into expression vectors, such that the 3' end of the putative promoter fragment corresponded to the 3'-most bp of the 5' untranslated region of the corresponding chytrid gene (that is, the 3' end of each promoter fragment was the nucleotide immediately upstream of the initiating ATG codon of the identified gene).

TABLE 2

Promoters isolated from *Aurantiochytrium* strain SGI-i886. When marked "short", the promoters were shortened from the 5' end of the corresponding full-length promoters.

| Gene Name | Promoter Length (hp) | SEQ ID NO | Expression Construct |
|---|---|---|---|
| Neighbor of BRCA1 gene 1 (NBR1), transcript variant 1; allele 1 | 1057 | SEQ ID NO: 1 | pSGI-JU-80-1 |
| Neighbor of BRCA1 gene 1 (NBR1), transcript variant 1; allele 6 | 1000 | SEQ ID NO: 2 | pSGI-JU-80-6 |
| Eft2p GTPasel translation elongation factor 2 (EF-2); allele 3 | 927 | SEQ ID NO: 3 | pSGI-JU-81-3 |
| Eft2p GTPasel translation elongation factor 2 (EF-2); allele 8 | 924 | SEQ ID NO: 4 | pSGI-JU-81-8 |
| 40S ribosomal protein S3a (S3-a); allele 2 | 655 | SEQ ID NO: 5 | pSGI-JU-82-2 |
| 40S ribosomal protein S3a (S3-a); allele 5 | 655 | SEQ ID NO: 6 | pSGI-JU-82-5 |
| Eukaryotic translation initiation factor 5A isoform IV (IF-5a); allele 1 | 1000 | SEQ ID NO: 7 | pSGI-JU-83-1 |
| Eukaryotic translation initiation factor 5A isoform IV (IF-5a); allele 2 | 1004 | SEQ ID NO: 8 | pSGI-JU-83-2 |
| 60S ribosomal protein L9; Conserved predicted protein (RPL9); allele 1 | 860 | SEQ ID NO: 9 | pSGI-JU-84-1 |
| 60S ribosomal protein L9; Conserved predicted protein (RPL9); allele 6 | 864 | SEQ ID NO: 10 | pSGI-JU-84-6 |
| Actin A complement of Actin-1/3 (ActA); allele 3 | 492 | SEQ ID NO: 11 | pSGI-JU-85-3 |
| Actin A complement of Actin-1/3 (ActA); allele 6 | 492 | SEQ ID NO: 12 | pSGI-JU-85-6 |
| Actin A complement of Actin-1/3 (ActA); allele 8 | 492 | SEQ ID NO: 13 | pSGI-JU-85-8 |
| Heat shock protein 70 (hsp70) | 1000 | SEQ ID NO: 14 | pSGI-JU-86 |
| Translation elongation factor 1-alpha (EF-1a); allele 4 | 1031 | SEQ ID NO: 15 | pSGI-JU-87-4 |
| Translation elongation factor 1-alpha (EF-1a); allele 7 | 1026 | SEQ ID NO: 16 | pSGI-JU-87-7 |
| 60S ribosomal protein L26 (RPL26); allele 5 | 1000 | SEQ ID NO: 17 | pSGI-JU-88-5 |
| 60S ribosomal protein L26 (RPL26); allele 7 | 996 | SEQ ID NO: 18 | pSGI-JU-88-7 |
| Tubulin alpha (Tubα); allele 1 | 1002 | SEQ ID NO: 19 | pSGI-JU-89-1 |
| Tubulin alpha (Tubα); allele 6 | 997 | SEQ ID NO: 20 | pSGI-JU-89-6 |
| Actin (Act); allele 4 | 1784 | SEQ ID NO: 33 | pSGI-JU-180-4 |
| Actin (Act); allele 5 | 1776 | SEQ ID NO: 34 | pSGI-JU-180-5 |
| Actin (Act); allele 6 | 1776 | SEQ ID NO: 35 | pSGI-JU-180-6 |
| Elongation factor 1-alpha 1 (EF1alpha) | 2048 | SEQ ID NO: 36 | pSGI-JU-181 |
| 60S ribosomal protein L6 (RPL6) | 1792 | SEQ ID NO: 37 | pSGI-JU-182 |
| Actin depolymerase (Adp); allele A | 1739 | SEQ ID NO: 38 | pSGI-JU-183A |
| Actin depolymerase (Adp); allele B | 1729 | SEQ ID NO: 39 | pSGI-JU-183B |
| Adenosylhomocysteinase (AHC) | 1885 | SEQ ID NO: 40 | pSGI-JU-184 |
| Alternative oxidase (AOX); allele B | 2015 | SEQ ID NO: 41 | pSGI-JU-185B |
| Alternative oxidase (AOX); allele C | 1961 | SEQ ID NO: 42 | pSGI-JU-185C |
| Cytochrome C oxidase (cox); allele A | 1764 | SEQ ID NO: 43 | pSGI-JU-186A |
| Cytochrome C oxidase (cox); allele C | 1764 | SEQ ID NO: 44 | pSGI-JU-186C |
| Elongation factor 1-beta (EF1beta) | 1774 | SEQ ID NO: 45 | pSGI-JU-187 |
| Fa ATP synthase (faas) | 1973 | SEQ ID NO: 46 | pSGI-JU-188 |
| Heavy metal associated domain (HMA); allele A | 1971 | SEQ ID NO: 47 | pSGI-JU-189A |
| Heavy metal associated domain (HMA); allele B | 1930 | SEQ ID NO: 48 | pSGI-JU-189B |
| Mitochondrial chaperonin 60 (hsp60); allele A | 1888 | SEQ ID NO: 49 | pSGI-JU-190A |
| Mitochondrial chaperonin 60 (hsp60); allele B | 1838 | SEQ ID NO: 50 | pSGI-JU-190B |
| Phosphoddylinsositol 3-kinase (P13K); allele A | 1635 | SEQ ID NO: 51 | pSGI-JU-191A |
| Phosphotidvlinsositol 3-kinase (P13K); allele C | 1637 | SEQ ID NO: 52 | pSGI-JU-191B |
| 60s ribososomal protein 11 (RPL11); allele B | 1840 | SEQ ID NO: 53 | pSGI-JU-192B |
| 60s ribososomal protein 11 (RPL11); allele C | 1844 | SEQ ID NO: 54 | pSGI-JU-192C |
| Small nuclear ribonucleoprotein (snRNP) | 1890 | SEQ ID NO: 55 | pSGI-JU-193 |
| Transcriptionally-controlled tumor protein homolog (TCTP) | 1956 | SEQ ID NO: 56 | pSGI-JU-194 |
| Tetraspanin (Tsp): allele A | 1700 | SEQ ID NO: 57 | pSGI-JU-195A |
| Tetraspanin (Tsp): allele B | 1680 | SEQ ID NO: 58 | pSGI-JU-195B |
| Tubulin alpha (Tubα-738) | 738 | SEQ ID NO: 59 | pSGI-JU-196 |
| Tubulin alpha (Tubα-522) | 522 | SEQ ID NO: 60 | pSGI-JU-197 |
| Actin (act-1176) | 1176 | SEQ ID NO: 61 | pSGI-JU-198 |
| Actin (act-776) | 776 | SEQ ID NO: 62 | pSGI-JU-199 |
| Actin (act-557) | 557 | SEQ ID NO: 63 | pSGI-JU-200 |
| Fa ATP synthase short (faas-776) | 776 | SEQ ID NO: 64 | pSGI-JU-188A-short |
| Heavy metal associated domain short (HMA-796) | 796 | SEQ ID NO: 65 | pSGI-JU-189A-short |
| Mitochondrial chaperonin 60 short (hsp60-) | 788 | SEQ ID NO: 66 | pSGI-JU-190A-short |
| Phosphotidylinsositol 3-kinase short (PI3K-752) | 752 | SEQ ID NO: 67 | pSGI-JU-191C-short |
| 60s ribososomal protein 11 short (RPL11-699) | 699 | SEQ ID NO: 68 | pSGI-JU-192B-short |
| Tetraspanin short (Tsp-749) | 749 | SEQ ID NO: 69 | pSGI-JU-195-short |
| Actin depolymerase-short (Adp-830) | 830 | SEQ ID NO: 70 | 183A-short-short |

TABLE 3

| Promoters isolated from *Schizochytritum* strain SGI-i94. | | | |
|---|---|---|---|
| Gene Name | Length | SEQ ID NO | Expression Construct |
| Transcriptionally-controlled tumor protein homolog (TCTP) | 1000 | SEQ ID NO: 21 | pSGI-JU-98 |
| Acetyl-coenzyme A synthetase 2 (ACS2) | 1163 | SEQ ID NO: 22 | pSGI-JU-99 |
| Tubulin alpha (Tubα) | 872 | SEQ ID NO: 23 | pSGI-JU-101 |
| Heat shock protein 70 (hsp70) | 1004 | SEQ ID NO: 24 | pSGI-JU-102 |
| Transcription elongation factor 3 (EF-3) | 1000 | SEQ ID NO: 25 | pSGI-JU-103 |
| Hexose transporter 1 (HXT1) | 1000 | SEQ ID NO: 26 | pSGI-JU-105 |
| Catalase (cat) | 1018 | SEQ ID NO: 27 | pSGI-JU-106 |
| 60S ribosomal protein L9 (RPL9) | 994 | SEQ ID NO: 28 | pSGI-JU-107 |
| 40s ribosomal protein S3a (RPS3a) | 1000 | SEQ ID NO: 29 | pSGI-JU-108 |
| Tubulin beta chain (Tubβ) | 1000 | SEQ ID NO: 30 | pSGI-JU-109 |
| Superoxide dismutase (SOD) | 976 | SEQ ID NO: 31 | pSGI-JU-110 |
| Phosphoglycerate kinase (PGK) | 1033 | SEQ ID NO: 32 | pSGI-JU-111 |

The promoters provided in Tables 2 and 3 were cloned upstream of the reporter gene TurboGFP (SEQ ID NO:169; Evrogen, Moscow. Russia) to generate expression vectors for evaluation of promoter function in transgenic labyrinthulomycetes strains. The vectors also carried the nptII marker gene (SEQ ID NO:170) for selection of transformants on paromomycin-containing media. For cloning the promoter fragments into the expression vector backbone as described for various promoters below, the primer sequences provided in TABLE 4 were used.

TABLE 4

| Primers used in synthesizing labyrinthulomycetes promoter expression constructs. | | |
|---|---|---|
| Primer name | Primer sequence | SEQ ID NO |
| oSGI-JU-0336 | tgagagtgcaccataGGTTGGATTTCTCCTTTTTGCGTC | SEQ ID NO: 79 |
| oSGI-JU-0337 | ctcgtcgctacCATGTGACAACGGCCAGGAC | SEQ ID NO: 80 |
| oSGI-JU-0338 | tgagagtgcaccataGTTAGCGCAGACCTAGCTGTATC | SEQ ID NO: 81 |
| oSGI-JU-0339 | ctcgtcgctctcCATCTTGCTTTGCGATTTGTAGAGC | SEQ ID NO: 82 |
| oSGI-JU-0340 | tgagagtgcaccataGCGAACGCCATAATCAGCG | SEQ ID NO: 83 |
| oSGI-JU-0341 | ctcgtcgctacCATGGTTGCCTACTTCGCG | SEQ ID NO: 84 |
| oSGI-JU-0342 | tgagagtgcaccataCCGCGCAAAACCGCCTTAATC | SEQ ID NO: 85 |
| oSGI-JU-0343 | ctcgtcgctctcCATTTTTGATAAGTTTTGGGACTCGACG | SEQ ID NO: 86 |
| oSGI-JU-0344 | tgagagtgcaccataTCCCTTTTAGCCAATTTGCATATCTTCTAC | SEQ ID NO: 87 |
| oSGI-JU-0345 | ctcgtcgctacCATCTTGCCTGTCGCGCTG | SEQ ID NO: 88 |
| oSGI-JU-0346 | tgagagtgcaccataGGTGTCCTCACCCTCAAGTAC | SEQ ID NO: 89 |
| oSGI-JU-0347 | ctcgtcgctctcCATCTCCTCGTCGAAGTCCTG | SEQ ID NO: 90 |
| oSGI-JU-0350 | tgagagtgcaccataTCAATGTCCATCATATTATCATTACGAGTCATG | SEQ ID NO: 91 |
| oSGI-JU-0351 | ctcgtcgctacCATGATGCTCTAGATTACTTGATGAATCTACTTAC | SEQ ID NO: 92 |
| oSGI-JU-0352 | tgagagtgcaccataACGAGGAGCGAAGGTAGGTG | SEQ ID NO: 93 |
| oSGI-JU-0353 | ctcgtcgctctcCATGGTGGTCTTGTCGTCCATC | SEQ ID NO: 94 |
| oSGI-JU-0356 | tgagagtgcaccataAGCAGCTTCAAGCCATCATCAC | SEQ ID NO: 95 |
| oSGI-JU-0357 | ctcgtcgctacCATCGTGCGCGGGAGCTTG | SEQ ID NO: 96 |
| oSGI-JU-0358 | tgagagtgcaccataGGAGGGAGGCATGAAAACAAAG | SEQ ID NO: 97 |
| oSGI-JU-0359 | ctcgtcgctctcCATTTTGCTTGAGGTTGGAGTTTCG | SEQ ID NO: 98 |
| oSGI-JU-0392 | tgagagtgcaccataAAGGATGAGGCTGGTTTCAGAAAAC | SEQ ID NO: 99 |
| oSGI-JU-0394 | tgagagtgcaccataGCAGGGGTGCTAGTATTTTATACTATCTG | SEQ ID NO: 100 |
| oSGI-JU-0399 | tgagagtgcaccataAGAAGTATTAAAAAAAGGACCGGATGAAAG | SEQ ID NO: 101 |

TABLE 4-continued

Primers used in synthesizing labyrinthulomycetes promoter expression constructs.

| Primer name | Primer sequence | SEQ ID NO |
|---|---|---|
| oSGI-JU-0401 | tgagagtgcaccataACTTTTCAACTTGAGATGCACCAC | SEQ ID NO: 102 |
| oSGI-JU-0403 | tgagagtgcaccataGATGAATGAAAGAATGAAAGAATGAAAGAATCG | SEQ ID NO: 103 |
| oSGI-JU-0407 | tgagagtgcaccataCTCAAACTCGGCAAACTTGGTAAATG | SEQ ID NO: 104 |
| oSGI-JU-0409 | tgagagtgcaccataAGAAGCCAAGGTATCTACCAGC | SEQ ID NO: 105 |
| oSGI-JU-0411 | tgagagtgcaccataTCGAGGACACAACCAACTCAAG | SEQ ID NO: 106 |
| oSGI-JU-0413 | tgagagtgcaccataCTTCGAAGTACTACTTTGTAGATCCTAG | SEQ ID NO: 107 |
| oSGI-JU-0415 | tgagagtgcaccataCGAATGTTGGGAACTACAGAATCATTG | SEQ ID NO: 108 |
| oSGI-JU-0417 | tgagagtgcaccataACCGGAAGCCTGGATATGTATC | SEQ ID NO: 109 |
| oSGI-JU-0419 | tgagagtgcaccataACCAACAACTGCACTAACCAAG | SEQ ID NO: 110 |
| oSGI-JU-0434 | tctcgtcgctacCATCTTCTTGAGAGCGGAAAGGG | SEQ ID NO: 111 |
| oSGI-JU-0435 | tctcgtcgctctcCATTTTGCTTGAGGTTGGAGTTTCG | SEQ ID NO: 112 |
| oSGI-JU-0436 | tctcgtcgctctcCATTGTGTTCTTAAGTTAAAAACTTGACTTGAAAATC | SEQ ID NO: 113 |
| oSGI-JU-0437 | tctcgtcgctacCATCTTGCTAAGTGTCTTACTTCTGC | SEQ ID NO: 114 |
| oSGI-JU-0438 | tctcgtcgctctcCATTGTGCTAACTACAGGTACGTACG | SEQ ID NO: 115 |
| oSGI-JU-0440 | tctcgtcgctctcCATCTTGAAACCAAGGTGAGGTTC | SEQ ID NO: 116 |
| oSGI-JU-0441 | tctcgtcgctctcCATGCCGATTTGTCCTGCCCG | SEQ ID NO: 117 |
| oSGI-JU-0442 | tctcgtcgctacCATCTTGCCTGTCGCGCTGCAC | SEQ ID NO: 118 |
| oSGI-JU-0443 | tctcgtcgctacCATGGTTGCCTACTTCGCGCAAG | SEQ ID NO: 119 |
| oSGI-JU-0444 | tctcgtcctctcCATCTTTTATTAGTATCGCGAAGCTAGAAG | SEQ ID NO: 120 |
| oSGI-JU-0445 | tctcgtcgctacCATGATGCTTGCTTGAAGACTTGG | SEQ ID NO: 121 |
| oSGI-JU-0446 | tctcgtcgctacCATCTTGCCAGGCTTGCAGG | SEQ ID NO: 122 |
| oSGI-JU-0800 | actgagagtgcaccatatgcTCGCGACTTTACGTGTTCTATG | SEQ ID NO: 123 |
| oSGI-JU-0801 | ccgctctcgtcgctacCATTTTGCTAGTTGGGTGCTTG | SEQ ID NO: 124 |
| oSGI-JU-0808 | actgagagtgcaccatatgcGTCCAACAACAGAGCGCATAG | SEQ ID NO: 125 |
| oSGI-JU-0809 | ccgactcgtcgctctcCATTTTGTTTGGTGCTAGTAGCTTC | SEQ ID NO: 126 |
| oSGI-JU-0812 | actgagagtgcaccatatgcCATTACTCCAATCCCTGAACACG | SEQ ID NO: 127 |
| oSGI-JU-0813 | ccgctctcgtcgctacCATCTTGCCTGTCGCGCTGCAC | SEQ ID NO: 128 |
| oSGI-JU-0837 | actgagagtgcaccatatgcTGTGATAGCGAGTTGTGCGAG | SEQ ID NO: 129 |
| oSGI-JU-0838 | ccgactcgtcgctctccaGGTGTCAAGATAGAAGTGGTGTC | SEQ ID NO: 130 |
| oSGI-JU-0841 | actgagagtgcaccatatgcCGCCGCTCATAGTGTAAACTC | SEQ ID NO: 131 |
| oSGI-JU-0842 | ccgctctcgtcgctaccatCTTGTCTGTGTCTTCGCTAAAC | SEQ ID NO: 132 |
| oSGI-JU-0845 | actgagagtgcaccatatgcTGGGAGCTATGGAGTCTTGGA | SEQ ID NO: 133 |
| oSGI-JU-0846 | ccgactcgtcgctctccaCTTGACTACTTTGTAGAGACTTGGAC | SEQ ID NO: 134 |
| oSGI-JU-0849 | actgagagtgcaccatatgcAGAATGGTTTTCGAAGAGGCAG | SEQ ID NO: 135 |
| oSGI-JU-0850 | ccgctctcgtcgctaccatAACGAGTTAGGCGCTTGGC | SEQ ID NO: 136 |
| oSGI-JU-0853 | actgagagtgcaccatatgcTCTCCAGAAATGACACACCGC | SEQ ID NO: 137 |
| oSGI-JU-0854 | ccgactcgtcgctctccatTTTGCTTGGCAAAGTTTAACTTG | SEQ ID NO: 138 |
| oSGI-JU-0858 | actgagagtgcaccatatgcAGCGCAACAGCCAAATCTAC | SEQ ID NO: 139 |

TABLE 4-continued

Primers used in synthesizing labyrinthulomycetes promoter expression constructs.

| Primer name | Primer sequence | SEQ ID NO |
|---|---|---|
| oSGI-JU-0859 | ccgctctcgtcgctaccatCTTGCCCAAAATCTATCTGTGTG | SEQ ID NO: 140 |
| oSGI-JU-0862 | actgagagtgcaccatatgcCTTGCTGACCTTGCGATTG | SEQ ID NO: 141 |
| oSGI-JU-0863 | ccgactcgtcgctctccaGGTATTTTCTACGTTATGCATCG | SEQ ID NO: 142 |
| oSGI-JU-0866 | actgagagtgcaccatatgcAGCGACCATGAACTACACATC | SEQ ID NO: 143 |
| oSGI-JU-0867 | ccgctctcgtcgctaccatTTTTATTTGTGTTTTGTTTTGTCGCC | SEQ ID NO: 144 |
| oSGI-JU-0870 | actgagagtgcaccatatgcCCCTTCAACACGAACTCCAAG | SEQ ID NO: 145 |
| oSGI-JU-0871 | ccgactcgtcgctctccatCGTGCCCCGAAGATAGC | SEQ ID NO: 146 |
| oSGI-JU-0874 | actgagagtgcaccatatgcGAAGCGTTTGGTTGTAGCGAC | SEQ ID NO: 147 |
| oSGI-JU-0875 | ccgctctcgtcgctaccatGGTGCCTAAGAAAGAAAGCAAC | SEQ ID NO: 148 |
| oSGI-JU-0878 | actgagagtgcaccatatgcGTCTTCTGTGCCTGCATCTG | SEQ ID NO: 149 |
| oSGI-JU-0879 | ccgactcgtcgctctccatGGTGGAGGCGGCGGCGTC | SEQ ID NO: 150 |
| oSGI-JU-0880 | actgagagtgcaccatatgcTTATTCATCGACTGACTGGCCT | SEQ ID NO: 151 |
| oSGI-JU-0881 | ccgctctcgtcgctaccatCTTCTGGAGAGCGGAAAGG | SEQ ID NO: 152 |
| oSGI-JU-0884 | actgagagtgcaccatatgcAGAACGGCGTGGAAAAGTTG | SEQ ID NO: 153 |
| oSGI-JU-0885 | ccgactcgtcgctctccaCTTGCTGCTTTGGATTTATTCAC | SEQ ID NO: 154 |
| oSGI-JU-0888 | actgagagtgcaccatatgcTCAGTCACTCACGCATTCAG | SEQ ID NO: 155 |
| oSGI-JU-0889 | actgagagtgcaccatatgcATTCCTGTTCCCCTCCCATC | SEQ ID NO: 156 |
| oSGI-JU-0890 | actgagagtgcaccatatgcACAGACAAACAAGGGAGCAAG | SEQ ID NO: 157 |
| oSGI-JU-0891 | actgagagtgcaccatatgcAATGAACGCCAACGAGAGAC | SEQ ID NO: 158 |
| oSGI-JU-0892 | actgagagtgcaccatatgcAGAAAACAGAAGAGTAGGTAGCG | SEQ ID NO: 159 |
| PF266 | ggcgcacgtgattgcgaataccgcuccacGTTTAAACaaactcgttcgtggctgagc | SEQ ID NO: 160 |
| PF267 | ggcgcacgtgattgcgaataccgcttccacGTTTAAACaatatgagcgatagaaagtgtgc | SEQ ID NO: 161 |
| PF268 | ggcgcacgtgattgcgaataccgcttccacGTTTAAACacgttatcgcgaagtcaatcc | SEQ ID NO: 162 |
| PF269 | ggccacgtgattgcgaataccgcttccacGTTTAAACtcctatcactctatctttcatcagg | SEQ ID NO: 163 |
| PF270 | ggcgcacgtgattgcgaataccttccacGTTTAAACagagttcctcctcctttcgacc | SEQ ID NO: 164 |
| PF271 | CGTATGTTGTGTGGAATTGTGAGCG | SEQ ID NO: 165 |
| PF274 | ggcgcacgtgattgcgaataccgcaccacGTTTAAACgtccttcccaccaatctcgg | SEQ ID NO: 166 |
| oSGI-JU-0334 | atgccccgggtaccgACGCCTTAGATACATTGATGAG | SEQ ID NO: 167 |
| oSGI-JU-0364 | tgagagtgcaccatatgcATGgaagcgacgagagcg | SEQ ID NO: 168 |

Construction of Expression Vectors pSGI-JU-80-pSGI-JU-89 Containing Promoter Sequences Derived from *Aurantiochytrium* sp. Strain SGI-i886.

Promoter sequences from labyrinthulomycetes strain SGI-i886 that were associated with the genes whose transcript abundance was evaluated in Example 2 (TABLE 1) were cloned upstream of the reporter gene TurboGFP to generate expression vectors pSGI-JU-80-pSGI-JU-89 (TABLE 5). Each of the resulting expression vectors also carried the nptII marker gene for selection of transformants on paromomycin-containing agar media. These constructs were generated by assembling two PCR products: (1) a PCR product carrying the promoter sequence amplified from SGI-i886 genomic DNA using PCR primers indicated in TABLE 5 (primer sequences provided in TABLE 4), and (2) a PCR product carrying the TurboGFP and SV40 terminator amplified using pTurboGFP plasmid DNA (Evrogen) as template and PCR primers oSGI-JU-101 and oSGI-JU-334 (TABLE 4). The two PCR products were cloned into pSGI-JU-74 (FIG. 1), a pUC19 based cloning vector that carried a neomycin phosphotransferase marker gene (nptII) gene (SEQ ID NO:170) for selection of labyrinthulomycetes transformants on paromomycin-containing media. The PCR-derived insert sequences were confirmed by Sanger sequencing.

TABLE 5

*Aurantiochytrium* sp. strain SGI-i886 promoter regions identified by gene, expression constructs for promoter evaluation, and cloning primers.

| Promoter | Expression Construct | Cloning Primers Used |
|---|---|---|
| Neighbor of BRCA1 gene 1 (NBR1), transcript variant 1; allele 1 (SEQ ID NO: 1) | pSGI-JU-80-1 | oSGI-JU-0336 oSGI-JU-0337 |
| Neighbor of BRCA1 gene 1 (NBR1), transcript variant 1; allele 6 (SEQ ID NO: 2) | pSGI-JU-80-6 | |
| Eft2p GTPasel translation elongation factor 2 (EF-2); allele 3 (SEQ ID NO: 3) | pSGI-JU-81-3 | oSGI-JU-0338 oSGI-JU-0339 |
| Eft2p GTPasel translation elongation factor 2 (EF-2); allele 8 (SEQ ID NO: 4) | pSGI-JU-81-8 | |
| 40S ribosomal protein S3a (S3-a); allele 2 (SEQ ID NO: 5) | pSGI-JU-82-2 | oSGI-JU-0340 |
| 40S ribosomal protein S3a (S3-a); allele 5 (SEQ ID NO: 6) | pSGI-JU-82-5 | oSGI-JU-0341 |
| Eukaryotic translation initiation factor 5A isoform IV (IF-5a); allele 1 (SEQ ID NO: 7) | pSGI-JU-83-1 | oSGI-JU-0342 oSGI-JU-0343 |
| Eukaryotic translation initiation factor 5A isoform IV (IF-5a); allele 2 (SEQ ID NO: 8) | pSGI-JU-83-2 | |
| 60S ribosomal protein L9; Conserved predicted protein (RPL9); allele 1 (SEQ ID NO: 9) | pSGI-JU-84-1 | oSGI-JU-0344 oSGI-JU-0345 |
| 60S ribosomal protein L9; Conserved predicted protein (RPL9); allele 6 (SEQ ID NO: 10) | pSGI-JU-84-6 | |
| Actin A complement of Actin-1/3 (ActA); allele 3 (SEQ ID NO: 11) | pSGI-JU-85-3 | oSGI-JU-0346 |
| Actin A complement of Actin-1/3 (ActA); allele 6 (SEQ ID NO: 12) | pSGI-JU-85-6 | oSGI-JU-0347 |
| Actin A complement of Actin-1/3 (ActA); allele 8 (SEQ ID NO: 13) | pSGI-JU-85-8 | |
| Heat shock protein 70 (hsp70) (SEQ ID NO: 14) | pSGI-JU-86 | oSGI-JU-0350 oSGI-JU-0351 |
| Translation elongation factor 1-alpha (EF-1a); allele 4 (SEQ ID NO: 15) | pSGI-JU-87-4 | oSGI-JU-0352 |
| Translation elongation factor 1-alpha (EF-1a); allele 7 (SEQ ID NO: 16) | pSGI-JU-87-7 | oSGI-JU-0353 |
| 60S ribosomal protein L26 (RPL26); allele 5 (SEQ ID NO: 17) | pSGI-JU-88-5 | oSGI-JU-0356 |
| 60S ribosomal protein L26 (RPL26); allele 7 (SEQ ID NO: 18) | pSGI-JU-88-7 | oSGI-JU-0357 |
| Tubulin alpha (Tubα); allele 1 (SEQ ID NO: 19) | pSGI-JU-89-1 | oSGI-JU-0358 |
| Tubulin alpha (Tubα); allele 6 (SEQ ID NO: 20) | pSGI-JU-89-6 | oSGI-JU-0359 |

Construction of the Vector Backbone pSGI-JU-79

A promoter-less reporter gene TurboGFP (SEQ ID NO: 169; Evrogen, Moscow, Shagin et al., *Mol. Biol. Evol.,* 21 (5):841-50, 2004) and a SV40 terminator (SEQ ID NO):78) from simian virus was cloned into pSGI-JU-74 (FIG. 1), a pUC19 based cloning vector that carried a neomycin phosphotransferase marker gene (nptII) gene (SEQ ID NO: 170), to provide an expression construct for evaluating function of promoters inserted upstream of the TurboGFP gene. An NsiI site was engineered at the 5' end of the TurboGFP gene to facilitate cloning of promoter sequences upstream of the reporter gene. A PCR product carrying the TurboGFP reporter gene and a SV40 terminator was generated using pTurboGFP plasmid DNA (Evrogen, Moscow. Russia) as a template and PCR primers oSGI-JU-364 and oSGI-JU-334 containing the restriction digestion sites NdeI and SadI (TABLE 4). PCR primer oSGI-JU-364 introduced the NsiI site at the 5' end of the TurboGFP gene. The amplified PCR product was cloned into the pSGI-JU-74 vector to generate vector pSGI-JU-79 (FIG. 2), which was pre-digested with restriction enzymes NdeI and SacI using GeneArt® Seamless Cloning and Assembly procedure (Life Technologies, Carlsbad, Calif.). The PCR-derived insert sequences were confirmed by Sanger sequencing.

Construction of Expression Vectors pSGI-JU-98-pSGI-JU-111 Containing Promoter Sequences Derived from *Schizochytrium* sp. Strain SGI-i94.

A number of promoter sequences from labyrinthulomycetes strain SGI-i94 (Table 3) were cloned upstream of the reporter gene TurboGFP to generate expression vectors pSGI-JU-98-pSGI-JU-111 (TABLE 6). It was observed that the nucleotide sequence of the SGI-i94 tubulin alpha chain promoter (SEQ ID NO:23) exhibited >96% sequence identity to the SGI-i886 tubulin alpha chain promoter (pSGI-JU-89; SEQ ID NOs:19 and 20). Each of the resulting expression vectors also carried the nptII marker gene for selection of transformants on paromomycin-containing agar media. These constructs were generated by cloning a PCR product carrying the promoter sequence, amplified from SGI-i94 genomic DNA using the PCR primers indicated in TABLE 6, below (primer sequences provided in TABLE 4), into an NsiI-digested plasmid pSGI-JU-79 using GeneArt® Seamless Cloning and Assembly procedure (Life Technologies). The PCR-derived insert sequences were confirmed by Sanger sequencing.

TABLE 6

*Schizochytrium* sp. strain SGI-i94 promoter regions identified by gene, expression constructs for promoter evaluation, and cloning primers.

| Promoter | Expression Construct | Cloning Primers Used |
|---|---|---|
| Transcriptionally-controlled tumor protein homolog (TCTP) (SEQ ID NO: 21) | pSGI-JU-98 | oSGI-JU-0392 oSGI-JU-0434 |
| Acetyl-coenzyme A synthetase 2 (ACS2) (SEQ ID NO: 22) | pSGI-JU-99 | oSGI-JU-0399 oSGI-JU-0436 |

TABLE 6-continued

*Schizochytrium* sp. strain SGI-i94 promoter regions identified by gene, expression constructs for promoter evaluation, and cloning primers.

| Promoter | Expression Construct | Cloning Primers Used |
|---|---|---|
| Tubulin alpha (Tubα) (SEQ ID NO: 23) | pSGI-JU-101 | oSGI-JU-0394<br>oSGI-JU-0435 |
| Heat shock protein 70 (hsp70) (SEQ ID NO: 24) | pSGI-JU-102 | oSGI-JU-0401<br>oSGI-JU-0437 |
| Transcription elongation factor 3 (EF-3) (SEQ ID NO: 25) | pSGI-JU-103 | oSGI-JU-0403<br>oSGI-JU-0438 |
| Hexose transporter 1 (HXT1) (SEQ ID NO: 26) | pSGI-JU-105 | oSGI-JU-0407<br>oSGI-JU-0440 |
| Catalase (cat) (SEQ ID NO: 27) | pSGI-JU-106 | oSGI-JU-0409<br>oSGI-JU-0441 |
| 60S ribosornalroteinl L9 (RPL9) (SEQ ID NO: 28) | pSGI-JU-107 | oSGI-JU-0411<br>oSGI-JU-0442 |
| 40s ribosomal protein S3a (RPS3a) (SEQ ID NO: 29) | pSGI-JU-108 | oSGI-JU-0413<br>oSGI-JU-0443 |
| Tubulin beta chain (Tubβ) (SEQ ID NO: 30) | pSGI-JU-109 | oSGI-JU-0415<br>oSGI-JU-0444 |
| Superoxide dismutase (SOD) (SEQ ID NO: 31) | pSGI-JU-110 | oSGI-JU-0417<br>oSGI-JU-0445 |
| Phosphoglycerate kinase (PGK) (SEQ ID NO: 32) | pSGI-JU-111 | oSGI-JU-0419<br>oSGI-JU-0446 |

Figure 2:
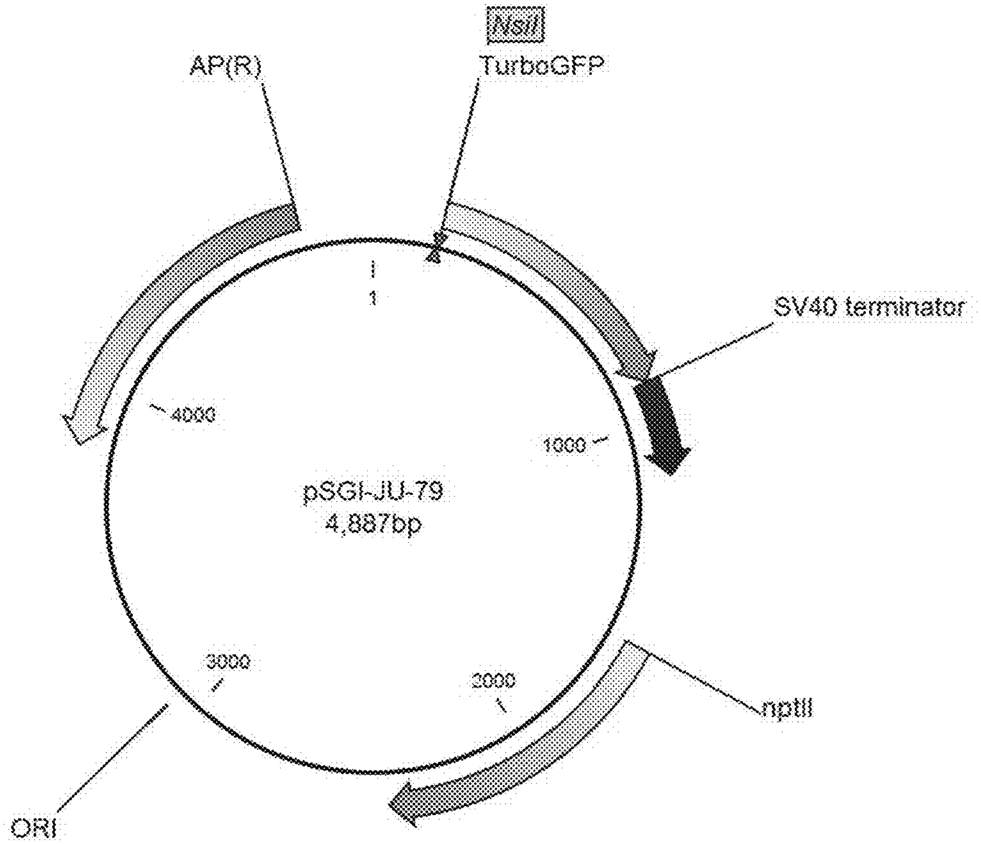
FIG. 2 is plasmid map for expression vector pSGI-JU-79 used to make promoter expression constructs described in Example 3.

Construction of Expression Vectors pSGI-JU-80-pSGI-JU-195.

pSGI-JU-180-pSGI-JU-195 were expression vectors in which various promoter sequences (approximately 1.5-2 kb in length) from the *Aurantiochytrium* sp. strain SGI-i886 (TABLE 2) were operably cloned upstream of the TurboGFP (SEQ ID NO:169) in pSGI-JU-79 (FIG. 2). Each of these expression vectors also carried the nptII marker gene (SEQ ID NO: 170) for selection of transformants on paromomycin-containing agar media. These constructs were generated by cloning a PCR product carrying the promoter sequence, amplified from SGI-i886 genomic DNA using the PCR primers indicated in TABLE 7 (primer sequences provided in TABLE 4), into an NsiI-digested plasmid pSGI-JU-79 using Gibson Assembly® cloning procedure (SGI-DNA. La Jolla. Calif.). The PCR-derived insert sequences were confirmed by Sanger sequencing.

TABLE 7

*Aurantiochytrium* sp. strain SGI-i886 promoter regions identified by gene, expression constructs for promoter evaluation, and cloning primers.

| Promoter | Expression Construct | Cloning Primers Used |
|---|---|---|
| Actin (Act); allele 4 (SEQ ID NO: 33) | pSGI-JU-180-4 | oSGI-JU-0800<br>oSGI-JU-0801 |
| Actin (Act); allele 5 (SEQ ID NO: 34) | pSGI-JU-180-5 | oSGI-JU-0800<br>oSGI-JU-0801 |
| Actin (Act); allele 6 (SEQ ID NO: 35) | pSGI-JU-180-6 | oSGI-JU-0800<br>oSGI-JU-0801 |
| Elongation factor 1-alpha 1 (EF1alpha) (SEQ ID NO: 36) | pSGI-JU-181 | oSGI-JU-0808<br>oSGI-JU-0809 |
| 60 S ribosomal protein L6 (RPL6) (SEQ ID NO: 37) | pSGI-JU-182 | oSGI-JU-0812<br>oSGI-JU-0813 |
| Actin depolymerase (Adp); allele A (SEQ ID NO: 38) | pSGI-JU-183A | oSGI-JU-0837<br>oSGI-JU-0838 |
| Actin depolymerase (Adp); allele B (SEQ ID NO: 39) | pSGI-JU-183B | oSGI-JU-0837<br>oSGI-JU-0838 |
| Adenosylhomocysteinase (AHC) (SEQ ID NO: 40) | pSGI-JU-184 | oSGI-JU-0841<br>oSGI-JU-0842 |
| Alternative oxidase (AOX); allele B (SEQ ID NO: 41) | pSGI-JU-185B | oSGI-JU-0845<br>oSGI-JU-0846 |
| Alternative oxidase (AOX); allele C (SEQ ID NO: 42) | pSGI-JU-185C | oSGI-JU-0845<br>oSGI-JU-0846 |
| Cytochrome C oxidase (cox); allele A (SEQ ID NO: 43) | pSGI-JU-186A | oSGI-JU-0849<br>oSGI-JU-0850 |
| Cytochrome C oxidase (cox); allele C (SEQ ID NO: 44) | pSGI-JU-186C | oSGI-JU-0849<br>oSGI-JU-0850 |
| Elongation factor 1-beta (EF1beta) (SEQ ID NO: 45) | pSGI-JU-187 | oSGI-JU-0853<br>oSGI-JU-0854 |
| Fa ATP synthase (faas) (SEQ ID NO: 46) | pSGI-JU-188 | oSGI-JU-0858<br>oSGI-JU-0859 |

TABLE 7-continued

*Aurantiochytrium* sp. strain SGI-i886 promoter regions identified by gene, expression constructs for promoter evaluation, and cloning primers.

| Promoter | Expression Construct | Cloning Primers Used |
|---|---|---|
| Heavy metal associated domain (HMA); allele A (SEQ ID NO: 47) | pSGI-JU-189A | oSGI-JU-0862<br>oSGI-JU-0863 |
| Heavy metal associated domain (HMA); allele B (SEQ ID NO: 48) | pSGI-JU-189B | oSGI-JU-0862<br>oSGI-JU-0863 |
| Mitochondrial chaperonin 60 (hsp60); allele A (SEQ ID NO: 49) | pSGI-JU-190A | oSGI-JU-0866<br>oSGI-JU-0867 |
| Mitochondrial chaperonin 60 (hsp60); allele B (SEQ ID NO: 50) | pSGI-JU-190B | oSGI-JU-0866<br>oSGI-JU-0867 |
| Phosphotidylinsositol 3-kinase (PI3K); allele A (SEQ ID NO: 51) | pSGI-JU-191A | oSGI-JU-0870<br>oSGI-JU-0871 |
| Phosphotidylinsositol 3-kinase (PI3K); allele C (SEQ ID NO: 52) | pSGI-JU-191C | oSGI-JU-0870<br>oSGI-JU-0871 |
| 60 s ribososomal protein 11 (RPLA11); allele B (SEQ ID NO: 53) | pSGI-JU-192B | oSGI-JU-0874<br>oSGI-JU-0875 |
| 60 s ribososomal protein 11 (RPL11) allele C (SEQ ID NO: 54) | pSGI-JU-192C | oSGI-JU-0874<br>oSGI-JU-0875 |
| Small nuclear ribonucleoprotein (snRNP) (SEQ ID NO: 55) | pSGI-JU-193 | oSGI-JU-0878<br>oSGI-JU-0879 |
| Transcriptionally-controlled tumor protein homolog (TCTP) (SEQ ID NO: 56) | pSGI-JU-194 | oSGI-JU-0880<br>oSGI-JU-0881 |
| Tetraspanin (Tsp); allele A (SEQ ID NO: 57) | pSGI-JU-195A | oSGI-JU-0884<br>oSGI-JU-0885 |
| Tetraspanin (Tsp); allele B (SEQ ID NO: 58) | pSGI-JU-195B | oSGI-JU-0884<br>oSGI-JU-0885 |

Construction of Expression Vectors Carrying Shortened Variants of Promoter from *Aurantiochytrium* sp. Strain SGI-i886.

pSGI-JU-196 and pSGI-JU-197 (TABLE 2) were expression vectors in which a full-length tubulin-alpha promoter from labyrinthulomycetes strain SGI-i886 (SEQ ID NO:20) was shortened from its 5' end to a length of 738 bp (SEQ ID NO: 196) and 522 bp (SEQ ID NO: 197), respectively. The promoters were shortened from the 5' end of the full-length promoter. Each of these expression vectors also carried the nptII marker gene (SEQ ID NO: 170) for selection of transformants on paromomycin-containing agar media. These constructs were generated by cloning PCR products carrying the promoter shortened promoter sequences (SEQ ID NO:196 and SEQ ID NO:197), which were individually amplified from the pSGI-JU-89-6 plasmid DNA template using the PCR primers indicated in TABLE 8 (primer sequences provided in TABLE 4), into an NsiI-digested pSGI-JU-79 vector using the Gibson Assembly® cloning procedure (Gibson et al. (2009) *Nature Methods* 6: 343-345; Gibson (2011) Methods in Enzymology 498: 349-361; SGI-DNA, La Jolla. CA). The PCR-derived insert sequences were confirmed by Sanger sequencing.

pSGI-JU-198, pSGI-JU-199, and pSGI-JU-200 (TABLE 2) were expression vectors in which a full-length actin promoter from *Aurantiochytrium* sp. strain SGI-i886 (SEQ ID NO:34) was shortened from its 5' end to a length of 1176 bp (SEQ ID NO:61), 776 bp (SEQ ID NO:62), and 557 bp (SEQ ID NO:63), respectively. Each of these expression vectors also carried the nptII marker gene (SEQ ID NO:170) for selection of labyrinthulomycetes transformants on paromomycin-containing agar media. These constructs were generated by cloning a PCR product carrying the shortened promoter sequence, which was amplified from pSGI-JU-180-5 plasmid DNA template using the PCR primers indicated in TABLE 8 (primer sequences provided in TABLE 4), into an NsiI-digested pSGI-JU-79 vector using the Gibson Assembly® cloning procedure. The PCR-derived insert sequences were confirmed by Sanger sequencing.

TABLE 8

Shortened promoters derived from *Aurantiochytrium* sp. strain SGI-i886 promoter regions identified by gene, expression constructs for promoter evaluation, and cloning primers.

| Promoter | Construct | Primers Used |
|---|---|---|
| Tubulin alpha (Tubα-738) (SEQ ID NO: 59) | pSGI-JU-196 | oSGI-JU-0888<br>oSGI-JU-0359 |
| Tubulin alpha (Tubα-522) (SEQ ID NO: 60) | pSGI-JU-197 | oSGI-JU-0889<br>oSGI-JU-0359 |
| Actin (act-1176) (SEQ ID NO: 61) | pSGI-JU-198 | oSGI-JU-0890<br>oSGI-JU-0801 |
| Actin (act-776) (SEQ ID NO: 62) | pSGI-JU-199 | oSGI-JU-0891<br>oSGI-JU-0801 |
| Actin (act-557) (SEQ ID NO: 63) | pSGI-JU-200 | oSGI-JU-0892<br>oSGI-JU-0801 |

Example 4

Genetic Transformation of Labyrinthulomycetes Cells

In a typical transformation experiment, labyrinthulomycetes cells were transformed as follows.

Day 1: Labyrinthulomycetes cells were grown in 50 mL of FM002 medium in a baffled 250 mL flask overnight at 30° C. under agitation at 150 rpm.

Day 2: Cultured cells from 0.5 mL of the culture were pelleted and suspended in a volume of FM002 that was 50 times the pellet volume. Fifty microliters of cell suspension was used to inoculate 50 mL of FM002 in a baffled 250 mL flask, and grown overnight at 30° C. and 150 rpm.

Day 3: Cells of 50 mL of the overnight culture were pelleted by centrifugation at 2,000×g for 5 minutes, suspended in 20 mL of 1 M mannitol, and transferred to a 125 mL flask. In a next step, 200 μL of 1 M $CaCl_2$) and 500 μL of Protease XIV (10 mg/mL, Sigma, P6911) were added, followed by incubation at 30° C. under agitation at 100 rpm for 4 hours. From this point forward, wide-bore tips were used and cell cultures are kept on ice. The cultured cells were pelleted by centrifugation at 2,000×g for 5 minutes. The volume of cell pellet was noted before the cells were suspended in 10 mL cold 10% glycerol. Cells were pelleted by centrifugation at 2,000×g for 5 minutes one more time, and suspended in a volume of electroporation medium (Mirus Ingenio Buffer) that was 4 times the pellet volume, 100 μL of suspended cells was added to a pre-chilled cuvette containing DNA (5-10 μg) and gently mixed. Electroporation of cells was carried out using 500 V, 200Ω, and 25 μF, followed by addition of 1 mL of GY (17 g/L Instant Ocean, 30 g/L glucose, and 10 g/L yeast extract) to the cuvette and transfer of contents to a 15 ml culture tube. Electroporated cells were allowed to recover overnight at 30° C. with continuous agitation at 150 rpm. Recovered cells were subsequently plated on selection media (200-250 μL/plate) and further incubated at 30° C.

Example 5

Evaluation of Promoters Derived Introduced into *Aurantiochytrium* sp. SGI-i886

Each of the candidate promoters described above was cloned upstream of the reporter gene TurboGFP in an expression vector that also carried an nptII gene for resistance to the antibiotic paromomycin. The expression vectors were constructed as described in Example 3 above. These resulting expression vectors were then linearized using a restriction site located in the vector sequence, and subsequently transformed into labyrinthulomycetes cells according to the general procedure described in Example 4.

Figure 3:
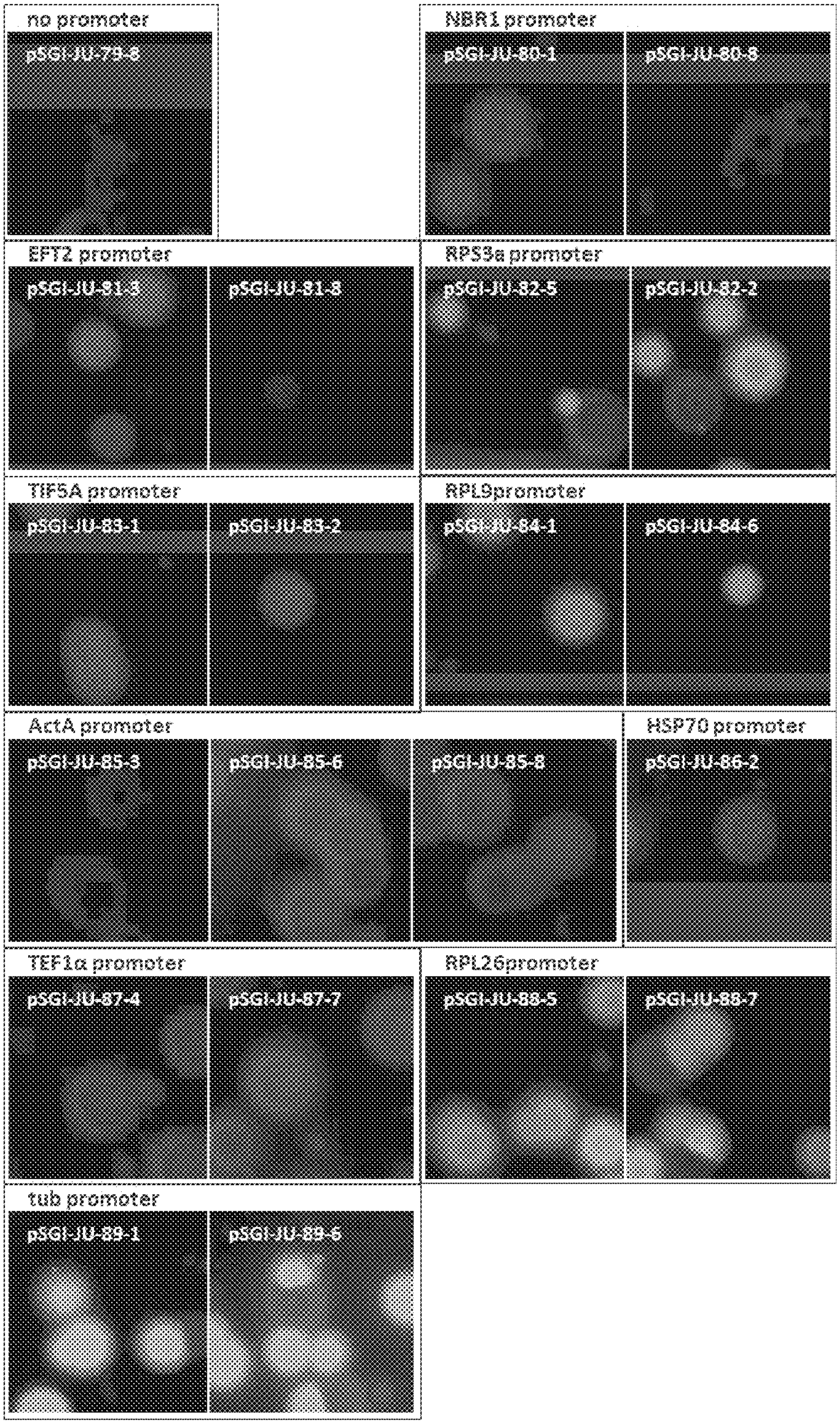
FIG. 3 is a representation of fluorescence microscopic images analyzing TurboGFP signals for labyrinthulomycetes colonies that were transformed with expression constructs in which TurboGFP expression was placed under control of various promoters. For each construct, the promoter sequence is indicated by the construct name as provided in TABLE 2. Fluorescent signals were detected and/or quantified using a Typhoon FLA 9000 system (GE Healthcare Life Sciences). All scanning and image analysis were done using the ImageQuant software with the same settings/values.

The relative strength of each promoter was evaluated based on the expression of the TurboGFP reporter using fluorescence microscopy. Fluorescence signals of the transformed colonies were examined using the Typhoon™ FLA9000 system (GE Healthcare Life Sciences) with 473 nm laser and LPB filter with EMT set to 550V. As can be seen in FIG. 3 and TABLE 9, the promoters were observed exhibiting various levels of activity.

TABLE 9

Relative strength of promoters from *Aurantiochytrium* sp. strain SGI-i886 as determined by fluorescent microscopy

| Construct | No. of allele analyzed | Corresponding gene, Promoter Sequence ID | Relative strength |
|---|---|---|---|
| pSGI-JU-79 | N/A | Control construct (no promoter sequence insert) | N/A |
| pSGI-JU-80-1, -6 | 2 | Neighbor of BRCA1 gene 1 (NBR1), transcript variant 1 (SEQ ID NO: 1, SEQ ID NO: 2) | + |
| pSGU-JU-81-3, -8 | 2 | Eft2p GTPaseI translation elongation factor 2 (EF-2) (SEQ ID NO: 3, SEQ ID NO: 4) | + |
| pSGI-JU-82-2, -5 | 2 | 40S ribosomal protein S3a (S3-a) (SEQ ID NO: 5, SEQ ID NO: 6) | ++ |
| pSGU-JU-83-1, -2 | 2 | Eukaryotic translation initiation factor 5A isoform IV (IF-5a) (SEQ ID NO: 7, SEQ ID NO: 8) | + |
| pSGI-JU-84-1, -6 | 2 | 60S ribosomal protein L9 (RPL9) (SEQ ID NO: 9, SEQ ID NO: 10) | ++ |
| pSGI-JU-85-3, -6, -8 | 3 | Actin A complement of Actin-1/3 (ActA) (SEQ ID NO: 1, SEQ ID NO: 12, SEQ ID NO: 13) | + |
| pSGI-JU-86 | 1 | Heat shock protein 70 (hsp70) (SEQ ID NO: 14) | + |
| pSGI-JU-87-4, -7 | 2 | Translation elongation factor 1-alpha (EF-1a) (SEQ ID NO: 15, SEQ ID NO: 16) | + |
| pSGI-JU-88-5, -7 | 2 | 60S ribosomal. protein L26 (RPL26) (SEQ ID NO: 17, SEQ ID NO: 18) | ++ |
| pSGI-JU-89-1, -6 | 2 | Tubulin alpha (Tub-α) (SEQ ID NO: 19, SEQ ID NO: 20) | ++++ |
| pSGI-JU-189A, B | 2 | Heavy metal associated domain (HMA) (SEQ ID NO: 47, SEQ ID NO: 48) | ++/++ |
| pSGI-JU-190A, B | 2 | Mitochondrial chaperonin 60 (hsp60) (SEQ ID NO: 49, SEQ ID NO: 50) | ++++/++++ |
| pSGI-JU-191A, C | 2 | Phosphotidylinsositol 3-kinase (PI3K) (SEQ ID NO: 51, SEQ ID NO: 52) | ++/+++ |
| pSGI-JU-192B, C | 2 | 60s ribososomal protein 11 (RPL11) (SEQ ID NO: 53, SEQ ID NO: 54) | +++/+++ |
| pSGI-JU-193 | 1 | Small nuclear ribonucleoprotein (snRNP) (SEQ ID NO: 55) | − |
| pSGI-JU-194 | 1 | Transcriptionally-controlled tumor protein homolog (TCTP) (SEQ ID NO: 56) | + |
| pSGI-JU-195A, B | 2 | Tetraspanin (Tsp) (SEQ ID NO: 57, SEQ ID NO: 58) | +++/+++ |

The strongest promoters observed in this assay were the promoters from the tubulin alpha gene (SEQ ID NO:19 and SEQ ID NO:20, in expression constructs pSGI-JU-89-1 and pSGI-JU-89-6, respectively) and the mitochondrial chaperonin 60 (hsp60) gene promoters (SEQ ID NO:49 and SEQ ID NO:50, in expression constructs pSGI-JU-190A and pSGI-JU-190B, respectively). Expression levels using the 60s ribososomal protein 11 (RPL11) promoters (SEQ ID NO:53 and SEQ ID NO:54, in expression constructs pSGI-JU-192B and pSGI-JU-192C, respectively), Tetraspanin (Tsp) promoters (SEQ ID NO:57 and SEQ ID NO:58, in expression constructs pSGI-JU-195A and pSGI-JU-195B, respectively) and phosphatidylinositol 3-kinase (PI3K) promoters (SEQ ID NO:53 and SEQ ID NO:54, in expression constructs pSGI-JU-191A and pSGI-JU-191C, respectively) also demonstrated moderately high expression of GFP as evaluated by fluorescence, while the ribosomal RPS3a promoter (SEQ ID NO:5 and SEQ ID NO:6, in expression constructs pSGI-JU-82-2 and pSGI-JU-82-6, respectively), RPL9 promoters (SEQ ID NO:9 and SEQ ID NO:10, in expression constructs pSGI-JU-84-1 and pSGI-JU-84-6, respectively), and RPL26 promoters (SEQ ID NO:17 and SEQ ID NO:18, in expression constructs pSGI-JU-88-5 and pSGI-JU-88-7, respectively) were observed exhibiting medium level expression. Expression levels of the "neighbor of BRCA1 gene 1" (NBR1), transcript variant 1 gene promoters (SEQ ID NO:1 and SEQ ID NO:2, in expression constructs pSGI-JU-80-1 and pSGI-JU-80-6, respectively), the eft2p GTPase translation elongation factor 2 (EF-2) gene promoters (SEQ ID NO:3 and SEQ ID NO:4, in expression vectors pSGI-JU-81-3 and pSGI-JU-81-8, respectively), eukaryotic translation initiation factor 5A isoform IV (IF-5a) promoters (SEQ ID NO:7 and SEQ ID NO:8, in expression constructs pSGI-JU-83-1 and pSGI-JU-83-2, respectively), actin A complement of Actin-1/3 (ActA) promoters (SEQ ID NO:11, SEQ ID NO:12, and SEQ ID NO:13, in expression vectors pSGI-JU-85-3, pSGI-JU-85-6 and pSGI-JU-85-8, respectively), the heat shock protein 70 (hsp70) promoter (SEQ ID NO:14, in expression vector pSGI-JU-86) and translation elongation factor 1-alpha (EF-1a) promoters (SEQ ID NO:15 and SEQ ID NO:16, in expression vectors pSGI-JU-87-4 and pSGI-JU-87-7, respectively) were relatively low in this GFP expression assay.

Example 6

Evaluation of Promoters Derived from *Schizochytrium* sp. SGI-i94 in *Aurantiochytrium* sp. SGI-i886

This Example describes the experimental characterization and evaluation of several promoter sequences initially derived from *Schizochytrium* sp. strain SGI-i94 and subsequently introduced into *Aurantiochytrium* sp. strain SGI-i886, using fluorescent microscopy techniques. The Example also describes experimental evaluation of several terminators from *S. cerevisiae* in combination with various promoters from strain SGI-i94.

As described in Example 5 above and provided in TABLE 9, the reporter gene TurboGFP when under control of a tubulin alpha promoter, as well as for example, the mitochondrial hsp60 promoters (SEQ ID NO:49 and SEQ ID NO:50), and an SV40 terminator (in pSGI-JU-89-6) could produce high levels of expression in recombinant SGI-i886 cells, indicating that the tubulin alpha promoter from SGI-i886 and SV40 terminator from simian virus could be used as good source of regulatory elements for high expression of heterologous gene sequences in recombinant labyrinthulomycetes cells. To identify additional promoters and terminators having these highly desirable characteristics, as described in Example 3, additional constructs were generated in which various promoter sequences from strain SGI-i94 (TABLE 6) were each cloned upstream of the reporter gene TurboGFP. Similarly, additional constructs were generated in which the SV40 terminator downstream of TurboGFP in pSGI-JU-89-6 was replaced with various terminators from *S. cerevisiae* (TABLE 10). These expression vectors were then linearized using a restriction site located in the vector sequence, and subsequently transformed into the SGI-886 strain according to the general procedure described in Example 4. The relative strength of each promoter was evaluated based on the expression of the TurboGFP reporter using fluorescence microscopy. Fluorescence signals of the transformed colonies were examined using the Typhoon™ FLA9000 system (GE Healthcare Life Sciences) with 473 nm laser and long pass blue (LPB) filter with the electron multiplier tube (EMT) set to 550V.

TABLE 10

Terminators from *Saccharomyces cerevisiae*

| Construct | Corresponding Gene | SEQ ID NO |
|---|---|---|
| pSGI-JU-124 | Alcohol dehydrogenase 1 (ADH1) | SEQ ID NO: 71 |
| pSGI-JU-125 | Enolase II (ENO2) | SEQ ID NO: 72 |
| pSGI-JU-126 | Pyruvate decarboxylase 1 (PDC1) | SEQ ID NO: 73 |
| pSGI-JU-127 | 3-phosphoglycerate kinase (PGK1) | SEQ ID NO: 74 |
| pSGI-JU-128 | Glyceraldehyde-3-phosphate dehydrogenase (TDH3) | SEQ ID NO: 75 |
| pSGI-JU-129 | Translational elongation factor EF-1 alpha (TEF1) | SEQ ID NO: 76 |
| pSGI-JU-89-6 | Cytochrome C isoform 1 (CYC1) | SEQ ID NO: 77 |

Figure 4:
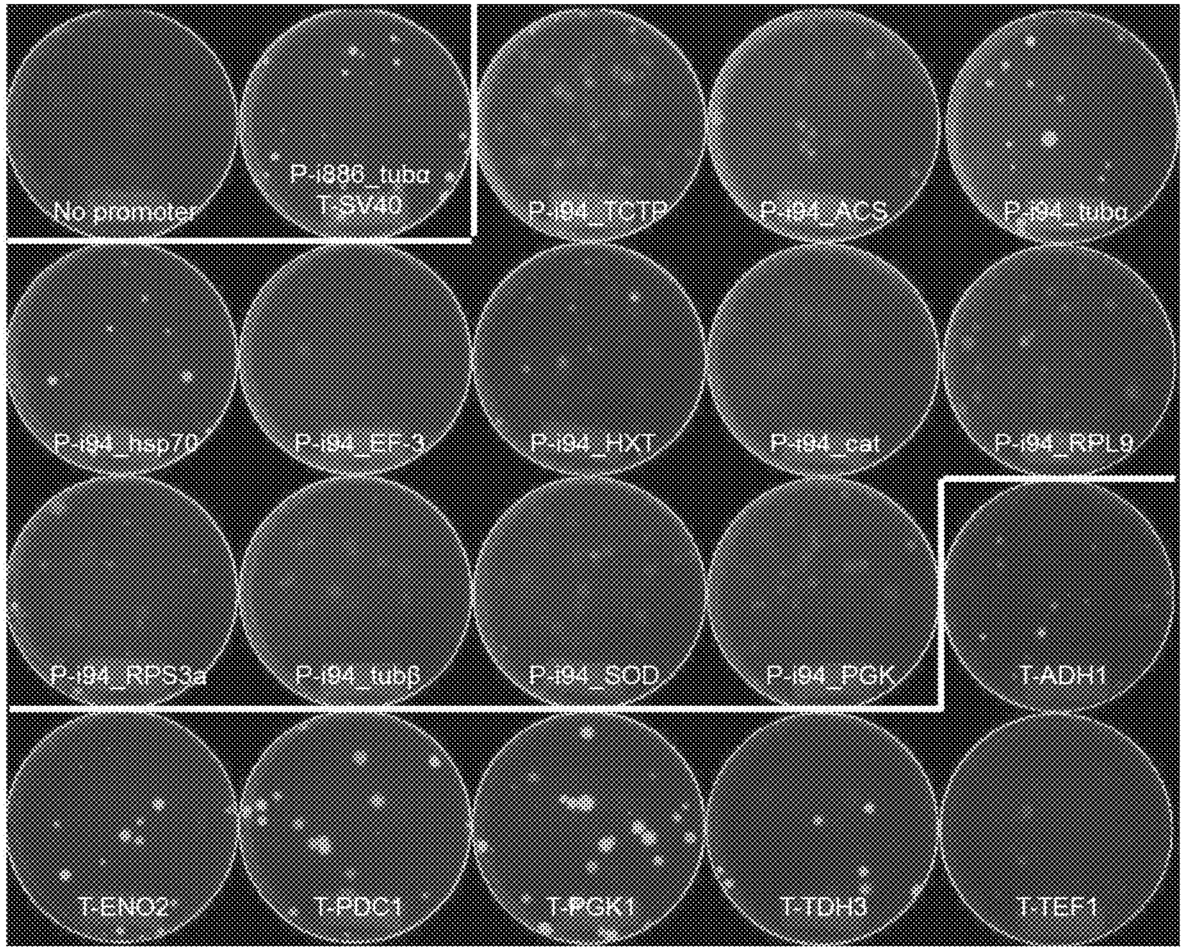
FIG. 4 is a representation of fluorescence microscopic images analyzing TurboGFP signals for labyrinthulomycetes colonies that were transformed with expression constructs in which TurboGFP expression was placed under control of various promoters and terminators. For each construct, the promoter and terminator are indicated by a 'P-' or 'T-', respectively, in front of the construct name. Fluorescent signals were detected and/or quantified using a Typhoon FLA 9000 system (GE Healthcare Life Sciences). All scanning and image analysis were done using the ImageQuant software with the same settings/values.

As reported in TABLE 11 and illustrated in FIG. 4 the promoters isolated from strain SGI-i94 all demonstrated some ability to direct expression of the GFP, and were observed to exhibit various levels of activity in recombinant SGI-i886 cells when compared to the positive control promoter, which was the tubulin alpha chain promoter isolated from SGI-i886 (SEQ ID NO:23). In particular, although there were significant variations in intensity of fluorescent signals among the transformants of the same construct, fluorescent signals with significantly high intensity were observed with the reporter gene TurboGFP being expressed using promoters corresponding to the tubulin alpha chain gene (SEQ ID NO:23) and the hsp7 gene of strain SGI-i94 (SEQ ID NO:24). The hexose transporter protein promoter (SEQ ID NO:26) displayed moderate activity in this assay.

TABLE 11

Relative strength of the promoter sequences derived from *Schizochytrium* sp. strain SGI-i94 and tested in recombinant *Aurantiochytrium* sp. strain SGI-i886.

| Construct | Promoter Sequence | Corresponding gene | Relative strength |
|---|---|---|---|
| pSGI-JU-98 | SEQ ID NO: 21 | Transcriptionally-controlled tumor protein homolog (TCTP) | + |
| pSGI-JU-99 | SEQ ID NO: 22 | Acetyl-coenzyme A synthetase 2 (ACS2) | + |
| pSGI-JU-101 | SEQ ID NO: 23 | Tubulin alpha (Tub-α) | ++++ |
| pSGI-JU-102 | SEQ ID NO: 24 | Heat shock protein 70 (hsp70) | +++ |

TABLE 11-continued

| Relative strength of the promoter sequences derived from *Schizochytrium* sp. strain SGI-i94 and tested in recombinant *Aurantiochytrium* sp. strain SGI-i886. | | | |
|---|---|---|---|
| Construct | Promoter Sequence | Corresponding gene | Relative strength |
| pSGI-JU-103 | SEQ ID NO: 25 | Transcription elongation factor 3 (EF-3) | + |
| pSGI-JU-105 | SEQ ID NO: 26 | Hexose transporter 1 (HXT1) | ++ |
| pSGI-JU-106 | SEQ ID NO: 27 | Catalase (cat) | + |
| pSGI-JU-107 | SEQ ID NO: 28 | 60 S ribosomal protein L9 (RPL9) | + |
| pSGI-JU-108 | SEQ ID NO: 29 | 40 s ribosomal protein S3a (RPS3a) | + |
| pSGI-JU-109 | SEQ ID NO: 30 | Tubulin beta chain (Tub-β) | + |
| pSGI-JU-110 | SEQ ID NO: 31 | Superoxide dismutase (SOD) | + |
| pSGI-JU-111 | SEQ ID NO: 32 | Phosphoglycerate kinase (PGK) | + |

Additionally, an enhancement in fluorescent signal intensities was observed with the PGK1, ENO2 and PDC1 terminators. A similar level of fluorescence was observed with the TDH3 terminator while a decrease in expression was observed with the each of the ADH1 and TEF1 terminators.

Example 7

Evaluation of Promoters Derived from *Aurantiochytrium* sp. SGI-i886 Using Paromomycin Resistance Gene nptII This Example describes the experimental evaluation of several promoter sequences derived from strain SGI-i886 for their potential use as selectable marker in the context of genetic transformation. While the use of fluorescent report proteins, such as TurboGFP as described above, is generally considered a reliable way to identify and screen for promoters functional in a particular cell or species, it was also considered important that they be tested in the context of transformation because most of these promoters would be used to drive the expression of a selectable marker or a biochemical pathway gene in genetic transformation procedures. Therefore, the promoters from the actin depolymerase (Adp) gene (alleles A and B, SEQ ID NO:38 and SEQ ID NO:39, of expression constructs pSGI-JU-183A and pSGI-JU-183B, respectively); the promoter from the Fa ATP synthase (faas) gene (SEQ ID NO:46) of expression construct pSGI-JU-188; the promoter from the heavy metal associated domain (HMA) (SEQ ID NO:47) of expression construct pSGI-JU-189A; promoters from the mitochondrial chaperonin 60 (hsp60) gene (SEQ ID NO:49 and SEQ ID NO:50 of expression constructs pSGI-JU-190A and pSGI-JU-190B); the phosphatidylinositol 3-kinase (PI3K) promoter (SEQ ID NO:54) of expression construct pSGI-JU-191C, the 60s ribosomal protein 11 (RPL11) promoter (SEQ ID NO:53) of expression construct pSGI-JU-192B, and the Tetraspanin (Tsp) promoter (SEQ ID NO:58) of expression construct pSGI-JU-195B, all of which were initially shown to be produce significant TurboGFP signals as described in Example 4 (TABLE 9), were further tested for their ability to confer paromomycin resistance when used to drive expression of a paromomycin-resistance gene, nptII, and thus support cell growth on selective media. For this purpose, using standard molecular biology techniques a paromomycin-resistance gene, nptII (SEQ ID NO:170), was operably linked at the 3' end of each of the foregoing promoter sequences in place of the TurboGFP gene. Each of the promoter sequences was directly PCR-amplified from its respective expression vector using appropriate forward and reverse primers shown in TABLE 12. PCR primer W171, which had vector homology and was designed to hybridize just upstream of the promoter, was a common forward primer for all promoter sequences except that oSGI-JU-0858 was used for pSGI-JU-188A. Each of the PCR-amplified products was agarose gel-purified and cloned into pSGI-JU-74 (FIG. 1), which was pre-digested with restriction enzymes NdeI and BstXI, using Gibson® Assembly procedure (SGI-DNA, La Jolla, CA). These two restriction sites are located immediately upstream to the nptII gene, and thus cloning each promoter sequence between these two sites allows the promoter to drive the expression of the antibiotic-resistance gene. The PCR-derived insert sequences of the resulting constructs were also confirmed by Sanger sequencing.

TABLE 12

| Primers for cloning promoters upstream of the nptII gene | | |
|---|---|---|
| Primer Name | Primer Sequence | SEQ ID NO |
| W171 | ATCAGAGCAGATTGTACTGAGAGTGCAC | SEQ ID NO: 171 |
| W172 | gcgtgcaatccatcttgttcaatccccatGGTGTCAAGATAGAAGTGGTGTCAA | SEQ ID NO: 172 |
| W173 | gcgtgcaatccatcttgttcaatccccatCTTGCCCAAAATCTATCTGTGTGAAACGC | SEQ ID NO: 173 |
| W174 | gtgcaatccatcagttcaatccccatGGTATTTTCTACGTTATGCATCGATTCATATTT | SEQ ID NO: 174 |
| W175 | cgtgcaatccatcttcaatccccatTTTTATTTGTGTTTTGTTTTGTCGCCTGTGGA | SEQ ID NO: 175 |
| W176 | gcgtgcaatccatcttgttcaatccccatCGTGCCCCGAAGATAGCTCGCTC | SEQ ID NO: 176 |
| W177 | gcgtgcaatccatcttggttcaatccccatGGTGCCTAAGAAAGAAAGCAACTAGCTCC | SEQ ID NO: 177 |
| W178 | gcgtgcaatccatcttgttcaatccccatCTTGCTGCTTTGGATTTATTCACTTGACGT | SEQ ID NO: 178 |

TABLE 12-continued

| Primers for cloning promoters upstream of the nptII gene | | |
|---|---|---|
| Primer Name | Primer Sequence | SEQ ID NO |
| W179 | gcgtgcaatccatcttgttcaatccccatTTTGCTTGAGGTTGGAGTTTCGAAAACTAC | SEQ ID NO: 179 |
| oSGI-JU-0858 | actgagagtgcaccatatgcAGCGCAACAGCCAAATCTAC | SEQ ID NO: 139 |

Each of the resulting constructs which retained the number designations of the original FP expression constructs of TABLE 2, was linearized, transformed into SGI-i886, and plated onto selection agar plates supplemented with paromomycin at 2 g/L. All of the promoters tested as described above showed an ability to confer paromomycin resistance to transformed cells, but to slightly different extents in terms of the number of colonies resulting from the transformations (the same amount of each linearized constructs was transformed into the target strain of interest, i.e. SGI-i886). Based on the number of obtained transformants, the promoters from the mitochondrial hsp60 gene (SEQ ID NO:49 and SEQ ID NO:50, in constructs “190A” and “190B”); the PI3K gene (SEQ ID NO:52) in construct “191C”, and the 60s RPL11 gene (SEQ ID NO:53) of transformation construct “192B” were determined to be somewhat better than the control promoter, which was a full-length tubulin promoter from SGI-i886 (886Tp), whereas the promoters from the Adp gene (SEQ ID NO:38 and SEQ ID NO:39, in transformation constructs “183A” and “183B”); the faas gene (SEQ ID NO:46) in transformation construct “188”, the HMA gene (SEQ ID NO:47) in construct “189A”: and the (Tsp) gene (SEQ ID NO:58, in construct “195B”) were similar to the control (full-length tubulin promoter from SGI-i886) in yielding transformants.

Example 8

Evaluation of Promoter Activity of Deletion Variants Using Paromomycin Resistance Reporter Gene nptII The lengths of the promoters enabling paromomycin resistance described in Example 7 above ranged from 1500 bp to 2000 bp. In order to identify shorter variants of the promoters described in Example 7, an allele of each of the promoters was chosen (pSGI-JU-183A, pSGI-JU-188, pSGI-JU-189A, pSGI-JU-190A, pSGI-JU-191C, pSGI-JU-192B, and pSGI-JU-195B) and subjected to a shortening procedure from the 5' end to lengths ranging from approximately 500 bp to 800 bp. The promoter sequence shortening was achieved by using standard PCR-based methods. The PCR-derived sequences of the resulting shortened promoters were also confirmed by Sanger sequencing. Corresponding expression constructs were built, in which nptII was placed at the 3' end of each of the shortened promoters, and subsequently tested for their potential to confer resistance and thus cell growth.

TABLE 13

Relative strength of the deletion variants of various promoter sequences derived from *Aurantiochytrium* sp. strain SGI-i886

| Promoter | Construct | Primers Used | Relative strength |
|---|---|---|---|
| Tubulin alpha (Tubα-738) (SEQ ID NO: 59) | pSGI-JU-196 | oSGI-JU-0888 oSGI-JU-0359 | ++++ |
| Tubulin alpha (Tubα-522) (SEQ ID NO: 60) | pSGI-JU-197 | oSGI-JU-0889 oSG1-JU-0359 | – |
| Actin (act-1176) (SEQ ID NO: 61) | pSGI-JU-198 | oSGI-JU-0890 oSGI-JU-0801 | ++++ |
| Actin (act-776) (SEQ ID NO: 62) | pSGI-JU-199 | oSGI-JU-0891 oSGI-JU-0801 | + |
| Actin (act-557) (SEQ ID NO: 63) | pSGI-JU-200 | oSGI-JU-0892 oSGI-JU-0801 | ++++ |
| Fa ATP synthase short (faas-776) (SEQ ID NO: 64) | pSGI-JU-188-short | PF271 PF266 | – |
| Heavy metal associated domain short (HMA-796) (SEQ ID NO: 65) | pSGI-JU-189-short | PF271 PF267 | ++ |
| Mitochondrial chaperonin 60 short (hsp60-788) (SEQ ID NO: 66) | pSGI-JU-190-short | PF271 PF268 | ++++ |
| Phosphotidylinsositol 3-kinase short (PI3K-752) (SEQ ID NO: 67) | pSGI-JU-191-short | PF271 PF269 | +++ |
| 60 s ribososomal protein 11 short (RPL11-699) (SEQ ID NO: 68) | pSGI-JU-192-short | PF271 PF274 | +++ |
| Tetraspanin short (Tsp-749) (SEQ ID NO: 69) | pSGI-JU-195-short | PF271 PF270 | +++ |
| Actin depolymerase-short (Adp-830) (SEQ ID NO: 70) | 183-short | PF271 PF265 | ++ |

Each of the resulting constructs was linearized, transformed into SGI-i886, and plated onto selection agar plates supplemented with paromomycin at 2 g/L. With the exception for the shortened version of the promoter from pSGI-JU-188 which did not result in colonies, all other shortened promoter sequences resulted in paromomycin resistance but to slightly different extents in terms of the number of colonies resulting from the transformations (TABLE 13). The relative strengths of these shortened promoter sequences also appeared to be similar to those of their longer counterparts, where the result of the full-length promoter in pSGI-JU-183A (“full”) was used as a reference for comparison.

Example 9

Identification of Lipogenic Promoters in Chytrid Strain SGI-i886

This Example describes the experimental characterization and evaluation of several promoter sequences derived from strain SGI-i886 that are active during lipogenesis based on average coverage of the cDNA in next-generation sequencing (NGS) data of the transcriptomes of the strain SGI-i886 during mid- to late-log phase of growth.

Replicate flasks (n=2) of strain SGI-i886 were grown in nitrogen-deplete and control (that is, nitrogen-replete)

media, respectively. Each flask was sampled for transcriptomics analysis at 0-hour, 2-hour, and 24-hour time points. A total of 12 polyA-selected mRNA samples were prepared for next-generation RNA sequencing. RNA isolation and preparation of next-generation sequencing were performed by using the procedures described in Example 2 above.

The average sequencing coverage, shown for 13 putative lipogenic promoters in TABLE 14, measured in terms of FPKM according to Mortazavi et al. (*Nature Methods* 5:621-628, 2008), corresponds to the transcript abundance of each gene in each sample. In these RNA sequencing experiments, the relative expression of a given transcript was predicted to be proportional to the number of cDNA fragments that originated from it.

TABLE 14

Listing of genes whose promoters were assessed for expression strength during lipogenic phase. Control_02 and Control_24 were FPKM values for indicated transcripts at 2-and 24-hour time points, respectively, after being diluted back into fresh growth medium. The 2-hour time point indicates transcript levels at mid-growth stage while the 24-hour time point indicate transcript levels at a stationary phase (nutrient deplete).

| Promoter SEQ | | FPKM | | Log2 |
|---|---|---|---|---|
| ID NO | Gene Description | Control_02 | Control_24 | (24 vs 02) |
| 180 | Molecular chaperone (Small heat shock protein) | 1586.5 | 7084.8 | 2.2 |
| — | NAD(P)-binding Rossmann-fold domains | 500.3 | 3664.6 | 2.9 |
| 181 | Elicitin-like protein 6 (Precursor) | 148.4 | 3527.9 | 4.6 |
| 182 | NADH-ubiquinone reductase complex 1 MLRQ subunit | 18.0 | 2523.0 | 7.1 |
| 183 | Glyceraldehyde 3-phosphate dehydrogenase, NAD binding domain | 359.2 | 1763.1 | 2.3 |
| 184 | Fructose-bisphosphate aldolase, cytoplasmic isozyme | 235.0 | 1034.8 | 2.1 |
| 190 | NAD(P)-binding Rossmann-fold domains | 93.7 | 964.7 | 3.4 |
| 185 | Acc1 acetyl-CoA carboxylase | 65.7 | 945.1 | 3.8 |
| 186 | MFS transporter, sugar porter (SP) family (Mfsp) | 72.4 | 603.6 | 3.1 |
| — | Phosphatidylinositol kinase | 113.8 | 578.7 | 2.3 |
| 189 | Fatty acid synthase alpha subunit reductase | 48.2 | 565.6 | 3.6 |
| 187 | Carnitine O-palmitoyltransferase 2 | 48.5 | 538.0 | 3.5 |
| 188 | Ferredoxin reductase-like, C-terminal NADP-linked domain | 35.4 | 519.1 | 3.9 |

The ability of these promoters to control expression of the reporter gene TurboGFP during lipogenic phase was assessed. The use of this dataset for lipogenic promoters were further validated by the presence of promoter sequences corresponding to the lipid biosynthesis genes acetyl-CoA carboxylase and fatty acid synthase among the putative lipogenic promoters. Both of these genes were expected to be upregulated during the lipogenic phase. In addition, it was observed that the omega-3 PUFA synthase genes were also induced in this dataset (see, TABLE 15).

TABLE 15

Expression levels of omega-3 PUFA synthase genes in transcriptomic dataset

| Gene | FPKM | | Log2 |
|---|---|---|---|
| Description | Control_02 | Control_24 | (24 vs 02) |
| Omega-3 polyunsaturated fatty acid synthase PfaA | 197.3 | 1249.0 | 2.7 |
| Omega-3 polyunsaturated fatty acid synthase PfaD | 183.2 | 837.5 | 2.2 |
| Omega-3 polyunsaturated fatty acid synthase PfaC | 136.1 | 677.1 | 2.3 |

TABLE 15-continued

Expression levels of omega-3 PUFA synthase genes in transcriptomic dataset

| Gene | FPKM | | Log2 |
|---|---|---|---|
| Description | Control_02 | Control_24 | (24 vs 02) |
| Omega-3 polyunsaturated fatty acid synthase PfaD | 79.3 | 379.5 | 2.3 |
| Omega-3 polyunsaturated fatty acid synthase PfaD | 73.2 | 304.3 | 2.1 |
| Omega-3 polyunsaturated fatty acid synthase PfaA | 43.2 | 560.2 | 3.7 |

TABLE 15-continued

Expression levels of omega-3 PUFA synthase genes in transcriptomic dataset

| Gene | FPKM | | Log2 |
|---|---|---|---|
| Description | Control_02 | Control_24 | (24 vs 02) |
| Omega-3 polyunsaturated fatty acid synthase PfaC | 23.5 | 165.6 | 2.8 |
| Omega-3 polyunsaturated fatty acid synthase PfaA | 780.2 | 7104.6 | 3.2 |

Construction of Expression Vectors Carrying Lipogenic Promoters.

The ability of these promoters to express heterologous genes during lipogenic phase was assessed as follows. Approximately 3 kb of the sequence extending upstream (5') of the initiating methionine codon (that is, native start codon) of the corresponding genes were selected as comprising promoters. To evaluate their ability to control expression of an operably linked heterologous gene, these promoter sequences were cloned upstream of the reporter gene TurboGFP to generate expression vectors pSGI-CC-002-6, 8-13, which are listed in Table 16. These constructs were generated by cloning PCR products carrying the corresponding promoter sequences (which were individually amplified from genomic DNA template of the strain SGI-i886 using primers indicated in Table 16) into an NsiI-digested pSGI-CC-001 vector using Gibson Assembly® cloning procedure (SGI-DNA, La Jolla, Calif.). All of the PCR-derived insert sequences were confirmed by Sanger sequencing. The cloning vector pSGI-CC-001 was a plasmid that carried the reporter gene TurboGFP and an SV40 terminator without a promoter sequence. An NsiI site was engineered at the 5' end of the TurboGFP gene to facilitate cloning of the promoter sequences upstream of the reporter gene. The vector pSGI-CC-001 also carries the hph marker gene for selection of chytrid transformants on hygromycin.

TABLE 16

Expression cassettes and vectors carrying lipogenic promoters

| Construct Name | Promoter Length (bp) | SEQ ID NO |
|---|---|---|
| pSGI-CC-002 | 3032 | 180 |
| pSGI-CC-003 | 3001 | 181 |
| pSGI-CC-004 | 3044 | 182 |
| pSGI-CC-005 | 3000 | 183 |
| pSGI-CC-006 | 3001 | 184 |
| pSGI-CC-008 | 2971 | 185 |
| pSGI-CC-009 | 2971 | 186 |
| pSGI-CC-010 | 3044 | 187 |
| pSGI-CC-011 | 3017 | 188 |
| pSGI-CC-012 | 3054 | 189 |
| pSGI-CC-013 | 2966 | 190 |

The resulting constructs were then transformed into a wild type *Aurantiochytrium* strain (WH-06267). GFP expression in multiple independent transformants was assessed as the cell cultures were transitioned into lipogenic phase in a 24-well microbioreactor (Micro-24; Pall Corporation). The statuses of the various promoters are summarized in TABLE 16. For the Micro-24 experiment, cultures were initially grown to mid-growth in FM005 (which is a defined media with low C:N ratio), then shifted to lipogenic media FM006 (which is a defined media with high C:N ratio) at an OD740=1.4. Once in FM006, the cultures were placed in a Micro-24 (Isett et al. *Biotechnol. Bioengineer.* 98:1017-1028, 2007) (DO=50%, 650 rpm, 30° C.). Samples were taken at various time points and average fluorescence on the green channel (TurboGFP) in each sample was assessed using the Guava flow cytometer. The results for promoters tested to date are shown in FIGS. 5-7 (also see TABLE 17).

Figure 5:
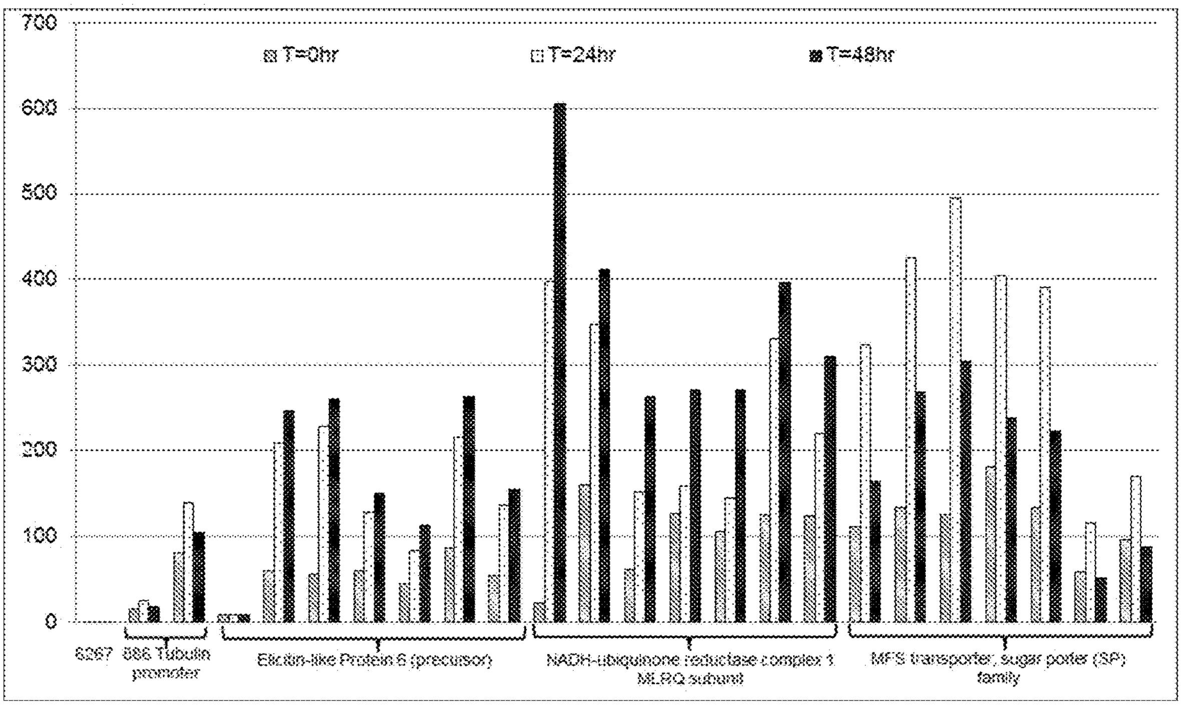
FIG. 5 graphically summarizes the results from experiments evaluating the ability of three candidate lipogenic promoters to control expression of the reporter gene TurboGFP during lipogenic phase. Samples were taken at 0-hr, 24-hr, and 48-hr time points and average fluorescence on the green channel (TurboGFP) in each sample was assessed using the Guava flow cytometer. Control cells were wild type chytrid cells (WH-06267) and transgenic chytrid cells carrying a TurboGFP reporter gene expressed under control of α-tubulin promoter. In this experiment, the cultures were grown in FM006 medium instead of FM005.

FIG. 5 graphically summarizes the results from experiments evaluating the ability of three candidate lipogenic promoters to direct expression of a heterologous nucleic acid sequence; Elicitin-like protein 6 (Precursor), NADH-ubiquinone reductase complex 1 MLRQ subunit (Nurp), or MFS transporter, sugar porter (SP) family (Mfsp); to control expression of the reporter gene TurboGFP during lipogenic phase. Samples were taken at 0-hr, 2-hr, 24-hr, and 48-hr time points and average fluorescence on the green channel (TurboGFP) in each sample was assessed using the Guava flow cytometer. Control cells were wild type chytrid cells (WH-06267) and transgenic chytrid cells carrying a TurboGFP reporter gene expressed under control of α-tubulin promoter. In this experiment, the cultures were initially grown in FM006 medium instead of FM005.

Figure 6:
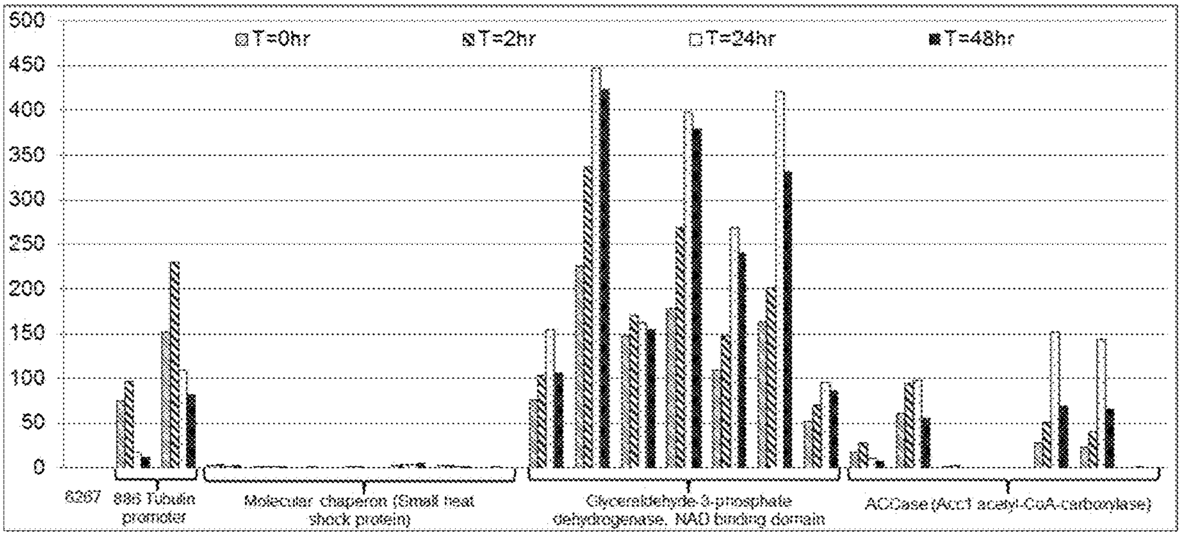
FIG. 6 graphically summarizes the results from experiments evaluating the ability of three candidate lipogenic promoters to control expression of the reporter gene TurboGFP during lipogenic phase. Samples were taken at 0-hr, 2-hr, 24-hr, and 48-hr time points and average fluorescence on the green channel (TurboGFP) in each sample was assessed using the Guava flow cytometer. Control cells were wild type chytrid cells (WH-06267) and transgenic chytrid cells carrying a TurboGFP reporter gene expressed under control of α-tubulin promoter.

FIG. 6 graphically summarizes the results from experiments evaluating the ability of three candidate lipogenic promoters to direct expression of a heterologous nucleic acid sequence; Molecular chaperone (Small heat shock protein) (SEQ ID NO:180), Glyceraldehyde 3-phosphate dehydrogenase. NAD binding domain (SEQ ID NO:183), or ACCase (Acc1 acetyl-CoA carboxylase) (SEQ ID NO:185); to control expression of the reporter gene TurboGFP during lipogenic phase. Samples were taken at 0-hr, 2-hr, 24-hr. and 48-hr time points and average fluorescence on the green channel (TurboGFP) in each sample was assessed using the Guava flow cytometer. Control cells were wild type chytrid cells (W H-06267) and transgenic chytrid cells carrying a TurboGFP reporter gene expressed under control of α-tubulin promoter.

Figure 7:
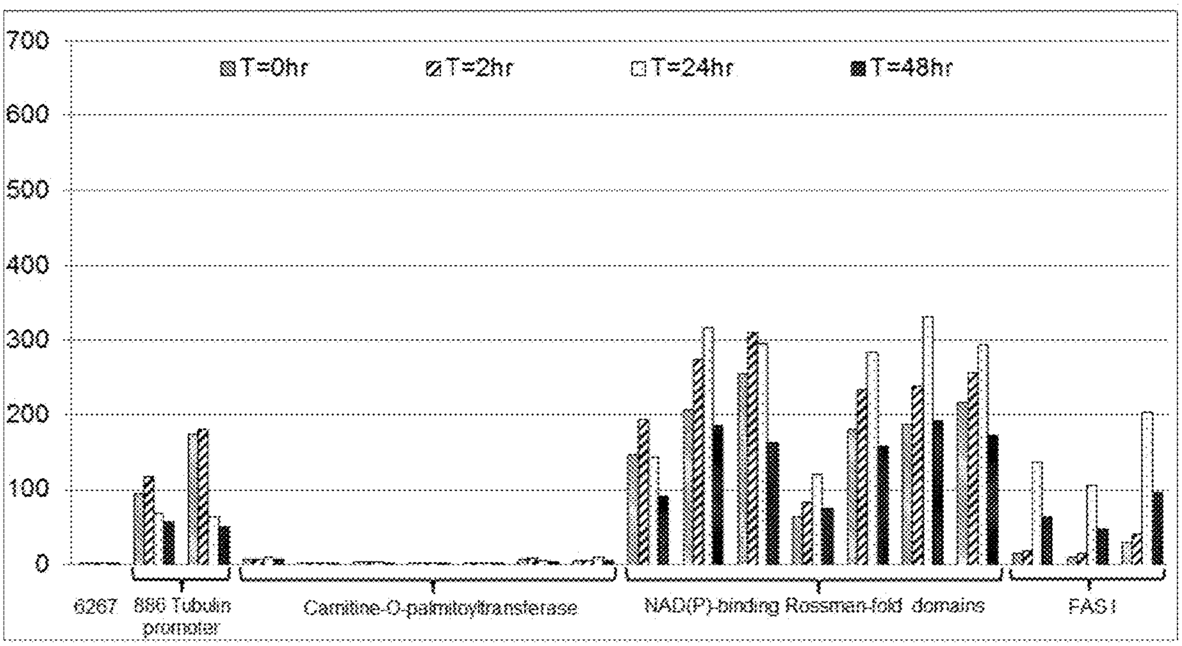
FIG. 7 graphically summarizes the results from experiments evaluating the ability of three candidate lipogenic promoters to control expression of the reporter gene TurboGFP during lipogenic phase. Samples were taken at 0-hr, 2-hr, 24-hr, and 48-hr time points and average fluorescence on the green channel (TurboGFP) in each sample was assessed using the Guava flow cytometer. Control cells were wild type chytrid cells (WH-06267) and transgenic chytrid cells carrying a TurboGFP reporter gene expressed under control of α-tubulin promoter.

FIG. 7 graphically summarizes the results from experiments evaluating the ability of three candidate lipogenic promoters to direct expression of a heterologous nucleic acid sequence; Carnitine O-palmitoyltransferase 2. NAD(P)-binding Rossmann-fold domains (Nrfp), or FAS I (Fatty acid synthase alpha subunit reductase); to control expression of the reporter gene TurboGFP during lipogenic phase. Samples were taken at 0-hr, 2-hr, 24-hr, and 48-hr time points and average fluorescence on the green channel (TurboGFP) in each sample was assessed using the Guava flow cytometer. Control cells were wild type chytrid (*Aurantiochytrium*) cells (WH-06267) and transgenic chytrid cells carrying a TurboGFP reporter gene expressed under control of α-tubulin promoter.

TABLE 17

Listing of genes whose promoters were assessed for expression during lipogenic phase. When tested in Micro-24 system for GFP expression, a qualitative score of −, +, ++, +++, ++++ are given (also see FIGS. 5-7).

| Gene Description | GFP expression | Construct | SEQ ID NO |
|---|---|---|---|
| Molecular chaperone (Small heat shock protein) | − | pSGI-CC-002 | 180 |
| Elicitin-like protein 6 (Precursor) | ++* | pSGI-CC-003 | 181 |
| NADH-ubiquinone reductase complex 1 MLRQ subunit (Nurp) | ++++* | pSGI-CC-004 | 182 |
| Glyceraldehyde 3-phosphate dehydrogenase, NAD binding domain | +++ | pSGI-CC-005 | 183 |
| Fructose-bisphosphate aldolase, cytoplasmic isozyme | | pSGI-CC-006 | 184 |
| NAD(P)-binding Rossmann-fold domains | ++ | pSGI-CC-013 | 190 |
| Acc1 acetyl-CoA carboxylase | + | pSGI-CC-008 | 185 |
| MFS transporter, sugar porter (SP) family | +++* | pSGI-CC-009 | 186 |
| Fatty acid synthase alpha subunit reductase | + | pSGI-CC-012 | 189 |
| Carnitine O-palmitoyltransferase 2 | − | pSGI-CC-010 | 187 |
| Ferredoxin reductase-like, C-terminal NADP-linked domain | | pSGI-CC-011 | 188 |

*The Micro-24 analysis for these promoters used the FM006 growth medium for the growth stage prior to the cultures being transitioned into the Micro-24 microbioreactor.

Based on these assays, the Nurp promoter (SEQ ID NO:182), the Gpdp promoter (SEQ ID NO:183), and the Msfp promoter (SEQ ID NO:186) demonstrated strong activity under lipogenic culture conditions.

Example 10

Identification of Constitutive Promoters in Chytrids

This Example describes the experimental characterization and evaluation of several strong promoter sequences derived from chytrids. Transcriptomics study was performed as described in Examples 2 and 9 on three independent genetically engineered strains: GH-15002, GH-15003, and GH-SGI-F-15120.

The strains GH-SGI-F-15002. GH-SGI-F-15003 and GH-SGI-F-15120 were each cultured and characterized in 2-L fed-batch fermentation. Samples for RNA were taken in mid-growth stage, several hours after initiation of lipid phase, and 1-2 days after initiation of lipid phase. Total RNA was extracted from each sample using the Ambion RiboPure™ RNA Purification Kit for yeast (Catalog #AM1926). PolyA-selected mRNA samples were prepared for next-generation RNA sequencing. The transcriptomics data generated from next-generation RNA sequencing was subsequently examined to identify genes that were highly expressed during 2-L fed-batch fermentation. The average sequencing coverage (FPKM), shown for 12 candidate strong promoters in TABLE 18, was a measure of relative transcriptional levels of the corresponding genes. It was observed that two of the genes for which lipogenic promoters were described previously in Example 9, NADH-ubiquinone reductase complex 1 MLRQ subunit (Nurp) and glyceraldehyde-3-phosphate dehydrogenase, type I (Gpdp) were also identified in this experiment. Also identified in this experiment were genes encoding subunits of the PUFA-PKS pathway (e.g., PfaA, PfaC) and several genes known to be involved in lipid biosynthesis and accumulation (e.g., GPAT1, DGAT, and Fas1p). The remaining eleven genes were not specifically involved in biosynthesis of polyunsaturated fatty acids.

Construction of Expression Vectors Carrying Constitutive Promoters Driving Expression of a Delta 17 Desaturase Gene.

Construction of pSGI-EO-001: pSGI-EO-001 was the base vector that contained the Δ17 desaturase gene without a promoter. An AleI site was engineered at the start codon of the Δ17 desaturase gene to facilitated cloning of promoter sequences upstream of the reporter gene. The Δ17 desaturase gene is followed by the tdh3 terminator. This vector also carries the bsr marker gene for selection of chytrid transformants on Blasticidin.

Construction of pSGI-EO-003-013: pSGI-EO-003-013 are plasmids where various potential promoter sequences (~3 kb) from chytrid isolate SGI-i886 was cloned upstream of Δ17 desaturase. These constructs were generated by cloning a PCR product carrying the promoter sequence (amplified from genomic DNA using primers indicated in Table XYZ) into AleI-digested vector pSGI-EO-001 using Gibson Assembly® cloning. PCR-derived promoter sequences were all confirmed by MiSeq sequencing except for pSGI-EO-009 which was confirmed by Sanger sequencing.

pSGI-EO-014: pSGI-EO-014 is a plasmid where the Gpdp promoter (SEQ ID NO:183) was cloned upstream of Δ17 desaturase. The promoter sequence was amplified using primers oSGI-JU-1797 & oSGI-JU-1809 from pSGI-JU-354, a plasmid into which the promoter had been previously cloned. The PCR-derived promoter sequence was confirmed by MiSeq sequencing.

TABLE 18

Highly expressed genes identified from 2-L fermentation transcriptomics data.

| | | GH-15002 | | | GH-15003 | | | GH-SGI-F-15120 | | |
|---|---|---|---|---|---|---|---|---|---|---|
| Gene Description | Gene Name | 10 h | 30.5 h | 46.5 h | 10 h | 30.5 h | 46.5 h | 28 h | 45 h | 71.5 h |
| Omega-3 polyunsaturated fatty acid synthase subunit, PfaA (3' end) | pfaA | 5698.1 | 5392.2 | 4812.3 | 3677.0 | 4961.1 | 3549.7 | 2667.5 | 7420.0 | 19565.3 |
| Lysophosphatidylcholine acyltransferase 1 | PLAT2 | 1359.5 | 3225.2 | 1957.7 | 962.2 | 3208.2 | 1713.6 | 1313.8 | 4907.1 | 4540.6 |
| Polyketide-type polyunsaturated fatty acid synthase PfaA (5' end) | pfaA | 659.4 | 1256.4 | 951.2 | 643.2 | 1434.9 | 1166.6 | 2453.6 | 4856.7 | 3922.4 |
| Actin beta/gamma 1 | Actin | 3415.7 | 2482.4 | 1239.2 | 2743.1 | 1976.6 | 1528.3 | 1240.9 | 1310.0 | 3218.1 |
| Heat shock cognate 70 | Hsp70 | 13797.1 | 5084.7 | 4251.0 | 8105.4 | 4650.8 | 4648.7 | 4500.7 | 2723.4 | 2958.8 |
| Glutamine synthetase root isozyme 1 | Gln-Syn | 1156.4 | 1652.1 | 1204.6 | 473.6 | 1289.0 | 1199.5 | 143.9 | 2595.7 | 2375.7 |
| P-loop containing nucleoside triphosphate hydrolases | TEF | 28986.2 | 10776.1 | 13253.1 | 27467.1 | 9094.0 | 11234.2 | 8086.2 | 2585.8 | 2137.3 |
| Heat shock protein 90 | Hsp90 | 7878.6 | 2729.6 | 2522.6 | 4440.3 | 2092.0 | 2252.5 | 3306.5 | 1815.6 | 2087.1 |
| Actin depolymerizing proteins | Act Depol | 6107.8 | 6049.2 | 4432.3 | 6004.3 | 5982.4 | 4541.3 | 1758.3 | 1868.7 | 2058.7 |
| 40S ribosomal protein S3a | Rps3a | 13753.5 | 1853.8 | 4065.6 | 8564.3 | 1105.2 | 2365.0 | 6912.4 | 1865.1 | 2014.3 |
| 40S ribosomal protein S8 | Rps8 | 34438.3 | 4873.7 | 9499.7 | 24796.7 | 3910.6 | 7059.5 | 4307.1 | 1308.2 | 1724.1 |
| 60S ribosomal protein L8 | Rpl8 | 8484.9 | 1205.3 | 2481.3 | 6835.0 | 857.0 | 1842.8 | 3974.6 | 1245.2 | 1550.9 |
| Voltage-dependent anion-selective channel protein 3 isoform 1 | Vac | 5558.9 | 3977.5 | 2221.5 | 5954.1 | 4225.5 | 2584.0 | 2037.4 | 1614.1 | 1487.3 |
| Omega-3 polyunsaturated fatty acid synthase subunit, PfaC (pfaC; DH) | PfaC | 737.7 | 1619.2 | 1136.1 | 827.5 | 1516.0 | 1477.9 | 1420.8 | 2879.1 | 1273.2 |
| NADH-ubiquinone reductase complex 1 MLRQ subunit | Nurp | 426.8 | 3946.1 | 1288.8 | 590.4 | 3507.6 | 1556.2 | 13.6 | 314.9 | 515.3 |
| Glycerol-3-phosphate acyltransferase 9 isoform 1 | GPAT1 | 134.4 | 190.0 | 125.8 | 90.8 | 207.3 | 124.0 | 101.1 | 424.7 | 514.5 |
| glyceraldehyde-3-phosphate dehydrogenase, type I | Gpdp | 959.8 | 1236.9 | 470.1 | 940.3 | 1170.1 | 538.6 | 604.9 | 664.9 | 428.3 |
| Diacylglycerol O-acyltransferase 2B | DGAT | 74.6 | 102.4 | 76.8 | 54.1 | 91.0 | 66.2 | 37.0 | 54.9 | 56.9 |
| FAS2_PENPA Fatty acid synthase subunit alpha | Fas1p | 126.6 | 319.5 | 145.8 | 113.3 | 220.7 | 205.8 | 64.2 | 92.7 | 46.8 |

pSGI-EO-027: pSGI-EO-027 is a plasmid where the pfaA promoter was cloned upstream of Δ17 desaturase. The promoter sequence was amplified using primers oSGI-JU-1830 & oSGI-JU-1852 from pSM-20, a plasmid into which the promoter had been earlier cloned. The PCR-derived promoter sequence was confirmed by Sanger sequencing.

TABLE 19

Expression constructs carrying strong constitutive promoters identified by gene name and SEQ ID

| Construct Name | Gene Name | Promoter Length (hp) | SEQ ID NO |
|---|---|---|---|
| pSGI-EO-027 | PfaA | 3070 | 191 |
| pSGI-EO-003 | Hsp90 | 3073 | 192 |
| pSGI-EO-004 | Rps8 | 2942 | 193 |
| pSGI-EO-005 | Gln-syn | 3112 | 194 |
| pSGI-EO-006 | Actin | 3101 | 195 |
| pSGI-EO-007 | Hsp70 | 3063 | 196 |
| pSGI-EO-008 | Vac | 3033 | 197 |
| pSGI-EO-009 | Plat2 | 3193 | 198 |
| pSGI-EO-010 | TEF | 3017 | 199 |
| pSGI-EO-011 | Rps3a | 2986 | 700 |
| pSGI-EO-012 | Rpl8 | 2956 | 201 |
| pSGI-EO-013 | Act Depol | 2918 | 202 |
| pSGI-EO-014 | Gpdp | 3001 | 183 |

Each of the expression constructs listed in Table 19 was transformed into the ARA producing strain GH-15311 according to the transformation procedure described in Example 4 above. The ARA producing strain GH-15311 was a ΔPfaA chytrid strain transformed with three expression cassettes each of which carried coding sequences of elongase-/desaturase (Elo/Des) fatty acid synthetic pathway genes. A brief description of the Elo/Des expression cassettes is shown in Table 20.

TABLE 20

Summary of elongase/desaturase gene cassettes introduced into the ARA producing strain GH-15311. The nucleotide sequences of Msfp promoter, Nurp promoter, and Nrfp promoter are provided in the Sequence Listing as SEQ ID NO: 186, SEQ ID NO: 182, and SEQ ID NO: 190, respectively.

| Cassettes | promoter | gene | terminator | marker | Description |
|---|---|---|---|---|---|
| pSGI-JU-353 | Mfsp | Δ12des13 | pgk1t | nptII | Genes for conversion of C16:0 to C18:2 (Linoleic acid) using lipogenic promoters. |
| | Nurp | Δ9des14 | eno2t | | |
| | Nrfp | C16elo17 | sv40t | | |
| pSG1-JU-354 | Mfsp | Δ5des2 | pgk1t | hph | Genes for conversion of C18:2 (Linoleic acid) to EPA using lipogenic promoters. |
| | Nurp | Δ6elo6 | eno2t | | |
| | Nrfp | Δ6des9 | sv40t | | |
| | Gpdp | ω3des23 | tdh3t | | |
| pSGI-JU-355 | Mfsp | Δ5des2 | pgk1t | hph | Genes for conversion of C18:2 (Linoleic acid) to ARA using lipogenic promoters. |
| | Nurp | Δ6elo6 | eno2t | | |
| | Nrfp | Δ6des9 | sv40t | | |

A summary of results from the transformation of the expression constructs listed in Table 19 into the ARA producing strain GH-15311 is presented in Table 21.

TABLE 21

Summary of experiments transforming the ARA producing strain GH-15311 with a gene encoding Δ17 desaturase placed under control of various strong constitutive promoters

| Promoter | SEQ ID NO: | Construct Name | No transformants examined |
|---|---|---|---|
| PfaA | 191 | pSI-EO-027 | 3 |
| Hsp90 | 192 | pSI-EO-003 | 1 |
| Rps8 | 193 | pSI-EO-004 | 6 |
| Gln-syn | 194 | pSI-EO-005 | 7 |
| Actin | 195 | pSI-EO-006 | 11 |
| Hsp70 | 196 | pSI-EO-007 | 3 |
| Vac | 197 | pSI-EO-008 | 6 |
| Plat2 | 198 | pSI-EO-009 | 6 |
| TEF | 199 | pSI-EO-010 | 1 |
| Rps3a | 200 | pSI-EO-011 | 6 |
| Rpl8 | 201 | pSI-EO-012 | 6 |
| Act depol | 202 | pSI-EO-013 | 10 |
| Gpdp | 183 | pSI-EO-014 | 8 |

Transformants were examined for their ability to modulate PUFA production by using Micro-24 fermentation procedure. For each construct, at least 6 independent transformants were tested when possible. When fewer than 6 transformants were available, all transformants were tested. In the Micro-24 assays, the cells were grown to about half density in FM005 growth medium for approximately one day, then pelleted and resuspended in FM006 medium. The results (ARA and EPA titers) are shown in Figure Table 22.

TABLE 22

ARA and EPA contents (% TOC) of GH-15311 and transformants carrying a Δ17 desaturase gene placed under control of various promoters. Promoters used and transformant clone ID are indicated. Clone GH-15311 L and R were two cultures of background strain GH-15311 used as controls. Cultures were grown in growth medium (FM2; rich media) and transitioned to lipogenesis media (FM006; low N:C ratio). Samples were taken 72 hours after transition to lipogenesis medium and analyzed by GC-FAME.

| Strain/Promoter | Transformant ID | ARA | EPA |
|---|---|---|---|
| Control: 15311 | L | 20.14% | 0.63% |
| | R | 21.92% | 0.45% |
| Act Depol | p3 #1 | 10.94% | 2.45% |
| (SEQ ID NO: 202) | p3 #2 | 8.18% | 0.77% |
| | p3 #6 | 8.21% | 5.08% |
| | p3 #7 | 7.26% | 3.43% |
| Actin | p1 #19 | 5.93% | 5.93% |
| (SEQ ID NO: 195) | p1 #20 | 5.17% | 6.79% |
| | p1 #22 | 11.21% | 4.00% |
| | p1 #23 | 7.13% | 3.61% |
| | p1 #24 | 9.83% | 2.32% |
| Gln-Syn | p1 #12 | 9.68% | 0.17% |
| Gpdp | p3 #10 | 0.15% | 9.35% |
| (SEQ ID NO: 183) | p3 #11 | 1.70% | 11.97% |
| | p3 #12 | 0.70% | 8.06% |
| Plat2 | p2 #1 | 0.90% | 11.59% |
| (SEQ ID NO: 198) | p2 #2 | 0.95% | 8.61% |
| | p2 #3 | 1.05% | 8.39% |
| | p2 #4 | 0.00% | 6.91% |
| | p2 #5 | 0.84% | 8.59% |
| | p2 #6 | 0.44% | 16.41% |
| Rpl8 | p2 #23 | 12.91% | 1.96% |
| (SEQ ID NO: 201) | p2 #24 | 6.31% | 3.29% |
| | p2 #25 | 8.62% | 0.35% |
| | p2 #26 | 5.53% | 5.26% |
| | p2 #27 | 11.08% | 1.18% |
| | p2 #28 | 18.30% | 2.08% |
| Rps3a | p2 #17 | 16.24% | 5.47% |
| (SEQ ID NO: 200) | p2 #18 | 15.46% | 3.95% |
| | p2 #19 | 6.29% | 4.50% |
| | p2 #20 | 4.14% | 14.81% |
| | p2 #21 | 9.76% | 8.80% |
| | p2 #22 | 8.58% | 2.58% |
| Rps8 | p1 #6 | 2.17% | 7.31% |
| (SEQ ID NO: 193) | p1 #7 | 6.77% | 4.29% |
| | p1 #8 | 2.78% | 8.04% |
| | p1 #9 | 11.22% | 8.86% |
| | p1 #10 | 1.11% | 8.86% |
| | p1 #11 | 15.23% | 2.13% |
| TEF (SEQ ID NO: 199) | p2 #12 | 3.60% | 17.94% |

TABLE 23

ARA and EPA contents (% TOC) of GH-15311 and chytrid transformants carrying a Δ17 desaturase gene placed under control of various promoters. Promoters used and transformant clone ID are indicated. Clone EO01C6 was a no promoter control. Cultures were grown in growth medium (FM2; rich media) and transitioned to lipogenesis media (FM006; low N:C ratio). Samples were taken 72 hours after transition to lipogenesis medium and analyzed by GC-FAME.

| Strain/ Promoter | Transformant ID | ARA | EPA |
|---|---|---|---|
| — | 15311 | 20.14% | 0.63% |
| — | EO0106 | 21.92% | 0.45% |
| hsp90 | EO03C1 | 10.94% | 2.45% |
| Gln-syn | EO05C12 | 8.18% | 0.77% |
| | EO05C13 | 8.21% | 5.08% |
| | EO05C14 | 7.26% | 3.43% |
| | EO05C3 | 5.93% | 5.93% |
| | EO05C8 | 5.17% | 6.79% |
| | EO05C9 | 11.21% | 4.00% |
| actin | EO06C10 | 7.13% | 3.61% |
| | EO06C11 | 9.83% | 2.32% |

TABLE 23-continued

ARA and EPA contents (% TOC) of GH-15311 and chytrid transformants carrying a Δ17 desaturase gene placed under control of various promoters. Promoters used and transformant clone ID are indicated. Clone EO01C6 was a no promoter control. Cultures were grown in growth medium (FM2; rich media) and transitioned to lipogenesis media (FM006; low N:C ratio). Samples were taken 72 hours after transition to lipogenesis medium and analyzed by GC-FAME.

| Strain/ Promoter | Transformant ID | ARA | EPA |
|---|---|---|---|
| | EO06C4 | 9.68% | 0.17% |
| | EO06C5 | 0.15% | 9.35% |
| | EO06C6 | 1.70% | 11.97% |
| | EO06C7 | 0.70% | 8.06% |
| hsp70 | EO07C4 | 0.90% | 11.59% |
| | EO07C6 | 0.95% | 8.61% |
| | EO07JC1 | 1.05% | 8.39% |
| vac | EO08JC1 | 0.00% | 6.91% |
| | EO08JC2 | 0.84% | 8.59% |
| | EO08JC3 | 0.44% | 16.41% |
| | EO08JC4 | 12.91% | 1.96% |

TABLE 23-continued

ARA and EPA contents (% TOC) of GH-15311 and chytrid transformants carrying a Δ17 desaturase gene placed under control of various promoters. Promoters used and transformant clone ID are indicated. Clone EO01C6 was a no promoter control. Cultures were grown in growth medium (FM2; rich media) and transitioned to lipogenesis media (FM006; low N:C ratio). Samples were taken 72 hours after transition to lipogenesis medium and analyzed by GC-FAME.

| Strain/ Promoter | Transformant ID | ARA | EPA |
|---|---|---|---|
| | EO08JC6 | 6.31% | 3.29% |
| | EO08JC7 | 8.67,% | 0.35% |
| act depol | EO13C11 | 5.53% | 5.26% |
| | EO13C7 | 11.08% | 1.18% |
| | EO13C9 | 1.8.30% | 2.08% |
| | EO13JC1 | 16.24% | 5.47% |
| | EO13JC2 | 15.46% | 3.95% |
| | EO13JC3 | 6.29% | 4.50% |
| gpdp | EO14JC1 | 4.14% | 14.81% |
| | EO14JC3 | 9.76% | 8.80% |
| | EO14JC4 | 8.58% | 2.58% |
| | EO14JC6 | 2.17% | 7.31% |
| | EO14JC7 | 6.77% | 4.29% |

TABLE 23-continued

ARA and EPA contents (% TOC) of GH-15311 and chytrid transformants carrying a Δ17 desaturase gene placed under control of various promoters. Promoters used and transformant clone ID are indicated. Clone EO01C6 was a no promoter control. Cultures were grown in growth medium (FM2; rich media) and transitioned to lipogenesis media (FM006; low N:C ratio). Samples were taken 72 hours after transition to lipogenesis medium and analyzed by GC-FAME.

| Strain/ Promoter | Transformant ID | ARA | EPA |
|---|---|---|---|
| pfaA | EO27C4 | 2.78% | 8.04% |
| | EO27C6 | 11.22% | 8.86% |
| | EO27C8 | 1.11% | 8.86% |

As shown in Tables 22 and 23, it was observed that most of the ARA is converted to EPA in strains expressing Δ17 desaturase using promoter sequences corresponding to the Gpdp, Plat2, TEF, Hsp90, Hsp70, Vac, and PfaA genes. Most of the other promoter constructs resulted in some conversion of ARA to EPA indicating that they are active but likely not as strong. Under lipogenic conditions, the Plat2 promoter (SEQ ID NO:198) and the pfaA promoter (SEQ ID NO:191) demonstrated strong activity along with the previously assessed Nurp promoter (SEQ ID NO:182), Gpdp promoter (SEQ ID NO:183), and Msfp promoter (SEQ ID NO:186) which also demonstrated strong activity under lipogenic culture conditions.

While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

What is claimed is:

1. A nucleic acid construct comprising a nucleic acid sequence that comprises a polynucleotide having promoter activity, wherein the polynucleotide comprises at least 98% sequence identity to the nucleic acid sequence of SEQ ID NO: 63; wherein the polynucleotide is operably linked to a heterologous nucleic acid sequence.

2. The nucleic acid construct of claim 1, wherein the promoter is functional in a *Schizochytrium* or *Aurantiochytrium* cell.

3. The nucleic acid construct of claim 1, wherein said heterologous nucleic acid sequence encodes a polypeptide or a functional RNA.

4. The nucleic acid construct of claim 3, wherein said heterologous nucleic acid sequence encodes a functional RNA selected from the group consisting of a ribosomal RNA, a tRNA, a ribozyme, a transactivating (tr) RNA of a CRISPR system, a crispr (cr) RNA of a CRISPR system, a chimeric guide RNA of a CRISPR system, a micro RNA, an interfering RNA (RNAi) molecule, a short hairpin (sh) RNA, and an antisense RNA molecule.

5. The nucleic acid construct of claim 1, wherein said heterologous nucleic acid sequence is operably linked to a terminator.

6. The nucleic acid construct of claim 5, wherein the terminator comprises a sequence having at least 90% sequence identity to a sequence selected from the group consisting of SE ID NOs: 71-78.

7. The nucleic acid construct of claim 1, wherein the promoter is functional in a Labyrinthulomycetes cell.

8. The nucleic acid construct of claim 3, wherein said construct is an expression cassette or a vector.

9. The nucleic acid construct of claim 3, wherein the heterologous nucleic acid sequence encodes a transcription factor; a DNA binding protein; a splicing factor; a nuclease; a cas protein; a recombinase; a G protein; a nucleotide cyclase; a phosphodiesterase; a kinase; a polypeptide that participates in protein secretion; a polypeptide that participates in protein trafficking; a structural protein; a hormone; a cytokine; an antibody; a transporter; an enzyme having lipolytic activity; a thioesterase; an amidase; a lipase; a fatty acid synthase; a component of a fatty acid synthase complex; a pfaA polypeptide; a pfaB polypeptide; a pfaC polypeptide; a pfaD polypeptide; a pfaE polypeptide; an acyl-CoA synthetase; an acyl-ACP synthetase; an acyl carrier protein; an acyl-CoA carboxylase; an acyl transferase; an enzyme that participates in glycolysis; a dehydrogenase; an enzyme of the TCA cycle; a fatty acid desaturase; or a fatty acid elongase.

10. The nucleic acid construct of claim 3, wherein said heterologous nucleic acid sequence further comprises a selectable marker ene or a reporter gene.

11. The nucleic construct of claim 10, wherein said selectable marker gene is selected from the group consisting of a gene conferring resistance to an antibiotic; a gene conferring resistance to an herbicide; a gene encoding acetyl CoA carboxylase (ACCase); a gene encoding acetohydroxy acid synthase (ahas); a gene encoding acetolactate synthase; a gene encoding aminoglycoside phosphotransferase; a gene encoding anthranilate synthase; a gene encoding bromoxynil nitrilase; a gene encoding cytochrome P450-NADH-cytochrome P450 oxidoreductase; a gene encoding dalapon dehalogenase; a gene encoding dihydropteroate synthase; a gene encoding a class I 5-enolpyruvylshikimate-3-phosphate synthase (EPSPS); a gene encoding a class II EPSPS (aroA); a gene encoding a non-class I II EPSPS; a gene encoding glutathione reductase; a gene encoding glyphosate acetyltransferase; a gene encoding glyphosate oxidoreductase; a gene encoding hydroxyphenylpyruvate dehydrogenase; a gene encoding hydroxy-phenylpyruvate dioxygenase; a gene encoding isoprenyl pyrophosphate isomerase; a gene encoding lycopene cyclase; a gene encoding phosphinothricin acetyl transferase; a gene encoding phytoene desaturase; a gene encoding prenyl transferase; a gene encoding protoporphyrin oxidase; a gene encoding superoxide dismutase; a gene encoding arg7; a gene encoding his3; a gene encoding hisD; a gene encoding hisG; a gene encoding manA; a gene encoding nitl; a gene encoding trpB; a gene encoding uidA; a gene encoding xylA; a gene encoding a dihydrofolate reductase gene; a gene encoding a mannose-6-phosphate isomerase gene; a gene encoding a nitrate reductase gene; a gene encoding an ornithine decarboxylase gene; a gene encoding a thymidine kinase gene; a gene encoding a 2-deoxyglucose resistance gene; and a gene encoding an R-locus gene.

12. A method of transforming a eukaryotic cell, comprising:

(i) introducing into a eukaryotic cell the nucleic acid construct of claim 5; and (ii) selecting or screening for a transformed eukaryotic cell.

13. The method according to claim 12, wherein the nucleic acid construct is introduced by a biolistic procedure or electroporation.

14. A recombinant eukaryotic cell produced by the method of claim 12.

15. A recombinant cell comprising the nucleic acid construct of claim 1.

16. The recombinant cell of claim 15, wherein said nucleic acid construct is stably integrated into the genome of said recombinant cell.

17. The recombinant cell of claim 15, wherein the recombinant cell is a Labyrinthulomycetes cell.

18. The recombinant cell of claim 17, wherein said Labyrinthulomycetes cell is of a microorganism selected from the group consisting of an *Aplanochytrium*, an *Aurantiochytrium*, a *Diplophrys*, a *Japonochytrium*, an *Oblongichytrium*, a *Schizochytrium*, a *Thraustochytrium*, and an *Ulkenia* microorganism.

* * * * *

SEQUENCE LISTING

```
<160> NUMBER OF SEQ ID NOS: 204

<210> SEQ ID NO 1
<211> LENGTH: 1057
<212> TYPE: DNA
<213> ORGANISM: Aurantiochytrium sp.
<220> FEATURE:
<221> NAME/KEY: misc_feature
<223> OTHER INFORMATION: pSGI-JU-80-1
<220> FEATURE:
<221> NAME/KEY: misc_feature
<223> OTHER INFORMATION: SG1EUKS126945 Neighbor of BRCA1 gene 1 (NBR1);
      transcript variant 1 promoter; allele 1

<400> SEQUENCE: 1

ggttggattt ctcctttttg cgtcaaacca aaaggaaaag cgccttgcca agatcgggct     60

cgatgtagct gctgcgaaaa aggtgtctcg tgatgaggcc cttgctttcg aatatgaaat    120

tctcgcaaag ctttcgccga ccgaggttgc tattgcactc ctgaactatc gcatcaagcc    180

tggtaagctc ttgaagtctg gtcttggccg cctcgggtat acaatgaagc tcgctaagaa    240

ggcattcaag ggtggtcctt acggtgtgaa ggcccacaag aagatgatga agaaggccca    300

caaggcgcac aagaagatga aaggaggcaa gcatatgcgt cctgaccatc cttgggcaca    360

tgggcctggt gggcaccacg gtcatcatca cggtcgtcat ggactaggtg gtgggtttcg    420

aggtggtcgc cacggtggat tcggtggtca tgtacctttt gaaggtccag aaggtgcccc    480

ccgccacaga ggccccccacc acggaggccc ccaccacgga ggcccccacc acggaggccc    540
```

-continued

```
tcaccacgga ggccccccacc acggaggccc ccgccatgga ggccctcacc acggtggtcg    600

catgcatttt ggcggtggtc ctcttggtat gatgggtcac cctggctgcc ctcctcctcc    660

tccctttgag catcagcata gtgaagctcg catgcctgtg gatagtgaag tccacggagg    720

acctgctgct ggttttggtg gctgggcccc tcatatgggc cgtggcggtc gtggcggtcg    780

cggtcgcgcg ggctttggcg gacggggtgg acacatgttt catcccggtt ttatggctgg    840

ccctttttgct cctcctcccc cgaagaatca caatggggaa agcagcagtg acgatgaggg    900

cgagaacgag aagttttctg gcgctggcca ctttggtctg tctggacact ggggcggtat    960

gatgtggcat ggtggacatc atggacatca tggccgtggc cctcgtcacg ctcaccatgg   1020

aggacttggc tttggaggtg gtcctggccg ttgtcac                           1057
```

<210> SEQ ID NO 2
<211> LENGTH: 1000
<212> TYPE: DNA
<213> ORGANISM: Aurantiochytrium sp.
<220> FEATURE:
<221> NAME/KEY: misc_feature
<223> OTHER INFORMATION: pSGI-JU-80-6
<220> FEATURE:
<221> NAME/KEY: misc_feature
<223> OTHER INFORMATION: SG1EUKS126945 Neighbor of BRCA1 gene 1 (NBR1); transcript variant 1 promoter; allele 6

<400> SEQUENCE: 2

```
ggttggattt ctccttttttg cgtcaaacca aaaggaaaag cgccttgcca agatcgggct     60

cgatgtcgct gctgcgaaaa aggtgtctcg tgatgaggcc cttgctttcg aatatgaaat    120

tctcgcaaag ctttcgccga ccgaggttgc gattgcactc ctgaactatc gcatcaagcc    180

tggtaagctc atgaagtctg gtcttggccg cctcgggtat acaatgaagc tcgctaagaa    240

ggcattcaag ggtggtcctt acggtgtgaa ggcctacaag aagatgatga agaaggccca    300

caaggcgcac aagaagatga aaggaggcaa gcatatgcgt cctgaccatc cttgggcaca    360

tgggcctggt gggcaccacg gtcatcatca cgctcgtcat ggactaggtg gtgggtttcg    420

aggtggtcgc cacggtggat tcggtggtca tgtacctttt gaaggtccag aaggtgcccc    480

ccgccacgga ggccctcacc acggtggccc tcaccacggt ggccccccacc acggtggccc    540

ccgccacgga ggccctcacc acggtggccc tctaggtatg atgggtcacc ctggctgccc    600

tcctcctcct ccctttgagc atcagcatag tgaagctcgc atgcctgtgg atagtgaagt    660

ccacagagga cctgctgctg gttttggtgg ctgggcccct catatgggcc gtggcggtcg    720

tcgcggtcgc gcgggctttg gcggaccggg tgggcacatg tttcatcccg gttttatggc    780

tggccctttt gctcctcctc ccccgaagaa tcacaattgg gaaagcagca gtgacgatga    840

gggtgagaac gagaagtttt ctggcgctgg ccactttggt ctgcctggac actggggcgg    900

tatgatgtgg catggtggac atcatggaca tcatggccgt ggccctcgtc acgctcatca    960

tggaggacta ggctttggag gtggtcctgg ccgttgtcac                         1000
```

<210> SEQ ID NO 3
<211> LENGTH: 927
<212> TYPE: DNA
<213> ORGANISM: Aurantiochytrium sp.
<220> FEATURE:
<221> NAME/KEY: misc_feature
<223> OTHER INFORMATION: pSGI-JU-81-3
<220> FEATURE:
<221> NAME/KEY: misc_feature
<223> OTHER INFORMATION: SG1EUKS110153 Eft2p GTpase translation elongation factor 2 (EF-2) promoter; allele 3

<400> SEQUENCE: 3
gttagcgcag acctagctgt atcgcctatc tggcctaggc cccctccgcc cagcattcct 60
ttctttctct ctctttcgcc tccactcatt cacgcccttt cttctccagc agaccccttt 120
ggcgatattg tcgaggtagg tgcttcatca tcatccgagg gcgacgcgcg gaggcgggcg 180
gggcgggcgg ccaggcgctg ctcgggcgca ggcactacgc tgcacgcaca tctagacctg 240
cagcggcggg ctgcaatccg cggtctacag gacaggtgcg gcagcatgga gctcattccc 300
gctcgcatgt ggccagtctg ccaaccaacc aaccaccttc tctcctctcc catacataga 360
catacatggc gaggccaatg cacatgcgtg cggaaggccg agggcaggag ggaagcggat 420
agcgaggagc agacaggaca ccgcgaggag tagcggcagc cgtgtatcat ccatcacctg 480
ggaagtggag cagagaccag attcgattga accattggtt aaaagagaag ttttcttttt 540
cttttctttt tgctgcttgc tgtatccatc tggctaaggc tctgctaccc agttgactag 600
gagtatatgg atttctctac tttctctggg agactatctt tccgtttgct tctttggagt 660
ggtctttctg cctcttctct ccccgaatgc ccaataggct caaacgtatg caaacaaaca 720
tgtcatggtg gagacgagga ggaagggaga gaacattcgc cttgcgcgcc catttttgtt 780
tgaaggattt gatttgaaga atggtcaact aactgtatac tttgtgaaca aattgcgtct 840
ttgatattga taacaacagg gattttgtac cggaaccgca gcggatttag tagttgagcc 900
cctcggctct acaaatcgca aagcaag 927

<210> SEQ ID NO 4
<211> LENGTH: 924
<212> TYPE: DNA
<213> ORGANISM: Aurantiochytrium sp.
<220> FEATURE:
<221> NAME/KEY: misc_feature
<223> OTHER INFORMATION: pSGI-JU-81-8
<220> FEATURE:
<221> NAME/KEY: misc_feature
<223> OTHER INFORMATION: SG1EUKS110153 Eft2p GTpase translation
elongation factor 2 (EF-2) promoter; allele 8

<400> SEQUENCE: 4
gttagcgcag acctagctgt atcccctatc tggcctaggc cccctccgcc cagcattcct 60
ttctttctct ctctttcgcc tccactcatt cacgcccttt cttctccagc agaccccttt 120
ggcgatattg tcgaggtagg tgcttcatca tcatccgagg gcgacgcgcg gaggcgggcg 180
gggcgggcgg ccaggcgctg ctcgggcgca ggcactacgc tgcacgcaca tctagacctg 240
cagcggcggg ctgcaatccg cggtctacag gacaggtgcg gcagcatgga gcttattccc 300
gctcgcatgt ggccagtctg ccaaccaacc aaccaccttc tctcctctct catacataga 360
catacatggc gaggccaatg cacatgcgtg cggaaggccg agggcaggag ggaagcggat 420
agtgaggagc atacaggaca ccgcgaggag tagcggcagc cgtgtatcat ccatcacctg 480
ggaagtggag cagaaaccag attcgattga accattggtt aaaagagaag ttttcttttt 540
cttttctttt tactgcttgc tgtatccatc tggttaagac tctgctaccc agttgaatag 600
gagtacatgg atttctctac tttctctggg agactatctt tccgtttgct tctttggagt 660
ggtctttctg cctcttctct ccccgaatgc ccaataggct caaacgtatg caaacatgtc 720
atggtggaga ggaggaggaa gggagagaac attcgccttg cgcgcccatt tttgtttgaa 780
cgatttgatt tgaagaatgg tcaactaact gtatactttg tgaacaaatt gtgtctttga 840
tattgataac aacagggatt ttgtaccgga accgcagcgg atttagtagt ttgagcccct 900

```
cggctctaca aatcgcaaag caag                                          924


<210> SEQ ID NO 5
<211> LENGTH: 655
<212> TYPE: DNA
<213> ORGANISM: Aurantiochytrium sp.
<220> FEATURE:
<221> NAME/KEY: misc_feature
<223> OTHER INFORMATION: pSGI-JU-82-2
<220> FEATURE:
<221> NAME/KEY: misc_feature
<223> OTHER INFORMATION: SG1EUKS117138 40S ribosomal protein S3a
      promoter; allele 2

<400> SEQUENCE: 5

gcgaacgcca taatcagcgg tcttgccacc gacctccctc cacatccttg tttatctaat     60

gccgcagcaa tataggttct ctctaacact taaccatggc caccagttcc tctcatgaag    120

cgctttgata cctgcgcaac gctttttcag cctggctgct tccacagaat ctccttaatt    180

accctgtcta aacctcatta acctccttat attttaaggt gagtcaaatc tgcacaactc    240

cttttcagtc tacttaatca cctccttcat ttccctttac gcagtatcta ttaaggcggt    300

tctcccctca aactagggtt taaccctagg cggaacgcag ctgaccttcg gcgcagatgc    360

gcgcctaaat gagagtgcgg attttgcctt tttgtattta atatgagctg cggatggcct    420

tgcaagcagg gcgtaaatgg gtggaggaaa gaaaggagtg gaggggcgcg gccactagct    480

agaggtatct gactcttatg agcgctgggc gagcggcggg gcatgtaggt gtgttctaag    540

ggtctattag aggtaacgcg gggaatggtg caggggcggc gaggaagagc agacgggcat    600

ccttcaattc aattcgggtt ggttgacgtg caggacttgc gcgaagtagg caacc         655


<210> SEQ ID NO 6
<211> LENGTH: 655
<212> TYPE: DNA
<213> ORGANISM: Aurantiochytrium sp.
<220> FEATURE:
<221> NAME/KEY: misc_feature
<223> OTHER INFORMATION: pSGI-JU-82-5
<220> FEATURE:
<221> NAME/KEY: misc_feature
<223> OTHER INFORMATION: SG1EUKS117138 40S ribosomal protein S3a
      promoter; allele 5

<400> SEQUENCE: 6

gcgaacgcca taatcagcgg tcttgccacc gacctccctc cacatccttg tttatctaat     60

gccgcagcaa tataggttct ctctaacact taaccatggc caccagttcc tctcatgaag    120

cgctttgata cctgcgcaac gctttttcag cctggctgct tccacagaat ctccttaatt    180

accctgtcta aacctcatta acctccttat attttaaggt gagtcaaatc tgcacaactc    240

cttttcagtc tacttaatca cctccttcat ttccctttac gcagtatcta ttaaggcggt    300

tctcccctca aactagggtt taaccctagg cggaacgcag ctgaccttcg gcgcagatgc    360

gcgcctaaat gagagtgcgg attttgcctt tttgtattta atatgagctg cggatggcct    420

tgcaagcagg gcgtaaatgg gtggaggaaa gaaaggagtg gaggggcgcg gccactagct    480

agaggtatct gactcttatg agcgctgggc gagcggcggg gcatgtaggt gtgttctaag    540

ggtctattag aggtaacgcg gggaatggtg caggggcggc gaggaagagc agacgggcat    600

ccttcaattc aattcgggtt ggttgacgtg caggacttgc gcgaagtagg caacc         655


<210> SEQ ID NO 7
```

-continued

```
<211> LENGTH: 1000
<212> TYPE: DNA
<213> ORGANISM: Aurantiochytrium sp.
<220> FEATURE:
<221> NAME/KEY: misc_feature
<223> OTHER INFORMATION: pSGI-JU-83-1
<220> FEATURE:
<221> NAME/KEY: misc_feature
<223> OTHER INFORMATION: SG1EUKS124238 Eukaryotic translation initiation
      factor 5A isoform IV promoter; allele 1

<400> SEQUENCE: 7

ccgcgcaaaa ccgccttaat caccctcctt gaggcggagg ttggcgatta aggtggcttt     60

caatcagatg caccttaata tacctaccac cggccgcggt tgtccatata agaaggaggg    120

ctttttctg cacgaccagg caggattaag gtgcactttc gccgccacac aaacatgtat    180

tcttcttttc agggcgcctc atcacgagca gactcacatc caccaggttc atcaggtacg    240

tgcgacgacg agctcgcttg ggcggggcgt gcggctcccc tggcggcgct gtgcggcctc    300

gtggtcgtgc atattcttac gttctggggc tcgcggcttt ctgtccctgc cgtgcggtcg    360

cttcatgggc gggatgccgc atggagacga ggcggcctca gcttctttgc ttgtctctct    420

gtttgtctct ctttctttct aaatcagtta gctgtctgtg gtctgtgagc ttgcggcttt    480

gctactctct cgacgggtag cactatggaa ccagcactgg ctagcagaga ccggtcacgt    540

ggctcgcggc gcccgatcct ggagcgtgtc ggaagttctc tggatcgagt gattgattaa    600

cttatttatt aatcacgctg gtttctcttc ttctcttcct ctctctttta ttgtcagttt    660

cttctctttc ttctcctgat tgatacggag tattgatcag gtgctgccct gttcaatgaa    720

gaggatatcg agggagtaat gatggaggaa tgacgaaggg atgattgaag aatccggaga    780

gtgccggcac agtctctgca tagtaggaga atgatcttgg aaaggaacga ggacagaacc    840

aaaacggaag gagaacgtgc aggcaaggcg agtatatatg caagggaggt gtttatatta    900

tctatcacat gaaaatgaca agaaactaac cgtgaagttc attgattttt gcgaacaaaa    960

cagatttacg tagatcgtcg agtcccaaaa cttatcaaaa                         1000


<210> SEQ ID NO 8
<211> LENGTH: 1004
<212> TYPE: DNA
<213> ORGANISM: Aurantiochytrium sp.
<220> FEATURE:
<221> NAME/KEY: misc_feature
<223> OTHER INFORMATION: pSGI-JU-83-2
<220> FEATURE:
<221> NAME/KEY: misc_feature
<223> OTHER INFORMATION: SG1EUKS124238 Eukaryotic translation initiation
      factor 5A isoform IV promoter; allele 2

<400> SEQUENCE: 8

ccgcgcaaaa ccgccttaat caccctcctt gaggcggagg ttggcgatta aggtggcttt     60

taatcagacg caccttaata tacctaccac cggccgcggt tggccatata agaaggaggg    120

ctttttctg cacgaccagg caggattaag gtgcactttc gccgccacac aaacatgtat    180

tcttcttttc agggcgcctc atctcgagca gactcacatc caccaggttc atcaggtacg    240

tgcgacgacg agctcgcttg ggcggggcgt gcggctcccc tggcggcgct gtgcggcctc    300

gtggtcgtgc atattcttac gttctggggc tcgcggcttt ctggccctgc cgtgcggtcg    360

cttcatgggc gggatgccgc atggagacga ggcggcctca gcttctttgc ttgtctctct    420

gttcgtcgct ctctttcatt ctaaatcagt tagctgtctg tggtctgcga gcttgcggct    480

ttgctactct cttgacgggt agcactatgg aaccagcact ggctagcaga gaccggtcac    540
```

```
gtggctcgcg gcgcccgatc ctggagcgtg tcgggaggtt ctgtggatcg agtgattgat    600

tgacttttt tattaatcac gctggtttct cttcttctct tcctctctct tttattgtca    660

gtttcctctc tttcttctcc tgattgatac ggagtattga tcaggtgctg ccctgtgcga    720

tgaagaggat atcgagggag taacgatgga ggaatgacga agggaggatt gaagaatccg    780

gggagtgccg gcacagtctc tgcagagtag gagaatgatc ttggaaagga acgaggacag    840

aaccaaaacg gaaggagaac gtgcaggcga ggcgaatata tatgcaaggg aggtgtttat    900

attatctatc acatgaaaat gacaagaaac taaccgtgaa gttcattgat ttttgcgaac    960

aaaacagatt taagtagatc gtcgagtccc aaaacttatc aaaa                   1004

<210> SEQ ID NO 9
<211> LENGTH: 860
<212> TYPE: DNA
<213> ORGANISM: Aurantiochytrium sp.
<220> FEATURE:
<221> NAME/KEY: misc_feature
<223> OTHER INFORMATION: pSGI-JU-84-1
<220> FEATURE:
<221> NAME/KEY: misc_feature
<223> OTHER INFORMATION: SG1EUKS121571; 60S ribosomal protein L9;
      Conserved protein promoter; allele 1

<400> SEQUENCE: 9

tcccttttag ccaatttgca tatcttctac taccttctcg ctatgaccta acgaggaaac     60

catcagactc tcagaacaac ccatttattg aggagaaagt caactctcac tccttctact    120

acttgtacta aaatgtaagg cacgtatcat ctcaggtacc tacagtctgt atgtattatg    180

aaacaatgta gttgcctacc tacccattag ttctatgatg ccagaattcg tgccggctgt    240

tcacttcggc tcttggtcct ttctctgaga tagcctcttc acctggcaac ttctacacat    300

ccattcacag ctccaaacag aaagaccctc gctcctcgtg tgcatgagtt ggtcacattc    360

aatacctcat cctcaatcaa tcaatcaatc aatcaatcaa tcaatcaatc aatcaatcaa    420

tcaatcaatc aatcaatcaa tcaatcaatc aatcaatcaa tcaatcaatc aatcaatcaa    480

tcaatcaaat tatcagttat acagctccac aatagactat accgccgcac agccttctct    540

acagtaaagt attcaccttt acaatagagc aaacccatag ccaaagccgc ctttaaaccc    600

aagctcttta gatggcccct gtccaaccag attcccaaac attccccctg ttcccccata    660

tgtgccgagt tgattcgctt tcgggcgcgg tgtttgggag aggggttagg gtgaattagt    720

tacggcgcat tggggcgccg aagagttgtc tggctgcgca agaggggggg caggaaggga    780

gagcagagaa gggcgcgatt ggcggcggca gaccacaaga gcttggctag gcttggaaag    840

cgtgcagcgc gacaggcaag                                               860

<210> SEQ ID NO 10
<211> LENGTH: 864
<212> TYPE: DNA
<213> ORGANISM: Aurantiochytrium sp.
<220> FEATURE:
<221> NAME/KEY: misc_feature
<223> OTHER INFORMATION: pSGI-JU-84-6
<220> FEATURE:
<221> NAME/KEY: misc_feature
<223> OTHER INFORMATION: SG1EUKS121571; 60S ribosomal protein L9;
      Conserved protein promoter; allele 6

<400> SEQUENCE: 10

tcccttttag ccaatttgca tatcttctac taccttctcg ctatgaccta acgaggaaac     60
```

-continued

```
catcagactc tcagaacaac ccatttattg aggagaaagt caactctcac tccttctact    120

acttgtacta aaatgtaagg cacgtatcat ctcaggtacc tacagtctgt atgtattatg    180

aaacaatgta gttgcctacc tacccattag ttctatgatg ccagaattcg tgccggctgt    240

tcacttcggc tcttggtcct ttctctgaga tagcctcttc acctggcaac ttctacacat    300

ccattcacag ctccaaacag aaagaccctc gctcctcgtg tgcatgagtt ggtcacattc    360

aatacctcat cctcaatcaa tcaatcaatc aatcaatcaa tcaatcaatc aatcaatcaa    420

tcaatcaatc aatcaatcaa tcaatcaatc aatcaatcaa tcaatcaatc aatcaatcaa    480

tcaatcaatc aaattatcag ttatacagct ccacaataga ctataccgcc gcacagcctt    540

ctctacagta aagtattcac ctttacaata gagcaaaccc atagccaaag ccgcctttaa    600

acccaagctc tttagatggc cctgtccaa ccagattccc aaacattccc cctgttcccc    660

catatgtgcc gagttgattc gctttcgggc gcggtgtttg ggagaggggt tagggtgaat    720

tagttacggc gcattggggc gccgaagagt tgtctggctg cgcaagaggg ggggcaggaa    780

gggagagcag agaagggcgc gattggcggc ggcagaccac aagagcttgg ctaggcttgg    840

aaagcgtgca gcgcgacagg caag                                            864


<210> SEQ ID NO 11
<211> LENGTH: 492
<212> TYPE: DNA
<213> ORGANISM: Aurantiochytrium sp.
<220> FEATURE:
<221> NAME/KEY: misc_feature
<223> OTHER INFORMATION: pSGI-JU-85-3
<220> FEATURE:
<221> NAME/KEY: misc_feature
<223> OTHER INFORMATION: SG1EUKS120942; Actin A (complement of
      Actin-1/3) promoter; allele 3

<400> SEQUENCE: 11

ggtgtcctca ccctcaagta ccccattgag cacggtatcg tgaccaactg ggacgacatg     60

gagaagatct ggcaccacac cttctacaac gagctccgcg ttgcccccga ggagcacccc    120

gttctcctca ccgaggcccc cctcaacccc aaggccaacc gtgagcgcat gacccagatc    180

atgttcgaga ccttcaacgt gcccgccatg tacgtcaaca tccaggccgt tctctccctc    240

tacgcctctg gtcgtaccac cggtgccgtc ctcgactctg gtgatggtgt cacccacacc    300

gtccccatct acgagggtta cgctctcccg cacgccgttc tccgtatcga tcttgccggc    360

cgtgacctca ccgactacat gatgaagatc ctcaccgagc gtggctactc cttcaccacc    420

accgccgagc gcgaaattgt tcgtgacatc aaggagaagc tcgcctacgt cgcccaggac    480

ttcgacgagg ag                                                        492


<210> SEQ ID NO 12
<211> LENGTH: 492
<212> TYPE: DNA
<213> ORGANISM: Aurantiochytrium sp.
<220> FEATURE:
<221> NAME/KEY: misc_feature
<223> OTHER INFORMATION: pSGI-JU-85-6
<220> FEATURE:
<221> NAME/KEY: misc_feature
<223> OTHER INFORMATION: SG1EUKS120942; Actin A (complement of
      Actin-1/3) promoter; allele 6

<400> SEQUENCE: 12

ggtgtcctca ccctcaagta ccccattgag cacggtatcg tgaccaactg ggacgacatg     60

gagaagatct ggcaccacac cttctacaac gagctccgcg tcgcccccga ggagcacccc    120
```

gttctcctca ccgaggcccc cctcaacccg aaggccaacc gtgagcgcat gacccagatc 180
atgttcgaga ccttcaacgt gcccgccatg tacgtcaaca tccaggctgt tctctccctc 240
tacgcctctg gtcgtaccac cggtgccgtc ctcgactctg gtgatggtgt cacccacacc 300
gtccccatct acgagggtta cgctctcccg cacgccgttc tccgtatcga tcttgccggc 360
cgtgacctca ccgactacat gatgaagatc ctcaccgagc gtggctactc cttcaccacc 420
accgccgagc gcgagattgt ccgtgacatc aaggagaagc ttgcctacgt cgcccaggac 480
ttcgacgagg ag 492

<210> SEQ ID NO 13
<211> LENGTH: 492
<212> TYPE: DNA
<213> ORGANISM: Aurantiochytrium sp.
<220> FEATURE:
<221> NAME/KEY: misc_feature
<223> OTHER INFORMATION: pSGI-JU-85-8
<220> FEATURE:
<221> NAME/KEY: misc_feature
<223> OTHER INFORMATION: SG1EUKS120942; Actin A (complement of Actin-1/3) promoter; allele 8

<400> SEQUENCE: 13
ggtgtcctca ccctcaagta ccccattgag cacggtatcg tgaccaactg ggacgacatg 60
gagaagatct ggcaccacac cttctacaac gagctccgcg tcgcccccga ggagcacccc 120
gttctcctca ccgaggcccc cctcaacccg aaggccaacc gtgagcgcat gacccagatc 180
atgttcgaga ccttcaacgt gcccgccatg tacgtcaaca tccaggctgt tctctccctc 240
tacgcctctg gtcgtaccac cggtgccgtc ctcgactctg gtgatggtgt cacccacacc 300
gtccccatct acgagggata cgctctcccg cacgccgttc tccgtatcga tcttgccggc 360
cgtgacctca ccgactacat gatgaagatc ctcaccgagc gtggctactc cttcaccacc 420
accgccgagc gcgaaattgt ccgtgacatc aaggagaagc tcgcctacgt cgcccaggac 480
ttcgacgagg ag 492

<210> SEQ ID NO 14
<211> LENGTH: 1000
<212> TYPE: DNA
<213> ORGANISM: Aurantiochytrium sp.
<220> FEATURE:
<221> NAME/KEY: misc_feature
<223> OTHER INFORMATION: pSGI-JU-86
<220> FEATURE:
<221> NAME/KEY: misc_feature
<223> OTHER INFORMATION: SG1EUKS101561; Heat shock protein 70 promoter

<400> SEQUENCE: 14
tcaatgtcca tcatattatc attacgagtc atgggttcta ctgagtgcta tgcagctgct 60
aggaggtaga aggtgcctaa gcgttgctaa gggagagcgc gaaatgaaga attcttttaa 120
ctcggatcgc tttctgcgaa aagggtcgtt cgtttggatt taaaagaggc actgctaggg 180
ataagggtag gaggcccttt agggtggggg agagtcatcg acatgtgcgg ccctcgttgg 240
cccttattag ttaagggaga ataatcgatg atttgttgat tgattgattg attgattgat 300
tgatttgttg atttgttgat ttgttgattt gttgatttgt tgattgattg atcacagcgc 360
aatcgatgaa tgaatgagtg atgaagagtg aatagtgatg gaatgaatga tcgatgtgat 420
gatacatacc gaagagaaaa gaaagaagaa aaggatgcgt atctacagtt agctagctag 480
ttggttagct agtgtttagt tagaaggagg aaacagcttc gatgaaaaga gaggtcgatg 540

```
cactagaggg catatagagg taacagtagg agtggcggcg atactgtgaa agcaggtgct    600

gtgaatagtg agtgagtgat ggtttatgtt tgtttgaaga agtgttctcg atcaatgaat    660

gaatgagtga atgaatgaaa gagaaagaaa caacaaagaa agaaggaaag aaaggaagaa    720

gagatataca tatgtatgta tatgtatgta tgtatgtata ggtatgtata ggtatgtagg    780

ataaacagaa agagaagcaa agctccaacg tgttctagac gtcgagcgag tctgctgtct    840

ccgcttgcgt ctgcactggg ttgttgaaag accctctttg ttgagattct tttgccactc    900

gctcctgttg tgacctgacc gcggtcgctt cgcttcttct cgctcgctag ctcgtcgtcg    960

gtaggcaagt aagtagattc atcaagtaat ctagagcatc                          1000
```

```
<210> SEQ ID NO 15
<211> LENGTH: 1031
<212> TYPE: DNA
<213> ORGANISM: Aurantiochytrium sp.
<220> FEATURE:
<221> NAME/KEY: misc_feature
<223> OTHER INFORMATION: pSGI-JU-87-4
<220> FEATURE:
<221> NAME/KEY: misc_feature
<223> OTHER INFORMATION: SG1EUKS142913; Translation elongation factor
      1-alpha promoter; allele 4

<400> SEQUENCE: 15

acgaggagcg aaggtaggtg accaccgacg actacgacca cgaccacgac cacagccacg     60

gcggctgcag ccacgggacg cctcgcatgg cagcgcatca gcaccagcaa cgacagctgc    120

gaggagcgca gggccgatct ggacgcgccg gagccgcacg accaatgccg acgcaacgct    180

gattcttctg gattacctct acacatgcat atatgtgtag aggtgcggat gaaatgccct    240

gcgaataaat gaatggcttc gagtttgcct gccgtatgct cgaaagtgcg tgtgcagaca    300

caggcacgac cgagaggaca acagtctgtg cttacctcac cagcacattc ttgcaacgcc    360

atacgaagca cgcgaaatct tgtggctcag agaggaaggc attcgtgtac gggaacgtgg    420

ggaacgctat caatttggaa ttcaaaatga gtgaaccaga caactaactg tgacttgaac    480

tgttgctcca cgcatcaaaa ccaaaccctt aacagaagta gaccagttcg aagctactag    540

caccaaacaa aatgggcaag acgaaggagc acgtcaacct tgtcgtcatc ggccacgtcg    600

atgccggcaa gtccaccacc accggccact tgatctacaa gtgcggtggt atcgacaagc    660

gtaccatcga gaagttcgag aaggaggccg ccgagctcgg taagggttcc ttcaagtacg    720

catgggttct tgacaagctc aaggccgagc gtgagcgtgg tatcaccatc gatatcgctc    780

tctggaagtt cgagtccccc aagttcgact tcaccgtcat cgatgccccc ggtcaccgtg    840

atttcatcaa gaacatgatt accggtacct cccaggccga tgttgccgtt ctcgtcattg    900

actcttccca gggtggtttc gaggccggta tcgccaagga tggccagacc cgtgagcacg    960

ctctcctcgc cttcaccctc ggtatccagc agatcatcgt cgccgtcaac aagatggacg   1020

acaagaccac c                                                        1031
```

```
<210> SEQ ID NO 16
<211> LENGTH: 1026
<212> TYPE: DNA
<213> ORGANISM: Aurantiochytrium sp.
<220> FEATURE:
<221> NAME/KEY: misc_feature
<223> OTHER INFORMATION: pSGI-JU-87-7
<220> FEATURE:
<221> NAME/KEY: misc_feature
<223> OTHER INFORMATION: SG1EUKS142913; Translation elongation factor
```

1-alpha promoter; allele 7

<400> SEQUENCE: 16
acgaggagcg aaggtaggtg accaccgacg accacgacca cgaccacagc cacggcggct 60
gcagccacgg gacgcctcgc atggcagcgc agcagcacca gcaacgacag ctgcgaggag 120
cgcagggccg atctggatgc gccggagccg aacgaccaat gccgaagcaa cgctgattct 180
tctggattcg ctctatatat gcatatatgt gtagaggagc ggatgaaatg gcctgcgaat 240
aaatgaatgg cttggagttt gcttgccgta tgctcaaaag tgcgtgtgca gacacaggca 300
cgaccgagcg gacaacagtc tgtgcttacc tcaccagcac attcttgcaa cgccatacaa 360
agcacgcgaa atcttgtagc tcagagcgaa aggcattcgt ggtacgggaa tgtggggaac 420
actatcaaat tggaattcag aatgagtgaa ccagacaact aactgtgact tgaactgttg 480
ctccacgcat caaaaccaaa cccttaacag aagtagacca gttcgaagct actagcacca 540
aacaaaatgg gcaagacgaa ggagcacgtc aaccttgtcg tcatcggcca cgtcgatgcc 600
ggcaagtcca ccaccaccgg ccacttgatc tacaagtgcg gtggtatcga caagcgtacc 660
atcgagaagt tcgagaagga ggccgccgag ctcggtaagg gttccttcaa gtacgcatgg 720
gttcttgaca agctcaaggc cgagcgtgag cgtggtatca ccatcgatat cgctctctgg 780
aagttcgagt cccccaagtt cgacttcacc gtcatcgatg cccccggtca ccgtgatttc 840
atcaagaaca tgattaccgg tacctcccag gccgatgtcg ccgttctcgt tattgactct 900
tcccagggtg gtttcgaggc cggtatcgcc aaggatggcc agacccgtga gcacgctctt 960
ctcgccttca ccctcggtat ccagcagatc atcgtcgccg tcaacaagat ggacgacaag 1020
accacc 1026

<210> SEQ ID NO 17
<211> LENGTH: 1000
<212> TYPE: DNA
<213> ORGANISM: Aurantiochytrium sp.
<220> FEATURE:
<221> NAME/KEY: misc_feature
<223> OTHER INFORMATION: pSGI-JU-88-5
<220> FEATURE:
<221> NAME/KEY: misc_feature
<223> OTHER INFORMATION: SG1EUKS123094; 60S ribosomal protein L26
promoter; allele 5

<400> SEQUENCE: 17
agcagcttca agccatcatc acatcatgcg ggaagttggg acatgctcta cgcggccatc 60
tgccaacgaa gacgtgcaaa cttcgaaaca gagctctggc acccccgcca aacgaaccaa 120
agcaaaatcg ccgtgagcct tggcataccc aagtatcgag ttaatgcaaa gcccgtcaag 180
ccaagctcac tgcactccga agcaagtctt tctactgaaa cgatgtgttc cctgtctaca 240
agtcgagcat agaacacaca gcccagcctc cagtacaagc cgtgtctaca tccatcgcag 300
acatttcgtc aaaccttcct gaaagagctg caacgcacac acagacagag acagagacag 360
agacagagac acacccttga ttccacatgg aagccatcgt tcacgccatt ccttaatctc 420
tcctccaaag gttcattgaa ggacaggagg gaaataaatc tcatgtaatt ccaaagtcca 480
tttcatacca tccatcggcc tagcctgaac caattcctga tcaaacacca ccattcgaaa 540
gcctcaattt ttctcttcgt ctcgaggccc tcccagcctc tttcgaaacc gttgagaccg 600
tcttctacgc atcgtcgcac gcgtcctgcc gctcccttct gctctcacca gtcccacttg 660
ccgccctctg cgccccctct ccccttgttc cctctgttac ctctgttccc ccatagcttt 720

```
cctcctccgt gcgtctcgca cacgcactcg attattattt aggtaccccc tagggttagg    780

tttccacgga atcgaaggcg atatttatat ggggatagag gggggcgggg caggaagggg    840

ggcatgaaag gatatggctc accgccatcg gcgccaccca agcgcgggaa gaggaagggg    900

gtagagtggg agaaggcgcg aagggcggcg gcggcgtgaa tagacaggaa acaaacggag    960

accaaggcag ccgtcagcgc agcacaagct cccgcgcacg                         1000


<210> SEQ ID NO 18
<211> LENGTH: 996
<212> TYPE: DNA
<213> ORGANISM: Aurantiochytrium sp.
<220> FEATURE:
<221> NAME/KEY: misc_feature
<223> OTHER INFORMATION: pSGI-JU-88-7
<220> FEATURE:
<221> NAME/KEY: misc_feature
<223> OTHER INFORMATION: SG1EUKS123094; 60S ribosomal protein L26
      promoter; allele 7

<400> SEQUENCE: 18

agcagcttca agccatcatc acatcatgcg ggaagttggg acatgctcta cgcggccatc     60

tgccaacgaa gacgtgcaaa cttcgaaaca gagctctggc acccccgcca aacgaaccaa    120

agcaaaatcg ccgtgagcct tggcataccc aagtatcgag ttaatgcaaa gcccgtcaag    180

gcaagctcac tgcactccga agcaagtctt tctactgaaa cgatgtgttc cctgtctaca    240

agtcgagcat agaacacaca gcccatcctc cagtacaagc cgtgtctaca tccatcgcag    300

acatttcgtc aaaccttcct gaaagagctg caacgcacac acacagacag agacagagac    360

agagacacac gcttgattcc acatggatgc catcgttcac gccattcctt aatctctcct    420

ccaaaggttc attgaaggac aggagggaaa taaatctcat gtaattccaa agtccatttc    480

ataccatcca tcagcctagc ctgaaccaat tcctgatcaa acaccaccat tcgaaagcct    540

caatttttct cttcgtctca aggccctccc agcctctttc gaaaccgttg agaccgtctt    600

ctacgcatca tcgcacgcgt cctgccgctc ccttctgctc tcaccagtcc cacttgccgc    660

cctctgcgcc ccctctcccc ttgttccctc cgttacctaa gttcccccgt agctttcctc    720

ctccgtgcgt ctcgcacacg cactcgatta ttattcaggt actccctagg gttaggtttc    780

cacggaattg aaggcgacat ttatatgggg atagaggggg gcggggcagg aaggggggca    840

tgaaaggata tggctcaccg ccatcggcgc cacccaagcg cgggaagagg aagggggtag    900

agtgggagaa ggcgcgaagg gcggcggcgg cgtgaataga caggaaacaa acggagacca    960

aggcagccgt cagcgcagca caagctcccg cgcacg                              996


<210> SEQ ID NO 19
<211> LENGTH: 1002
<212> TYPE: DNA
<213> ORGANISM: Aurantiochytrium sp.
<220> FEATURE:
<221> NAME/KEY: misc_feature
<223> OTHER INFORMATION: pSGI-JU-89-1
<220> FEATURE:
<221> NAME/KEY: misc_feature
<223> OTHER INFORMATION: SG1EUKS109854; Tubulin alpha chain promoter;
      allele 1

<400> SEQUENCE: 19

ggagggaggc atgaaaacaa agttgttaaa actgaacgag gcgaaagaaa gcgccggagc     60

aatggaagac acaatatgag tagtaggtag caggtcccta cagccagcca ctcaatcata    120

cgagaagtct gcgcaggggt gctagtattt tatagtatct ggatgctagg aggcaagact    180
```

-continued

```
tcttttgcct gtctgtttgt ctatctggct acccctattg tatcttatat cccaaacact    240

agggctccct cacctgcaac agtcagtcac tcacgcattc agtatatact aaggctcacc    300

tagactaatc cataagcagc caatccgttc cgcgctcgcg ccggtagaag caaccggacc    360

atacggaggt cttagtgttt aggttatatg ggctatgtct tatcggtggg ccgttataca    420

cgccgcgctg gaagctcctc tactttgtga ggagtttcac ttataatgta tgatcgggat    480

tcctgttccc ctcccatcca ctgggtgcaa aattcaactc cctcacaaaa agtgcattat    540

ataaatatat gtaaaggcaa cggtcgctac ctctaagtac actgaggata taaacaagag    600

caagatggaa gttttcagta tttgttgtga ggaacaccac tggaggccaa aacaggcctc    660

ttagagggtt ctccactggc aagcctcgac ggtttggcgc agagtgaggg cagcaaactt    720

tgccgcatcg cagcaaatct caatcagcct tttgacggtc gtgcctaaca acacgccgtt    780

caccccaagc cttactttgc cttcgtgcat tgtcctcgag tatcgtaagt ttgattcgct    840

ttcattcgct tccatccact ccggttgtag caaaagcaaa gcagcgttgt gcggctctct    900

caaggtttgg ccctgatgcg atcgaagagc ataaactaac tagcctccgt cttggtttcg    960

tttcacagtt aagtagtttt cgaaactcca acctcaagca aa                      1002
```

```
<210> SEQ ID NO 20
<211> LENGTH: 997
<212> TYPE: DNA
<213> ORGANISM: Aurantiochytrium sp.
<220> FEATURE:
<221> NAME/KEY: misc_feature
<223> OTHER INFORMATION: pSGI-JU-89-6
<220> FEATURE:
<221> NAME/KEY: misc_feature
<223> OTHER INFORMATION: SG1EUKS109854; Tubulin alpha chain promoter;
      allele 6

<400> SEQUENCE: 20
```

```
ggagggaggc atgaaaacaa agttgttaaa actaaacgag gcgaaagaaa gcggcggagc     60

aatggtagac acaatatgag taggtagcag gtccctacag ccagccactc aatcatacga    120

ggagtctatg caggggtgct agtattttat agtatctgga tgctaagagg cacgacttct    180

tccgcctgtc tgtttgtcta tctggctacc cctattgtat cttatatcct aaacactagg    240

gctccctcac cagcaacagt cagtcactca cgcattcagt ttatactaag gctcacctag    300

actaatccat aagcagccaa tccgttccgc gctcgcgccg gtagaagcaa ccggaccata    360

cggaggtctt aatgtttagg ttatatggac tatgtcttat cggtgggccg ttatacacgc    420

cgcgctggaa gctcctctac tttgtgagga gtttcactta taatgaatga tcgggattcc    480

tgttcccctc ccatccactg ggtgcaaaac tcaactccct cacaaaaagt gtattctata    540

aatatatgta aaagcaacgg tcgctacctc taagtacact gatgatataa acaagagcaa    600

gatggaagtt ttcagtgttt gttgtgagga acagcactgg aggccaaaac aagcctctta    660

gaaagttctc cactggcaag cttcgacggt ttggcgcaga gtgagggcag caaactttgc    720

cgcatcgcag caaatctcaa tcagcctttt gacggtcgtg cctaacaaca cgccgttcac    780

cccaagcctt actttgcctt cgtgcattgt cctcgagtat cgtaagtttg attcgctttc    840

attcgcttcc atccactccg gttgtagcaa aagcaaagca gcgttgtgcg gctctcaagg    900

tttggccctg atgcgaccga cgagcataaa ctaactagcc tccgtcttgg tttcgtttca    960

cagtaaagta gttttcgaaa ctccaacctc aagcaaa                             997
```

<210> SEQ ID NO 21
<211> LENGTH: 1000
<212> TYPE: DNA
<213> ORGANISM: Schizochytrium sp.
<220> FEATURE:
<221> NAME/KEY: misc_feature
<223> OTHER INFORMATION: pSGI-JU-98
<220> FEATURE:
<221> NAME/KEY: misc_feature
<223> OTHER INFORMATION: i94 TCTP promoter

<400> SEQUENCE: 21

```
aaggatgagg ctggtttcag aaaacccggt gaaccgccac gcaggcaatc aatcgtctta      60

taaccgtaat aaaccgtcac aggttcactc acggctgttc gcacctcacg caccttcaga     120

tcgagctgta gaactcgact acacacgcac gctctctaca ccattgcaat cgcgatgcac     180

gcgacgcctc aggcatctcc tttcgggagg tggccgggaa cctaggagcg tgtgttcctg     240

gtgctgcttt cgccaatccg tggcccggtt ctcgcaggac tccttctgca aagacttcaa     300

tccatcttga gcacctcgat ctcaagatcg ctgattcttc ggtccacgat tcttgaaagc     360

gggctcgatc gcacactctg gactcattaa ggggcacatt taaggtcttt ccaccacaga     420

acgttctgaa cagcacgtgg cattcagttt ccctccttaa cctccactgg cgaacccgcc     480

ctcctacttc actgtcccat taaggcggaa atgagtggct gatgcagtcg tgacccgctt     540

tctccctgct aaggtccctc ttgccacgca gaaccttgca actcccactg cctcacatcg     600

acccatgttc cttgtgaggg agtccagaat gctctaggtg aggcgcttta tttcggctcc     660

agtggcgtgt gaggcagaaa gataccccct gtgtgggcgt ttttatgcgg ctccaatatg     720

cgggtgcgcc cagtggggct gggaggggga agccaaagtt tgtgcagcag tggtgccggc     780

ggcgttggac tagtcgcagc cagtcatcgg gacttaggtg cctgggtagg ggtgtcttag     840

ggcgcggcta ggcgaaactc tgcgttggag gatcctgcgg agaagggcga aagaggggaa     900

aaggcggatg agcgtatgaa ggcacgggaa ggagcggcaa cagactcgca atcagcagtg     960

gagtttacag acgtcgtgac ccctttccgc tctcaagaag                          1000
```

<210> SEQ ID NO 22
<211> LENGTH: 1163
<212> TYPE: DNA
<213> ORGANISM: Schizochytrium sp.
<220> FEATURE:
<221> NAME/KEY: misc_feature
<223> OTHER INFORMATION: pSGI-JU-99
<220> FEATURE:
<221> NAME/KEY: misc_feature
<223> OTHER INFORMATION: i94 ACS2 promoter

<400> SEQUENCE: 22

```
agaagtatta aaaaaaggac cggatgaaag aaaaattgcc ttgaaaggat agaagaactt      60

caaaagaata gtgggttttc aaaagacaca gcaaaagaag gaaagaaaga aagaaagaga     120

gaaagaaaga aagaaagaaa gaaagaaaga aagaaagaaa gaaagaaaga aagaaagaaa     180

gaaagaaaga aagaaagaaa gaaagaaaga aagaaagaaa gaaagaaaga aagaaagaaa     240

gaaagaaaga aagaaagaaa gaaagaaaga aagaaagaaa gaaagaaaga aagaaaagga     300

aagtgagaac tggcgtcaaa agaaattgaa agagtctgac tctgtggaag aaagcttgga     360

agaagaaagc ggatagaggg gcgaaattaa ggggaagaag agagaacgaa aggtgggcct     420

ccactgggcc actcagaggc agtggaaaga gagggaggaa gagtgagaaa gctggaggga     480

tgggactgct agagagagct aagtggaggc taggcatgaa gatagtaaaa ggcgcagagc     540
```

-continued

```
cgcagacaag gctttggctt gcctcgctcc cattgccagc aaactcgaaa cctcgaaggc    600

gaccgaggaa aagcaaaccc caaacaccgc tcgcctcaac taggtacgtc aacaagaaag    660

cccaacgaag atgatcagcc aagacagtcg gcctgccgtg ctgctgctgc tgctgctgct    720

gctgctgcct gcttgatgca tatatactgc tcttgcatga tatgagaagc agcagcaaca    780

gccgtatgta taatcgatca tcttgttcca tgattccaca catctgtcat actgggcaga    840

ggaatgggaa catctccctg ctcttgaatg ggctagaaca ggagaagtcg aagcacttgc    900

tgctctctgc cagcgtcttc acgcttggcg tgcagcggta ggtgctgcaa acttctctct    960

acatatgtct agaatagcga cttgggaact cctcagctgc tcgatatatg acaatggcga   1020

tattgcatgc ttgctatctt tcttgaagat gaacagaaca actgacattt gagtcacccg   1080

aatgaaccgt aatcccccta cagcaaagca aaaagatcaa cttgtactag attttcaagt   1140

caagttttta acttaagaac aca                                           1163
```

```
<210> SEQ ID NO 23
<211> LENGTH: 872
<212> TYPE: DNA
<213> ORGANISM: Schizochytrium sp.
<220> FEATURE:
<221> NAME/KEY: misc_feature
<223> OTHER INFORMATION: pSGI-JU-101
<220> FEATURE:
<221> NAME/KEY: misc_feature
<223> OTHER INFORMATION: i94 tubulin alpha promoter

<400> SEQUENCE: 23

gcaggggtgc tagtatttta tactatctgg atgctaggag gcaagacttc ttttgcctgt     60

ctgtctgttt gtctatctgg ctacccctat tgtatcttat atcccaaaca ctagggctcc    120

ctcacctgca acagtcagtc actcacgcat tcagtatata ctaaggctca cctagactaa    180

tccataagca gccaatccgt tccgcgctcg cgccggtaga agcaaccgga ccatacggag    240

gtcttagtgt ttaggttata tgggctatgt cttatcggtg ggccgttata cacgccgcgc    300

tggaagctcc tctactttgt gaggagtttc acttataatg tatgatcggg attcctgttc    360

ccctcccatc cactgggtgc aaaattcaac tccctcacaa aaagtgcatt atataaatat    420

atgtaaaggc aacggtcgct acctctaagt acactgagga tataaacaag agcaagatgg    480

aagttttcag tatttgttgt gaggaacacc actggaggcc aaaacaggcc tcttagaggg    540

ttctccactg gcaagcctcg acggtttggc gcagagtgag ggcagcaaac tttgccgcat    600

cgcagcaaat ctcaatcagc cttttgacgg tcgtgcctaa caacacgccg ttcaccccaa    660

gccttacttt gccttcgtgc attgtcctcg agtatcgtaa gtttgattcg ctttcattcg    720

cttccatcca ctccggtcgt agcaaaagca aagcagcgtt gtgcggctct caaggtttag    780

ccctgatgcg atcgaagagc ataaactaac tagcctccgt cttggtttcg tttcacagtt    840

aagtagtttt cgaaactcca acctcaagca aa                                  872
```

```
<210> SEQ ID NO 24
<211> LENGTH: 1004
<212> TYPE: DNA
<213> ORGANISM: Schizochytrium sp.
<220> FEATURE:
<221> NAME/KEY: misc_feature
<223> OTHER INFORMATION: pSGI-JU-102
<220> FEATURE:
<221> NAME/KEY: misc_feature
<223> OTHER INFORMATION: i94 hsp70 promoter

<400> SEQUENCE: 24
```

```
actttttcaac ttgagatgca ccaccctctg caagacgacc cagagacagc aaagaccgct     60
atcaccgcac ctgaagaggc ttcggaagcg atgatgtgaa cacttgattg tactgcgagt    120
catcgttcat gaggattcat gacttggaat tctgtgaatc tgatgataga gttggaagag    180
catggttttg taggtactta ctaagttgaa ctacgtacta ctacttcact aagctttaca    240
tgtacaacta tactttaccc ctcaatttga aaatttgaat tttgaaaaat acagtagtga    300
ctatgccatc tgaactttac aagggggctt aatagaagtc atgccgagtc cgaagcagtt    360
ctttgcagtt cttccataac aactgttatg aatataccat taggaacgtt ctggaacgtt    420
tacgtatgtg ttctggaacg ctcttaatta aaaaataatt cttaatattt taaatgtttt    480
aattatttaa aaagcacctt taaaagtttt taatgtattt ctagccccgg ccgttgaagc    540
taagaaggaa aagcccctta ttttggaagg taagccttat tacagcatac tctttcatgc    600
ccttaataag gtgcaaaaga tgatctttct agaatctttg gcaaagagga ttctaccctt    660
cgcgaagacc ctcaagaatc cgctagtact caaatagtga ctatagtagg gactaagaac    720
aatctggatg gcttagacag tgttcgtgaa ggtctctggt tgcaagttga tagacataat    780
atgagcgaaa agtgaatcca tgattgccta atgagccgag ctcaataagt ttcaaacaga    840
aaagaatgaa ggagagcaca accaactaag agtaagataa gagtaccaag gagtgccagc    900
tggtgaagag caccaagagc cacagacttg aagaagcaaa ccccaaaccg caatcagaag    960
cgaacagtaa aagttacagt agcagaagta agacacttag caag                     1004
```

<210> SEQ ID NO 25
<211> LENGTH: 1000
<212> TYPE: DNA
<213> ORGANISM: Schizochytrium sp.
<220> FEATURE:
<221> NAME/KEY: misc_feature
<223> OTHER INFORMATION: pSGI-JU-103
<220> FEATURE:
<221> NAME/KEY: misc_feature
<223> OTHER INFORMATION: i94 EF-3 promoter

<400> SEQUENCE: 25

```
gatgaatgaa agaatgaaag aatgaaagaa tcgattgatt gattgattga tggataaatg     60
gatgcgtgga aagtaagctc cggacgatcg gctggatgtg taggggcctg caaggggtgc    120
cgagcattca tgcagcaata ggtgtagcct tctgttgaat attggtgatg cacagagata    180
aatggtcaac agaaaagcgg cagcaatttg tacaaccttt cctttcctgt cctttccttt    240
tttctatttt agtttcagtt caaggttttc aaaggctgct ttcatgattg taattaaatt    300
tagtttcatt taaaaacttt taaaaaataa aaaataaatc gagagaaagc tctggtttta    360
aaaagaaaaa gcgtggaatc tcaaacggtt tgccgctagt agctagatag ggataaaagg    420
taaggcatta gtagtagcta cgtagctgcg ctaactaacc accgtcggtg tgagggggtg    480
ggctgtgggg aggaagagtg agggcgactt cttcctcctc tcataaacga aggcggaaga    540
agcccgtttg tgagagggcc cctcgcaaaa gaggcagaaa cttggcgcgt ttgggagaca    600
gggaggaggg ggtgtgagag gacaagtgtt cagaggggct tgggaggaga gaatgatgat    660
gaagaagaag aagaagaaga agaagaagaa agaggaggaa ctgatgggcc cattcgatgg    720
tgcattcgca gaccaagcaa acccgaaact cgagcaggcc aaggagaact gactgactga    780
ctcggttgac ctggcgcaga accgttgcct gattagcaag cagcaaagcc ggaacccagc    840
gcacccgccc tcttgaagaa gctagcaagc aagcaagcaa gtaagcacaa gtcggcgcag    900
```

```
caacagaacc caggtagcag gtagcaagtg catttgttac gaaggaaagc gaaagcggta    960

gtagattaaa aggtgtacgt acgtacctgt agttagcaca                         1000


<210> SEQ ID NO 26
<211> LENGTH: 1000
<212> TYPE: DNA
<213> ORGANISM: Schizochytrium sp.
<220> FEATURE:
<221> NAME/KEY: misc_feature
<223> OTHER INFORMATION: pSGI-JU-105
<220> FEATURE:
<221> NAME/KEY: misc_feature
<223> OTHER INFORMATION: i94 HXT1 promoter

<400> SEQUENCE: 26

ctcaaactcg gcaaacttgg taaatggcca acatagaatt aggacactca ttcgagctaa     60

cagaaaggag tggacaagcg gatgctgtcc ccagctgggt ttcccggtac cttgcgtctt    120

tctctaaagt tcctcaattt ttcttcagtt ttagctgagc aagttgcaag tcgcgtacgc    180

ctcgcaggcc caagaagaag atggattcga ggacgtgaaa acgcttctgg atgacacgca    240

agagaaggat ttgctccgac tttgcagcga ggcatcatca tattgtacgt tttaaaatta    300

tattttatag attggaagcg gttggtgatc gcttctttaa gaatttttag tctcaagatt    360

gaaagaactt gtgacttttg catctgctat gtttttgaga aggtggtttt caactcgaag    420

aggaatggtc gatggcgagt tttgcgcagt ggtgacagag tcgacggctg agagaaaact    480

ctagaattgt attgcttcct acatgagaga gttgtgaatt ccagaaacta ccacagagag    540

atcttgaaga aattattaga gatgagagga cactcgaaaa tccaagaacg ccgtgctacc    600

gtctccttgc agtagttaga cctagagata taatataaat gcgtggcaca ctttcatacg    660

catagcacga gtacgctgac taaactaccc actgcagaaa agaactaaaa ttaaggccag    720

tgtgctcaca gctaccttcc actagattaa tttctcagaa aaggctaaga acaaaaactt    780

ttttccttct ctcctttcgg gaaagtaaag caatgcatgg catcgcagca gcatatggat    840

gcaagcaaag caaaaccaaa actcgaagtc caaatcctgg gatctaaatt tcattgactg    900

ggctactaag gacctctgat tttcagttat agaattagac tctttgagtg tatcaggaga    960

tactaactca aaagtaagtg aacctcacct tggtttcaag                         1000


<210> SEQ ID NO 27
<211> LENGTH: 1018
<212> TYPE: DNA
<213> ORGANISM: Schizochytrium sp.
<220> FEATURE:
<221> NAME/KEY: misc_feature
<223> OTHER INFORMATION: pSGI-JU-106
<220> FEATURE:
<221> NAME/KEY: misc_feature
<223> OTHER INFORMATION: i94 catalase promoter

<400> SEQUENCE: 27

agaagccaag gtatctacca gcagcagctc gggtgctgag gaacacagga agtaagaagg     60

aagcaagaat attgctgctt gctccacctg cggcctctcc gtcttgactc ctggcagttc    120

aactcgttcg accaacttgc cagatattcg aatgccttgg acatcgtcac atctcgaggc    180

ctgtgctgcg ccaacttcaa cctggaggac agaaacagct atagaggatc ttgaagacca    240

gaacatggag gaggtgggag gagcgctggc gctcctcttg gggtcaggct cgcggccctt    300

gggacgcagt ggcgtgtgat gcaatgcatg tgcgatgagc ttcaatgctt cagtgaagcg    360

tacggcttaa agggaacgca tgatggcctt attgcaggcc agaggctcac tgcttagagc    420
```

```
tctacaatag aacactacaa aatggaacag atttgagtaa caaggctgtc aaggtctttt    480

cttcacggca acagacatgc cgtcttgtca gcccaaactt taggtttcaa gctttgacgc    540

gataatttag tcaagttcgc gccggtgaca ttgagaaggc tagtttttct atctagtgaa    600

aaaaaaaatg tttaaaataa ttatgacaga tatagcaatg agtagtgagt gtcagcgtgg    660

ccatacatgg agtatctcag tctctgcctc ggcttgaagc ttttactgct cagtgactcc    720

ctcaaatgga caaagaatct gagttttaga agttgttacc aactattccg tcttgtgata    780

ataagtaatt aattaattaa ttatataaaa gacgaagacg aagaagaaga agaagaagag    840

aaagtaaaaa gaagagaaac gggaaaagaa aaagaaagga attaatatta tcacgcagtc    900

agaacttcag aactttagaa cccatcagtg gcgaatgttt caagagaaca tttataatca    960

tcaggcaaat gaaaagggtg tatcgacttg aagaaaatca cgggcaggac aaatcggc     1018
```

<210> SEQ ID NO 28
<211> LENGTH: 994
<212> TYPE: DNA
<213> ORGANISM: Schizochytrium sp.
<220> FEATURE:
<221> NAME/KEY: misc_feature
<223> OTHER INFORMATION: pSGI-JU-107
<220> FEATURE:
<221> NAME/KEY: misc_feature
<223> OTHER INFORMATION: i94 60S ribosomal protein RPL9 promoter

<400> SEQUENCE: 28

```
tcgaggacac aaccaactca aggtcgtcat acgaggagcg cactgctcgt gggccctttg     60

gttgttgcat tataaatcgc ataagaaaga acgaacgaac taatttgctt tggccatcac    120

ttgtaatgga ataggtattt tgccttttcg tcctttggtg tccctccctt ttagccaatt    180

tgcatatctt cttctacctt ctcgacctaa cgaggaaacc atcagactct cagaacaacc    240

catttatcga ggagaaagtc aactctcact ccttctacta cttgtactaa aatgtaaggc    300

acgtatcatc tcaggtacct acagtctgta tgtattatga aacaatgtag ttgcctacct    360

acccattagt tctatgatgc cagaattcgt gccggctgtt cacttcggct cttggtcctt    420

tctctgagat agcctcttca cctggcaact tctacacatc cattcacagc tccaaacggc    480

aaccagagaa gaatcacaga aagaccctcg ttattgtgtg catgagttgg tcacattcaa    540

tacctcatcc tcaatcaatc aatcaatcaa tcaatcaatc aatcaatcaa tcaatcaatc    600

aatcaatcaa tcaatcaatc aatttatcag ttatacagct ccacaataga ctataccacc    660

acacagcctt ctctacagta aagtattcac ctttacaata gagcaaaccc atagccaaag    720

ccgcctttac acccaagctc tttagatggc ccctgtccaa ccagattccc aaacattccc    780

cctgttcccc catatgtgcc gagttgattc gctttcgggc gcggtgtttg ggagaggggt    840

tagggtgaat tagttccggc gcattggggc gccgaagagt tgtctggctg cgcaagaggg    900

ggggcaggaa gggagagcag agaagggcgc gattggcggc ggcagaccac aagagcttgg    960

ctaggcttgg aaagcgtgca gcgcgacagg caag                                994
```

<210> SEQ ID NO 29
<211> LENGTH: 1000
<212> TYPE: DNA
<213> ORGANISM: Schizochytrium sp.
<220> FEATURE:
<221> NAME/KEY: misc_feature
<223> OTHER INFORMATION: pSGI-JU-108
<220> FEATURE:
<221> NAME/KEY: misc_feature
<223> OTHER INFORMATION: i94 40S ribosomal protein RPS3a promoter

<400> SEQUENCE: 29
cttcgaagta ctactttgta gatcctagct agtaagtaat taatgatgta taggttctac 60
atagaaaagg ggagacctcg gtagtataca cgtatacact gtcatatgta aatagatagc 120
aaatccaggg ccacggggaa ttatggccta tgtcccatga caacataaca gagttcggta 180
taataggtac aagtaagaga tcaatagggg atatagtagc cactagcaag cagctcttca 240
ggtgcgcggg caccgtttgt tgctatattg cgcttgtgtc atttgctaaa ctaaacgaac 300
tgatgatgag gagtgcgcac atttcctcgc gctttcttg ctgttgcgaa cgccataatc 360
agcggtcttg ccaccgacct ccctccacat ccttgtttat ctaatgccgc agcaatatag 420
gttctctcta acacttaacc atggccacca gttcctctca tgaagcgctt tgatacctgc 480
gcaacgcttt ttcagcctgg ctgcttgcac agaatctcct taattaccct gtctaaaccc 540
cattaacctc cttatatttt aaggtgagtc aaatctgcac aactcctttt cagtctactt 600
aatcacctcc ttcatttccc tttacgcact atctattaag gcggttctcc cctcaaacta 660
gggtttaacc ctaggcggaa cgcagctgac cttcggcgca gatgcgcgcc taaaagagag 720
tgcggatttt gccttttttgt atttaatatg agctgcggat ggccttgcaa gcagggcgta 780
aatgggtgga ggaaagaaag gagtggaggg gcgcggccac tagctagagg tatctgactc 840
ttatgagcgc tgggcgagcg gcggggcatg taggtgtatt ctaagggtct attagaggta 900
acgcggggaa tggtgcaggg gcggcgagga agagcagacg ggcatccttc aattcaattc 960
gggttggttg acgtgcagga cttgcgcgaa gtaggcaacc 1000

<210> SEQ ID NO 30
<211> LENGTH: 1000
<212> TYPE: DNA
<213> ORGANISM: Schizochytrium sp.
<220> FEATURE:
<221> NAME/KEY: misc_feature
<223> OTHER INFORMATION: pSGI-JU-109
<220> FEATURE:
<221> NAME/KEY: misc_feature
<223> OTHER INFORMATION: i94 tubulin beta promoter

<400> SEQUENCE: 30
cgaatgttgg gaactacaga atcattgcga aaggaggtgg ttggaaaggg gagaaacaat 60
tgcgacggat gaggaacgaa gactccgtcg gccatacgaa ggaagaggca aagagcggga 120
gaaagaaatt gacgcttcaa cagacaggcg acaagtcgag ttaaataaag agccctttttt 180
ggacggattg agagggagat cgcgaggtct ttgagcatta attctccctt tttgttcttt 240
gaacttttta ctttcgatat ttttatttta tttaaagata aaaattgtct tttagtataa 300
taaaatttac ctcttttttt taaaaaaaaa atttgaaaat aataataata ataaaactgg 360
aaggtttttt cttttcactt ttgagaacaa ataaaagttg cgaaaatagt aattgaaatt 420
tattttaaaa aacagaggtc agatcccagt gctgacagag gtagtggcag tggcgcccag 480
agatcaccaa agaggaagaa attaacagag atctacctag gaagaaaggg cctgtagtgg 540
aaggatttga aaagttgttg ggaggagagg caaatatcgc gaaacccact gattattaga 600
taggcagagt aaagagaggg gatgtgaggg gcgggcgagg gtctgtctaa ccgctcagct 660
ggcgcgagaa taatgatatg aagtttctct ttgttttgct gttgcatatg atggagcata 720
gttatgagag aatgaaagcg ataaaagagg gtgttggtgg cgttggcggg tgagccagac 780
atagtttggg cagcaaacct tgaattgatt tgagtagtag gctgtgcgtt gagcaagcag 840

```
tctgtcttcg cctcgtgcga gcagtagtaa gggaggcagc agccacagca gcagcaacag    900

cagcagcaaa agactcggcg cccgtcgtcg atcgagagat ttttgaaggc aaagcatcaa    960

gtcaagagtc gagcttctag cttcgcgata ctaataaaag                         1000
```

<210> SEQ ID NO 31
<211> LENGTH: 976
<212> TYPE: DNA
<213> ORGANISM: Schizochytrium sp.
<220> FEATURE:
<221> NAME/KEY: misc_feature
<223> OTHER INFORMATION: pSGI-JU-110
<220> FEATURE:
<221> NAME/KEY: misc_feature
<223> OTHER INFORMATION: i94 superoxide dismutase (SOD) promoter

<400> SEQUENCE: 31

```
accggaagcc tggatatgta tctccggcga tgacttggat tattttctct ttttttcttt     60

ttcttttttc gtattttttt tactgactca tttcatccta ctttttttcgt tgttatatag   120

tctccacata cagaagttca aggctacaca gcagcatagg ataggtatct gatattggcg   180

tagcaacttt gctcgctcct ccagcgacta tctactagca ggtagcaaaa ataaattata   240

tcttcttaat ctataatata tgtagagtag gcgtgaatat tatctgccat aaggctattt   300

ctatttactt tttttatttc aagaagaaca ggtaactagg atcactgcta gctcgtctct   360

ataggtattc gagtctctac ttcatttgct ccgcgccagg ccaggctgaa aacctttcct   420

tcttcaaaaa aatatataca tgttctatat agcaaagaac cagttgaaga tagcagttat   480

gatgttcaac tagttagacc tagtatagaa atgctatact gcacttgcta aaggttatat   540

agttagtgct aggcaggtag ggtgcctgtt aaattcaatt tcgtttgtcc taaattttga   600

aatggatgaa attaaaaaat atatatattt aaaaaaaatc actttcattt taatgttatt   660

tattatcgtg atatcagtat cttagttgac ctatcaacca tctattgtca ctcttaagac   720

tctccaggag acagaaaagg tgaaagagga agaagaggat acttttacct gcagcagcat   780

ttgcagtacc tgtagtgtat ctactacata ggtagagaat tagatagata atagatgagg   840

aaatagatac agacatagat agattaagag aaagcagagg aagcattgta actaagccaa   900

agacaccact tcacaggcag caaaccaaga attaaattcc tttcctccgt ctaaaccaag   960

tcttcaagca agcatc                                                    976
```

<210> SEQ ID NO 32
<211> LENGTH: 1033
<212> TYPE: DNA
<213> ORGANISM: Schizochytrium sp.
<220> FEATURE:
<221> NAME/KEY: misc_feature
<223> OTHER INFORMATION: pSGI-JU-111
<220> FEATURE:
<221> NAME/KEY: misc_feature
<223> OTHER INFORMATION: i94 phosphoglycerate kinase (PGK) promoter

<400> SEQUENCE: 32

```
accaacaact gcactaacca agcagaggcc gccgactgtt ctttcgtctt gacccacggc     60

cctcgcgcat gagccgtcca ccatcgtaaa caaaatctac atttactccg tgctcctcct   120

tataggtacc taatgatgac gcaaaacaat aacaacaacg tagtcaatta attgatccat   180

atatctatct ttctttagct aatgcaatag atactaagaa aagatacaag caagcgtccc   240

acaggatcta tccaacttcc gtggtgcccc cctctgcatc caaagagcct ctctcttccc   300
```

```
cggcctttct gcccagaggg gggtcttcct aagagtgtgg atgtccctgc ttcccgccct    360

aatgaggccc aggatctttc tcaatatttc aaagacggcg cgaagcacta cacatccacg    420

agagatagat cacttctgct cttcttctgc cttcgggcct cgctctcgca gccgcggccg    480

ccgaaccgcg agctggcggg cctcgagggg ggcggcggcc aggcccggag cctcagagcg    540

cggggcggcg gccgcggagc tgaagaatcg acgatggttt gtttcaaagc tcaagttcaa    600

cttcgagatg gtcgatgttc ttttcctctg ttcttgttgg tcagattagg agaacaccct    660

attactacaa tcacgcactt tcactagcat caccctggcg ttgatatcgt ggagatggca    720

gggtgaaaga atgtgctacg ttcttcagta atggcgatta tgggacatga aaatgataat    780

ttgaaatcgc tcattacact acattagagt agcaggtagt aggtagtagg tagaaagata    840

gaacagagtt tggaacagag aattggcgta ggccgcgctt agagtaaacg gtaggggtcg    900

cgaaggaagg atacgacgga agggatttga aagtgatttg aatcagagcc tcgagtgaag    960

aaaagcttcg gcaaacacga aactatatct atcgcgaaga gattcgttcg agtggacctg   1020

caagcctggc aag                                                      1033
```

<210> SEQ ID NO 33
<211> LENGTH: 1784
<212> TYPE: DNA
<213> ORGANISM: Aurantiochytrium sp.
<220> FEATURE:
<221> NAME/KEY: misc_feature
<223> OTHER INFORMATION: pSGI-JU-180-4
<220> FEATURE:
<221> NAME/KEY: misc_feature
<223> OTHER INFORMATION: i886 actin promoter; allele 4

<400> SEQUENCE: 33

```
tcgcgacttt acgtgttcta tgttataaaa gcaaaaggaa cagcagcttc tgcagaacat     60

attatgaaaa gtcctttttt ctaatggtat ggaaaagaaa aacatacaaa ctagagagat    120

ggtaccttac ggtacgcact ggcgcagcta ggtgtacgcg tagcagtgtt gtagacttcg    180

gaaagaatca aggtttttta aatggagaaa acagcgtctg tgaagggggg taggtgtgta    240

agaagtattg cattacatct cgtccgtcat ataaaaactg aatataaaac ataaagctta    300

aggactactg tacttcatcg attgactgat ctactgattt actcgagtga tgccgctgcg    360

tttgtgcggt tggacagcga tagctatagc gacttgcccc cttgcgtacc agagagtgag    420

tgcgcgagtg aacgcttcgt cgagtaaggg tgattgtgga tgatggattc tcgacggatc    480

gatggattgt ttgctttgta tccttcgagt ttattttttt tttttttttt ttttacttct    540

ttcctaaagt aaaagtcgat taatcaatca aatcactgtg acgtgagata gcagaaacaa    600

gtaaataaac agacaaacaa gggagcaaga cagacgggca atgtcacact gccgtcggtg    660

tgtagcggcg cgacgagtat tgactgacgc gtgtgcgcac aaccttgatt tttagctgat    720

tagctgttaa gccaggtaca caaaacatcc attcatacat ccaaagaaga tgcaaccata    780

aatacataca cccgtgagtg cataaatagc ccgcctccag acagatcggg cggcctctga    840

cgcggagtgt gcgagcaaag agcgcgattt acacatttat cgacagcgaa ggatcgctca    900

atccacaaaa aagaaaataa aaataaaaaa tcctaaaatc atacctccac ctccgacaga    960

tcagacttct gaaagaggaa ttttgaaaga acttagaaag aaagaaagaa tgaacgccaa   1020

cgagagactc attcattctc ctcctcgcct ttatctcgaa gggttcaaaa ggggcgccgc   1080

tagggacaag actagtgata tggtagagcc cagcaaagtt ttaattaaaa gctaaagtat   1140

atataacata ttgaaaatta ttctattgta aagctaaaaa ttaaaagtat aatagatgcc   1200
```

ctatattaaa caatttttat ctaactaaga aaacagaaga gtaggtagcg aaaattggaa 1260
ctggggtggc aagagagttc acactttctt ttcgtaagtt cttttggata aggaagttag 1320
tgagttgttt agttgtgcta tccgtatgtt tccatttgac tgtctgtgta tctatctgtt 1380
tgactcactc actcatcttt tcacaattct cgcaagtgaa gggggggcat cttgactttc 1440
tcgcgatttt cttcaagacc cccctcctgc cccactgggg tgctttactg aggcgaaagc 1500
tctagtttga tatggaaagg aggtacagtt aggaggaaga ggggtgtgtt tgtgaggggg 1560
aaatgaggca gcagtccggg tgcccctcag aggcagtggt gatgagagga agtgtgaggg 1620
ggtgaatttc gaaaggatcc tccttaagtg gaggcattcg ggagagggtg cctgccagct 1680
ggcggtatcg tggtcgcgac ggctgcgctc caggatcagc aaacccgcaa cctcaagctc 1740
aagaagcaac aacacagtag cagaacaagc acccaactag caaa 1784

<210> SEQ ID NO 34
<211> LENGTH: 1776
<212> TYPE: DNA
<213> ORGANISM: Aurantiochytrium sp.
<220> FEATURE:
<221> NAME/KEY: misc_feature
<223> OTHER INFORMATION: pSGI-JU-180-5
<220> FEATURE:
<221> NAME/KEY: misc_feature
<223> OTHER INFORMATION: i886 actin promoter; allele 5

<400> SEQUENCE: 34
tcgcgacttt acgtgttcta tgttataaaa gcaaaaggaa cagcagcttc tgcagaacat 60
attatgaaaa gtcctttttt ctaatggtat ggaaaagaaa aacatacaaa ctagagagat 120
ggtaccttac ggtacgcact ggcgcagcta ggtgtacgcg tagcagtgtt gtagactttg 180
gaaagaatca aggtttttta aatggagaaa acagcgtctg tgaagggggg taggtgtgta 240
agaagtattg cattacatct cgtccgtcat acaaaaactg aataaaaaca taaagcttaa 300
ggactactgt acttcatcga ttgactgatc tgctgattta ctcgagtgat gccgctgcgt 360
ttgtgcggtt ggacagctat agcgacttgc ccccttgcgt accagagagt gagtgcgcga 420
gtgaacgctt cgtcgagtaa gggtgattgt ggatgatgga ttctcgacgg atcgatggat 480
tgtttgcttt gtatccttcg agtttatttt tttttttttt ttttttactt ctttcctaaa 540
gtaaaagtcg attaatcaat caaatcactg tgacgtgaga tagcagaaac aagtaaataa 600
acagacaaac aagggagcaa gacagacggg caatgtcaca ctgccgtcgg tgtgtagcgg 660
cgcgacgagt attgactgac gcgtgtgcgc acaaccttga tttttagctg attagctgtt 720
aagccaggta cacaaaacat ccattcatac atccaaagaa gatgcaacca taaatacata 780
cacccgtgag tgcataaata gcccgcctcc agacagatcg ggcggcctct gacgcggagt 840
gtgcgagcaa agagcgcgat ttacacattt atcgacagcg aaggatcgct caatccacaa 900
aaaagaaaat aaaaataaaa aatcctaaaa tcatacctcc acctccgaca gatcagactt 960
ctgaaagagg aattttgaaa gaacttagaa agaaagaaag aatgaacgcc aacgagagac 1020
tcattcattc tcctcctcgc ctttatctcg aagggttcaa aaggggcgcc gctagggaca 1080
agactagtga tatggtagag cccagcaaag ttttaattaa aagctaaagt atatataaca 1140
tattgaaaat tattctattg taaagctaaa aattaaaagt ataatagatg ccctatatta 1200
aacaattttt atctaactaa gaaaacagaa gagtaggtag cgaaaattgg aactggggtg 1260
gcaagagagt tcacactttc ttttcgtaag ttcttttgga taaggaagtt agtgagttgt 1320

-continued

```
ttagttgtgc tatccgtatg tttccatttg actgtctgtg tatctatctg tttgactcac   1380

tcactcatct tttcacaatt ctcgcaagtg aaggggggc atcttgactt tctcgcgatt   1440

ttcttcaaga cccccctcct gccccactgg ggtgctttac tgaggcgaaa gctctagttt   1500

gatatggaaa ggaggtacag ttaggaggaa gaggggtgtg tttgtgaggg ggaaatgagg   1560

cagcagtccg ggtgcccctc agaggcagtg gtgatgagag gaagtgtgag ggggtgaatt   1620

tcgaaaggat cctccttaag tggaggcatt cgagagaggg tgcctgccag ctggcggtat   1680

cgtggtcgcg acggctgcgc tccaggatca gcaaacccgc aacctcaagc tcaagaagca   1740

acaacacagt agcagaacaa gcacccaact agcaaa                             1776


<210> SEQ ID NO 35
<211> LENGTH: 1776
<212> TYPE: DNA
<213> ORGANISM: Aurantiochytrium sp.
<220> FEATURE:
<221> NAME/KEY: misc_feature
<223> OTHER INFORMATION: pSGI-JU-180-6
<220> FEATURE:
<221> NAME/KEY: misc_feature
<223> OTHER INFORMATION: i886 actin promoter; allele 6

<400> SEQUENCE: 35

tcgcgacttt acgtgttcta tgttataaaa gcaaaaggaa cagcagcttc tgcagaacat     60

gttatgaaaa gtcctttttt ctaatggtat ggaaaagaaa aacatacaaa ctagagagat    120

ggtaccttac ggtacgcact ggcgcagcta ggtgtacgcg tagcagtgtt gtagactttg    180

gaaagaatca aggtttttta aatggagaaa acagcgtctg tgaagggggg taggtgtgta    240

agaagtattg cattacatct cgtccgtcat acaaaaactg aataaaaaca taaagcttaa    300

ggactactgt acttcatcga ttgactgatc tgctgattta ctcgagtgat gccgctgcgt    360

ttgtgcggtt ggacagctat agcgacttgc ccccttgcgt accagagagt gagtgcgcga    420

gtgaacgctt cgtcgagtaa gggtgattgt ggatgatgga ttctcgacgg atcgatggat    480

tgtttgcttt gtatccttcg agtttatttt tatttttatt ttattttta ttctttccta    540

aagtaaaagt cgattaatca atcaaatcac tgtgacgtga gatagcagaa acaagtaaat    600

aaacagacaa acaagggagc aagacagacg ggcaatgtca cactgccgtc ggtgtgtagc    660

ggcgcgacga gtattgactg ccgtgtgtgc acaaccttga tttttagctg attagctgtt    720

aagccaggta cacaaaacat ccattcatac atccaaagaa gatgcaacca taaatacata    780

cacccgtgag tgcataaata gcccgcctcc agacagatcg ggcggcctct gacgcggagt    840

gtgggagcaa agagcgcgat ttacacattt atcgacagcg aaggatcgct caatccacaa    900

aaaagaaaat aaaaataaaa aatcctaaaa tcatacctcc acctccgaca gatcagactt    960

ctgaaagagg aattttgaaa gaacttagaa agaaagaaag aatgaacgcc aacgagagac   1020

tcattcattc tcctcctcgc ctttatctcg aagggttcaa aaggggcgcc gctagggaca   1080

agactagtga tatggtagag cccagcaaag ttttaattaa aagctaaagt atatataaca   1140

tattgaaaat tattctattg taaagctaaa aattaaaagt ataatagatg ccctatatta   1200

aacaattttt atctaactaa gaaaacagaa gagtaggtag cgaaaattgg aactggggtg   1260

gcaagagagt tcacactttc ttttcgtaag ttcttttgga tgaggaagtt agtgagttgt   1320

ttagttgagc tatccgtatg tttccatttg actgtctgtg tatctatctg tttgactcac   1380

tcactcatct tttcacaatt ctcgcaagtg aaggggggc atcttgactt tctcgcgatt   1440

ttcttcaaga cccccctcct gccccactgg ggtgctttac tgaggcgaaa gctctagttt   1500
```

```
gatatggaaa ggaggtacag ttaggaggaa gaggggtgtg tttgtgaggg ggaaatgagg   1560

cagcagtccg ggtgcccctc agaggcagtg gtgatgagag gaagtgtgag ggggtgaatt   1620

tcgaaaggat cctccttaag tggaggcatt cgagagaggg tgcctgccag ctggcggtat   1680

cgtggtcgcg acggctgcgc tccaggatca gcaaacccgc aacctcaagc tcaagaagca   1740

acaacacagt agcagaacaa gcacccaact agcaaa                             1776
```

<210> SEQ ID NO 36
<211> LENGTH: 2048
<212> TYPE: DNA
<213> ORGANISM: Aurantiochytrium sp.
<220> FEATURE:
<221> NAME/KEY: misc_feature
<223> OTHER INFORMATION: pSGI-JU-181
<220> FEATURE:
<221> NAME/KEY: misc_feature
<223> OTHER INFORMATION: i886 Elongation factor (EF1) alpha promoter

<400> SEQUENCE: 36

```
gtccaacaac agagcgcata gaagatgtta tccaggtaag gctgcaataa tacgcagttt     60

gagttttcta ttttaaaagt aagtttaaaa cttaaaaatt tcatacttat gcatgctatt    120

caaaataaga ttgtatcatc ctaaagtatt cttcttctcg ttcttcttct aatcggaaca    180

gagacaactt tggtgggttt gcgggccttt gagagaaaga aaaaaaactc tcaaaagaaa    240

ccaggcttcc gaggccgact tgcgcagctc tggattgagg ttccttcgat cgctcgcttc    300

accttcctgg cccgcgcatg cctcgctctg ggtacacagc tgagtgagtg agcgaaagat    360

gagcgaatga atgcaatatt tttctatttt ctattcattt aactgtactt aattaattga    420

ttattgattg attgattgat tgattgattg attgattaat gactctcgct tctgagaata    480

catctgttct catcttcatc gtcacgtcag aatggaagga tgagaaatga aaagaattcg    540

atcactttcc cgccttcttg ctagctcatg ctcctttccc gccaaaaaga aagaagagga    600

aagcaccccg aagaaaagaa agaaatcacc caaacaccct cctccttcct cgtccacaga    660

cagctcagaa taatgaaagc tatctttcca tcgctcttga cctaactctc tttctgctcc    720

tgtaaattca tccaacaaat gtttagtctc agaaacccat ctgcctcata ctactactta    780

ctaccttcct tacttgaaag caggcaggct cacggccagc ttggcagata ggatagttct    840

catatctatt gctgatcgtt cccgtttctt tctcaaagca aagtcttttc tcttcattcc    900

ttttcttttt cttttctttt caggctctcc acgttttcag gagtagtaca tttgctactt    960

agtaattaga aagcttagta ctttttgctt ttctggattc tgaagacttg gaaatagaaa   1020

gaaattaaaa atctttttct tctttctttc agcctttgct ggactccctc gcacgcctcc   1080

ttcttcccca gccatccatc agcgggcact ccacccgcgc ttcaacgctc gctcgagtgc   1140

gtgcttattt gccttcaacg cggcgcggcg gttaatatag tcccagcact ccttaagggg   1200

ggcatcgcag ggattatctt tttaaaacct gtcacggagt tacattttcc ctcgcatcaa   1260

agtgttcccg gccgcgtcgc acatctaagt tttataacct acacccctcg tggggtaggg   1320

gcgaattcta tgtacacagc acctcagaac ttgcgcgcgt tccgtgacaa atgaggggtg   1380

tggcggcgca ttcggccgca tcgccacatt cagatatcta acatacccccc ccttcgcgat   1440

gagtggcagg cgaggcggat tcgctcgcga gaggcgaggt gccacagcag accagtaacg   1500

aggagccaag gtaggtgacc accgacgact acgaccacga ccacgaccac agccacggcg   1560

gctgcagcca cgggacgcct cgcatggcag cgcatcagca ccagcaacga cagctgcgag   1620
```

-continued

```
gagcgcaggg ccgatctgga cgcgccggag ccgcacgacc aatgccgacg caacgctgat   1680

tcttctggat tacctctaca catgcatata tgtgtagagg tgcggatgaa atgccctgcg   1740

aataaatgaa tggcttcgag tttgcctgcc gtatgctcga aagtgcgtgt gcagacacag   1800

gcacgaccga gaggacaaca gtctgtgctt acctcaccag cacattcttg caacgccata   1860

cgaagcacgc gaaatcttgt ggctcagaga ggaaggcatt cgtgtacggg aacgtgggga   1920

acgctatcaa tttggaattc aaaatgagtg aaccagacaa ctaactgtga cttgaactgt   1980

tgctccacgc atcaaaacca aacccttaac agaagtagac cagttcgaag ctactagcac   2040

caaacaaa                                                            2048


<210> SEQ ID NO 37
<211> LENGTH: 1792
<212> TYPE: DNA
<213> ORGANISM: Aurantiochytrium sp.
<220> FEATURE:
<221> NAME/KEY: misc_feature
<223> OTHER INFORMATION: pSGI-JU-182
<220> FEATURE:
<221> NAME/KEY: misc_feature
<223> OTHER INFORMATION: i886 60S ribosomal protein L6 (RPL6) promoter

<400> SEQUENCE: 37

cattactcca atccctgaac acggcttggt tctacgcttc tccatacttc tgagctgctc     60

tagccagccc gtcaagagat aattttacag ggatcttcct tctaatagaa agacatacat    120

ctatagaaag gctttaagaa agctacctac tgcaactaac acctaaaatg tgacggaatc    180

gtcgtcacct caaaactaca actaaaatta ctacccttac ctgtgactaa gaaaaaaaat    240

atactacgat tacaaatctc accttggcat tattatcttc acattagttc atatccacgt    300

gactaaaagt gcaggctact gatggtaaaa tatcttcgtt attgcacatt cttgcagagt    360

tgacatccac gatatctgag aactatcact accaaaccac ctagtaggta cccagctagc    420

cgttatgatc taatgatccc tatagaggac gttttacaaa ggtcccttcg tattggtggt    480

tccgagttgc gtcacgctag aactcggtag atcctttcta gttctacgtc gaagcaacag    540

tacaaagccc agcactacta ctagagtttc atagctggta gatacctacc taccttggtg    600

tttggtagtt gatatataga caaaggtaac acccttatat agttgattta tgaagtagct    660

ttgggcaaca tgtgcttctt cttctattac tactaggtac tcacctagtg acaacagtca    720

gtcatgtttg gctactgctt cgccatcatg aacacgtccg accactttga ggacacaacc    780

aactcaaggt cgtcatacga ggagcactgc tcgtgggccc tttggttgtt gcattataaa    840

tcgcataaga aagaacgaac gaactaattt gctttggcca tcacttgtaa tggaataggt    900

attttgcctt ttcgtccttt ggtgtccctc ccttttagcc aatttgcata tcttctacta    960

ccttctcgct atgacctaac gaggaaacca tcagactctc agaacaaccc atttattgag   1020

gagaaagtca actctcactc cttctactac ttgtactaaa atgtaaggca cgtatcatct   1080

caggtaccta cagtctgtat gtattatgaa acaatgtagt tgcctaccta cccattagtt   1140

ctatgatgcc agaattcgtg ccggctgttc acttcggctc ttggtccttt ctctgagata   1200

gcctcttcac ctggcaactt ctacacatcc attcacagct ccaaacagaa agaccctcgc   1260

tcctcgtgtg catgagttgg tcacattcaa tacctcatcc tcaatcaatc aatcaatcaa   1320

tcaatcaatc aatcaatcaa tcaatcaatc aatcaatcaa tcaatcaatc aatcaatcaa   1380

tcaatcaatc aatcaatcaa tcaatcaatc aatcaatcaa attatcagtt atacagctcc   1440

acaatagact ataccgccgc acagccttct ctacagtaaa gtattcacct ttacaataga   1500
```

-continued gcaaacccat agccaaagcc gcctttaaac ccaagctctt tagatggccc ctgtccaacc 1560
agattcccaa acattccccc tgttccccca tatgtgccga gttgattcgc tttcgggcgc 1620
ggtgtttggg agaggggtta gggtgaatta gttacggcgc attggggcgc cgaagagttg 1680
tctggctgcg caagaggggg ggcaggaagg gagagcagag aagggcgcga ttggcggcgg 1740
cagaccacaa gagcttggct aggcttggaa agcgtgcagc gcgacaggca ac 1792

<210> SEQ ID NO 38
<211> LENGTH: 1739
<212> TYPE: DNA
<213> ORGANISM: Aurantiochytrium sp.
<220> FEATURE:
<221> NAME/KEY: misc_feature
<223> OTHER INFORMATION: pSGI-JU-183A
<220> FEATURE:
<221> NAME/KEY: misc_feature
<223> OTHER INFORMATION: i886 actin depolymerase promoter (ADP); allele A; short

<400> SEQUENCE: 38
tgtgatagcg agttgtgcga ggtggcaccg cctttctttg caacagccag gaagagagaa 60
ggcctgccat tctgcctatt acaatgaatg tatgtatgtg tacgtgcttg cttgcttgca 120
agatagggct aaaagcgaag gaaaaggaac tttgaaagaa gcgcgctagg ggtgggtagg 180
actcgcttag gcgcggctag ccgttcttat cgcgctgtct atcccagcag ttgtagagtt 240
tccgctttct ccaaatgtga tcctttcttc ttatcacgat tgctctattc gtctcgagtt 300
ctgagcctct cgatgacgat ggtgatcatg acgataacgg cgatgctgtc attgctgctg 360
ctgctgctga tgatgatggt ggtggtggcg gtgggtccta ggccatctcc agctacgcgt 420
ttcttgcttc ggtgtatcag ccagctcggc ttctgtcggc gaactgagct gtccttctcg 480
acgaatcgct atcctccgca aaagttctgc caaaggtttg ttccatttcg aactaaaaac 540
aatcgatgaa agaaagtaaa tgattttaca tttaaaatag gaaaaagagg taaatagaca 600
cttagctaag aaaaacaggc tttaaagtaa acataaaaca aataaaacga tgattgattg 660
atctgcaaaa gcaagaagaa ggaaagactg actgcctgct gcaaattgct gttgacctga 720
atgcaaatga atgaatgaat gaatgaatga atgaatgatc tcgtactcta cgacacttcg 780
gcggcctctg tagatcgctc gcctgctccc tctctccctc gctccgtccc ctctgagcga 840
agcaaataaa ggagccacag gcaaattgtc catctttctg tggatagatc aatcgcacac 900
acattcgttc gtttgctacc tactttcagt acctgaaatt aaaattagaa taggtaattc 960
gaggcaatct tgcacataca catatatata tttacataaa taatcccaaa gacaggagcc 1020
gcactttcct acgattgatt ttttaattaa ttaacctttt aaaaactaat ttaatttgag 1080
aagtaaatga aaaagaagaa aagaaacacc tcctgctact aaaagttcct cttgtgacga 1140
gtcttcgtcc atagcacaac acacataaca gatcgattga gaaacaaagg aaacaagcag 1200
aggaagctcc tactagcagc ggtaagggac tcttacgccg gcaagttagg ggaatgtggg 1260
gaacgcagtc tgcacatccg gaggtggcca actcagcgtc ctgcgcctcc tctgtgactg 1320
gctacactgt gaaacttttt actcacaaag gggtgtgctc tccccagtgc gtaacttccc 1380
gcactctgat tgttaaaaag gtacttcctc agaggttcta cagaaaatac tcccgccaca 1440
ggccaatgtt tgttaacatc aatacaacag acgaaagtat ttgttgagag tacaaagtga 1500
tagaggggga gagggagtga gggaagctgt gggagtgagt ctgagaggag aaaggtgaga 1560
aagatatagg atatatttat agacagagtg gttgagagga gaggcgttgg tatctgtgtg 1620

-continued gttctcctct catcttccac tgggacaaag tcttcctcat gcttcgaagt cgtgcagacc 1680
cactactaca tttgaattct actttcgtct cttcttgaca ccacttctat cttgacacc 1739

<210> SEQ ID NO 39
<211> LENGTH: 1729
<212> TYPE: DNA
<213> ORGANISM: Aurantiochytrium sp.
<220> FEATURE:
<221> NAME/KEY: misc_feature
<223> OTHER INFORMATION: pSGI-JU-183B
<220> FEATURE:
<221> NAME/KEY: misc_feature
<223> OTHER INFORMATION: i886 actin depolymerase promoter; allele B

<400> SEQUENCE: 39
tgtgatagcg agttgtgcga ggtggcacag tctttctttg caaggcagcc agccagccag 60
ccaggaagag agaaggcctg ccattctgcc tattacaatg tatgtatgtg tacgtgcttg 120
cttgcttgct tgcttgcttg caagataggg ctaaaagcga aggaaaaaga actttgcgct 180
aggggctggt taggactcgc ttacgtgcgg ctagccgttc ttatcgcgct gtctatccca 240
gcagttgtag agtttccgct ttctccaaat gtgatccttt cttcttatca cgattgctct 300
attcgtctcg agttctgagc ctctcgatga cgatggtgat catgacgata acggcgatgc 360
tgttattgct gctgctgctg ctgctgatga tgatggtggc ggtgggtcct aggccatctc 420
cagctacgcg tttcttgctt cggtgtatca gccagctcgg cttctgtcgg cgaactgagc 480
tgtccttctc gacgaatcgc tatcctccgc aaaagttctg ccaaaggttt gttccatttc 540
gaactaaaaa caatcgatga aagtaaatga ttttacattt aaaataggaa aaagaagtaa 600
atagacactt agctaagaaa aacaggcttt aaagtaaaca taaaacaaat aaaacgatga 660
ttgattgatc tgcgcagaca aaagaaggaa agactgactg actgactgcc tgctgcaaat 720
tgctgttgac ctgaatgcaa atgaatgaat gaatgatctc gtactctacg acacttcggc 780
ggcctctata gatcgctcgc ctgctccctc tctccctcgc tccgtcccct ctgaacgaag 840
caaataaagg agccacaggc aaattgtcca tctttctgtg gatagatcaa tcgcacacac 900
attcgtttgc tacctacttt cagtacctga aattaaaatt agaataggta atttgaggta 960
atcttgcaca tatacatata tatatttata taaataatcc caaagacagg agcctcactt 1020
tcctacgatt gattttttaa ttaacttttt aaaaactaat ttaatttgag aagtaaatga 1080
aaaagaagaa aagaaacacc tcctgctgct aaaagttcct cttgtgacga gtcttcgtcc 1140
ataacacaac acacataaca gattgattga gaaacaaagg aaacaagcag aggaagctcc 1200
tactagcagc ggtaaggaac tcttacgccg gcaagttagg ggaacgtggg gaacacagtc 1260
tgcacatccg gaggtggcca actcagcgtc ctgcgcctcc tctgtgactg ggtacactgt 1320
aaaacttttt actcacaaag gggtgtgctc tctgcagtgc gtaacttccc gcactctgat 1380
tgttaaaaag gtacttcctc agaggttcta cagaaaatac tcccgccaca ggccaatgtt 1440
tgttaacatc aatacaacag atgaaagtat ttgtccagag tacacagtga tagatagtga 1500
gagggagtga gggaagctgt gggagtgagt ctgagaggag aaaggtggga aagatatagg 1560
atatattaat agacagagtg gttgagagga gagacgtggg tatctgtgtg gttctcctct 1620
catcttccac tgggacaagg tcttcctcat gcttcgaagt cgtgcagacc cactactaca 1680
tttgaattct actttcgtct cttcttgaca ccacttctat cttgacacc 1729

<210> SEQ ID NO 40

<211> LENGTH: 1885
<212> TYPE: DNA
<213> ORGANISM: Aurantiochytrium sp.
<220> FEATURE:
<221> NAME/KEY: misc_feature
<223> OTHER INFORMATION: pSGI-JU-184
<220> FEATURE:
<221> NAME/KEY: misc_feature
<223> OTHER INFORMATION: i886 Adenosyl homocysteinase (AHC) promoter

<400> SEQUENCE: 40

```
cgccgctcat agtgtaaact cataagccta agtactccag ccctctcagc cagccactct     60
tgcggctctt tccaacagta aaaagaaaaa atcgtcgtta ggagtggcct tctagtaccc    120
ggctacaggg agactatggt actgctacaa ttgttactct ttttcttatc ttttgttttt    180
taattaatca tcttattcat tttgttttag ttaattaata gttcgcagca agaaaggagc    240
gggtaggtag aagaggcttt gtgaacttga agatcctcgc gaggaattct gctttgatgg    300
cgcaacctcg cacaggcaga gctgtgctcc gcagcaacgc gagccagcct ctttccgaag    360
tggcctggag aaaactctgc agctcctgaa cgctccctgc tttggaaact aggaagcgcc    420
ggccaagtca gcgatgcggt tcgaagggct ttacacactg agacagaact tcttcgcatt    480
tctattttat ttttatttaa ttttgttttt gtagatcaaa agatgctgat tgatgccggc    540
ctaccagtga actcgagttg cagcaggtta tacgcgctac gcagaggcag caagctcctg    600
gcgaccttgg aatcctcgtg gcgagctagg tgcctaccgg ctgggagaag gacgagaaga    660
gcgctccaag caacggagca gaacacaaga ggcccaggcc gctttctcta gagagcgcga    720
cgatgatgta cataatcctc gcagtaggag acagctaaga agtcctatcc tggaaagaag    780
gacccagaga agaaattgat cgaactgcaa attgcaaaag ctagccactt tgattctctg    840
agtcgatgat acacgaatca cgctgggcga agaaagattc cgctcctccc agagctctcg    900
aaggaggagg tggctaaacc gcctgcctat ctgaaggccc gcaagcttgt cgagctcaga    960
gtcgcgatca agagaaggcc cttgaatgta aaaaaagagt tcaacttggt tccagcctgt   1020
attgcgcaat gtcggcgcct tgcgcattca tcgcattcaa tcacagcaac acactaagat   1080
aatcgacacg aacacccacc ctacacccct ccaacccagg cacaaagcgc tgcgctgcat   1140
acacacaggg acacaggaag gtggtcctga gggcagaaga acgccccctc ggaggcctcg   1200
ctcgcggtgg cgacgatggc gatgacagag atggggaacg cggggagctg gcatccggag   1260
tcaatttgtg gcgccagagg tgtatgtgaa gaggggaaag aatctttatg tgagtcgcgt   1320
ctacgcaatc tggagccact ggagtttttg tgtggtagtg aagagtactc attagttgac   1380
agtgtgggac tgagggtgtt gaagtaaagc tttttcaact tgtgatgtca tagttttaaa   1440
ctcactcgag ggaagctgaa accttctctg tttaaaattg ccagtggtgt tagaggcagt   1500
ggctttggtg aagaacatct acagctgtgg tgattttcaa ggcagagggg taccaacggg   1560
attcgagcgg gggcagaggg cgagcaccac caaccttgtg aggtgactat ttgaaaagag   1620
aggaagaaag aaagggaaaa gaaatagaaa aaaagaaata caacgcgtaa gcagaggagc   1680
ggagattgtt ggcgcagcgt tgaagattta aaaatatttg aatttttgaa tatttgaaag   1740
aattacctaa gtagctagcc acctccctat ctgaaggttg agagaatggt tgtgaccgaa   1800
gaagatggat gatccaagca gagctccagc agacccgaaa cacttcgaag tcgctaccgt   1860
tcagtttagc gaagacacag acaag                                         1885
```

<210> SEQ ID NO 41
<211> LENGTH: 2015

<212> TYPE: DNA
<213> ORGANISM: Aurantiochytrium sp.
<220> FEATURE:
<221> NAME/KEY: misc_feature
<223> OTHER INFORMATION: pSGI-JU-185B
<220> FEATURE:
<221> NAME/KEY: misc_feature
<223> OTHER INFORMATION: i886 alternative oxidase (AOX) promoter; allele B

<400> SEQUENCE: 41

```
tgggagctat ggagtcttgg aaaatcgtta ttaagtttca aatctaaagc tataggcttc     60
gttgttctgc ggcggttggc gatcggtgat tcgtcagatt acgtagatac atacatacat    120
acctagtttg taacaaagtt caatcttaaa atttaacgcc agagatgaaa ggcatgagaa    180
aaccaggaca acgcaagagg gacgaagagc agtatcaaaa gcaccagggg gtgcggggca    240
gacggagagc gcgcgaaggt gatagatggc cctgcggtgg ggaggattta tgatccaaat    300
gaggtcccgc tttcgatatg tttttcgatt tttcattttg ttgacctgaa ttgtaaattt    360
taaaaaacat ttttaacaaa aatgaaaaca gtgtttttcc tttctttaaa ataaaaataa    420
acagtggtac ccaatacacg actagtatgt aattctgaaa agcagagttt taaagctcag    480
gtctccttag cccttggtga tcgtagcgta cctcccatat acaggtccta cctgcatact    540
atggtacaca aatgttaaaa gaatatgtct gattgttaca ggcgctcagc tagtacctca    600
tagcacagaa agagggctgt gaaagtaacg aaaagggaag gcgaactgcc tgagatgtga    660
aagatgaaaa gaaagaatag caggcacggt ttcgacaaaa aataaaagaa aaactgaaag    720
aaaaaagttg ccaaaagcaa gttgggagct caggcaactt ggctttctcg cggtgaaaat    780
gcgcggtgtt tgaggtgacc tcagcgcgca cctgtctaaa tggtgggggc acgaggctcg    840
agccgacaca ttggctcagc cacgctgacc tcgagcgcgt tcacggcgat ggtaagaatt    900
cgagcgaacg ggtgaggggt cgaacttcgc atgagtggaa tgctggatgg atagaacatg    960
actcagcaag ttgaattata tgagtagttc taccttcttt ctttcgttct tggaaataag   1020
atttaaaaaa aattaaaaac gattataggt aatctttgat tttatttata aaaagctaaa   1080
caaataggat cttaaaactc tcaggattag aataatcgtg aatgatgaag aaccgcaagc   1140
gaaaggcgaa ggacctccgg attctcgcac cccgaagagg ctctcggcag ctcagcgctc   1200
gtcctgacta gatttaaatt ctccgcgagg ccaatgtgcc gcaagccaca gtctgcggga   1260
gtagccatga gaacgaacga ataccttggt tcgtctggag aggagagccg aagatcatca   1320
tccctttcca aagaccgcct atcgttttat agaaataatt tttttaataa tgctcgaatg   1380
gggagtgaac agacaaatat ctaagcgagc ctattctaaa ctgtagcacc ccccgtgtct   1440
atgataagac cgtgactatt attgccttgg tttccgcggc caagttttcc tgccttcagc   1500
cacgaggaaa ttggccattg acgctgcgct gtgagaggaa gatggccaag gacacaaggg   1560
tacttgcgct ctacaaagtg gtgactgctt agtttattga agattgattg actgattgac   1620
tgactgactg actgtgatgc gatgtgatgg atcaatcgtg gcgatactta tgcaagtgct   1680
aagaacttcc cgaaagcaaa gaaaattgga gggccatcca acccacaggc ggtagggttc   1740
atttaagaga aaaggtaggg gtggaaaccc gtactggtga gcaggaaggt gagttttgca   1800
tgaagagcag cacaacgaaa gtggcagcag aagcaaaccc gcaactcatc gcaacagcga   1860
taagctcaag agcaaaagaa gaaacctcaa agcattcgaa gccgcgagac aagaatagca   1920
aaccccaaac tcagggattt cgatcgaaga ctcacaatag caatagcgat agcaagaagc   1980
actagagaag tccaagtctc tacaaagtag tcaag                              2015
```

<210> SEQ ID NO 42
<211> LENGTH: 1961
<212> TYPE: DNA
<213> ORGANISM: Aurantiochytrium sp.
<220> FEATURE:
<221> NAME/KEY: misc_feature
<223> OTHER INFORMATION: pSGI-JU-185C
<220> FEATURE:
<221> NAME/KEY: misc_feature
<223> OTHER INFORMATION: i886 alternative oxidase (AOX) promoter; allele
C

<400> SEQUENCE: 42

```
tgggagctat ggagtcttgg aaatcgttat taagtttcaa atccaaagcg ataggcttcg     60

ttgttctgcg gcggttggcg atcggtgatt cgtcagatta cgtagataca gacataccta    120

gtttgtaaca aagttcaatt gtaaaattta acgccagaga tgaaaggcat gagaaaacca    180

ggacaacgca agagggacga agagcagtat caaaagcacc agggggtgcg gggcagacgg    240

agagcgcgcg aaggtgatag atggccctgc ggtggggagg atttatgatc caaatgaggt    300

cccgctttcg atatgttttt cgatttttca ttttcttgaa cctgaattgt aaactttaaa    360

aaacattaaa aaaaaatgaa aacagtgttt tttctttctt taaaataaaa ataaacagtg    420

gtacccaata catgactagt atgtaattct gaaaagcaga gttttaaagc tcaggtctcc    480

ttagcccgca tactatggta cacaaatgtt aaaagaatat gtctgattgt tacagccgct    540

cagctagtac ctcatagcac agaaagaggg ctgtgaaagt aacgaaaagg gaaggcgaac    600

tgcctgagat gtgaacgatg aaaagaaaga atagcaggca gggtttcgac aaaaaataaa    660

agaaaaactg aaagaaaaaa gttgccaaaa gcaagttggg agctcaggca acttggcttt    720

ctcgcggtga aaatgcgcgg tgtttgaggt gacctcagcg cgcacctgtc taaatggtgg    780

gggcacgagg ctcgagccga cacattggct cagccacgct gacctcgagc gcgttcacgg    840

cgatggtaag aattcgagcg aacgggtgag gggtcgaact tcgcatgagt ggaatgctgg    900

atggatagaa catgactcag caagttgaat tatgagtagt tctaccttct ttctttcgtt    960

cttggaaata agatttaaaa aaaaaatgat aggtaatctt caattttatt tataaaaagc   1020

taaacaaata ggatcttaaa actctcagga ttagaataat cgtgaatgat gaagaaccgc   1080

aagcgaaagg cgaaggacct ccggattctc gcaccccgaa gaggctctcg gcagctcagc   1140

gctcgtcctg actaggttta aattctccgc gaggccaatg tgccgcaagc cacggtctgc   1200

gggactagcc atgagaacga acgaatacct tggttcgtct ggagaggaga gccgaagatc   1260

atcatccctt tccaaagacc gcctatcgtt ttatagaaat aattttttta ataatgctcg   1320

aatggggagt gaacagacaa atatctaagc gagcctattc taaactatag caccccccgt   1380

gtctatgata agaccgtgac tattattgcc ttggtttccg cggccaagtt ttcctgccta   1440

cagccacgag gaagttggcc attgacgctg tgctgtgaga ggaagaaggc caaggacaca   1500

aggatacttg cgctctacat agtggtgact gcttagttta ttgaagattg attgactgat   1560

tgactgactg actgactgtg atgcgatgtg atggatcaat cgtggcgata cttttatgca   1620

agtgctaaga acttcccgaa agcaaagaaa attggagggc catccaaccc acaggcggta   1680

gggttcattt aagagaaaag gtaggggtgg aagcccgtac tggtgagcag gaaggtgagt   1740

tttgcatgaa gagcagcaca acgaaagtgg cagcagaagc aaacccgcaa ctcatcgcaa   1800

cagcgataag ctcaacagca aaagaagaaa cctcaaagca ttcgaagccg cgagacaaga   1860

atagcaaacc ccaaactcag ggatttcgat cgaagactca caatagcaat agcgatagca   1920
```

-continued

```
agaagcacta gagaagtcca agtctctaca aagtagtcaa g                  1961


<210> SEQ ID NO 43
<211> LENGTH: 1764
<212> TYPE: DNA
<213> ORGANISM: Aurantiochytrium sp.
<220> FEATURE:
<221> NAME/KEY: misc_feature
<223> OTHER INFORMATION: pSGI-JU-186A
<220> FEATURE:
<221> NAME/KEY: misc_feature
<223> OTHER INFORMATION: i886 cytochrome C oxidase (COX) promoter;
      allele A

<400> SEQUENCE: 43

agaatggttt tcgaagaggc agggcacttc ttggcaaaag ctcaagaatt cggtctacca     60

caaatccgtc cttacggttt tcacgtttgt agggtccata acgatgctgg agttgaagtg    120

cggccagctt ttccattgta cgctctgatg ccataaattt gcctgaaaca aggtcatgca    180

cagcttgaat atatcgaagc ctcaaaattc cagggtctcg agagtgcaga aggccatcaa    240

cgaaggtgat aatccgtaag aagatcttat aacatcgtac tgcccaggtt tcaatgcggt    300

cttgctccgg aataatagct tctttacgct tgccgtcgag attagctaca attgagaagt    360

attgtgcaac tctatcgcta tcaacgaggc ccataacacg agccataccc ttacatacat    420

cctttaaaaa taaaggagat cagcacaata caacgccatt tgtgtcgcgc aagttagttt    480

gtcatttagg tgatcaggtg ccttggtacc actacctcaa agcgcgcaat ttcaaggtca    540

aatttaagca gatgctttgc tcaatagaat tcagcaacag aatttgcatt taacttgcaa    600

gttctgttac gaatagtttc aacatataat tcatcgctgc ttttttgatg caattctgtg    660

tgcttgcgta tccccaggat tttacatccc ctccttcggc tggtccgctc agccgaatga    720

actcaccttc gctgtgctgt ctgagctaag ttccagctct tcgcacgtgt ggtctaacag    780

gaagacctgt agcttcatgt tggccatatt tgccaactgc tgccacgtat tctcgcctca    840

ccctgagcgc gagtgtgagc agccgctttg ctgcagcaac ctcaacagca atgcaaacaa    900

atgaagaaaa aatcgcacat ggtatatatt ttttgctttt taaaatttta attagaatca    960

aaatacaaaa acaaataata tactgtaaag gaaggtacaa acctagttga accattccaa   1020

aacttcgtga gttctaagca caagtgaaac aaactatatt aacagagaca gaacaagcca   1080

cattaccacc aaataaactt aagaaacaga ctctagtaaa atagcaaagg aaaaccgagc   1140

aaaacatgca cgttaaactc tattcactta ctcggtatct aaccatttgc ctaaccactc   1200

tgctattaac atcatagtaa tctcctcaaa ctaatactac tccaatgacc tcatctacag   1260

catcgcatgt catactgggg tctctatgtt acaaccatag tagcgtactg gtaggctttt   1320

ataatccttt attcctacgg tgtcttttag gaagagggac acacactctg cgcccctccc   1380

aattaaaata cagcgtacta aattcgatca ctcagctatc tccgttactc ttttcctttt   1440

cgtacactcg tcttgctaac tcatctggac tgcacaactc gtgtttatta ttcactgagc   1500

tgagaggcag atttcagttt ctaatgccac tgtttaaccc ttcacaccct atccttttac   1560

ctctgttacc actgaaaata tttatctaca agaaagcagg aggtgcagta aaaatctgca   1620

aaaatgccca caaagggtct cactatacac tgaaaagtag agagggagat agtgttagtg   1680

gatggagggg ggcagtgaga ggggcctcca ctggcagctg ctgctgctct ctcgagtcca   1740

tggccgccaa gcgcctaact cgtc                                          1764
```

<210> SEQ ID NO 44
<211> LENGTH: 1764
<212> TYPE: DNA
<213> ORGANISM: Aurantiochytrium sp.
<220> FEATURE:
<221> NAME/KEY: misc_feature
<223> OTHER INFORMATION: pSGI-JU-186C
<220> FEATURE:
<221> NAME/KEY: misc_feature
<223> OTHER INFORMATION: i886 cytochrome C oxidase (COX) promoter; allele C

<400> SEQUENCE: 44

```
agaatggttt tcgaagaggc agggcacttc ttggcaaaag ctcaagaatt cggtctacca     60

caaatccgtc cttacggttt tcacgtttgt agggtccata acgatgctgg agttgaagtg    120

cggccagctt ttccattgta cgctctgatg ccataaattt gcctgaaaca aggtcatgca    180

cagcttgaat atatcgaagc ctcaaaattc cagggtctcg agagtgcaga aggccatcaa    240

cgaaggtgat aatccgtaag aagatcttat aacatcgtac tgcccaggtt tcaatgcggt    300

cttgctccgg aataatagct tctttacgct tgccgtcgag attagctaca attgagaagt    360

attgtgcaac tctatcgcta tcaacgaggc ccataacacg agccataccc ttacatacat    420

cctttaaaaa taaaggagat cagcacaata caacgccatt tgtgtcgcgc aagttagttt    480

gtcatttagg tgatcaggtg ccttggtacc actacctcaa agcgcgcaat ttcaaggtca    540

aatttaagca gatgctttgc tcaatagaat tcagcaacag aatttgcatt taacttgcaa    600

gttctgttac gaatagtttc aacatataat tcatcgctgc ttttttgatg caattctgtg    660

tgcttgcgta tccccaggat tttacatccc ctccttcggc tggtccgctc agccgaatga    720

actcaccttc gctgtgctgt ctgagctaag ttccagctct tcgcacgtgt ggtctaacag    780

gaagacctgt agcttcatgt tggccatatt tgccaactgc tgccacgtat tctcgcctca    840

ccctgagcgc gagtgtgagc agccgctttg ctgcagcaac ctcaacagca atgcaaacaa    900

atgaagaaaa aatcgcacat ggtatatatt ttttgctttt taaaatttta attagaatca    960

aaatacaaaa acaaataata tactgtaaag gaaggtacaa acctagttga accattccaa   1020

aacttcgtga gttctaagca caagtgaaac aaactatatt aacagagaca gaacaagcca   1080

cattaccacc aaataaactt aagaaacaga ctctagtaaa atagcaaagg aaaaccgagc   1140

aaaacatgca cgttaaactc tattcactta ctcggtatct aaccatttgc ctaaccactc   1200

tgctattaac atcatagtaa tctcctcaaa ctaatactac tccaatgacc tcatctacag   1260

catcgcatgt catactgggg tctctatgtt acaaccatag tagcgtactg gtaggctttt   1320

ataatccttt attcctacgg tgtcttttag gaagagggac acacactctg cgcccctccc   1380

aattaaaata cagcgtacta aattcgatca ctcagctatc tccgttactc tttccctttt   1440

tgtacactcg tcttgctaac tcatctggac tgcacaactc gtgtttatgg tacactgagc   1500

tgagaggaag atttcggttt ctaatgccac tgttcaaccc ttcacaccct atcctttcac   1560

ctctgttacc actgaaaata tttatctaca agaaagcagg gggcgcagta aaaatctgca   1620

aaaatgccca caaagcgtct cacaacacac tggaaaatta agagggagat agtgtcagtg   1680

gatggagggg ggcagtgaga ggggcctcca ctggcagctg ctgctgctct ctcgagtcca   1740

tggccgccaa gcgcctaact cgtt                                          1764
```

<210> SEQ ID NO 45
<211> LENGTH: 1774
<212> TYPE: DNA
<213> ORGANISM: Aurantiochytrium sp.

<220> FEATURE:
<221> NAME/KEY: misc_feature
<223> OTHER INFORMATION: pSGI-JU-187
<220> FEATURE:
<221> NAME/KEY: misc_feature
<223> OTHER INFORMATION: i886 Elongation factor (EF1) beta promoter

<400> SEQUENCE: 45
tctccagaaa tgacacaccg catcataagt tcactttcaa actttgagaa tctcccctaa 60
tattttaatt cacaaagcat tttattctat tctaaaagtg acttgcagca cgtacttctc 120
ttggaaatag ttgaccttgt caattgtaaa attgattgaa aatgtgctgt cacctcgcgc 180
tgttttgaga cttgtagatc taagtttgct taagtacatg tcgatggcta aaaaagtata 240
ccgtaactcc tcgagttagg tctacaactc tgaatcatgt ttctttagat acattaccat 300
tagtactcag tgattaattt gagacaaggt gcatacattc aacacaattc tatctagcct 360
tttgcatcgt cttagagcca aagtcacatt atatgcggac ggtagtactg atgacacatg 420
ccataaagga gacataaccc caaaaacacc tgcaactctt ttttagacag acaagcgcag 480
gtgattcatc gaaacctcac caaacagcat attaaaccat cacattcacc gtttgcttgt 540
cagaataata cctggcgaca aatttacaat aataaatatg ttccttacat ccgcttgcgt 600
tgattctgag gcactggttt tcactctctt gcatcagaga cacgcttgct cgcttgctta 660
aacaatcgcg tcaaaactcc tgaaacacag gcatcccagt gctttctgat gtacccagca 720
attaaaaagg cagaagcgct gaggaactcc gagtcagtcc agaactattc gtttcataac 780
gagtcctcgt gctttcgtta cgtgtaacct ccaagcggtc ggtcgcgtgt tcgcgaaggg 840
acgtctttgc ctaccagacc ccgcgtcatc atcccatctt tacaaagttc catccccgtg 900
gccttgtgcg attgtgtctc cggaatcttt ggcgccacag aatttgctcg cgacgtaggg 960
cccagctatc caaaacggta gccctagttg ttggtggtgg gagctcgatc ttgcgtcaaa 1020
gagaaagaac ttgctttctt tcttgctttt ttgctctctt tctcgatctc gtttgctctg 1080
gcgctatcct cgcgaggcct ctcttcgcct ctgcgctgcg tcctgggctc cgaaaggcgg 1140
ctttgcctgc gcgggacgag ccatgacaga ggcatcaggc agaggagcgg cgaaggggcg 1200
aagaatttta gaaaagaaga aaagaagaaa agaagaaaag aagaaaagaa gaaaagcctc 1260
agagagaaaa gaagagaaga cagagtgagt gattcgaagt ctccgtcaga gagcagaaaa 1320
gagtcgggcc agctagcgat acgggtagaa gtggatagga ctgcggcgaa agtagttatt 1380
atgagttgtt tctttctttg tttctttctt tgtttctttg tttgtttgtt ccgtgtatca 1440
aagtagatac tatagctagt ggtggtagtg gtagagtaag gggtaggcag gtgcttgtgt 1500
aggtagatag atagaagata gatagataga tagataggta tagatagata gatagtgtag 1560
acctatctgt ctatgtctct gtatgtatag tatactttgt gaaaggtgga aagaagtaat 1620
gtttgtttct ctctctttaa gtatgtagta tggaggaaag atgaaaggag aggaaatcga 1680
tgatattgat ggattgattg attacttgga gcagcagatc tgcatcatcg ccttcatccg 1740
tatcccgaag ccaagttaaa ctttgccaag caaa 1774

<210> SEQ ID NO 46
<211> LENGTH: 1973
<212> TYPE: DNA
<213> ORGANISM: Aurantiochytrium sp.
<220> FEATURE:
<221> NAME/KEY: misc_feature
<223> OTHER INFORMATION: pSGI-JU-188
<220> FEATURE:
<221> NAME/KEY: misc_feature -continued
<223> OTHER INFORMATION: i886 Fa ATP synthase (faas) promoter; short

<400> SEQUENCE: 46

```
agcgcaacag ccaaatctac cctcggaatt cccttcctgg cgcactccca gcccctgctc     60
agccccactt tgcacacacg cccacccttc gttaccaatt cataacttta ctcccgctca    120
aagttaccct ttgataccgc gcattgttac ctattagtag cattgcagct cgccctgccg    180
cggcactgcc ggcccggggg ttgatagcat ggcggccagt agagcgctcg tgggcggagt    240
gcggagcgtc tgaggcgctg cggaggccgt gtaaagcggc cggaagggac agaaaggggc    300
caaggacagg cagcctaaga ggtgtttgag aggacagctt tggaggcatc gatgaagaag    360
agctcggcat aagaaacgcg atattggcca aagcaatgct ccctcggcgg ctccctgcgg    420
ccgcgtcgct gcgtgccggc gaatctcggg cccactcggg tcaaccttaa atcggtttcc    480
agcgaagccc cgagaggggc acacactgag agccacagtc acagtggtga tcagtagaga    540
aacaggctgc gcagggaaga gtataggagg ggtgcagtcc ggcaaaagta ggggaagaga    600
gacgggcaaa aggaaaaaca taggtaagcc cgtgaggagg gaaagccagt ggagcgtatc    660
tgcggctggg agctgctgca aaggccattg tggcagcaga ccgcttgcta gtccaactcc    720
gctcgtgctc gctcgcttct tcgccgcagg tacgtgcagt gcgacgcgcg ggccgccgcc    780
ggtggtgtgc gtgcgtgact gagagcgccc gccgcccccg ctccgccgtc accaccggtc    840
gaccgcccgc ggcgccatgg aggcgccatt catgtgggca tgagcgcctg tcgaggctgg    900
cgaaagccgc cttcgtgatc cttctctact aagcttcctc gctccttagc tgcttcgcaa    960
gggctttcgt ggcaactgtg gtcgtgcaca atgctcgcaa aggacgcctc gcgcgacctg   1020
agccgcggtg ccgcgatccg catactcgcg catattggat atattgagat attcgtatat   1080
catttatatg cgagatgaga tgcgcatgtg tggatgcgat caatgcagtg caatgcgata   1140
caacaatgcc gatcttcaaa gcacacttgc agaggcaagt gcatctgggt atcggccaaa   1200
ctcgttcgtg gctgttgcat tggtcctaga tcacaatgcc ttaaggcttg ggtgacagct   1260
ggctggatgg ttgccaggat cctattattt cttattatta gttcgtctag gtgagggttc   1320
acttgatctt gatcattcaa tcgattcatt gcacatgcac gcaattgctc agtgggaaag   1380
cagtcgcgtg agcaatggtg gtgagatcac aacaaggttc ctgcaagcta cgatgggttt   1440
cgtgcaatgt gtgcagatac tactaatgtg tctcgatctt tgttggcaga ctcctagagc   1500
acactaatga ttcctaggaa aggtggtgga ttgtgctagg atggttgcag gtctatttat   1560
ttgcctgaac ccagaagagt acaatcatgt tgtgatgtta atttgcacac catcaacagt   1620
ccactgaagg atcctcggta gattatttga aagcttgtct caccatttat gatgaactgt   1680
atagatatat aataggagtc aatgagggaa ggaatcgatg acaaatactg ttttgataca   1740
aaagcagtag tcgctcaacg agccacatgg aaaagaaaga tacaccgttt ttgatttgat   1800
atccgaagaa attgggtatt cagttcaaaa ccactatctt ggttgtgtat tgattatatt   1860
tgtttgtttg tttgcagtga agataactaa ccggaaactc gctccccact ccactccacc   1920
cttacctgaa tcctatttcg ttatgcgttt cacacagata gattttgggc aag           1973
```

<210> SEQ ID NO 47
<211> LENGTH: 1971
<212> TYPE: DNA
<213> ORGANISM: Aurantiochytrium sp.
<220> FEATURE:
<221> NAME/KEY: misc_feature
<223> OTHER INFORMATION: pSGI-JU-189A
<220> FEATURE:

<221> NAME/KEY: misc_feature
<223> OTHER INFORMATION: i886 Heavy metal associated domain (HMA
promoter); allele A; short

<400> SEQUENCE: 47

```
cttgctgacc ttgcgattgc acccttcatc gaccgtctct ctgttgtgct tccccactac     60

cgctcatttg atccttttcc tgctgactgc gctgaggttt ctcgcattgt tcgcatgtac    120

gaggaggtga aaacccgccc cgctttccaa acaaccgcac aagaccccga gtactatatt    180

catgcgtatt cctcctacgg agaacctaag cgggagatta aagcctcctt gtaaggaaat    240

ctataattcg agcgagcttc actcgaaatg cattgatgga tttatgagtt agtgatagta    300

agtatagaga gacggtgcag aatttacgat atcgccaaac tacatggtta ttaggtatct    360

cgcatttgcc accaagtact gtttttcttt gtttttttcaa aggtgtgggc atagtctttc    420

tgcttgcttc tctgttttct agtctttctg cttgcttctc tgttttctaa ttaatctttt    480

tgataaaagt catttagaac aaagcataaa ataaaatttc aatctctgca aagaaccatt    540

ttgtacaaag gagttcagtc ttagcatcca tgtctctagc cgaaagttgt cgtgaaggca    600

actatgaaga gttctatgtc gcctaaattc cctgacgtgt tcatacaaca tcactcagct    660

atttctacga ccaacacttg gtaatctcac gcaaacattt acttcctctt cctactttgg    720

cattggccac ttgaattgtc ctcttcgtca tttatatgaa acccgcggga ctcggattgc    780

aaaccttact aaaccctaac aacataagaa catctctgaa tgcgcagctc tttgttacta    840

ctttcacaca aagtgcgtac gtagacgcgc gcctcccaaa gctatggttc tgaatcaaaa    900

ccctgattgt catcaaacgt cacttctcaa agcaaaatat ttaataataa tcaaatcttc    960

cgggccctta aattgccgcc ctagctcatt gatagtctat agcagtggtt tagcacgttt   1020

ccacttacct gcttgaatat atttcttggg gtccatatct cgcgtcacta tgtagtaagt   1080

agtaggtagt acaatgagtt atagaatcct tcggtgcaac tttcgaaaga tgctttgaca   1140

caacttctca caaaactttg attacataac agagtaatat gttgcgatag aaagtgtgca   1200

tgtaaattat accaccaatg agatataggg agagcacatt ctaaaatttt tagcttattc   1260

taccttgtac cttcatcgtc cggttctgtt tctccagcta ataggttacc tcatcaagat   1320

tgaaaagttg gtcatttcta gtctctatcc attccttcac ctgcattggt ttctcgaaac   1380

attcggcaag atcccgtaaa accactcgca aaagagtgcc gatgcatttg attttactta   1440

acgtcacttt catatgtatc agtaaaagtt agttatgtgg ggcctatatt aactttgata   1500

attaaaaaaa aagaaaaaaa agaaagaagt acttaatacc tttcatagtc ctatgcttta   1560

tctttaatag aagcgaagct gctcaaccaa atcagtcagc caggcaaaac agaaaccaaa   1620

cgatcgagcg cagccgactt ttcatttgct actcgaagag cattcaacat tgtacgttgg   1680

cgatatggca tcgctgggag gcaggtagct gtaatggaga gctatctttg cgacgtggtc   1740

gggtcctcga gtgatgaagc cgaggtgaac aaacttttgc cctcctcta ccatggtact    1800

ccttgttttg agaagacatt agtagctact gcacttaagc cgagctgacg ttcctttgag   1860

gcttgaatgt agcgatattt ctcgccatgg aggaaggatg acgtttattc tagtagacta   1920

actctgtaga tggggggaaa atatgaatcg atgcataacg tagaaaatac c            1971
```

<210> SEQ ID NO 48
<211> LENGTH: 1930
<212> TYPE: DNA
<213> ORGANISM: Aurantiochytrium sp.
<220> FEATURE:
<221> NAME/KEY: misc_feature -continued
<223> OTHER INFORMATION: pSGI-JU-189B
<220> FEATURE:
<221> NAME/KEY: misc_feature
<223> OTHER INFORMATION: i886 Heavy metal associated domain (HMA)
promoter; allele B

<400> SEQUENCE: 48
cttgctgacc ttgcgattgc acccttcatc gaccgtctct ctgttgtgct tccccactac 60
cgctcatttg atccttttcc tgctgactgc gctgaggttt ctcgcattgt tcgcatgtac 120
gaggaggtga aaacccgccc cgctttccaa acaaccgcac aagaccccga gtactatatt 180
catgcgtatt cctcctacgg agaacctaag cgggagatta aagcctcctt gtaaggaaat 240
ctataatacg agcgagcttc actcgaaatg cattgatgga tttatgagtt agtgatagta 300
agtatagaga gacggtgcag aatttacgat atcgccaaac tacatggtta ttaggtatct 360
cgcatttgcc accaagtact gtttttcttt gtttttttcaa aggtgtgggc atagtctttc 420
tgcttgcttc tctgttttct aattaatctt ttttataaga gtcatttaga acaaagcgta 480
aaataaaatt tcaatctctg cgaagaacca ttgtgtacaa aggagttcag tcttagcatc 540
catgtctcta gccgaaagtt gtcgtgaagg caactatgaa gagttctatg tcgtctacat 600
tccctgacgt gttcatacaa catcactcag ctatttctac gaccaacact tggtaatcgc 660
acgcaaacat ttactccctc ttcctacttt ggcattggcc acttgaattg tcctcttcgt 720
catttacatg aaacccgcgg gactcggatt gcaaaccctta ctaaacccta acaacataag 780
aacatctctg aatgcgcagc tctttttact actttcacac aaagtgcgta cgtagacgcg 840
tgcctcccaa agctatggtt ctgaatcaaa accctgattg tcatcaaacg tcacttctca 900
aagcaaaata tttaataata aacaaatctt ccgggcacta aaattgccgc cctagctcat 960
tgatagtcta tagcagtggt tgagcacgtt tccacttacc tgcttggcta tatttcttgt 1020
ggtccatgtc tcgcgtcact atgtagtaag tagtaggtag tacaataagt tatagaatcc 1080
tttggtgcga ctttcgaaag atgctttgac acaacttctc acaaaacttt gattacaaaa 1140
cagagtaata tgttgcgata gaaagtgtgc atgtaaatta taccaccaat gagatatagg 1200
gagagcacat tctaaatttt ttagcttatt ctaccttgta ccttcatcgt ccggttctgt 1260
ttctccagct aataggatac ctcatcaaga ttgaaaaaat ggtcatttct agtttctatc 1320
cattccttca cctgcgttgg tttctcgaaa cattcggcaa gatcccgtaa aaccactcgc 1380
aaaagagtgc cgatgcattt gattttactt aacgtcactt tcatctgtat cagtaaaagt 1440
tagttatgtg gggcctatat taactttgat aaaaaaaaaa ttaaaaaaag aagtacttaa 1500
tacctttcat agtcctatgc tttatcttta atagaagctg ctcaaccaaa tcagtcagcc 1560
aggcaaaaca gaaaccaaac gatcgagcgc agccgacttt tcatttgcta ctcgaagagc 1620
attcaacatt gtacgttggc gatatggcat cgctgggagg caggtagctg taatggagag 1680
ctatctttgc gacgtggtcg ggtcctcgag tgatgaagcc gaggtgaaca aacttttgcc 1740
ccttctctac catggtactc cttgttttga gaagacatta gtagctactg cacttaagcc 1800
gagctgacgt tcctttgagg cttggatgta gcgatgtttc tcgccatgga ggaaggatga 1860
cgtttattct agtagactaa ctctgtgcat gggggaaaaa tatgaatcga tgcataacgt 1920
agaaaatacc 1930

<210> SEQ ID NO 49
<211> LENGTH: 1888
<212> TYPE: DNA
<213> ORGANISM: Aurantiochytrium sp.

<220> FEATURE:
<221> NAME/KEY: misc_feature
<223> OTHER INFORMATION: pSGI-JU-190A
<220> FEATURE:
<221> NAME/KEY: misc_feature
<223> OTHER INFORMATION: i886 mitochondrial chaperonin 60 promoter
(hsp60); allele A; short

<400> SEQUENCE: 49
agcgaccatg aactacacat cttcttcgcg atcgatcgat cgatcgattt gatgattgat 60
tgattcactg tcgagatcgc ggtgttctca agatgaatga agacttctta gtttgtttgc 120
agccgcaaga aatcagcgag agacctgaag acaaggaaaa cactgtaagg cctggaaatc 180
agggagaatg aatcatcggt ggctctggcc atgtgctgat tcgctcgcca cgaagcagga 240
gattactcag cttatgcgtg aagagccgcc tatcatacct ccgcagctga gaacggcgca 300
atagattgac ctctgagaac cgcaacgaat gaaatcagcc ctgaagaatc agatcaatca 360
atcaatcaat caatcgcaca tgagatttcc attagtttgc aatctctttc tagcgcactg 420
cctaagcgta gctaggcgag aagaaaagaa aaggaaagaa aaggaaacga agcattgcaa 480
atcaaatcgt cgcaaagcag gcaaaatctt gactacacta ggtaacatca cgacaaaggc 540
aaggcaaagc aaagcaaagc aaagcaaaac acatgatgat gtgtctgctc ctgaaagcgc 600
tttcttcaac ccgcggggaa aacaaggcgt aagtcaggtc aaaatttagc caagctctga 660
agaggggcga gacatttaga aaacacatgt agtaattcat taatttattc ataactgaga 720
ccatttctcg tcacccagaa gcaaaaaaga aaaaaaaaaa acagaacaga agaaaagaaa 780
aaaaaattaa aaaagaaaaa aaaattaaaa aagaaaagaa aattaaaaaa agaaaaaaag 840
aaaagaaaaa aaatgtaatg cggcgctgag atcgcgagta gaatcgcgca agacctgcaa 900
taaatgccct gcggccgatc cctcgtgagc atgccttaca attgccagcc tctcccctag 960
gccctgaagc cgacctcaga acaagacgtg caaagccaca gcccgactgc ctgctgcacg 1020
gatgagcctt ctctcactct tctcagtaag aaagaaacaa cgaaacaaag agacaaagct 1080
ctcctctttc ttccacattc acgttcttcg cgaagtcaat ccattccccg cgttccccaa 1140
atgagggttc gcggtcgaac ccgggggctg agaagggcct taaaagcgcg ggtttaaaga 1200
gggatcggga gcggcgggag acaagggatt aaggtggaag tggacccttt tccagaaggg 1260
agaaaagcac gagcgggaga ttgactggtg cagcagatcc cgaacgacgt cttcgacagg 1320
tacgtgcctc agattgaggt gccgctcatg cggcactgta ttcaagcgct ctagctggcc 1380
gccatgttgc tgccactctg tttgccgctc gcggccacac ggctgccgcc aggaccaccc 1440
accacccgct ccagctgccg tgagctgagc ttacctatgg acgcatgagc ggctccaagc 1500
cacacgtcct gtctggtgaa tatccaactt gacgtcgcgg ctttgtctcc atcattctag 1560
ctgcgaatct ggattgctga ggagatcatc gcttctgcgc ggtgtgacgc cggcttcagc 1620
cgcgatagat tgatttggat ggaagcgacc aagcagagcg tcgcatctcc ttaccgggta 1680
ttagggttct gtagatccaa aagacctagt ttatgtattg agtggcagag acgaaaaatt 1740
ggctcaggct aatttgaatg gctgtggcta agtccttaaa tgcttggtgg acaatcgatg 1800
gaagaagagc aaagtgaaca aaaaagactg acctttcaag tttaatttat ttgcaatcca 1860
caggcgacaa aacaaaacac aaataaaa 1888

<210> SEQ ID NO 50
<211> LENGTH: 1838
<212> TYPE: DNA
<213> ORGANISM: Aurantiochytrium sp.

<220> FEATURE:
<221> NAME/KEY: misc_feature
<223> OTHER INFORMATION: pSGI-JU-190B
<220> FEATURE:
<221> NAME/KEY: misc_feature
<223> OTHER INFORMATION: i886 mitochondrial chaperonin 60 (hsp60)
promoter; allele B

<400> SEQUENCE: 50
agcgaccatg aactacacat cttcttcgcg atcgatttga tgattgattg attcactgtc 60
gagatcgcgg tgttctcaag atgaatgaag acttcttagt ttgtttgcag ccgcaagaaa 120
tcagcgagag acctgaagac gaggaaaaca ctgtaaggcc tggaaatcag ggagaatgaa 180
tcatcggtgg ctctggccat gtgctaattc gctcgccacg aagcaggagc ttactcagct 240
tatgcgtgaa gagccgccta tcatacctcc gcagctgaga acggcgcaat agattggcct 300
ctgagaaccg caacgaatga aatcagccct gaagaatcag attaatcaat caattgatcg 360
cacatgagat ttccattagt ttgcaatctc tttctagcgc actgcctaag cgtagctagg 420
cgagaaaaaa ggaaaaggaa agaaaaggaa acgaagcatt gcaaatcaaa tcgacgcaaa 480
gcaggcaaaa tcttgactac actaggtaac atcacaacaa aggcaaggca aagcaaagca 540
aagcaaagca catgatgatg tgtctgctcc tgaaagcgct ttcttcaacc cgcggggaaa 600
acaaggctta agtcaggtca aaatttagcc aagctctgaa gaggggcgag acatttagaa 660
aacacatgta gtaattcatt aatttattca taactgagac catttctcgt cacccagaag 720
caaaaagaaa attaaaaaat taaaaaaaga aaaagaaaat taaaaaagaa aattaaaaaa 780
agaaaaagaa aaaaagaaaa aaagaaaaga aaaaaatgta atgcggcgct gagatcgcga 840
gtagaatcgc gcaagacctg caataaaagc cctgcggccg attcctcgtg agcatgcctt 900
acaattgcca gcctctcccc taggccctga agccgacctc agaacaagac gtgcaaagcc 960
acagcccgac tgcctgctgc acggatgagt cttctctcac tcttctcagt aagaaagaaa 1020
caaagaaaca aagctctcct ctttcttcca cattcacgtt cttcgcgaag tcaattcatt 1080
ccccgcgttc cccaaatgag ggttcgcggt cgaacctggc ggatgataag ggccttaaaa 1140
gcgtgggatt aaagagggat cgggagcggc gggaggtgag ggattaaggt ggaagtgaac 1200
ccttttccag aagggagaaa agcacgagcg ggagattgac tggtgcagca gatcccgaac 1260
gacgtcttcg acaggtacgt gcctacagat tgaggtgccg ctcatgcggc actgtattca 1320
agcgctctag ctggccgcca tgttgctgcc actctgtttg ccgctcacgg ccacacggct 1380
gccgccagga ccaccacccg ctccagctgc cgtgagctga gcttacctat ggacgcatga 1440
gcggctccaa gccacacgtc ctgtctggtg aatatccaac ttgacgtcgc ggctttgtct 1500
ccatccttct agctgcgaat ctggattgct gaggagatca tcgcttctgc gcggtgtgac 1560
gccggcttca gctgcgacag attgatttgg atggaagcga tgaagtagag cgtcgcatct 1620
ccttactggg tattagggtt ctgtagatcc aaaagaccta gtttatgtat tgagtggcag 1680
agacgaaaaa ttggctcagg ccaatttgaa tggctgtggc taaatctttg aatgcttggt 1740
gggcaatcaa tggaagaaga gcaaagtgaa caaaaagact aaccctcaag tttaatttat 1800
ttgcactcca caggcgacaa aacaaaacac aaataaaa 1838

<210> SEQ ID NO 51
<211> LENGTH: 1635
<212> TYPE: DNA
<213> ORGANISM: Aurantiochytrium sp.
<220> FEATURE:
<221> NAME/KEY: misc_feature
<223> OTHER INFORMATION: pSGI-JU-191A
<220> FEATURE:
<221> NAME/KEY: misc_feature
<223> OTHER INFORMATION: i886 Phosphotidylinsositol 3-kinase (PI3K)
promoter; allele A

<400> SEQUENCE: 51
cccttcaaca cgaactccaa ggtgtagtgc cggagcaata taaatcccct tgtttgtaat 60
caaagcccct aaggggctga ttccgagggc ttctcgaaca gataaaggac caactttctc 120
aagcttgcta caagcttgtt ctaagggcag agcatcttca ctaaagacaa aagtatccac 180
ttcccgcgct ttcacaacaa cagatgtatt tgcacccaag atctttccag taccggggct 240
tgggaactcc acacggataa gtacctctgt accagcaatc aggtcaaggt cgtcaaaaaa 300
tacattgaga tttttctccg aaccaagggc ctcaatcgac ttttcttgac agttttgctc 360
agactcatcg ctataattgt ggttatcttc acttccgttt tttccattac tagttgtcaa 420
ctttacacag agattaagca gcggaattcg tgaagtattc aagatgttaa cgcggactag 480
gtgggccttg ccttgggagc caggttgtac cttggctttg atccgcagac ctcttgtgac 540
atactcctcc atcataccat tcatgctctc catcattgag acgctttgct gtaaactttg 600
tcccatcttc gagaacgcac tccccactga agcttcaaga gccttgacgc tcgactgcaa 660
aattgacacg acatctgcag actgtggtgc tttcccagcc tcagtttctt cggagttttc 720
ctccgttgta gctccagtct tcgacatctc ctctgtcaca cgttcctgtg tcttgcaggc 780
ctcggtgcct ggcttctcgt ccatgcttgc aagtcctcct ctcacagtca attcctgtcg 840
ttcgcttttg cctaatcgct atcttccttg ccttccttca agttctccta tcactctatc 900
tttcatcagg ttaacatgaa gatcccgtcg ttagttatca gtaaccgcgg ctcttgcccg 960
tgcactagcc acggcataag tagtcctacc ttgcatcttt gcatcctcta cttctcacaa 1020
tcctatatat caatagcgag ctcctatatt gatcttctca gccgtccacc atgatcactt 1080
ccaaagcatg gcgaactcgg aattactcta ctactgcttg aaggtcgcaa tagttgcagt 1140
taagacaatt cctagcacct gaagagccca gcggatcttt tccaacgtaa ctcaagggca 1200
aaagctccaa agtagcaagc gccacgagtc agaattccaa ggtctcttcg aaaccccact 1260
cccatcaatg atgcctacac ttcctagtac ttaccatcct ctaaactcct acctatctgc 1320
ctagctctga ccctacctgt atcgtgtggc agcggaacct atggcacccg ttccgcaccc 1380
atttagagaa ccggcgcata actgcgccgt ataaccacac cgaggttagg gtatggttct 1440
tttgcgttcg acagtagtga tgaccagcgg tagcggtggc ggcgacgggc ttagggatag 1500
gctatactct aaatagggaa aacttgggtc gcaggaaaga ggcgaaaaca aggagagcga 1560
aggtggcaac cagaacagaa ggacagagag gccagacgag gagcttgcgc aggagcgagc 1620
tatcttcggg gcacc 1635

<210> SEQ ID NO 52
<211> LENGTH: 1637
<212> TYPE: DNA
<213> ORGANISM: Aurantiochytrium sp.
<220> FEATURE:
<221> NAME/KEY: misc_feature
<223> OTHER INFORMATION: pSGI-JU-191C
<220> FEATURE:
<221> NAME/KEY: misc_feature
<223> OTHER INFORMATION: i886 Phosphotidylinsositol 3-kinase (PI3K
promoter); allele C; short

<400> SEQUENCE: 52

```
cccttcaaca cgaactccaa ggtgtagtgc cggagcaata taaatcccct tgtttgtaat     60

caaagcccct aaggggctga ttccgagggc ttctcgaaca gataaaggac caactgtctc    120

aagcttgcta caagcttgtt ctaagggcag agcatcttca ctaaagacaa aagtatccac    180

ctcccgcgct ttcacaacaa ctgatctatt tgcacccaag atctttccag taccggggct    240

tgggaactcc acacggataa gtacctctgt accagtaatc aggtcaaggt cgtcaaaaaa    300

tacattgaga tttttctccg aaccaagggc ctcaatcgac ttttcttgac agttttgctc    360

agactcatcg ctataattgt ggttatcttc acttccgttt tttccattac tagttgtcaa    420

ctttacacag agattaagca gcggaattcg tgaagtattc aagatgttaa cgcggactag    480

gtgggccttg ccttgggagc caggttgtac cttggctttg atccgcagac ctcttgtgac    540

atactcctcc atcataccat tcatgctctc catcattgag acgctttgct gtaaactttg    600

tcccatcttc gagaacgcac tccccactga agcttcaaga gccttgacgc tcgactgcaa    660

aattgacacg acatctgcag actgtggtgc tttcccagcc tcagtttctt cggagttttc    720

ctccgttgta gctccagtct tcgacatctc ctctgtcaca cgttcctgtg tcttgcaggc    780

ctcggtgcct ggcttctcgt ccatgcttgc aagtcctcct ctcacagtca attcctgtcg    840

ttcgcttttg cctaatcgct atcttccttg ccttccttca agttctccta tcactctatc    900

tttcatcagg ttaacatgaa gatcccgtcg ttagttatca gtaaccgcgg ctcttgcccg    960

tgcactagcc acggcataag tagtcctacc ttgcatattt gcatccttac tacctcccac   1020

aatcctatat atcaatagcg agctcctata ttgatcttct cagccgtcca ccatgatcac   1080

ttccaaagca tggcgaactc ggaattactc tactactgct tgaaggtcgc aatagttgca   1140

gttaagacaa ttcctagcac ctgaagagcc cagcggatct tttccaacgt aactcaaggg   1200

caaaagctcc aaagtagcaa gcgccacgag tcagaattcc aaggtctctt cgaaacccca   1260

ctcccatcaa tgatgcctac acttcctagc acttaccatc ctctaaactc ctacctatct   1320

gcctagctct gaccctacct gtatcgtgtg gcagcggaac ctatggcacc cgttccgcac   1380

ccatttagag aaccggcgca taactgcgcc gtataaccac accgaggtta gggtatggtt   1440

cttttgcgtt cgacagtagt gatgaccagc ggtagcggtg gcggcgacgg gcttagggat   1500

aggctatact ctaaataggg aaaacttggg tcgcgggaaa gaggcgaaaa caaggagagc   1560

gaaggcggca accagaacag aaggacagag aggccagacg aggagcttgc gcaggagcga   1620

gctatcttcg gggcacg                                                  1637
```

<210> SEQ ID NO 53
<211> LENGTH: 1840
<212> TYPE: DNA
<213> ORGANISM: Aurantiochytrium sp.
<220> FEATURE:
<221> NAME/KEY: misc_feature
<223> OTHER INFORMATION: pSGI-JU-192B
<220> FEATURE:
<221> NAME/KEY: misc_feature
<223> OTHER INFORMATION: i886 60S ribososomal protein 11 (RPL11) promoter; allele B; short

<400> SEQUENCE: 53

```
gaagcgtttg gttgtagcga catcttcagc ttcagagcgc gtctgtttca aattgtgatt     60

tcgccagatg tatctcttct ttctcaggat gtttcgtttg agcgagtgtc agcagattca    120

aatagcgtat tgctagaagc atattttgca tgtggaggtc cggaacgatg tctgagagag    180

cacctttttct gaatgactta atctagagga ggaataacct cgctcacaat cccacaataa    240
```

atgaaattat acaactgcta cctgagaggg tgaaacaatg caaatgtgtg caaaaggaaa 300
ccgtgtaggc gttgtagtgt tatactatga aaatgacgct tcgttgtaaa tcctttcgcc 360
agttctgttg agactcctgt tcgagacttt tccatcaaaa ttgtaatgag gtatatcagg 420
ggaagacaag actttgaaaa gcaaaataca tttcctcatg cgcacaagtc ctccagagcc 480
agcactaatt accaccatgt tataacgttt ttctggctca ggattcgacc actgtgcagg 540
cttgcagaga tctaggagtc gaatattgtg ctcgttaaga ggttcaatgg gaagatcatc 600
ttcagcaaag ccaatttcat ctccaacagg acgtcctccc tcaagactca gaactgccca 660
acttgctcga gcaaaggttg aagcacacaa tcaaatagat gccacattac tcgaaatttc 720
gcctgttaga tttacacaag tccatagaac ccctataagg acatcctatc ttgaaactct 780
tgatcgctac ctaatgtaag aattgcatat accaaattat atcatgctct ttagttcttt 840
caagatcgcc agccactaaa ctttgatacc gagtccaggc cctgccagca gtcctttgcc 900
aatcaacaag cgcgttttgt ctcaagcggc tccactatgg ttattgtcgc cctccctgat 960
ggtttatctg tgaaaagtaa aaaccagccc taccagcaga actttaatat ctcgcaatct 1020
aaaataacaa aacttatatt attttcataa aaatcggcga gtcatctccg cagagatcga 1080
gctcataaat tatcccccga aatttccccg ctcccctcaa aaatacccct agtggcccac 1140
cgtccttctt tccaccaatc tcggcgcgtc ggtctccttc tcgcgtctaa ggactcctca 1200
ctgtagttcc tcacccatat tggtcctttt gactaagttg gtcccacttt agtgctgggg 1260
tccttcaagc ttctccaggc accccgcggt ctgttagcat ggggtactct ggttaccaac 1320
cacatctgca caactcattt tacgcgatca taattcccta gattccctag attccctata 1380
ttacccattt ttttctgaga acagaacgcc aacagttttg aacacactgc tcgtccagaa 1440
cggcaaaacg gaacagtaga acagagcgag gcagcaacct ccagaacctt tggaacctaa 1500
actagggttg aaaccctagt tttgatccta gtgtttacgg catcaaagtt ctaacacaaa 1560
atcaaggtaa cacagggaac tccggcgcac cactcctttg gcaagcaggg gtaacgcggg 1620
gaatattctt tcctggagga ggcgagaagg gatcggtggc ggagggggca gggcatcgtg 1680
gtgcgcggcg ggcttttaca agtaatgagg caataggggg gcatagtagg aaagtgggga 1740
gaggcgtgga aggcgacgag aggagagagg agcagagcac agacagactc ggacggagcg 1800
caacagcggc aggagctagt tgctttcttt cttaggcacc 1840

<210> SEQ ID NO 54
<211> LENGTH: 1844
<212> TYPE: DNA
<213> ORGANISM: Aurantiochytrium sp.
<220> FEATURE:
<221> NAME/KEY: misc_feature
<223> OTHER INFORMATION: pSGI-JU-192C
<220> FEATURE:
<221> NAME/KEY: misc_feature
<223> OTHER INFORMATION: i886 60S ribososomal protein 11 (RPL11) promoter; allele C

<400> SEQUENCE: 54
gaagcgtttg gttgtagcga catcttcagc ttcagagcgt gtctgtttca aattgcgatt 60
tcgccagatg tagctcttct ttctcaggat ttttcgtttg agcgagtgtc agcagattca 120
aatagcgtat tgctagaagc atattttgca tgtggaggtc cggaacgatg tctgagagag 180
caccttttct gaatgactta atctagagga ggaataacct cgctcacaat cccacaataa 240
atgaaattgt acaactgcta cctgagaggg tgaaacaatg caaatgtgtg caagaggaaa 300

```
ccgtgtaggc gttgtagtgt tatactatga aaatgacgct tcgttgtaaa tcctttcgcc    360

agttctgttg agactcctgt tcgagacttt tccttcgaaa ttgtaatgag gtatatcaga    420

ggaagacaag actttgaaaa gtaaaataca tttcctcatg cgcacaagtc ctccagagcc    480

agcactaatt accaccatgt tttaacgttt ttctggctca ggattcgacc actgtgcagg    540

cttgcagaga tctaggagtc gaatattgtg ctcgtcaaga ggttcaatgg gaagatcatc    600

ttcagcaaag ccaatttcat ctccaacagg acgtcctcgc tcaaaactca gagctgccca    660

acttgctcga gcaaaggttg aagcacacaa tcaaataggt gccacattac tcgaaatttc    720

gcctgctaga tttacacaag tccatagaac ccctataagg gcatcctatc ttgaaactct    780

tgatcgctac ctaatgtaag aattgcatat accaaattat atcatgctct ttagttcttt    840

caagatcgcc agccactaaa ctttgatacc gagtccaggc cctgccagca gtcctttgcc    900

aatcaacacg cgcgttttgt ctcaagcggc ttcactacgg ttattgtcgc cctccctgat    960

ggtttatctg tgagaagtaa aaaccagccc taccagcaga actttaatat ctcgcaatct   1020

aaaataacaa aacttatatt attttcataa aaatcggcga gtcatctccg cagagatcga   1080

gctcataaat tatcccccga aatttccccg ctcccctcaa aaatacccct agtggcccac   1140

cgtccttctt tccaccaatc ttcggcgcgt cagtctcctt ctcgcgtcta aggactcctc   1200

actgtagtcc ctcacccata ttggtccttt tgactaagtt agtcccactt tagtgctggg   1260

gtccttcaag cttctccagg caccccgcgg tctgtcagca tggggtactc tggttaccaa   1320

ccacatctgc acaactcatt ttatgcgatc ataattccct agattcccta gattccctat   1380

gttacccaat tttttttct aagaacagaa cgccaacagt tttgaacaca ctgcttgtcc   1440

agaacagcaa agcagaacag tagaacagag cgaggcagca acctccagaa cctttggaac   1500

ctaaactagg gttgaaaccc tagttttgat cctagtgttt acggcatcaa agttctaaca   1560

caaaatcaag gtaacacagg gaactccggc gcaccactcc tttggcaagc aggggtaacg   1620

cggggaatat tctttcctgg aggaggcgag aagggatcgg tggcggaggg ggcagggcat   1680

cgtggtgcgc ggcgggctct tacaagtaat gaggcaatag gggggcataa taggaaagtg   1740

gggagaggcg tggaaggcga cgagaggaga gaggagcaga gcacagacag actcggacgg   1800

agcgcaacag cggcaggagc tagttgcttt ctttcttagg cacc                    1844
```

```
<210> SEQ ID NO 55
<211> LENGTH: 1890
<212> TYPE: DNA
<213> ORGANISM: Aurantiochytrium sp.
<220> FEATURE:
<221> NAME/KEY: misc_feature
<223> OTHER INFORMATION: pSGI-JU-193
<220> FEATURE:
<221> NAME/KEY: misc_feature
<223> OTHER INFORMATION: i886 small nuclear ribonucleoprotein (snRNP)
      promoter

<400> SEQUENCE: 55
```

```
gtcttctgtg cctgcatctg caatcgtggg agcgtcttcg gcatctccaa agccgtccaa     60

gacgttgttg ggttctttgg ccatctcgtc gcgggaccgc ttcttggccg ccttctcgcc    120

agagttcttg acggatttag gcgccatgtt gcttttctcc gttcgtaatt tgacttacta    180

gagaaccctc ggccgcgaca gcctttgcgt tttaagtctc agttcgcacg gcctagactg    240

cgcaaggtcg cgaactctgt tttggcaagg cttcgaggcc acccacagaa gggggtatac    300

tggaacttta gtaaccgatt cgatcaggaa cgcattacta tctctattat atcgaatttt    360
```

-continued

```
ataatatcac tctctgaccc cttggcgccc accattcatc gtctgtatgg cacttgtatt    420

cttttgataa atgcgagtta tagagtgccc tcaaagtgtc tattggacta ttaggtagat    480

aggaagcata acgccaattt gatatagcac aaggaattgc tttcatatct caaaaaacta    540

taaattattc agggaaggac ttgcttcaac ttgaagcccg agcaaagtgc gaaggaagtc    600

tgataatcag aaaatctgac gatcttaatt aaattcatgt ttttgcttta tattttgact    660

agaattaatg aaaatattct gtgtaattcc aagccaacat gatgtgattg agctgttatt    720

cactggaaag gaagatacgc atagtcttgg tatttgttga ggccaagctc cactttattt    780

tgtaatcctc tgaaaaggta gtattatgat gcctagtttc aaaatggcca ccaagctgca    840

gtatttcata gaaatttata ctttgaggag aactgtacaa ggaatcattg ataagcttgc    900

caagtccttg aaaaagttac caacttttag gaatagtttg agatgtctca aagcacttat    960

tgaatgaatt cccgtttccc aaatttgaag tttaagtgcg ctttttttaat tcaacctgtc   1020

ttgtcgatgc ttcgcttatc acctcatatt gattgtcgag ctgatgaatc cagagccaaa   1080

gtacatatat ctaaagatta tcgtccctca ttattgtaca ccagagtttc tcatttggcg   1140

tcctaatcgt attgactcac caattctaag ccaattcatg ctctactagt agatcaaaag   1200

cttattaggg tgctactatc aaaaaactct aacgcttgcc agcctccctg gtgaggaatt   1260

gtttaattat caatatctgc ctaggtgtaa cctagtacct aggcactcca tcttgttctt   1320

cttcaagttc ttcacattcc tttctccagt cttgggttgc tttgcatcga ttgatgaact   1380

caatcctatt ccactcattc atttcctgct cctctcctcc tgttaacact accctagctc   1440

cacttaggcc cgccatatta cgccctattt gcgggctgct tcttcatgtg ttccctggag   1500

ttgacatcat caagttttct atgatccgtt ccactctatc tgtttgaaag aacaaccgat   1560

agaacaaagg tgcacaagca gagacgaatg gctggatggg gagcggcgtc ttcctagaga   1620

tgatgataga gtttgtgagg tggataataa caagtttgca atagaagcga ttgtctattt   1680

atatccattc aattgactgt gaaggtctat agagcaattg tatactgata ggtggagttt   1740

attgattgtg attatatttg atagagagat tgattgattg attgattgat tgattagaat   1800

tgctcgagga gggtctctct ctctctatca aacaaaccct ctccgtcgct gtcgtcgtcg   1860

ccgctaaacc tcgacgccgc cgcctccacc                                   1890
```

<210> SEQ ID NO 56
<211> LENGTH: 1956
<212> TYPE: DNA
<213> ORGANISM: Aurantiochytrium sp.
<220> FEATURE:
<221> NAME/KEY: misc_feature
<223> OTHER INFORMATION: pSGI-JU-194
<220> FEATURE:
<221> NAME/KEY: misc_feature
<223> OTHER INFORMATION: i886 transcriptionally-controlled tumor protein homolog (TCTP) promoter

<400> SEQUENCE: 56

```
ttattcatcg actgactggc cttggtgcct aggttcaatc attgcattcg ctggtggtct     60

gcgaatcatt aatgggattt gttatgccta cgtttcttac ctcaaaagat aaaaagatac    120

ataccaagat atacaactta atcaatttta actttcgcga ttttcggttc caaactatct    180

ccatccatca ctgagcactg agcacaattc cccaaagcaa actatcacca cactctagat    240

agctctacta gctagctagc tagtagatac aacaacaaat ctatataatt attcaaggat    300

atccttgttt atgatatgcc cctaacatca caacgagcat agccacgaca tttatttatt    360
```

```
ttatatgctc aagagcacac gtttctatct tggttactcc atttccacga taaggcatat    420

gtacatgtaa gttgcaaagc agcctcttgt tacgatcttg cgctcatcaa aaaagctagg    480

gacttatccc agagcttgcc gttttgcata tttgtttctg aggctcggga tttcgtctgt    540

tttgtattgg aacaactttc agggtcccca tgccagcact tgccacgagg tctgactagt    600

tgcgtcgctc tctgatctca aagtcatcga tacctgccta cctccagagg aagtcctttg    660

gtgcgtgagt ttcacaacca aaaacaggca cgccgctgcg agcgagtgac tccggcaagc    720

tcatccacct acatgtatgt ctccagagtc tattgtaagt ttggcatcct cctaagccat    780

ctagctcacc agatagctct agcttagagg tacgccgtcg acgcccaatc tattcattcc    840

ttcattcatc cactgcaatg caatgcagtg caatggtgat tatggagtcc acgccaagat    900

tcacgagtgt gttgtggcag ataagtcaac ccagcgatgg ccaagtcagt caggtaaagg    960

atgaggctgc ttttagaaaa cccgatgaac cgccacgcag gcaatcaatc gtcttataac   1020

cgtaataaac cctcacaggt tcactcacgg ctgttcgcac ctcacgcacc ttcagatcga   1080

gctgtagaac tcgactacac acgcacgctc tctacaccat tgcaatcgcg atgcacgcga   1140

cgcctcgggc atctcctttc gggaggtggc cgggcaccta ggaacgtgtg ttcctggcgc   1200

tgctttcgcc aatccgtggc ccggttctcg caggactcct tctgcaaaga cttcaatcca   1260

tcttgagcac ctcgatctca agatcgctga ttcttcggtc cacgattctt gaaagcgggc   1320

tcgatcgcac actctggact cattaagggg cacatttaag gtctttccac cacagaacgt   1380

tctgaacagc acgtggcatt cagtttccct ccttaacctc cactggcgaa cccgccctcc   1440

taccccactg tcccattaag gcggaaatga gtggctgatg cagtcgtgac ccgctttctc   1500

tctgctaagg tccctcttgc cacgcagaac cttgccactc ccactgcctc acatcgaccc   1560

atttttcttg tgagggagtg tagaacgctc taggtgtgtc actttgtttc ggccccagtg   1620

gcgtgtgagg cagaaagata ccccttgtgt gggcgttttt atgcggcttc aatatgcggg   1680

tgcgcccagt ggggctggga ggggggagcc aaagtttgtg cagcagtggg gccggcggcg   1740

ttggactagt cgcagccagt catcgggact taggtgcctg ggtaggggtg tcttagtgcg   1800

cggctaggcg aaactctgcg ttggaggatc ctgcggagaa gggcgaaaga ggggaaaagg   1860

cggatgagcg tatgaaggca cgggaaggag cggcaacaga ctcgcaatca gcagtggagt   1920

ttacagacgt cgtgacccct ttccgctctc cagaag                              1956
```

<210> SEQ ID NO 57
<211> LENGTH: 1700
<212> TYPE: DNA
<213> ORGANISM: Aurantiochytrium sp.
<220> FEATURE:
<221> NAME/KEY: misc_feature
<223> OTHER INFORMATION: pSGI-JU-195A
<220> FEATURE:
<221> NAME/KEY: misc_feature
<223> OTHER INFORMATION: i886 Tetraspanin promoter; allele A

<400> SEQUENCE: 57

```
agaacggcgt ggaaaagttg gcctcgaacg agcccggcat cggcatcggc atcccgtccc     60

gccccgtcgg gggggaagcg agctggcctg tcagtcagcc tcggcggctg gattatcctg    120

aaaacgcctc gaagcgaacc ctaggcatcg atttgccagc gcgcgaacac cctcatcagc    180

gccaacgtcg acgtggaggt gggcacgaag atggacctga gcatggacct gaagatgcat    240

ggacctgagg atgcatggaa atgaatgcac agcgaggagg gctttgtgtg tcgacgcggc    300

gctcgggaga ttctgccgca tgaagaagaa gaagaagcgg ccgcacgaag gagaaagcga    360
```

aaggttctct cgcgccgctc gatatgagga gaactcgaac tgcttcctat gcgctctttt 420
cttcagccgc ctccccaaag ttatcccata tctgatctga tcatcagcat taaattataa 480
ctgacaacag tagtttggaa tttcaagttt tacgctcttt ttaatttttg ttgttttcaa 540
ttttagaaaa tatgtgatct ttttcttcatc ctaaaaagag attgcttctt gcttggaggt 600
acatattata tatacgggtt cttctagcct gttgcctctt gaggggaaag agggacactg 660
aggggctcag agcatctctc aatcggcgcg gctcttggag acctggagcg ccctgggtgg 720
agatcacagg cgcctctgca cgtacgcgaa gctcggctgt ttggccgatc ctcaggttct 780
gcaggggttt agatcccacg gtcctcgagc tctttcgatc tttgcttgct atcttttgct 840
atcttttgct atcttttgca atctttcttt tgcgagatca ctcatcgttg tgatagatca 900
ttgctttcaa tggaacttcc tcctttttaa taagcttttc ttttctcgcg caggaaagag 960
ttcctcctcc tttcgaccct ttccttcgct gtttctcctc tgctgatcct ctcttccgcg 1020
cagcttccgc actcagacca ggatggcgac tgtgggagat taaaggagtt gctgcgggag 1080
attttaaggt gaggcgctgg cctctgtgag gatcaaagcc acacaaacat ggccagagga 1140
actcagaggc tctgtgggag tgagagtctc tgagactggt cagcaagcca tcgcaagaga 1200
ggagacttca tagactggtc ccttaccact tccaattagc tgatgagtca gtcattaaat 1260
agagataaac ttgaaggaag gaagggaagg aaggaaagaa gcgaagagga aagaaactga 1320
agacagttca gggttcatca tagtccttat atgacttttc gtcttgtttt tgaatattaa 1380
tcatcatatt attttttata attaaatata tttagttgtg aaaagctgat tgagaggatc 1440
gaatacaatt tttttcattc atgagagatg gaggaatcag caaaactgaa acgtgggcta 1500
gaagtcagca agcgaccatc ctgcttgcat cggtggctgc gaaccaaagt agtttgagcc 1560
gtcagcaaat cccgaattgc aaatcccaaa caggtcgtgc ctgtctcgaa gttcgtgccg 1620
gcaacagaag aggacggcaa tcgtccctaa cattgagagt gggacgtcca atcccaagtg 1680
aataaatcca aagcagcaag 1700

<210> SEQ ID NO 58
<211> LENGTH: 1680
<212> TYPE: DNA
<213> ORGANISM: Aurantiochytrium sp.
<220> FEATURE:
<221> NAME/KEY: misc_feature
<223> OTHER INFORMATION: pSGI-JU-195B
<220> FEATURE:
<221> NAME/KEY: misc_feature
<223> OTHER INFORMATION: i886 Tetraspanin promoter; allele B; short

<400> SEQUENCE: 58
agaacggcgt ggaaaagttg gcctcgaacg agcccggcat cggcatcccg tcccgccccg 60
tcggggagga agcgagctgg cctgtcagtc agccagccag cccacggatc ctgaaaacgc 120
ctcgaaccga gggcccgagg aaccctaggc atcgatttgc cagcgcgcga acaccctcat 180
cagcgccaac gtcgacgtga aggtgggcac gaagatggac ctgagcatgg acctgaagat 240
gcatggacct gaagatgcat ggaaatgaat gcacggggag gagggctttg tgtgtcgacg 300
cggcgctcgg gagattctgc cgcatgaaga agcggccgca cgaaggagaa agcgaaaggt 360
tctctcgcgc cgctcgatat gaggagaact cgaactgctt tctatgcgct cttttcttca 420
gccgcctctc caaagttatt ccatatctga tctgatcatc agtattaaat tataactgac 480
aacagtagtt ttgaattttt actctctttt taatttttgt tgtttttaat tttagaaaat 540

-continued atgtgatctt ttcttcatcc taaaaagaga ttgcttcttg cttggaggta catattatat 600
agacgggttc ttctagcctg ttgcctcttc aggggaaaga gggacactga ggagctcaga 660
gcatcgctca atcggcgcgg cccttggaga cttggagcgc tctgggtgga gatcacaggc 720
gcctctgcac gtacgcgaag ctcggctgtt tggccgatcc tcaggttctg cagaggttta 780
gatcccacgg tcctcgagtt ctttcgatct ttgcttgcta tcttttgcta tcttttgcaa 840
tcttttgcga gatcactcat cgttgtgata gatcgttgct ttcaatggaa cttcctcctt 900
tttaataagc ttttcttttc tcgcgcagga aagagttcct cctcctttcg accctttcct 960
tcgctgtttc tcctctgctg atcctctctt ccgcgcagct tccgcactca gaccaggatg 1020
acgactgtgg gagattagag gatttgctgc gggggatttt aaggcggggc gctggcctct 1080
gtgaggatca aagccacaca aacatggcca gagaaactaa gaggctctgt gggagtgaga 1140
gtctctgaga ctggtcagca agccatcgca agagaggaga cttcatagac tggtccctta 1200
ccacttccaa ttagctgatg agtcagtcat taaatagaga taaacttgaa ggaagaaagg 1260
aaggaaagaa gcaaagagga aagaaactga agacagttca gggttcatca tagtccttat 1320
atgacttttc gtcttgtttt tgaatattaa tcatcatatt attttttata attaaatata 1380
tttagttatg aaaagctgat tgagaggatc gaatacaatt tttttcattc atgagagatg 1440
gaggaatcag caaaactgaa acgtgggcta gaagtcagca agcgaccatc ctgcttgcat 1500
cggtggctgc gaaccaaatt agtttgagcc gtcagcaaat cccgaattgc aaatctcaaa 1560
caggtcgtgc ctgtctcgaa gttcgtgccg gcaacagaag aggacggcaa tcgtccctaa 1620
cattgagagt gagtagttct gtgggattgg acgtcaagtg aataaatcca aagcagcaag 1680

<210> SEQ ID NO 59
<211> LENGTH: 738
<212> TYPE: DNA
<213> ORGANISM: Aurantiochytrium sp.
<220> FEATURE:
<221> NAME/KEY: misc_feature
<223> OTHER INFORMATION: pSGI-JU-196
<220> FEATURE:
<221> NAME/KEY: misc_feature
<223> OTHER INFORMATION: i886 tubulin alpha (Tub-alpha-738bp) promoter
<220> FEATURE:
<221> NAME/KEY: misc_feature
<223> OTHER INFORMATION: portion of SEQ ID NO. 20

<400> SEQUENCE: 59
tcagtcactc acgcattcag tttatactaa ggctcaccta gactaatcca taagcagcca 60
atccgttccg cgctcgcgcc ggtagaagca accggaccat acggaggtct taatgtttag 120
gttatatgga ctatgtctta tcggtgggcc gttatacacg ccgcgctgga agctcctcta 180
ctttgtgagg agtttcactt ataatgaatg atcgggattc ctgttcccct cccatccact 240
gggtgcaaaa ctcaactccc tcacaaaaag tgtattctat aaatatatgt aaaagcaacg 300
gtcgctacct ctaagtacac tgatgatata aacaagagca agatggaagt tttcagtgtt 360
tgttgtgagg aacagcactg gaggccaaaa caagcctctt agaaagttct ccactggcaa 420
gcttcgacgg tttggcgcag agtgagggca gcaaactttg ccgcatcgca gcaaatctca 480
atcagccttt tgacggtcgt gcctaacaac acgccgttca ccccaagcct tactttgcct 540
tcgtgcattg tcctcgagta tcgtaagttt gattcgcttt cattcgcttc catccactcc 600
ggttgtagca aaagcaaagc agcgttgtgc ggctctcaag gtttggccct gatgcgaccg 660
acgagcataa actaactagc ctccgtcttg gtttcgtttc acagtaaagt agttttcgaa 720
actccaacct caagcaaa 738

<210> SEQ ID NO 60
<211> LENGTH: 522
<212> TYPE: DNA
<213> ORGANISM: Aurantiochytrium sp.
<220> FEATURE:
<221> NAME/KEY: misc_feature
<223> OTHER INFORMATION: pSGI-JU-197
<220> FEATURE:
<221> NAME/KEY: misc_feature
<223> OTHER INFORMATION: i886 tubulin alpha (Tub-alpha-522bp) promoter
<220> FEATURE:
<221> NAME/KEY: misc_feature
<223> OTHER INFORMATION: portion of SEQ ID NO. 20

<400> SEQUENCE: 60
attcctgttc ccctcccatc cactgggtgc aaaactcaac tccctcacaa aaagtgtatt 60
ctataaatat atgtaaaagc aacggtcgct acctctaagt acactgatga tataaacaag 120
agcaagatgg aagttttcag tgtttgttgt gaggaacagc actggaggcc aaaacaagcc 180
tcttagaaag ttctccactg gcaagcttcg acggtttggc gcagagtgag ggcagcaaac 240
tttgccgcat cgcagcaaat ctcaatcagc cttttgacgg tcgtgcctaa caacacgccg 300
ttcaccccaa gccttacttt gccttcgtgc attgtcctcg agtatcgtaa gtttgattcg 360
ctttcattcg cttccatcca ctccggttgt agcaaaagca aagcagcgtt gtgcggctct 420
caaggtttgg ccctgatgcg accgacgagc ataaactaac tagcctccgt cttggtttcg 480
tttcacagta aagtagtttt cgaaactcca acctcaagca aa 522

<210> SEQ ID NO 61
<211> LENGTH: 1176
<212> TYPE: DNA
<213> ORGANISM: Aurantiochytrium sp.
<220> FEATURE:
<221> NAME/KEY: misc_feature
<223> OTHER INFORMATION: pSGI-JU-198
<220> FEATURE:
<221> NAME/KEY: misc_feature
<223> OTHER INFORMATION: i886 actin (Act-1176bp) promoter
<220> FEATURE:
<221> NAME/KEY: misc_feature
<223> OTHER INFORMATION: portion of SEQ ID NO. 34

<400> SEQUENCE: 61
acagacaaac aagggagcaa gacagacggg caatgtcaca ctgccgtcgg tgtgtagcgg 60
cgcgacgagt attgactgac gcgtgtgcgc acaaccttga tttttagctg attagctgtt 120
aagccaggta cacaaaacat ccattcatac atccaaagaa gatgcaacca taaatacata 180
cacccgtgag tgcataaata gcccgcctcc agacagatcg ggcggcctct gacgcggagt 240
gtgcgagcaa agagcgcgat ttacacattt atcgacagcg aaggatcgct caatccacaa 300
aaaagaaaat aaaaataaaa aatcctaaaa tcatacctcc acctccgaca gatcagactt 360
ctgaaagagg aattttgaaa gaacttagaa agaaagaaag aatgaacgcc aacgagagac 420
tcattcattc tcctcctcgc ctttatctcg aagggttcaa aaggggcgcc gctagggaca 480
agactagtga tatggtagag cccagcaaag ttttaattaa aagctaaagt atatataaca 540
tattgaaaat tattctattg taaagctaaa aattaaaagt ataatagatg ccctatatta 600
aacaattttt atctaactaa gaaaacagaa gagtaggtag cgaaaattgg aactggggtg 660
gcaagagagt tcacactttc ttttcgtaag ttcttttgga taaggaagtt agtgagttgt 720
ttagttgtgc tatccgtatg tttccatttg actgtctgtg tatctatctg tttgactcac 780

```
tcactcatct tttcacaatt ctcgcaagtg aagggggggc atcttgactt tctcgcgatt    840

ttcttcaaga cccccctcct gccccactgg ggtgctttac tgaggcgaaa gctctagttt    900

gatatggaaa ggaggtacag ttaggaggaa gaggggtgtg tttgtgaggg ggaaatgagg    960

cagcagtccg ggtgcccctc agaggcagtg gtgatgagag gaagtgtgag gggtgaatt   1020

tcgaaaggat cctccttaag tggaggcatt cgagagaggg tgcctgccag ctggcggtat   1080

cgtggtcgcg acggctgcgc tccaggatca gcaaacccgc aacctcaagc tcaagaagca   1140

acaacacagt agcagaacaa gcacccaact agcaaa                              1176


<210> SEQ ID NO 62
<211> LENGTH: 776
<212> TYPE: DNA
<213> ORGANISM: Aurantiochytrium sp.
<220> FEATURE:
<221> NAME/KEY: misc_feature
<223> OTHER INFORMATION: pSGI-JU-199
<220> FEATURE:
<221> NAME/KEY: misc_feature
<223> OTHER INFORMATION: i886 actin (Act-776bp) promoter
<220> FEATURE:
<221> NAME/KEY: misc_feature
<223> OTHER INFORMATION: portion of SEQ ID NO. 34

<400> SEQUENCE: 62

aatgaacgcc aacgagagac tcattcattc tcctcctcgc ctttatctcg aagggttcaa     60

aaggggcgcc gctagggaca agactagtga tatggtagag cccagcaaag ttttaattaa    120

aagctaaagt atatataaca tattgaaaat tattctattg taaagctaaa aattaaaagt    180

ataatagatg ccctatatta aacaattttt atctaactaa gaaaacagaa gagtaggtag    240

cgaaaattgg aactggggtg gcaagagagt tcacactttc ttttcgtaag ttcttttgga    300

taaggaagtt agtgagttgt ttagttgtgc tatccgtatg tttccatttg actgtctgtg    360

tatctatctg tttgactcac tcactcatct tttcacaatt ctcgcaagtg aagggggggc    420

atcttgactt tctcgcgatt ttcttcaaga cccccctcct gccccactgg ggtgctttac    480

tgaggcgaaa gctctagttt gatatggaaa ggaggtacag ttaggaggaa gaggggtgtg    540

tttgtgaggg ggaaatgagg cagcagtccg ggtgcccctc agaggcagtg gtgatgagag    600

gaagtgtgag gggtgaattt tcgaaaggat cctccttaag tggaggcatt cgagagaggg    660

tgcctgccag ctggcggtat cgtggtcgcg acggctgcgc tccaggatca gcaaacccgc    720

aacctcaagc tcaagaagca acaacacagt agcagaacaa gcacccaact agcaaa        776


<210> SEQ ID NO 63
<211> LENGTH: 557
<212> TYPE: DNA
<213> ORGANISM: Aurantiochytrium sp.
<220> FEATURE:
<221> NAME/KEY: misc_feature
<223> OTHER INFORMATION: pSGI-JU-200
<220> FEATURE:
<221> NAME/KEY: misc_feature
<223> OTHER INFORMATION: i886 actin (Act-557bp) promoter
<220> FEATURE:
<221> NAME/KEY: misc_feature
<223> OTHER INFORMATION: portion of SEQ ID NO. 34

<400> SEQUENCE: 63

agaaaacaga agagtaggta gcgaaaattg gaactggggt ggcaagagag ttcacacttt     60

cttttcgtaa gttcttttgg ataaggaagt tagtgagttg tttagttgtg ctatccgtat    120
```

```
gtttccattt gactgtctgt gtatctatct gtttgactca ctcactcatc ttttcacaat    180

tctcgcaagt gaaggggggg catcttgact ttctcgcgat tttcttcaag acccccctcc    240

tgccccactg gggtgcttta ctgaggcgaa agctctagtt tgatatggaa aggaggtaca    300

gttaggagga agaggggtgt gtttgtgagg gggaaatgag gcagcagtcc gggtgcccct    360

cagaggcagt ggtgatgaga ggaagtgtga gggggtgaat ttcgaaagga tcctccttaa    420

gtggaggcat tcgagagagg gtgcctgcca gctggcggta tcgtggtcgc gacggctgcg    480

ctccaggatc agcaaacccg caacctcaag ctcaagaagc aacaacacag tagcagaaca    540

agcacccaac tagcaaa                                                   557
```

<210> SEQ ID NO 64
<211> LENGTH: 776
<212> TYPE: DNA
<213> ORGANISM: Aurantiochytrium sp.
<220> FEATURE:
<221> NAME/KEY: misc_feature
<223> OTHER INFORMATION: pSGI-JU-188-short
<220> FEATURE:
<221> NAME/KEY: misc_feature
<223> OTHER INFORMATION: i886 Fa ATP synthase (faas-776) promoter; shortened
<220> FEATURE:
<221> NAME/KEY: misc_feature
<223> OTHER INFORMATION: portion of SEQ ID NO. 46

<400> SEQUENCE: 64

```
aaactcgttc gtggctgttg cattggtcct agatcacaat gccttaaggc ttgggtgaca     60

gctggctgga tggttgccag gatcctatta tttcttatta ttagttcgtc taggtgaggg    120

ttcacttgat cttgatcatt caatcgattc attgcacatg cacgcaattg ctcagtggga    180

aagcagtcgc gtgagcaatg gtggtgagat cacaacaagg ttcctgcaag ctacgatggg    240

tttcgtgcaa tgtgtgcaga tactactaat gtgtctcgat ctttgttggc agactcctag    300

agcacactaa tgattcctag gaaaggtggt ggattgtgct aggatggttg caggtctatt    360

tatttgcctg aacccagaag agtacaatca tgttgtgatg ttaatttgca caccatcaac    420

agtccactga aggatcctcg gtagattatt tgaaagcttg tctcaccatt tatgatgaac    480

tgtatagata tataatagga gtcaatgagg gaaggaatcg atgacaaata ctgttttgat    540

acaaaagcag tagtcgctca acgagccaca tggaaaagaa agatacaccg tttttgattt    600

gatatccgaa gaaattgggt attcagttca aaaccactat cttggttgtg tattgattat    660

atttgtttgt ttgtttgcag tgaagataac taaccggaaa ctcgctcccc actccactcc    720

acccttacct gaatcctatt tcgttatgcg tttcacacag atagattttg ggcaag        776
```

<210> SEQ ID NO 65
<211> LENGTH: 796
<212> TYPE: DNA
<213> ORGANISM: Aurantiochytrium sp.
<220> FEATURE:
<221> NAME/KEY: misc_feature
<223> OTHER INFORMATION: pSGI-JU-189A-short
<220> FEATURE:
<221> NAME/KEY: misc_feature
<223> OTHER INFORMATION: i886 Heavy metal associated domain short (HMA-796); allele A
<220> FEATURE:
<221> NAME/KEY: misc_feature
<223> OTHER INFORMATION: portion of SEQ ID NO. 47

<400> SEQUENCE: 65

```
aatatgttgc gatagaaagt gtgcatgtaa attataccac caatgagata tagggagagc     60
```

```
acattctaaa atttttagct tattctacct tgtaccttca tcgtccggtt ctgtttctcc    120

agctaatagg ttacctcatc aagattgaaa agttggtcat ttctagtctc tatccattcc    180

ttcacctgca ttggtttctc gaaacattcg gcaagatccc gtaaaaccac tcgcaaaaga    240

gtgccgatgc atttgatttt acttaacgtc actttcatat gtatcagtaa aagttagtta    300

tgtggggcct atattaactt tgataattaa aaaaaaagaa aaaaaagaaa gaagtactta    360

ataccttca tagtcctatg ctttatcttt aatagaagcg aagctgctca accaaatcag    420

tcagccaggc aaaacagaaa ccaaacgatc gagcgcagcc gacttttcat ttgctactcg    480

aagagcattc aacattgtac gttggcgata tggcatcgct gggaggcagg tagctgtaat    540

ggagagctat ctttgcgacg tggtcgggtc ctcgagtgat gaagccgagg tgaacaaact    600

tttgcccctc ctctaccatg gtactccttg ttttgagaag acattagtag ctactgcact    660

taagccgagc tgacgttcct ttgaggcttg aatgtagcga tatttctcgc catggaggaa    720

ggatgacgtt tattctagta gactaactct gtagatgggg ggaaaatatg aatcgatgca    780

taacgtagaa aatacc                                                    796
```

<210> SEQ ID NO 66
<211> LENGTH: 788
<212> TYPE: DNA
<213> ORGANISM: Aurantiochytrium sp.
<220> FEATURE:
<221> NAME/KEY: misc_feature
<223> OTHER INFORMATION: pSGI-JU-190A-short
<220> FEATURE:
<221> NAME/KEY: misc_feature
<223> OTHER INFORMATION: i886 mitochondrial chaperonin 60 promoter (hsp60); allele A; short
<220> FEATURE:
<221> NAME/KEY: misc_feature
<223> OTHER INFORMATION: portion of SEQ ID NO. 49

<400> SEQUENCE: 66

```
acgttcttcg cgaagtcaat ccattccccg cgttccccaa atgagggttc gcggtcgaac     60

ccgggggctg agaagggcct taaaagcgcg ggtttaaaga gggatcggga gcggcgggag    120

acaagggatt aaggtggaag tggacccttt tccagaaggg agaaaagcac gagcgggaga    180

ttgactggtg cagcagatcc cgaacgacgt cttcgacagg tacgtgcctc agattgaggt    240

gccgctcatg cggcactgta ttcaagcgct ctagctggcc gccatgttgc tgccactctg    300

tttgccgctc gcggccacac ggctgccgcc aggaccaccc accacccgct ccagctgccg    360

tgagctgagc ttacctatgg acgcatgagc ggctccaagc cacacgtcct gtctggtgaa    420

tatccaactt gacgtcgcgg ctttgtctcc atcattctag ctgcgaatct ggattgctga    480

ggagatcatc gcttctgcgc ggtgtgacgc cggcttcagc cgcgatagat tgatttggat    540

ggaagcgacc aagcagagcg tcgcatctcc ttaccgggta ttagggttct gtagatccaa    600

aagacctagt ttatgtattg agtggcagag acgaaaaatt ggctcaggct aatttgaatg    660

gctgtggcta agtccttaaa tgcttggtgg acaatcgatg gaagaagagc aaagtgaaca    720

aaaaagactg acctttcaag tttaatttat ttgcaatcca caggcgacaa aacaaaacac    780

aaataaaa                                                             788
```

<210> SEQ ID NO 67
<211> LENGTH: 752
<212> TYPE: DNA
<213> ORGANISM: Aurantiochytrium sp.
<220> FEATURE:

<221> NAME/KEY: misc_feature
<223> OTHER INFORMATION: pSGI-JU-191C-short
<220> FEATURE:
<221> NAME/KEY: misc_feature
<223> OTHER INFORMATION: i886 Phosphotidylinsositol 3-kinase (PI3K promoter); allele C; short
<220> FEATURE:
<221> NAME/KEY: misc_feature
<223> OTHER INFORMATION: portion of SEQ ID NO. 52

<400> SEQUENCE: 67

```
tcctatcact ctatctttca tcaggttaac atgaagatcc cgtcgttagt tatcagtaac     60

cgcggctctt gcccgtgcac tagccacggc ataagtagtc ctaccttgca tatttgcatc    120

cttactacct cccacaatcc tatatatcaa tagcgagctc ctatattgat cttctcagcc    180

gtccaccatg atcacttcca aagcatggcg aactcggaat tactctacta ctgcttgaag    240

gtcgcaatag ttgcagttaa gacaattcct agcacctgaa gagcccagcg gatcttttcc    300

aacgtaactc aagggcaaaa gctccaaagt agcaagcgcc acgagtcaga attccaaggt    360

ctcttcgaaa ccccactccc atcaatgatg cctacacttc ctagcactta ccatcctcta    420

aactcctacc tatctgccta gctctgaccc tacctgtatc gtgtggcagc ggaacctatg    480

gcacccgttc cgcacccatt tagagaaccg gcgcataact gcgccgtata accacaccga    540

ggttagggta tggttctttt gcgttcgaca gtagtgatga ccagcggtag cggtggcggc    600

gacgggctta gggataggct atactctaaa tagggaaaac ttgggtcgcg ggaaagaggc    660

gaaaacaagg agagcgaagg cggcaaccag aacagaagga cagagaggcc agacgaggag    720

cttgcgcagg agcgagctat cttcggggca cg                                  752
```

<210> SEQ ID NO 68
<211> LENGTH: 699
<212> TYPE: DNA
<213> ORGANISM: Aurantiochytrium sp.
<220> FEATURE:
<221> NAME/KEY: misc_feature
<223> OTHER INFORMATION: pSGI-JU-192B-short
<220> FEATURE:
<221> NAME/KEY: misc_feature
<223> OTHER INFORMATION: i886 60S ribososomal protein 11 (RPL11) promoter; allele B; short
<220> FEATURE:
<221> NAME/KEY: misc_feature
<223> OTHER INFORMATION: portion of SEQ ID NO. 53

<400> SEQUENCE: 68

```
gtccttcttt ccaccaatct cggcgcgtcg gtctccttct cgcgtctaag gactcctcac     60

tgtagttcct cacccatatt ggtccttttg actaagttgg tcccacttta gtgctggggt    120

ccttcaagct tctccaggca ccccgcggtc tgttagcatg gggtactctg gttaccaacc    180

acatctgcac aactcatttt acgcgatcat aattccctag attccctaga ttccctatat    240

tacccatttt tttctgagaa cagaacgcca acagttttga acacactgct cgtccagaac    300

ggcaaaacgg aacagtagaa cagagcgagg cagcaacctc cagaaccttt ggaacctaaa    360

ctagggttga aaccctagtt ttgatcctag tgtttacggc atcaaagttc taacacaaaa    420

tcaaggtaac acagggaact ccggcgcacc actcctttgg caagcagggg taacgcgggg    480

aatattcttt cctggaggag gcgagaaggg atcggtggcg gagggggcag ggcatcgtgg    540

tgcgcggcgg gcttttacaa gtaatgaggc aatagggggg catagtagga aagtggggag    600

aggcgtggaa ggcgacgaga ggagagagga gcagagcaca gacagactcg gacggagcgc    660

aacagcggca ggagctagtt gctttctttc ttaggcacc                           699
```

<210> SEQ ID NO 69
<211> LENGTH: 749
<212> TYPE: DNA
<213> ORGANISM: Aurantiochytrium sp.
<220> FEATURE:
<221> NAME/KEY: misc_feature
<223> OTHER INFORMATION: pSGI-JU-195B-short
<220> FEATURE:
<221> NAME/KEY: misc_feature
<223> OTHER INFORMATION: i886 Tetraspanin promoter; allele B; short
<220> FEATURE:
<221> NAME/KEY: misc_feature
<223> OTHER INFORMATION: portion of SEQ ID NO. 58

<400> SEQUENCE: 69
agagttcctc ctcctttcga ccctttcctt cgctgtttct cctctgctga tcctctcttc 60
cgcgcagctt ccgcactcag accaggatga cgactgtggg agattagagg atttgctgcg 120
ggggatttta aggcggggcg ctggcctctg tgaggatcaa agccacacaa acatggccag 180
agaaactaag aggctctgtg ggagtgagag tctctgagac tggtcagcaa gccatcgcaa 240
gagaggagac ttcatagact ggtcccttac cacttccaat tagctgatga gtcagtcatt 300
aaatagagat aaacttgaag gaagaaagga aggaaagaag caaagaggaa agaaactgaa 360
gacagttcag ggttcatcat agtccttata tgacttttcg tcttgttttt gaatattaat 420
catcatatta tttttataa ttaaatatat ttagttatga aaagctgatt gagaggatcg 480
aatacaattt ttttcattca tgagagatgg aggaatcagc aaaactgaaa cgtgggctag 540
aagtcagcaa gcgaccatcc tgcttgcatc ggtggctgcg aaccaaatta gtttgagccg 600
tcagcaaatc ccgaattgca aatctcaaac aggtcgtgcc tgtctcgaag ttcgtgccgg 660
caacagaaga ggacggcaat cgtccctaac attgagagtg agtagttctg tgggattgga 720
cgtcaagtga ataaatccaa agcagcaag 749

<210> SEQ ID NO 70
<211> LENGTH: 830
<212> TYPE: DNA
<213> ORGANISM: Aurantiochytrium sp.
<220> FEATURE:
<221> NAME/KEY: misc_feature
<223> OTHER INFORMATION: pSGI-JU-183A-short
<220> FEATURE:
<221> NAME/KEY: misc_feature
<223> OTHER INFORMATION: i886 actin depolymerase promoter (ADP); allele A; short
<220> FEATURE:
<221> NAME/KEY: misc_feature
<223> OTHER INFORMATION: portion of SEQ ID NO. 38

<400> SEQUENCE: 70
cgtttgctac ctactttcag tacctgaaat taaaattaga ataggtaatt cgaggcaatc 60
ttgcacatac acatatatat atttacataa ataatcccaa agacaggagc cgcactttcc 120
tacgattgat tttttaatta attaaccttt taaaaactaa tttaatttga gaagtaaatg 180
aaaaagaaga aaagaaacac ctcctgctac taaaagttcc tcttgtgacg agtcttcgtc 240
catagcacaa cacacataac agatcgattg agaaacaaag gaaacaagca gaggaagctc 300
ctactagcag cggtaaggga ctcttacgcc ggcaagttag gggaatgtgg ggaacgcagt 360
ctgcacatcc ggaggtggcc aactcagcgt cctgcgcctc ctctgtgact ggctacactg 420
tgaaactttt tactcacaaa ggggtgtgct ctccccagtg cgtaacttcc cgcactctga 480
ttgttaaaaa ggtacttcct cagaggttct acagaaaata ctcccgccac aggccaatgt 540
ttgttaacat caatacaaca gacgaaagta tttgttgaga gtacaaagtg atagaggggg 600
agagggagtg agggaagctg tgggagtgag tctgagagga gaaaggtgag aaagatatag 660
gatatattta tagacagagt ggttgagagg agaggcgttg gtatctgtgt ggttctcctc 720
tcatcttcca ctgggacaaa gtcttcctca tgcttcgaag tcgtgcagac ccactactac 780
atttgaattc tactttcgtc tcttcttgac accacttcta tcttgacacc 830

<210> SEQ ID NO 71
<211> LENGTH: 102
<212> TYPE: DNA
<213> ORGANISM: Saccharomyces cerevisiae
<220> FEATURE:
<221> NAME/KEY: misc_feature
<223> OTHER INFORMATION: Alcohol dehydrogenase 1 (ADH1) terminator

<400> SEQUENCE: 71
gcgaatttct tatgatttat gatttttatt attaaataag ttataaaaaa aataagtgta 60
tacaaatttt aaagtgactc ttaggtttta aaacgaaaat tc 102

<210> SEQ ID NO 72
<211> LENGTH: 231
<212> TYPE: DNA
<213> ORGANISM: Saccharomyces cerevisiae
<220> FEATURE:
<221> NAME/KEY: misc_feature
<223> OTHER INFORMATION: Enolase II (ENO2) terminator

<400> SEQUENCE: 72
agtgctttta actaagaatt attagtcttt tctgcttatt ttttcatcat agttcagaac 60
actttatatt aacgaatagt ttatgaatct atttaggttt aaaaattgat acagttttat 120
aagttacttt ttcaaagact cgtgctgtct attgcataat gcactggaag gggaaaaaaa 180
aggtgcacac gcgtggcttt ttcttgaatt tgcagtttga aaaataacta c 231

<210> SEQ ID NO 73
<211> LENGTH: 371
<212> TYPE: DNA
<213> ORGANISM: Saccharomyces cerevisiae
<220> FEATURE:
<221> NAME/KEY: misc_feature
<223> OTHER INFORMATION: Pyruvate decarboxylase 1 (PDC1) terminator

<400> SEQUENCE: 73
gcgatttaat ctctaattat tagttaaagt tttataagca tttttatgta acgaaaaata 60
aattggttca tattattact gcactgtcac ttaccatgga aagaccagac aagaagttgc 120
cgacacgaca gtctgttgaa ttggcttaag tctgggtccg cttctttaca aatttgaaga 180
atttctctta aacgatatgt atattctttt cgttggaaaa gatgtcttcc aaaaaaaaaa 240
ccgatgaatt agtggaacca aggaaaaaaa aagaggtatc cttgattaag gaacactgtt 300
taaacagtgt ggtttccaaa accctgaaac tgcattagcg taatagaaga ctagacacct 360
cgatacaaat a 371

<210> SEQ ID NO 74
<211> LENGTH: 247
<212> TYPE: DNA
<213> ORGANISM: Saccharomyces cerevisiae
<220> FEATURE:
<221> NAME/KEY: misc_feature
<223> OTHER INFORMATION: 3-phosphoglycerate kinase (PGK1) terminator

<400> SEQUENCE: 74
attgaattga attgaaatcg atagatcaat ttttttcttt tctctttccc catcctttac 60
gctaaaataa tagtttattt tatttttttga atatttttta tttatatacg tatatataga 120
ctattattta tcttttaatg attattaaga tttttattaa aaaaaaattc gctcctcttt 180
taatgccttt atgcagtttt tttttcccat tcgatatttc tatgttcggg ttcagcgtat 240
tttaagt 247

<210> SEQ ID NO 75
<211> LENGTH: 580
<212> TYPE: DNA
<213> ORGANISM: Saccharomyces cerevisiae
<220> FEATURE:
<221> NAME/KEY: misc_feature
<223> OTHER INFORMATION: Glyceraldehyde-3-phosphate dehydrogenase (TDH3) terminator

<400> SEQUENCE: 75
gtgaatttac tttaaatctt gcatttaaat aaattttctt tttatagctt tatgacttag 60
tttcaattta tatactattt taatgacatt ttcgattcat tgattgaaag ctttgtgttt 120
tttcttgatg cgctattgca ttgttcttgt ctttttcgcc acatgtaata tctgtagtag 180
atacctgata cattgtggat gctgagtgaa attttagtta ataatggagg cgctcttaat 240
aattttgggg atattggctt ttttttttaa agtttacaaa tgaatttttt ccgccaggat 300
aacgattctg aagttactct tagcgttcct atcggtacag ccatcaaatc atgcctataa 360
atcatgccta tatttgcgtg cagtcagtat catctacatg aaaaaaactc ccgcaatttc 420
ttatagaata cgttgaaaat taaatgtacg cgccaagata agataacata tatctagatg 480
cagtaatata cacagattcc cgcggacgtg ggaaggaaaa aattagataa caaaatctga 540
gtgatatgga aattccgctg tatagctcat atctttccct 580

<210> SEQ ID NO 76
<211> LENGTH: 143
<212> TYPE: DNA
<213> ORGANISM: Saccharomyces cerevisiae
<220> FEATURE:
<221> NAME/KEY: misc_feature
<223> OTHER INFORMATION: Translational elongation factor EF-1 alpha (TEF1) terminator

<400> SEQUENCE: 76
ggagattgat aagacttttc tagttgcata tcttttatat ttaaatctta tctattagtt 60
aattttttgt aatttatcct tatatatagt ctggttattc taaaatatca tttcagtatc 120
taaaaattcc cctctttttt cag 143

<210> SEQ ID NO 77
<211> LENGTH: 217
<212> TYPE: DNA
<213> ORGANISM: Saccharomyces cerevisiae
<220> FEATURE:
<221> NAME/KEY: misc_feature
<223> OTHER INFORMATION: Cytochrome C isoform 1 (CYC1) terminator

<400> SEQUENCE: 77
acaggcccct tttcctttgt cgatatcatg taattagtta tgtcacgctt acattcacgc 60
cctcccccca catccgctct aaccgaaaag gaaggagtta gacaacctga agtctaggtc 120
cctatttatt tttttatagt tatgttagta ttaagaacgt tatttatatt tcaaattttt 180

-continued

```
cttttttttc tgtacaaacg cgtgtacgca tgtaaca                               217


<210> SEQ ID NO 78
<211> LENGTH: 250
<212> TYPE: DNA
<213> ORGANISM: Simian virus 40
<220> FEATURE:
<221> NAME/KEY: misc_feature
<223> OTHER INFORMATION: SV40 terminator

<400> SEQUENCE: 78

agcggccgcg actctagatc ataatcagcc ataccacatt tgtagaggtt ttacttgctt      60

taaaaaacct cccacacctc cccctgaacc tgaaacataa aatgaatgca attgttgttg     120

ttaacttgtt tattgcagct tataatggtt acaaataaag caatagcatc acaaatttca     180

caaataaagc atttttttca ctgcattcta gttgtggttt gtccaaactc atcaatgtat     240

cttaaggcgt                                                             250


<210> SEQ ID NO 79
<211> LENGTH: 39
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0336

<400> SEQUENCE: 79

tgagagtgca ccataggttg gatttctcct ttttgcgtc                              39


<210> SEQ ID NO 80
<211> LENGTH: 32
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0337

<400> SEQUENCE: 80

ctcgtcgctc tccatgtgac aacggccagg ac                                     32


<210> SEQ ID NO 81
<211> LENGTH: 38
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0338

<400> SEQUENCE: 81

tgagagtgca ccatagttag cgcagaccta gctgtatc                               38


<210> SEQ ID NO 82
<211> LENGTH: 37
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0339
```

<400> SEQUENCE: 82
ctcgtcgctc tccatcttgc tttgcgattt gtagagc 37

<210> SEQ ID NO 83
<211> LENGTH: 34
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0340

<400> SEQUENCE: 83
tgagagtgca ccatagcgaa cgccataatc agcg 34

<210> SEQ ID NO 84
<211> LENGTH: 31
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0341

<400> SEQUENCE: 84
ctcgtcgctc tccatggttg cctacttcgc g 31

<210> SEQ ID NO 85
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0342

<400> SEQUENCE: 85
tgagagtgca ccataccgcg caaaaccgcc ttaatc 36

<210> SEQ ID NO 86
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0343

<400> SEQUENCE: 86
ctcgtcgctc tccatttttg ataagttttg ggactcgacg 40

<210> SEQ ID NO 87
<211> LENGTH: 45
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0344

<400> SEQUENCE: 87
tgagagtgca ccatatccct tttagccaat ttgcatatct tctac 45

<210> SEQ ID NO 88
<211> LENGTH: 31
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0345

<400> SEQUENCE: 88
ctcgtcgctc tccatcttgc ctgtcgcgct g 31

<210> SEQ ID NO 89
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0346

<400> SEQUENCE: 89
tgagagtgca ccataggtgt cctcaccctc aagtac 36

<210> SEQ ID NO 90
<211> LENGTH: 33
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0347

<400> SEQUENCE: 90
ctcgtcgctc tccatctcct cgtcgaagtc ctg 33

<210> SEQ ID NO 91
<211> LENGTH: 48
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0350

<400> SEQUENCE: 91
tgagagtgca ccatatcaat gtccatcata ttatcattac gagtcatg 48

<210> SEQ ID NO 92
<211> LENGTH: 47
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0351

<400> SEQUENCE: 92
ctcgtcgctc tccatgatgc tctagattac ttgatgaatc tacttac 47

<210> SEQ ID NO 93
<211> LENGTH: 35
<212> TYPE: DNA

<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0352

<400> SEQUENCE: 93
tgagagtgca ccataacgag gagcgaaggt aggtg 35

<210> SEQ ID NO 94
<211> LENGTH: 34
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0353

<400> SEQUENCE: 94
ctcgtcgctc tccatggtgg tcttgtcgtc catc 34

<210> SEQ ID NO 95
<211> LENGTH: 37
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0356

<400> SEQUENCE: 95
tgagagtgca ccataagcag cttcaagcca tcatcac 37

<210> SEQ ID NO 96
<211> LENGTH: 31
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0357

<400> SEQUENCE: 96
ctcgtcgctc tccatcgtgc gcgggagctt g 31

<210> SEQ ID NO 97
<211> LENGTH: 37
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0358

<400> SEQUENCE: 97
tgagagtgca ccataggagg gaggcatgaa aacaaag 37

<210> SEQ ID NO 98
<211> LENGTH: 37
<212> TYPE: DNA
<213> ORGANISM: Artificial Sequence
<220> FEATURE:
<223> OTHER INFORMATION: Synthetic polynucleotide
<220> FEATURE:

<221> NAME/KEY: misc_feature
<223> OTHER INFORMATION: primer oSGI-JU-0359

<400> SEQUENCE: 98
ctcgtcgctc tccattttgc ttgaggttgg agtttcg 37

<210> SEQ ID NO 99
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0392

<400> SEQUENCE: 99
tgagagtgca ccataaagga tgaggctggt ttcagaaaac 40

<210> SEQ ID NO 100
<211> LENGTH: 44
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0394

<400> SEQUENCE: 100
tgagagtgca ccatagcagg ggtgctagta ttttatacta tctg 44

<210> SEQ ID NO 101
<211> LENGTH: 45
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0399

<400> SEQUENCE: 101
tgagagtgca ccataagaag tattaaaaaa aggaccggat gaaag 45

<210> SEQ ID NO 102
<211> LENGTH: 39
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0401

<400> SEQUENCE: 102
tgagagtgca ccataacttt tcaacttgag atgcaccac 39

<210> SEQ ID NO 103
<211> LENGTH: 48
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0403

<400> SEQUENCE: 103

```
tgagagtgca ccatagatga atgaaagaat gaaagaatga aagaatcg                48


<210> SEQ ID NO 104
<211> LENGTH: 41
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0407

<400> SEQUENCE: 104

tgagagtgca ccatactcaa actcggcaaa cttggtaaat g                       41


<210> SEQ ID NO 105
<211> LENGTH: 37
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0409

<400> SEQUENCE: 105

tgagagtgca ccataagaag ccaaggtatc taccagc                            37


<210> SEQ ID NO 106
<211> LENGTH: 37
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0411

<400> SEQUENCE: 106

tgagagtgca ccatatcgag gacacaacca actcaag                            37


<210> SEQ ID NO 107
<211> LENGTH: 43
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0413

<400> SEQUENCE: 107

tgagagtgca ccatacttcg aagtactact ttgtagatcc tag                     43


<210> SEQ ID NO 108
<211> LENGTH: 42
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0415

<400> SEQUENCE: 108

tgagagtgca ccatacgaat gttgggaact acagaatcat tg                      42
```

<210> SEQ ID NO 109
<211> LENGTH: 37
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0417

<400> SEQUENCE: 109
tgagagtgca ccataaccgg aagcctggat atgtatc 37

<210> SEQ ID NO 110
<211> LENGTH: 37
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0419

<400> SEQUENCE: 110
tgagagtgca ccataaccaa caactgcact aaccaag 37

<210> SEQ ID NO 111
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0434

<400> SEQUENCE: 111
tctcgtcgct ctccatcttc ttgagagcgg aaaggg 36

<210> SEQ ID NO 112
<211> LENGTH: 38
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0435

<400> SEQUENCE: 112
tctcgtcgct ctccattttg cttgaggttg gagtttcg 38

<210> SEQ ID NO 113
<211> LENGTH: 50
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0436

<400> SEQUENCE: 113
tctcgtcgct ctccattgtg ttcttaagtt aaaaacttga cttgaaaatc 50

<210> SEQ ID NO 114
<211> LENGTH: 39
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0437

<400> SEQUENCE: 114
tctcgtcgct ctccatcttg ctaagtgtct tacttctgc 39

<210> SEQ ID NO 115
<211> LENGTH: 39
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0438

<400> SEQUENCE: 115
tctcgtcgct ctccattgtg ctaactacag gtacgtacg 39

<210> SEQ ID NO 116
<211> LENGTH: 37
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0440

<400> SEQUENCE: 116
tctcgtcgct ctccatcttg aaaccaaggt gaggttc 37

<210> SEQ ID NO 117
<211> LENGTH: 34
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0441

<400> SEQUENCE: 117
tctcgtcgct ctccatgccg atttgtcctg cccg 34

<210> SEQ ID NO 118
<211> LENGTH: 35
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0442

<400> SEQUENCE: 118
tctcgtcgct ctccatcttg cctgtcgcgc tgcac 35

<210> SEQ ID NO 119
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0443

<400> SEQUENCE: 119
tctcgtcgct ctccatggtt gcctacttcg cgcaag 36

<210> SEQ ID NO 120
<211> LENGTH: 43
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0444

<400> SEQUENCE: 120
tctcgtcgct ctccatcttt tattagtatc gcgaagctag aag 43

<210> SEQ ID NO 121
<211> LENGTH: 37
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0445

<400> SEQUENCE: 121
tctcgtcgct ctccatgatg cttgcttgaa gacttgg 37

<210> SEQ ID NO 122
<211> LENGTH: 33
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0446

<400> SEQUENCE: 122
tctcgtcgct ctccatcttg ccaggcttgc agg 33

<210> SEQ ID NO 123
<211> LENGTH: 42
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0800

<400> SEQUENCE: 123
actgagagtg caccatatgc tcgcgacttt acgtgttcta tg 42

<210> SEQ ID NO 124
<211> LENGTH: 39
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0801

<400> SEQUENCE: 124

-continued ccgctctcgt cgctctccat tttgctagtt gggtgcttg 39

<210> SEQ ID NO 125
<211> LENGTH: 41
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0808

<400> SEQUENCE: 125
actgagagtg caccatatgc gtccaacaac agagcgcata g 41

<210> SEQ ID NO 126
<211> LENGTH: 42
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0809

<400> SEQUENCE: 126
ccgctctcgt cgctctccat tttgtttggt gctagtagct tc 42

<210> SEQ ID NO 127
<211> LENGTH: 43
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0812

<400> SEQUENCE: 127
actgagagtg caccatatgc cattactcca atccctgaac acg 43

<210> SEQ ID NO 128
<211> LENGTH: 39
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0813

<400> SEQUENCE: 128
ccgctctcgt cgctctccat cttgcctgtc gcgctgcac 39

<210> SEQ ID NO 129
<211> LENGTH: 41
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0837

<400> SEQUENCE: 129
actgagagtg caccatatgc tgtgatagcg agttgtgcga g 41

<210> SEQ ID NO 130

<211> LENGTH: 43
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0838

<400> SEQUENCE: 130
ccgctctcgt cgctctccat ggtgtcaaga tagaagtggt gtc 43

<210> SEQ ID NO 131
<211> LENGTH: 41
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0841

<400> SEQUENCE: 131
actgagagtg caccatatgc cgccgctcat agtgtaaact c 41

<210> SEQ ID NO 132
<211> LENGTH: 42
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0842

<400> SEQUENCE: 132
ccgctctcgt cgctctccat cttgtctgtg tcttcgctaa ac 42

<210> SEQ ID NO 133
<211> LENGTH: 41
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0845

<400> SEQUENCE: 133
actgagagtg caccatatgc tgggagctat ggagtcttgg a 41

<210> SEQ ID NO 134
<211> LENGTH: 46
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0846

<400> SEQUENCE: 134
ccgctctcgt cgctctccat cttgactact ttgtagagac ttggac 46

<210> SEQ ID NO 135
<211> LENGTH: 42
<212> TYPE: DNA
<213> ORGANISM: Artificial Sequence
<220> FEATURE:

<223> OTHER INFORMATION: Synthetic polynucleotide
<220> FEATURE:
<221> NAME/KEY: misc_feature
<223> OTHER INFORMATION: primer oSGI-JU-0849

<400> SEQUENCE: 135
actgagagtg caccatatgc agaatggttt tcgaagaggc ag 42

<210> SEQ ID NO 136
<211> LENGTH: 39
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0850

<400> SEQUENCE: 136
ccgctctcgt cgctctccat aacgagttag gcgcttggc 39

<210> SEQ ID NO 137
<211> LENGTH: 41
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0853

<400> SEQUENCE: 137
actgagagtg caccatatgc tctccagaaa tgacacaccg c 41

<210> SEQ ID NO 138
<211> LENGTH: 43
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0854

<400> SEQUENCE: 138
ccgctctcgt cgctctccat tttgcttggc aaagtttaac ttg 43

<210> SEQ ID NO 139
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0858

<400> SEQUENCE: 139
actgagagtg caccatatgc agcgcaacag ccaaatctac 40

<210> SEQ ID NO 140
<211> LENGTH: 43
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0859

<400> SEQUENCE: 140
ccgctctcgt cgctctccat cttgcccaaa atctatctgt gtg 43

<210> SEQ ID NO 141
<211> LENGTH: 39
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0862

<400> SEQUENCE: 141
actgagagtg caccatatgc cttgctgacc ttgcgattg 39

<210> SEQ ID NO 142
<211> LENGTH: 43
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0863

<400> SEQUENCE: 142
ccgctctcgt cgctctccat ggtattttct acgttatgca tcg 43

<210> SEQ ID NO 143
<211> LENGTH: 41
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0866

<400> SEQUENCE: 143
actgagagtg caccatatgc agcgaccatg aactacacat c 41

<210> SEQ ID NO 144
<211> LENGTH: 46
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0867

<400> SEQUENCE: 144
ccgctctcgt cgctctccat ttttatttgt gttttgtttt gtcgcc 46

<210> SEQ ID NO 145
<211> LENGTH: 41
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0870

<400> SEQUENCE: 145
actgagagtg caccatatgc cccttcaaca cgaactccaa g 41

<210> SEQ ID NO 146
<211> LENGTH: 37
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0871

<400> SEQUENCE: 146
ccgctctcgt cgctctccat cgtgccccga agatagc 37

<210> SEQ ID NO 147
<211> LENGTH: 41
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0874

<400> SEQUENCE: 147
actgagagtg caccatatgc gaagcgtttg gttgtagcga c 41

<210> SEQ ID NO 148
<211> LENGTH: 42
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0875

<400> SEQUENCE: 148
ccgctctcgt cgctctccat ggtgcctaag aaagaaagca ac 42

<210> SEQ ID NO 149
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0878

<400> SEQUENCE: 149
actgagagtg caccatatgc gtcttctgtg cctgcatctg 40

<210> SEQ ID NO 150
<211> LENGTH: 38
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0879

<400> SEQUENCE: 150
ccgctctcgt cgctctccat ggtggaggcg gcggcgtc 38

<210> SEQ ID NO 151
<211> LENGTH: 42

<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0880

<400> SEQUENCE: 151
actgagagtg caccatatgc ttattcatcg actgactggc ct 42

<210> SEQ ID NO 152
<211> LENGTH: 39
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0881

<400> SEQUENCE: 152
ccgctctcgt cgctctccat cttctggaga gcggaaagg 39

<210> SEQ ID NO 153
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0884

<400> SEQUENCE: 153
actgagagtg caccatatgc agaacggcgt ggaaaagttg 40

<210> SEQ ID NO 154
<211> LENGTH: 43
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0885

<400> SEQUENCE: 154
ccgctctcgt cgctctccat cttgctgctt tggatttatt cac 43

<210> SEQ ID NO 155
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0888

<400> SEQUENCE: 155
actgagagtg caccatatgc tcagtcactc acgcattcag 40

<210> SEQ ID NO 156
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0889

<400> SEQUENCE: 156
actgagagtg caccatatgc attcctgttc ccctcccatc 40

<210> SEQ ID NO 157
<211> LENGTH: 41
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0890

<400> SEQUENCE: 157
actgagagtg caccatatgc acagacaaac aagggagcaa g 41

<210> SEQ ID NO 158
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0891

<400> SEQUENCE: 158
actgagagtg caccatatgc aatgaacgcc aacgagagac 40

<210> SEQ ID NO 159
<211> LENGTH: 43
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0892

<400> SEQUENCE: 159
actgagagtg caccatatgc agaaaacaga agagtaggta gcg 43

<210> SEQ ID NO 160
<211> LENGTH: 59
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer PF266

<400> SEQUENCE: 160
ggcgcacgtg attgcgaata ccgcttccac gtttaaacaa actcgttcgt ggctgttgc 59

<210> SEQ ID NO 161
<211> LENGTH: 62
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer PF267

<400> SEQUENCE: 161
ggcgcacgtg attgcgaata ccgcttccac gtttaaacaa tatgttgcga tagaaagtgt 60
gc 62

<210> SEQ ID NO 162
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer PF268

<400> SEQUENCE: 162
ggcgcacgtg attgcgaata ccgcttccac gtttaaacac gttcttcgcg aagtcaatcc 60

<210> SEQ ID NO 163
<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer PF269

<400> SEQUENCE: 163
ggcgcacgtg attgcgaata ccgcttccac gtttaaactc ctatcactct atctttcatc 60
agg 63

<210> SEQ ID NO 164
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer PF270

<400> SEQUENCE: 164
ggcgcacgtg attgcgaata ccgcttccac gtttaaacag agttcctcct cctttcgacc 60

<210> SEQ ID NO 165
<211> LENGTH: 25
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer PF271

<400> SEQUENCE: 165
cgtatgttgt gtggaattgt gagcg 25

<210> SEQ ID NO 166
<211> LENGTH: 61
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer PF274

<400> SEQUENCE: 166
ggcgcacgtg attgcgaata ccgcttccac gtttaaacgt ccttctttcc accaatctcg 60
g 61

<210> SEQ ID NO 167
<211> LENGTH: 38
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0334

<400> SEQUENCE: 167
atgccccggg taccgacgcc ttaagataca ttgatgag 38

<210> SEQ ID NO 168
<211> LENGTH: 37
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer oSGI-JU-0364

<400> SEQUENCE: 168
tgagagtgca ccatatgcat ggagagcgac gagagcg 37

<210> SEQ ID NO 169
<211> LENGTH: 699
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: green fluorescent protein TurboGFP gene

<400> SEQUENCE: 169
atggagagcg acgagagcgg cctgcccgcc atggagatcg agtgccgcat caccggcacc 60
ctgaacggcg tggagttcga gctggtgggc ggcggagagg gcacccccga gcagggccgc 120
atgaccaaca agatgaagag caccaaaggc gccctgacct tcagccccta cctgctgagc 180
cacgtgatgg gctacggctt ctaccacttc ggcacctacc ccagcggcta cgagaacccc 240
ttcctgcacg ccatcaacaa cggcggctac accaacaccc gcatcgagaa gtacgaggac 300
ggcggcgtgc tgcacgtgag cttcagctac cgctacgagg ccggccgcgt gatcggcgac 360
ttcaaggtga tgggcaccgg cttccccgag gacagcgtga tcttcaccga caagatcatc 420
cgcagcaacg ccaccgtgga gcacctgcac cccatgggcg ataacgatct ggatggcagc 480
ttcacccgca ccttcagcct gcgcgacggc ggctactaca gctccgtggt ggacagccac 540
atgcacttca agagcgccat ccaccccagc atcctgcaga acgggggccc catgttcgcc 600
ttccgccgcg tggaggagga tcacagcaac accgagctgg gcatcgtgga gtaccagcac 660
gccttcaaga ccccggatgc agatgccggt gaagaataa 699

<210> SEQ ID NO 170
<211> LENGTH: 798
<212> TYPE: DNA
<213> ORGANISM: Artificial Sequence
<220> FEATURE:

<223> OTHER INFORMATION: Synthetic polynucleotide
<220> FEATURE:
<221> NAME/KEY: misc_feature
<223> OTHER INFORMATION: neomycin phosphotransferase marker gene NptII

<400> SEQUENCE: 170
atggggattg aacaagatgg attgcacgca ggttctccgg ccgcttgggt ggagaggcta 60
ttcggctatg actgggcaca acagacaatc ggctgctctg atgccgccgt gttccggctg 120
tcagcgcagg ggcgcccggt tctttttgtc aagaccgacc tgtccggtgc cctgaatgaa 180
ctgcaggacg aggcagcgcg gctatcgtgg ctggccacga cgggcgttcc ttgcgcagct 240
gtgctcgacg ttgtcactga agcgggaagg gactggctgc tattgggcga agtgccgggg 300
caggatctcc tgtcatctca ccttgctcct gccgagaaag tatccatcat ggctgatgca 360
atgcggcggc tgcatacgct tgatccggct acctgcccat tcgaccacca agcgaaacat 420
cgcatcgagc gagcacgtac tcggatggaa gccggtcttg tcgatcagga tgatctggac 480
gaagagcatc aggggctcgc gccagccgaa ctgttcgcca ggctcaaggc gcgcatgccc 540
gacggcgatg atctcgtcgt gacccatggc gatgcctgct tgccgaatat catggtggaa 600
aatggccgct tttctggatt catcgactgt ggccggctgg gtgtggcgga ccgctatcag 660
gacatagcgt tggctacccg tgatattgct gaagagcttg gcggcgaatg ggctgaccgc 720
ttcctcgtgc tttacggtat cgccgctccc gattcgcagc gcatcgcctt ctatcgcctt 780
cttgacgagt tcttctga 798

<210> SEQ ID NO 171
<211> LENGTH: 28
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Primer W171

<400> SEQUENCE: 171
atcagagcag attgtactga gagtgcac 28

<210> SEQ ID NO 172
<211> LENGTH: 54
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Primer W172

<400> SEQUENCE: 172
gcgtgcaatc catcttgttc aatccccatg gtgtcaagat agaagtggtg tcaa 54

<210> SEQ ID NO 173
<211> LENGTH: 58
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Primer W173

<400> SEQUENCE: 173
gcgtgcaatc catcttgttc aatccccatc ttgcccaaaa tctatctgtg tgaaacgc 58

<210> SEQ ID NO 174
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Primer W174

<400> SEQUENCE: 174
gtgcaatcca tcttgttcaa tccccatggt attttctacg ttatgcatcg attcatattt 60

<210> SEQ ID NO 175
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Primer W175

<400> SEQUENCE: 175
cgtgcaatcc atcttgttca atccccattt ttatttgtgt tttgttttgt cgcctgtgga 60

<210> SEQ ID NO 176
<211> LENGTH: 52
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Primer W176

<400> SEQUENCE: 176
gcgtgcaatc catcttgttc aatccccatc gtgccccgaa gatagctcgc tc 52

<210> SEQ ID NO 177
<211> LENGTH: 58
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Primer W177

<400> SEQUENCE: 177
gcgtgcaatc catcttgttc aatccccatg gtgcctaaga aagaaagcaa ctagctcc 58

<210> SEQ ID NO 178
<211> LENGTH: 59
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Primer W178

<400> SEQUENCE: 178
gcgtgcaatc catcttgttc aatccccatc ttgctgcttt ggatttattc acttgacgt 59

<210> SEQ ID NO 179
<211> LENGTH: 59

<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Primer W179

<400> SEQUENCE: 179
gcgtgcaatc catcttgttc aatccccatt ttgcttgagg ttggagtttc gaaaactac 59

<210> SEQ ID NO 180
<211> LENGTH: 3032
<212> TYPE: DNA
<213> ORGANISM: Aurantiochytrium sp.
<220> FEATURE:
<221> NAME/KEY: misc_feature
<223> OTHER INFORMATION: pSGI-CC-002
<220> FEATURE:
<221> NAME/KEY: misc_feature
<223> OTHER INFORMATION: SG2EUKT121025; Molecular chaperone (Small heat shock protein)

<400> SEQUENCE: 180
atccggaacg gtggctttga ttcgcgactc agagcaagca ttagaaattc ctctcgcaac 60
ctcagagcaa gttagtctca cgacatcacg aattctacat gacacggtag agatcgactt 120
gagcggaacc ccctccgata aagctaaccc tgatacaaac gcagatgcta gtaatgtaca 180
agtgatcaac cttccgcccg gaaattacag catctttgtc tcaagctttg ctattgtaga 240
catggctggc aacgtatacc cgggctctta cacctcagac acacctatca cttttcagat 300
aggcgttggt gcaggtgaca atgatgatga tgatgatgat gatgatgatg atggtgatga 360
tgagaattct tccttcagca tgagttctat tgtgtccatg ttcttttggg cttcaatctt 420
tggcgctatg gccgctgcag gttacgcaat tgcatctcaa gatcgcgacg aggacgactc 480
ttctgcgggg ggcgacgccc cgtcgagctt tcgcgaatct tttgccgatt cttggatgca 540
atttcgcgag tctgtgaatg atcgtctcgg acggggatct tctcccctgg ccccgggaga 600
ctacaccctt gaggacgacg atgaatacga agaggaggtc gtcggcgaga cagagatggc 660
tttgtacccg acgctgccct cagaaccgac tgcatcggca tcgcttctcg cgacggcttc 720
agatgtcacc gacaacgatg acgacgaggc cgttgtgggc gtcgcaaggc ccgaccacag 780
acttggcagg gtctaaactt cctttccgca gactcttact tctgtggaaa tcccgatgcc 840
accacttcaa cgacccttcg tgcaaccatg aatcttgaaa accaatttcg gcacaggcaa 900
tctagccaag cagcaagtag cctaggctag ctagactcgc caccttgtcc aaagatagac 960
tattttataa agacgctaaa tccacgctga tattctctgg cctttccact ctggcctttc 1020
cacagtagtg cttgtgtcga cttattgtga tgaaaaacgt tgttggtcca accttcggaa 1080
ctcggacgcc gcttggcctg cccgcccccc attagcagca tactactgct atcatcgaca 1140
agcttcttcg tactcgtgca tagctgcggt ggcggttgat tgtcgagtcc gtgcgatgcg 1200
tacgacggcc agccaggttg cttgagctcg gcaagatctt ccctcgtgaa cccgcaaagc 1260
ctcaagtgct tgtgtggtcc ttcctggtcg ggctcctcag tgaactgcac aaaggtcagt 1320
gtaggttccc gcgtaatggt cgccagaaac gactacctcg taagccctca aattgcaaag 1380
ccagccagcc agccagccag ccaaccaaca ccatgagggt tcgttcgacg tcaagctgac 1440
gaggtcgaac ttcgaccttg ccaaggacgc gctcggcatt ctcgggccat tcgcgtacgc 1500
ttgcgggagc cctcacgtcg ccgcgcacgc agagccatcg ctcctacagc aaccaacgga 1560
gtcccattcg atgtcttacg aagcagcagc atctatctgt tccacgtttt tctcttcatc 1620
tctcaaagag aacagaacac aagctaaaga tctttagccg cgaaactgcc cccccagctc 1680
tcccgcattt tatcctcctc acacgccacc acttgttcta gaacgttctt gcttcaggcc 1740
ccgcacctgg cctgcttggc gagcggaaaa ggcgtcccgc gaggtgctgc gtggcgcatc 1800
gcacccccca agctccgcag tggggacgca tttgattcgt cgcggctttg cgggcctgag 1860
tttgctgcgg ataagccgcc caaagcctgc ctgcccgggg ggaagctgcg gtctgcctgc 1920
gcctgcgccc ccttccgccg gcgccgcgaa ggcctttctc tgcgtccggg acgccgctct 1980
cctcaacttg agggccatct ccgtatgtct tcgagaactc gcactctcag atcgcgaaaa 2040
gggctttgaa aggaaatgat gcgaaatgaa acgaaacgaa acgaaacgaa acgcaacgaa 2100
acgaaacgaa acgcaacgaa acgcaacgaa atgcgaacgt gaaggtccaa aaggaaaaga 2160
aatcgaaaga agagacagag gaagagggac gaagagctct ggtcttactg gtagcaccgc 2220
tcattcgtga aacggtagca gtggccggta aggggatcct gcgtggggag gtcatatggt 2280
taagggtagg cgagcgttag ttgtgtgggg gaggggggtt agtatctttc tttctcgacg 2340
attctgaagg tctgaggttc cggcggatct tcaagttctg cggacgacgg cgcgaggttt 2400
ctctgtctga ggagagcgcc ggttctgagc cgaagcgcag aagaaggcgc tccggagcaa 2460
accgcctccc ctcaaaagac gcctttggag tctggaaatt cttggttctg ttctgctgga 2520
tgacgactga cttatgcggg gcttgggtgt aatacgtttg ttaccttcaa gttcgttctc 2580
ctttctttct ttctttcttt ctttccttct cttcctggag cgagggctag cgcttattta 2640
ggttaaaaga gtaggactgc tttcaaactt gctctccaga gagtttggaa aatagaattt 2700
tgatacttgt tttaaaactc ctttttattg agggacgcaa tcgatcgatc gatagataga 2760
tcaaatctcg aaaccttcgc aaagattggc ccgcgcagag atagatcttc gcgagtcttc 2820
tgacgggagc agcaactgct gctgtgaggg gagccctaag tgcctgccgg ggtagtggtg 2880
gttcgacaac accctggcga gcgagttacc gaacagtgag gcttttgaag agtcccgagc 2940
caactcgtgc gatcccctct aggaggctct acctgttata tatatttata tatataggtt 3000
cgtagaggtt aaggttgagg gatttggacg ca 3032

<210> SEQ ID NO 181
<211> LENGTH: 3001
<212> TYPE: DNA
<213> ORGANISM: Aurantiochytrium sp.
<220> FEATURE:
<221> NAME/KEY: misc_feature
<223> OTHER INFORMATION: pSGI-CC-003
<220> FEATURE:
<221> NAME/KEY: misc_feature
<223> OTHER INFORMATION: SG2EUKT124470; Elicitin-like protein 6 (Precursor)

<400> SEQUENCE: 181
gaataccgct tcctcaatga aaccctcata aaccggagtg ccttcgggag agtcccttta 60
gaatgaatat actttctcga aactttggct caagcctctt tcgaccaaaa cagcgcccca 120
ctcattgcat tcattcaaag tgcctgtcac aaatgcctgt gaagcagacc ccacgtagaa 180
aagagaatac gcctttaaaa agcagaaccg ctgcttgaat tgagcgactg ctttggcttg 240
ctttcacagc ttgctgcaga accagcgaaa agactttctt tcgccttggc tcatgcattc 300
attcattcat tcattcattc attcattcat tcattcattc attcattcat tcgttcgttc 360
attacctcct aagaagagtt ctgcctcttc cgctcttttg cgttcattct ccttcgcact 420

-continued

```
ctctgaaact tttctgagca tgattcatca aaatgaatgc atctatccta cagcactagc    480
actacgtagg caggtcctac ggcagctaga aggaggcgtc gctctacttc ccacgtgaga    540
ggagggagtc tgaacaacgc acgccatgcg aggggcccta ggcattcctc tagctggctg    600
ccagtccttc aggaatcaag ggatcacgca cattccaact ttgacaaacc cgctgttgca    660
atgcatcagt gatcgatcga ttcatggaaa gcttcgatgg tttgcgcgcc ttcttcgcct    720
ctgctctctc ttccaggcag cctgcatgcc ggagtcttgt aaggaagtgc ggaagtgagg    780
aagcaaggaa ggaagcagag ggaggaagtg aacaaacagc ggaaccaatg gataagatag    840
atcagccaag gaatgagtca gtgaatgaat gaatgaatga atgaatgaat gtatgtatgt    900
atgtatcaat gaatgaatga aatatcaatg aatgtatcaa taaatgaatg aaatatcaat    960
gaatgaatga aatatcaatc aatgtatcaa tgaatgaatg catagcatgt ctccccaaac   1020
actcacttca ttggagtgtc ttcttctttc cctgcagagt ggcaggtttg tacatacgtc   1080
ctcccatacc gcaacatatt cgtgccgctt ttctgtgtca gttcttcttt gtgcatccat   1140
cttcaattta tttgaatgca ataaatagat agatagatag gtagataaat aaataaataa   1200
ataaaaacct tcgtggatct tgattcgtcg ctcactttat tttcaagctg ccctttgttc   1260
ttttctactc gcacagcaga ataaagaaag aacttgcata atagaaaagc aaaccaaata   1320
ccaaagtcaa acttggaagt acttcttccg cgacatttat tccataacaa acaaactcca   1380
gtcacggcgg tgtgcctaga tacaggacac cgcgtagtcc gaaccatgtt tcatcattca   1440
tatgagacat tcaagctcaa gttcattcaa gttcatgcaa gttcattcct tgatcctttc   1500
ctgtggcaag ctcgctcgtc agttgcctgt caacctgtgg atggacgcgg cgacgttcga   1560
tcgacggcac ttcattcgcg caagccatcg ctcaatcggt ggcgccactg ctttctcgaa   1620
ggcgccctct caagtgcaca ttagagaatg cggagtgtga tttctacttt tctccacttt   1680
cttcgcgctt tttcctgcct cgtgcaaaag tgcgaaatcg atcgaccatt cctggcactc   1740
gctaggagtg cgctagggcc gcctagaggc gggcgtgcgc cttcactctt ttcgaatcga   1800
tcgactgatg gtttgaattc cttcctcttt gccgccgttc tcttctccac gcgaagagaa   1860
cgccgttcta gatttgagga aaagtggctt tcgcagagaa cgtgtttgtt catgcattca   1920
cgcaattgca ctttctccgc atctcagggc ttctgcggtg cgacggccgc tcagaacacc   1980
cgtgtggaca tcacgggccg taaaagaaag ctgtccatgg acctctcttc tcagcgctcg   2040
ctttcgcgtt gtcacggtcc gcagagaagg cgagttagat cctctcactt tgaacagcag   2100
aactacaaca gacgaactgg agagccatgt ttttttggtt tttgctcttt tggcgctttt   2160
tcttgtttta aaaccagcag aaccgtgtct cgtactgtca ccgcaggcta aagtagagga   2220
ggtggcgata acagacaagg tgatgaatct ggctgcgggt taacagttct cgcaagggct   2280
ctctggcgac agtggcagtc acgtgactga atgcaaaaaa aaatattaat ttaataaaaa   2340
taaaaataaa attaaaatgg aaggccgccg gaaactggaa tagaaataga cgggaatgca   2400
ctaattatgg ggtatatatc gtcgcgtgga gtgctgacga aggcgcctat agctgtttca   2460
aaccttgggc acagaagtac ggtctggttt gtgatatgct ttggactttc ttgcaaagga   2520
tttgctttga gcttgaaaat acttgtgtat gattacttgc ttttcttgtt tgtttgtttg   2580
tttgtttgtt tgtttgtttg ttcacttgat tttcattaac agcccgggaa gtaagaaaat   2640
atggtctgaa ttaaaaaaaa aagtgatgtt cccacttttc tctcatccta actcatccca   2700
gcttaaagag tatcttggcc gccctcttca agaatcgagg cgcgcttgat tggttaaaaa   2760
ttatgcatcg gggtccgtgc atcctgaaga agcaaagcaa acctgaaatt gtgtagccag   2820
```

ggctcagcaa aggagctctg gaccagcaca gctacccacg aaccacggcg agggcaccag 2880
aacctggtgc accccgcggc aacatcaaat ctcgaagaac tcctacgttg taataacaac 2940
aggagagggt tcatcaagaa ggaccttgaa tcacgggcaa tcaaagcagt tgccttgaac 3000
a 3001

<210> SEQ ID NO 182
<211> LENGTH: 3044
<212> TYPE: DNA
<213> ORGANISM: Aurantiochytrium sp.
<220> FEATURE:
<221> NAME/KEY: misc_feature
<223> OTHER INFORMATION: pSGI-CC-004
<220> FEATURE:
<221> NAME/KEY: misc_feature
<223> OTHER INFORMATION: SG2UEKT110570; NADH-ubiquinone reductase complex 1; MLRQ subunit; Nurp

<400> SEQUENCE: 182
cctgcaaaga catagacaca ttaggccagg acaattaatt tttctctgct tttctgacca 60
agttctcctt catcgcgagc acactgttct gatgaatacc ttagaacgta tataacctcc 120
gaatgatatt ttttattcct tttagagaag atgaattata attatttagg tctttgttaa 180
gaggcggatg ccaggtgaaa aatggcatgg ccaaggaacc accaagctcc taacacttca 240
agtgaagcaa accttccaca agccagcaaa gcacttcaac cagaagtctg gcgtctcagc 300
aagtcccctt cgagtgcttc tccggcggcc attacataca cgcaagtgac gacggttttt 360
gagcgcatct atggctgcgg tttgctccgg cgggccgcca gcaatgcaac caatatctat 420
gccagagcgt cctccaccaa gcagaaagag aattccaaac gccagattgg ggacctccag 480
cgtgcctatc cagatgcttc caccgtctac aaaagcatct ttggagggga cagcggcaaa 540
aggccgggct tgtgcgccct attggactgc cgagattcac tgcaagcctg ttctgtgagc 600
actaccgtgt tatccttttg cctaaattgg aaacctcaaa agttgacaag ataaatcaaa 660
gtctaaacag ctcgaatgat atgtcattcg ttggcgtgtg actagcgctc atttacaaag 720
ccgagccgag cttcccccct gccagtggtg caagctggcc atttgttgag aggattgcac 780
tgtcaaaaca tgtaatgaat gtggcaccta acagtcacaa caagctctga gcatgcaagg 840
tattcaaatg caccagatgc aaatacgctg ccgatcgtga tgtccacgcc gcccgaggcg 900
tccttttgtg ctacctgccc aaggacataa tttaaattca tgtctttgaa tcacgaatta 960
gttgttaaac tcgcgattgg gccttagtcc cacgtcacca taggaaatgc aagttttgca 1020
aattccctac cttctaccta cttgaagtga ctactcttaa atactcactc ccaggttgtc 1080
cacttagact ttaacctaag gtacccccctc aagctaggca tgtatatcaa atcactcgat 1140
cttcaacaag tcgagtatcc ttccatattc aactcatgca tgttcaagtt ggatacagac 1200
tccttaacaa tttactacct agtagtaaca gaatcagaca gatagtgaga tagacaatga 1260
gtaagttgtt taatagacgc gaaaattcct cgaataacgc aaagaggaag agtttcttcg 1320
aagactttaa aactattact gcctaggtcc tacttaggta catactagtg ggaacctaat 1380
tactactgtt atcttaccat gtagagaacg gctttttccg ctctcacctt tcaggtttgg 1440
aagacgcggt aggacagtag acgattatac aaggcaggca gaagcagaga gcgaagcctg 1500
gatcgcaaag ataagatcgc gcagatctaa aatcaacttg gcaagtgact gcaaatacac 1560
taccaaagac cacctactag aaacaaacca gtataggcca cgtaggctag aaggtacagg 1620
ctctctctca atctcaactc agttcacctg agataagaat cggttaacag cttcagagtt 1680

```
gtgattaatg aataacaagc aacagatcac acctacctac tgagtagact ggtaggaaac   1740

gccgtgaatt aacccaatgc cctccgacca accagaatac tggcggcagc ctccgaccca   1800

tcaagttttc aggtttggcg tccagaaggc gtagcgagaa tcgcactagc agaaagaagc   1860

tagctaatgc agcgtcggag gtaaaattac acgcatcaat gcgtgcttaa tcaatttact   1920

actctacaat aattctagta ggtagcgatg gccatggcgg tgatgatgat aaaagcaaag   1980

accatatacc tttacagctc agcctgaaag aaatgaaaca acttcgggag gcgaggccag   2040

aagaaagcgt tactacatag tacctacctt ccagctaagc gatctgaacc gtacgcagac   2100

cccgaagata aatacttgtg gacagttagt cggtgtcagt cgatatatcc tttgatatat   2160

ggtagcggcc tagtattact atgatctgcc taagaaccgg tctaaaatgc gactgttgga   2220

tattcaggtg tgatcatgac cgcggtactg ctgcctacct actactgaaa ggcacgtttg   2280

gtagggctag gtagtagtag tttatagtag ttatctacta tttgagggct aagtagtatt   2340

agtacatagg tgttgatttt aattttaact tttttagaga aacatttgat gttggttggt   2400

cctctcctac tgctaatggg taggcaccct actatcaaat cgaaagaatt ttaccagaga   2460

tatttctttc tgactgagtc aagtctttct ttctcactct cctgtctctt ttcttcgact   2520

cttccactct gcctaagaga cccgtcctcc tgcaaacact ttcaacccga cgtgtttgac   2580

tctcacaacg atgaggttct gtcttgatcc tgggctcctc tcaaggtttt aagctttcta   2640

gctttcgttt tgctttttcg tccctttaga gtttctcgtt tgtttgtagc tttaaacagc   2700

aaatcaagtc cctcttatct ctctctctcg ccctctctcg ccctctgtct ccctctatct   2760

ccctctgtct tcctctgtct ccctgtctcc ctctctgtct ctgtctccct ctgtcactct   2820

agttttcaag ctcttctcta tctcggtgct tgcttctctc caatgcccac tgtctctttt   2880

ccactgagct ttcactaaaa cgccaagatg accaaactga tcgatcaaaa gttgccatca   2940

aatctcaaac acctacccga gcgaaaaaca acaaccaaag tcatttaggt ggataatctc   3000

tttactccgt tcgggttgtt agcaagtcac tgttgccagg aaaa                    3044
```

<210> SEQ ID NO 183
<211> LENGTH: 3000
<212> TYPE: DNA
<213> ORGANISM: Aurantiochytrium sp.
<220> FEATURE:
<221> NAME/KEY: misc_feature
<223> OTHER INFORMATION: pSGI-CC-005
<220> FEATURE:
<221> NAME/KEY: misc_feature
<223> OTHER INFORMATION: SG2EUKT123280; Glyceraldehyde 3-phosphate dehydrogenase; NAD binding domain

<400> SEQUENCE: 183

```
tgcggttcaa gttcgaagag gcttgaccaa gcgctcccaa atctagcctc gtaaaaccta     60

ttttagaatt gcggaagctc cactaaaaca caggagatac ggcgaacatc tctgcgtagc    120

atcgcacggt ttcgcctcgt ttcaggatcc acagtttgtg tgaatatcta cctaccaaac    180

ccatggagag atgagattga aagattggca aaactactgc tactgggaat agaggcagcg    240

cacgctttcc aggctcaaag atattctggt tacccacgat ttctgcgtgg atgaagtggt    300

ttgagaagag cgctacgtcg tcttcgccgg ggccggcatc atcagttgtc atcggcggcc    360

gctacgagtt tgtcgggtct tttgccacaa atattgacta ctggtactag gcacctattt    420

tcctgcaaag attcgaggag gacgttggca aatggatgcc aggacgaact tcaaagtcca    480

gcttcatatt atcgagacgt gttgcaggat caatcagctc cgaagcacat tccctatcgt    540
```

```
gcttctcagg cctggcggga atgcgaaggt gcctactctc ttggtgcaca ctgcctctag    600
aggagcatcg cctccagata gtagcatctg gaaaacgatc tgctgaagtt ctgaagggga    660
gatgccgcca ggttcctgct ggtttgacct tggatttgca gctagtttct ttcgacgttt    720
acagtgacat cgaagtcgtc tggaaacacg atagcagacg aaatgttgcg aacctcatcc    780
tgcgccccgg caacctcccg gaaagccgac ggctggagcc acaaataagg aggcaagctt    840
tccgcgaagg cgtcgaagtc aatgagaagg acaactttcc gggttcgagg ccgccttcaa    900
cgacggcccg aggccgaaga cgaccatcca agaaacctaa aggaggccgt cttcgatata    960
caataatcaa aatcggccaa gtcgtagaca cgatttcaaa ttgctgagga gagcttcttt   1020
cggacaactg gcgtccttga gcatgtggtc aaagccggcg tcgaacctgg acgtcgaagg   1080
ccactgaggc tcaattcgtg aatgtgaatg cagcccacgc caaatcaaac cagagccgcg   1140
gaaataaatg ctcgagcctc catgagcgat tcatgatcac tcatcacttg aagataggta   1200
attgcacgct tcccaacttg aagggttctc agaaatccat aaccaatcca tcatgctcag   1260
gattacctac ttattctgcg ccggtgagtc agagaaattg ccaccgagga gcttgctagc   1320
tataccgagc caggcagagg cggctgaggg tttgtttgta ggcaggcagt ggttcttggc   1380
cgtgctcgcg ttttggccgt catcgatcta tcctcgtcaa tcatcgacgc agaggctaag   1440
aaggatttga ccaagcctcg ggcacccccc agctgcgcag ggacggaagg cgggcgagta   1500
tgtgacgacg cgctcagcag ggggtgaaag atccggactg ccatttgaac gagtagtaat   1560
ttggcgcagc tcacaattat ctttccggtc ctactgctac aacgctctct cccctgtcct   1620
atataccact agaggagagc tcgttcaagc tcttgatctt gtgaggactc cactgggatt   1680
tcccgacaca agaaagcgcc agtgaacaga gggagaagtg ggcctcgaag tagcggtatg   1740
attatgtgag ggacacgggg cggagttccg gcgttccctc aggccttcct ctctgcgcct   1800
caggcaagtt tctaggaaaa gtgattttgt ataataatct tgtatgaaaa tgtgaagcgc   1860
aagtgcgcag aacctagaaa atctaaaaca aaagaaaaaa gagatcgtca cccgagcagc   1920
agaatcaatt cactccaagg taagtaacgc gtgctgtgcg ggagcgcccc cggtcagtca   1980
gtgttggagc ttgggataag ttgcatctgc gcgaagggtt ggcccatcca tctcaagtcc   2040
tttcctggcg gtttcgcccg cgtcaccagc cgcctggtgc tcctgatgga tggggactct   2100
ggatggtcga aagaggatgt gttgtatcta tctgtctgat aaggtaaaag gggacggctt   2160
ctgtactttc cttcttcgtt cgctcccgat cgtgtcttct aggatgcgcg atttcgatgt   2220
gctgaagatt ccgagcaccg tatgctatgc cgtctccgtc ttgcctgtgt tggcggctag   2280
ctagcgctga gggttgtgga cggccttggg aattaggaaa agaaagatac tcgtgtcgtt   2340
gaaacgtcct gttctttttc ttttctagta ttttctattc cagtctttac tttctgttcc   2400
tttcatttca cttcaagtac atcgtcacct ttatcgatct agtgtgagcc taactgagcg   2460
tcctgtcatg tagcaggagg aactacagag gttccgactg gtacgaacaa acgaatcggc   2520
gaacggagag taggcatgaa gttgttgttg tccaagatca aaaagataga aacgaatatc   2580
tttcttgttc tgctacctac attgaaacgg acatgaaaga cgacaattct agatgaagac   2640
actgccaaaa gggaagaagc gctcggccac cgcagcaaga aaggcaagag agagaagata   2700
aagtaaattt tcgagagaac aaaagaaatg aatgcaggaa ggaaggaagg aggggaggta   2760
gtgaaagaac gcgtgacaag atttgtaatg aagaacatgg catgaaagaa cgaacagggg   2820
ggactgacga tttgagggac tgatgtgcgc aattgaatct tttcatttg cattgcggct   2880
```

-continued

```
gcggcggcaa acaaaacaaa aataattatt cggcattcac tttggttgcg ttgttggaca   2940

acataaccat aacagaaaca aaagcaagga aacctagcgc acacataaac accaagcaaa   3000


<210> SEQ ID NO 184
<211> LENGTH: 3001
<212> TYPE: DNA
<213> ORGANISM: Aurantiochytrium sp.
<220> FEATURE:
<221> NAME/KEY: misc_feature
<223> OTHER INFORMATION: pSGI-CC-006
<220> FEATURE:
<221> NAME/KEY: misc_feature
<223> OTHER INFORMATION: SG2EUKT121957; Fructose-bisphosphate aldolase,
      cytoplasmic isozyme
<220> FEATURE:
<221> NAME/KEY: misc_feature
<222> LOCATION: (1998)..(1998)
<223> OTHER INFORMATION: n is a, c, g, or t

<400> SEQUENCE: 184

cttcggatcg ccctttactc ggacttgcct cggcaataaa aaaaaagagg ccgctcacct     60

cacggcccag gatatctttg caatgccgtc caccaaattt gcacttctag atgctgttta    120

ttgctgaaga tgccgctcga gatgaaatag tccgagtgaa ttgttggtag aatttctttc    180

aatctacgat gcaacaaagc tccgaatccg gcgaggtccg agcgagtttt gctgtgcttt    240

tgtgccttcc ttagcgccgt ctctctttat atttctgcac ttaattttta cctctcgcca    300

cgtagacacg tcaggctact acctactata ctagcacaac tacaaggcaa aacttgagcc    360

tgatgagaac gttgtgctct tcaagacaat caagtcttcc tcttgctgcg atggcttgac    420

ttgcctccac tctttacgag agtgccaaag accggcacca aacaattgtt ataactaact    480

ccttgttcac gagtgctgtg ccagacgcct tacacaggaa agataagatc gctcgatacg    540

ctcccctgcg ccaggcaacc agccgccgag ctgggactgc tgctactttg ctatgctgct    600

acagccgagc aatctccgtt ctgcccgaca acaaacgaag aacacactct tgaaaggaat    660

cgaccgaaga ctttcgaaac gctacttggc caaattctac tgcgatgagg ccgagaagga    720

gcgctgccct cgtgagggct atcctctaat acgtagttgc tcgaacaata ttgaaagcca    780

caggagacaa gtttcgaagc gagttttgca aactttggag aactagaact cacaactttt    840

tcaacaacaa aaaaggagat ttctagcgag tcaatggagc accgtgcgcc acgcgctcgc    900

acaggcagaa gcaggtttgc tgcaaggtag tggaggtaca ggtctggtgc cagctttata    960

actgatgcgg gcaggcgtgg ttagctagtt tgttgatgct gacgttgtct tcgtcatgca   1020

acatcctgaa aagagcgaag atggattata taaaattcgt agacccagat ggactttgat   1080

tgagaggagc ttccatttta tgttttgttt tttagtgtgg gtagctcata tgctagtctt   1140

tttcctatgc cccgatagca ttctgtaact ttttaagctc gataggaaag tctatttcgt   1200

tcaagaacct gaaaatagga ctcatgcaga actatacgac aggatgccgt catttattca   1260

agactattat gaactagata gtactgtttg gcggacggca aatggaatta acgaaaaagg   1320

tattggttat atattagttc agaaagggta agttggtgaa atgggactct caattcgcat   1380

gatacttact ccaccaggag agatgatttc ttaagaagcc tgcaatggat ggtgctattt   1440

ttttaaaaat ggatatgcta agtcgcaacc caaggtagat ccaagtttgc cggtagtatt   1500

ggcatcgtct tagttctagg aaaagaatgt aaaacttgaa gttgtgaacg tggtgtctta   1560

gatcaagagc agctgtcgag aatcctggca ttttctttcg ctgagaaagc ctggcaatgt   1620

gctgagaaga ttagacttga catctcgtag ctaacagtgg aaatcatcat actctctctt   1680
```

ttcaactggg actcttcgtg ggttgatcta taacgagttc gtctctagag atgtaacgca 1740
gatgctcgaa cctgtctctt gtctcgtgcg aattccaaag ctatcttttt ataaacccaa 1800
gataaatgac aaaaccccat gggattttgt ccacatctat tctgaaacaa ctggctgtgt 1860
ctttcaatct cgatgacgcc ctagatcatt tgatcaggga agccgcaaat tggatctcca 1920
ccctaatgta actacttaca agaaacaata agagtctcaa aataccgttc acttcgagaa 1980
cgccagtttt ctgtcctngt ccattacaaa agataaaagg acaaactttc tctagttgac 2040
gcaagtatta caaagcctgt gccgacaaac ttgacccttc tcgttaccca atctacaaaa 2100
agtcagtcaa ttagcccgaa atgcctattc tcttgacact cgggtcaagt ctgctagctt 2160
atccaatact ttgctttatt ttttgtttgt ttatgtttta atttttttct ttaagtaatt 2220
agtcgggtta actcgtattg ttatgaggtg cattaaaaac agaagaactt gaaaattgtg 2280
gaaattgtcc taggtttatc ctaataagta tttcttttta aaaatttctg taaaacctaa 2340
agaaaagaaa aaagaaacga aaaaaacaag gtaatgtctt tgattaattt tattttgaat 2400
taaattaaag cattcatcac aatattgaag gcaataagaa aatgtgtttc tcccctgcag 2460
ttcaatccca ctctccatcc ataattcgta gccaagactc gtgtcgtggt cttccgcttt 2520
ctcaagttgg gccgttgttt tgcaaaagtc aacagtccac aacggccaaa gaaagtcctt 2580
cgagttaggt atgttcttta ataagaatct atgcttttct ttccaaaaga agaatcggac 2640
tcggactgac ctgacactca atattccaat gatttgatat atgtatgttc caaggcgcat 2700
gactactaat atcaatcaac acttactcta ccacccgccg aaaaaggaaa gctaaagggc 2760
ccctcaaaag aacgctaaag aacgcaaaag gcctcttttc tgccgcatct agaagaactt 2820
tcaaaggata aactgggcta aattgaggga ccccccggtt ctatatcttg agatgacact 2880
gggtctggta cagtatccat tttgaaaatg cacagataat gggtggctga ttggccagta 2940
tcgacagtaa aggaccacgt gaaatctgga gtggccagca gaagagagga atcttgacgg 3000
c 3001

<210> SEQ ID NO 185
<211> LENGTH: 2971
<212> TYPE: DNA
<213> ORGANISM: Aurantiochytrium sp.
<220> FEATURE:
<221> NAME/KEY: misc_feature
<223> OTHER INFORMATION: pSGI-CC-008
<220> FEATURE:
<221> NAME/KEY: misc_feature
<223> OTHER INFORMATION: SG2EUKT123754; Acc1 acetyl-CoA carboxylase

<400> SEQUENCE: 185
aggacctctt tatctgcggc tttgtaaata aaataaaatg attcaatgaa tgaatgaatg 60
tatgtgtgac atcatcactc ctcttttggt tccatcaagc actgcggtga gtgagctaag 120
ggttctccta gctagcgccg tactagcgta gtcctcatgc cccggagagc aaagcaaaag 180
acgcaataga cgacagatga cgctcgtcgc ctttttacca catcaaacca agggcccttg 240
agctacgcct tctaagcgcc cgctacctgc ctctacccac agagggcaaa tcttttcgcc 300
tctcaactaa cttcgatcaa gactaattaa aataatcaat catcgtaaac taccctcgag 360
cagttataaa aaccctgcca actttcatac agacatacag acatacttac ttacatacat 420
atatatgtac gtgctatcat gaaatgatat tgatatgtgt gttgcgagct gattataata 480
cggaagagcg cacacacatg agcgtatttt attcgctccg tcggccccac agacggacgt 540
attttattcg gcggagccca ttgcgtagca tcctgcgaac ccgcgacaaa gcagcggtcc 600

```
gatcgctcgc tcttctcgca gaggagcagg aagccggccg aggacgcggc tgaggacgcc    660
tcggctggtc gggaaggcgc tgctgcagcg tactccggaa accacggagc ggcagccttg    720
gagctcaggc gccgatcccg ccaaggcggc gacgcggcga tgatgcgcgg attggccaca    780
ttgcatcatc atcgatgacg agcggaacag aacgaaggaa gagggccccg cagaggacca    840
gaggacagag aggaataggg gcggccagag ggaaacagta ggggtaatct cccccacagt    900
gagtttttgg gaagatacct ggcgcacgtg cagtcacaat gacactgaca cttgaggaga    960
gcagtggaga gggaggagaa gaaggagagg tatctcgccc tgacgccatc acagcacttt   1020
atgcgagtaa gttgaaaaat gggaggacga gtgttttaaa tacatgtttg tatgttaact   1080
taaaaaagtt tttaattaaa caagaatggt tttgtttttc aatatccaaa gtcttggtac   1140
ctagtactta ggacttactt aaatgcttga gggttcgtac taccgagagt gctgttataa   1200
gttctagtct tgtttagttt caagtaagtt tttagttttc attctatttt gctataaaat   1260
aaagaaagat cttaaaggaa gagaagaaaa ccattcgaac aagaacaaag gataaggaac   1320
gaggatttgc tcgaacatct tactgcaaat tcggcgggca gagaggcttc gtggcagaag   1380
aaaaaaagaa agaaagaaag aaagaaagaa agaaagaaag aaagaaagag gaaaggagcc   1440
tggagaccta tcggcagtca gtctgtcagt cagtcagtca gccctctgta agaaggcaaa   1500
gtcagcccgc ttcgctgttt ccttttgtca gtcgctccgg agcgaacgct tcggctccat   1560
ctatggaagt aagggggtaa cttaaattta aattaagtaa ataaaaatat tgttaaaaaa   1620
aatagaaaaa attatttgta taaactatcc aactggcaga agatagctga gatagaactg   1680
gcaaaaaaag aatcgccgtt cgctactgag aaaattcgaa tagctaacac tatggagcat   1740
cgtttgcttc acttgctgcc aatagtactg cgatgatggt ctgagccctt ctcttcctcc   1800
caggcagatt caaattattt tctttgcgtg gtctacagag gagaagcaga aaagagagat   1860
gaggtttgct tgctacaaaa actttttgta aacgagaaag gaaaaaggaa ggaaaaaagg   1920
aaaaagagaa aggaaagaga atgaaattta gttttaaaaa gttttgaaaa aggaaagaga   1980
gaaatactcg ccaactcgag aagcaaatcc gcaactccag atcggagaca ttacacgcag   2040
cagcaccaga ctcctcgagg caccgaggcg tccggcagca gcagcgacaa aagcgacgaa   2100
agcggcagca agtcaagctc cgccacctct cactcaaggt acgtacagac acaggcacat   2160
acgcggtcgg tggccagccc gccaaggctc gaggagcccc agcaagcgcc atcgaccttg   2220
gaatttcaaa ttggacaaat tcgaaggcgg cgttgttttc ctctcctttt gccattacta   2280
ctccctgctg ctctgctctc cccgtttctt tgaaggcttt cgtgcagagc atatctatct   2340
gtctgtatct tcttgttctc tctccactgc ttggttggct ttttttggcc tagatagaag   2400
atgttctctt ctgctctctg ttgctttcga attattggac cctgggaggt aataataata   2460
ataataataa taaatcgatg ataaagcagt agaaaaacaa gagaagtgag agattaattg   2520
attgaaggaa gagggaagaa aacaggaaca aaagggcaca aaggaggtag aaaggagaga   2580
cgaaggctct gacgcaagcg agcgatatca tatcctgcgg tgcacagcga gtattggaaa   2640
cactacgtca gcaaagtgca taaggataat ttataggggg aaaagggcct tggcagcaga   2700
gtagcagcag cagtagcaaa gtccaaactc gggagtcgca agaggcgaca acgagcgctt   2760
ggacagattg atcctgaata ggagactgac tttgaattca cggcggcggc ctcactccgc   2820
atacacaaca acagcaacca cacaacacag cacaaagggt acaaacacgt tcccacttgt   2880
tgcagcaaag ctttctgttt ttttcaattc tctttgattt tttctgtatt tctgacgtca   2940
```

gcagcacagc agcaacaaat cttgaagcaa g 2971

<210> SEQ ID NO 186
<211> LENGTH: 2983
<212> TYPE: DNA
<213> ORGANISM: Aurantiochytrium sp.
<220> FEATURE:
<221> NAME/KEY: misc_feature
<223> OTHER INFORMATION: pSGI-CC-009
<220> FEATURE:
<221> NAME/KEY: misc_feature
<223> OTHER INFORMATION: SG2EUKT113004; MFS transporter, sugar porter
(SP) family

<400> SEQUENCE: 186
cttgtccaac tgcttctttc caacaaacca gccagcgagc tcgtttgcta ttcttttgaa 60
gttcgcggca gtagagattg aatcctacct ctacttccta tgttttcagg tcgatggcat 120
acgtacgtca cttttgtcag atctatcttc tcttttctgt tgccaatctg atcccaccta 180
ccagtccaat agtagctacc tacttagcac tcaaactgtt ttccaattca agagatcatg 240
agaattaatc gagctatttg ttgttttcca acttcagaat ggttgattcc cataaagcat 300
catgtctcca catcaacatc atgatcttca ttattcgagc tgcgaactct gaagaagggc 360
tgcctgtata ttctagcagt ccaatgcctt gctgctgctg gcggtggatg gaaactgggg 420
agtaaggtcc ccgaacgcat gtagatactg agtcaatgat agtaagctct ctctgcatgt 480
gactgaggat gaaggggcct tgaaatttac tttttattat gcctcacaaa tcgacgttca 540
tacgtgaaga tgatgataac gtagatgagc cgtctcggtt gaggttcagg gaggccgatc 600
ttgcgaactt gctgccgccg aaagctgcaa aagacacatc ctatagctag caaagacagc 660
agcagcagta gcccaatcct tcgaggctga caggctttgg ctatgggtta cttcgctgat 720
cggtcaattt tgggagaaca ttggtctcgc aacgaagcta tattcttcat gcttcattat 780
acatattcaa gttctcttaa aacatactaa atatatagaa tacctaaaca gattataaac 840
agattgcgtt gatatcataa agagatgacg gcgaacttga acagaacaag gcgaagccga 900
ggctatcatt ggcacaagag cacctggata ggaaggcgaa acctaaacat gcgatcggta 960
aacatagtgg ctccaagagg gaaagtggga agaactaatg gaaggaagac gaatatcggc 1020
tcggataaaa atatatttat cactcaagtt tcttttacaa tattttctac aaaaagaaga 1080
aaaagaaaca gaaaacgctc cttcgaaaag ttcaagcatt tgtcaaattg accattgtcc 1140
tcatgaagtc ttcttgccga aatggcagta ggcctaacag ctcgagccat gatgtacata 1200
agtcagaagg ccattttata gaaagtgata aaggttgaca gcacgaaata aagaacactt 1260
tgaaggccgc aggaatcggt ctgctctgac aaagaattaa gtcaacgtgt gatttctttc 1320
tcctactgaa tttcaaggga gtccaccagc catgaagtat atataccgcg aacgaagaat 1380
tagggacaaa actatcaaat tacaggatcc cgaagcaggc ttgagatgca tgactaactc 1440
ttcaacgttg tacatactag tcttatgcct tcactcacca tcttcatcaa taaattctca 1500
taaaactatt gtcattcacc ttctattgta ctaaacagtt tttacattct tcatcatttt 1560
aaaaattaaa ataggagcta ttaaagacat acgcaatgga tgccttacgc agatcatctc 1620
cgaaaataga ttaggctatc gcttgcagcc gtttcctccg atggtgccaa catagtcctc 1680
ttggcttcgg atgttgtctc ggggcgatac ggttgtccgg cacagcagct tgccgatgaa 1740
cttggagcac cttcgcctgt tttgtgttca ggccacctcg gaagacacgc ttatctcgct 1800
cgggtggacc aacctcgacg atcgatactc acaccagatt cgtagctgcc taaactcacg 1860

```
agcgaccccg gaataggtcc gagatctcgc acgtgaaact tgtctccccc aagatcagcg   1920

attcaggcaa tagataaagc atacgacaac atctgctgtg gacacagcat agcacggcct   1980

ggatcagctc aaactcagca aacttggtaa atggccaaca tagaattagg acactcactc   2040

gagctaacag aaaggagtgg acaagcggat gctgtcccca gctgggtttc ccggtacctt   2100

gcgtctttct caaaagttcc tcaatttttc ttcagtttta gctgagcaag ttgcaagtcg   2160

cgtacgcctc gcagccccaa gaagaagatg ggaggacgtg aaaacgcttc tggatgacac   2220

gcaagagaag gatttgctcc gactttgcag cgaggcatca tcatattgta cgttttaaaa   2280

ttatatttta tagattggaa gcggttggtg atcgcttctt ttagaatttt tagtctcaag   2340

attgaaagaa cttgtgactt ttgcatctgc tatgtttttg agaaggtggt tttcaactcg   2400

aagaggaatg ggcgatgacg agttttgcgc agtggtgaca gagtcgacgg ctgagagaaa   2460

actctagaat tgtattgctt cctacatgag agagttgtga attccagaaa ctaccacaga   2520

gagatcttga agaaattatt agagatgaga ggacactcga aaatccaaga acgcggtgct   2580

accgtctcct tgcagtagtt agacctagag atataatata aatgcgtggc acactttcat   2640

acgcatagca cgagtacgct gactaaacta cccactgcag aaaagaacta aaattaaggc   2700

cagtgtgctc acagctacct tccactagat taatttctca gaaaaggcta agaacaaaaa   2760

ctgttttcct tctctccttt cgggaaagta aagcaatgca tggcatcgca gcagcatatg   2820

gatgcaagca aagcaaaacc aaaactcgaa gtccaaatcc ttggatctaa atttcattgg   2880

ctgggctact aaggacctct gattttcagt tatagaatta gactctttga gtgtatcagg   2940

agatactaac tcaaaagtaa gtgaacctca ccttggtttc aag                     2983


<210> SEQ ID NO 187
<211> LENGTH: 3044
<212> TYPE: DNA
<213> ORGANISM: Aurantiochytrium sp.
<220> FEATURE:
<221> NAME/KEY: misc_feature
<223> OTHER INFORMATION: pSGI-CC-010
<220> FEATURE:
<221> NAME/KEY: misc_feature
<223> OTHER INFORMATION: SG2EUKT118935; Carnitine O-palmitoyltransferase
      2

<400> SEQUENCE: 187

gccttcgtgt cttggtttga gctgttcata cgaaataaat acacgaatga acgattaaag     60

cactcgtggc cttctgcaga ctcagagacc gtggattgtt ttgacgactc cagagcagct    120

taaaagaagt cagccagtag aaaaaccaca ttaggcaaca aaggccgtca gcagtggcag    180

tgatcgatgc gcacgcgtct ggatcaagaa agaattttga cactcgctca ctcactcgct    240

cactagtgac actcactcaa ctcgctcatc gatcggttct acgataattt taattagttc    300

actcagaaag cgttggctgc gcaggatagg ttcgacgcgt atgttgctgt gaggaagcag    360

gcgccaccaa aagcaaagct ttttgggtgt ctatctagaa gttgaaaacc caatctttcc    420

ctcatccgca agattctcaa aagtatgctt ctcatacgca gataatcaat tgatcatgct    480

tctgatacaa gcgatcgaat gaatagccac tgtgcgatgc tcgagacgaa gaattgtagc    540

gtacgtcatc cattaatcat gatctttgag tgggcgagag attgatttga tttgtttcca    600

cgacgacgac gacgacgacg acgacgatga gaatgaatga atgaatgaat gagaaggcgt    660

catacgttat tggctcacat catcgtcgtc atcggcgaaa tctgcatccg gcttgctcaa    720

tcaatcaata tggaggacgg aggtttgttt gctacagagc gaatcgtgaa agaagaaagc    780
```

-continued

```
cttccggggt atcttgcgat ggcgctctgt ttgtgtagct ggaccgacga cgcccggcga    840
gaagccgaca atacacgcct ccaaagacac acgctcctgc gattttcgtg atcttttctt    900
cgcatttacg gagtagtagg catcgcattc tccccttcgt ggagaacttt agattcttgc    960
ggttagattt tcatgtgttt ctgtttggct aaatatgttt ttggtaatag taatcaattg   1020
atagtgatga tgatagcagt aaactgatct ctgatacaat tttgaaattt gttctctatc   1080
taccgagggg atcctttttc atttttgaat aaccttgaaa ttttttttatt tttttttaaat   1140
gttcttttaa tatttctttt aatttattct ttaaattaaa ttaaactaaa aattagcctt   1200
cgtaaaaaga attaaggcaa ttgaatttta cttgctgcgt taatagaaca tgcaaagaac   1260
aactcctatc ccgataatag cgtttcgagt aagtagaatc acttttagct ggttagatag   1320
gaagctggga agatgaaaat gtctcgtgtt ccaaactgcc ctgaatcaga gaaagaacgg   1380
ggcggtctga cttttctatg ggcggactc tccgtttctc tcccgataaa gccttgagac   1440
caaggaatgc tatgcatatt ctttggatat ctgtctttcc tttgcttttt tctatctcaa   1500
agaaacgcgt gcatgaagag taacaggctt catggagtga ggtatgagat cgtaggacag   1560
tatatctaga acacctggaa ccgtgctaat gtatatgctt taagatacct ttaatgataa   1620
cattaggagt agctatcatc caggagatca tcatttagtg gcctcagaag gtctataacc   1680
ttctgtagag aggttaaaat acacgagaat agctttttcc ctatagtgtg tagcaaaata   1740
gtctactgta cgggaccgcg tatagtggag taaatgaatc agctcttcga agagaggcaa   1800
aagcagaggc aaaagcagcg gcaatcgcga actgcgacaa cttagggtcg cggaagggag   1860
gtacgtacgt accgtcgcgg ggtcgtgacg gcagggggag gtacgagcgg tagccgggta   1920
ggcgcgagag gtcttgcaga accgctttgg gagcgtgctg attcatcagt ctcagggcca   1980
agctcgagct tggtgggtca tctcagtcag attaccgcca ttgcggctgg agagcggacc   2040
tgcggcgaag aaggcctcgt gatcgcctct ggggaatcag ggaagcatgc ggaggtcctg   2100
gcgtggtgcg tgaaggggag cagggggcgc agcggaagcc tgccggctgg ccggtgaagc   2160
gctgatgttg atgatatcgt tgacgatgaa gtggctaacg tgaagatcgc tatctttctc   2220
atcttactgc tgttattact tcaatatggc atgtatccaa atgcaacaaa tgtaaccaat   2280
gtgtgctata attataatgt ctttgacggt gttctttttg gtgtgacttt ttggcgcttt   2340
tgtcgcgctt ggttatttgt ttaattttgt ttgcgcgttc tctttttttc tttttttctt   2400
tttttgtgcg ggcttaaaac gttttttgtt ttttgttttt gttttgatgc gaaaaaaatt   2460
tggtgtgaat tatggaatgt tttttctact ttgaaaaaaa attgttctct caactgtttc   2520
tggaattttt cgatttcatt cttcaattct tttttctttc ttttttaatt gacctctcgt   2580
acctctccct gctgaccctc tctgactgac tgacggaccg gcctctacga acgtggtgta   2640
atttcaatgc ggaatggcat taaactaaac tttgaacacg ccttccgacc gctcttttct   2700
tacaccacga acctttttcgc ctccaaactc actcactcct tctctctctc tccctctctc   2760
tccctctctc tgacacactc acccattgac tcacttgtgc tctctctctc acacacacac   2820
actaaaaacg aaaaacaaaa aacaaatcaa aatcaaaatc aactccgaaa acaaacaaac   2880
aaaactaaaa ctaatctcac ttcttaccca acaacctcgc agctagacta agccgcagag   2940
aggagagaga ggaaaaagaa agtttctttt cttcttcttc ttcttttttct caggaaagaa   3000
gaagcagtac tagaagtagt gaaactaaaa agaaaatcag cgtc                     3044
```

<210> SEQ ID NO 188
<211> LENGTH: 3017

```
<212> TYPE: DNA
<213> ORGANISM: Aurantiochytrium sp.
<220> FEATURE:
<221> NAME/KEY: misc_feature
<223> OTHER INFORMATION: pSGI-CC-011
<220> FEATURE:
<221> NAME/KEY: misc_feature
<223> OTHER INFORMATION: SG2EUKT108885; Ferredoxin reductase-like,
      C-terminal NADP-linked domain

<400> SEQUENCE: 188

atgctaccta cctccttttc aaaaggaggg ttctcttgtt ctttctaagg caatatcaac     60

tcattccttg ttcttcaggt gcagataata ataataggta gtttctagtt cgagtgaacg    120

atattgaaca ttagtgaaca atgtcagaat gaaaagaact cattttcttg tggagaaatc    180

catgtaaaaa catctttctg attgatgcac aaaacgaagc catcctcagt gtcctcagag    240

aaaagccaca gctaaaacaa gctaaatcaa acattttctt tcttgcacat tgataggata    300

tctaaagctt attagaagac tagccaaatt attatgtgct tgtgagcaaa aaccacatcc    360

aaaacacacg ttcaggaaat cccattgatg ataaaggtca gggagttcaa ctgatttatt    420

ttaacaggtc taaagtatga atctcaaaag atataaaact acaattgttt ttggattcct    480

caaattttct acaatcttat ctttacgatg ctattagata aactctcaaa gtattgcact    540

tcaattcgtt acggtcgatt gagctctgca agatttcttg ccaaacgccg atgataagca    600

aggattgagc ggtggctcgc tcaagtagat cttactgagc tccacgttga aagaataaat    660

tggtaattta cctcagaagc tttccagcga atccatcatt gctctcatct ctctctgggt    720

aaagtaacat ttgttgtgtt tttatgttct caaagcagca tgcactgcat agtagaatgc    780

aggaactgaa atgaaatctc catctgagca cctaatacct cgattgattc tttgacttcg    840

tttcgagata tttcaagttg tattggaatt ctcactcaat atataaccac tacatttatc    900

tgagtttcga tctgatgaac aaacaaattg tctaaactct attgaccata tttgagagat    960

ccgaatctca gcaaaataaa atatgaatac aacactaaat agttcgccat taagtcttac   1020

ttatctgtcc cacactaaaa ttacctttat gttcgcaaac tgaagtttct ttactactgc   1080

ctcccatgaa ctccggtctt cgtaagcgag aggtagtatc tggttcctct cttgcctcgc   1140

tctgcgtctt tgtcgcatgc gctgggatgg ctcaaggctt aatctgaata ctggcgagct   1200

ctttcatgaa tagatagaca gatttctggt cattctggca cacatacaac tcgcaaatgt   1260

gtagtaagta gcctcgaatg tatcgcatca taatcatcgt cgactcagcc aaagatgtga   1320

tcatcatcga ctcggccgaa gatacattct attgtagtct gtgcctgtcc tgtgcaaggc   1380

gtccgatggt ccgagcaccg tcccttgtga ccctccagga gtatctctgt cgtccctggt   1440

gatcgcacct aggaggtact acgtagagta agtagagaga ggagaagagg ccacacacag   1500

gctctaaaga aaaaaagaaa aatcttttct gggcttccta cgtaccggcc tacctaacac   1560

ttgacgcgat cgaaaagcgg agagaacttg aggaaatgtg atttccatag cccacaagtt   1620

tataattcga gacgacaact tgcgaactga ttctttatca agtttgattc actttgcttc   1680

gcgtaaaagg tctcaaaaaa attgagtcga gttggggaac aggattgttt gtgattgttt   1740

gtgattgttt gtttgtctat atttatgatt aaattccaaa gacaagagac cgacatgaag   1800

ttgacgttgg gactgatttg taaagatcgt cgcagatatc gaagggccca tagccagcct   1860

cgctggttgg tgctgcgatg gagattctga gtcatcacca ttcggtttat tttcgctctc   1920

ttcaggctga cgcctagctc aacttgagac acaggctgtc ccagagtcct gccaactaac   1980

tctctagaga ggtacttgtg gccggagaga tcaatttcat ttcatggtgg cttcgaagtt   2040
```

-continued

```
tcgagttgca gaggctgctt ggtcgactcg gaggccgcct ttctttggcc tccacctagc   2100

tagctagagc tagctgggtc cacgcatcag ccaatcttcc gagtccttcg cacacgtact   2160

cacacgaaga tgagctttga gtcggtgttc caccggcctt ccgagtatgc gaaatcttcg   2220

ccccaggctg gctggcctct ggttcgcagt ggaggtcgac gcagatggag taagccggcc   2280

ctgcgctagg cgtcgactct cagcgtctcc tcttgctgac aacctcaact cggacggctg   2340

agaacagcag cagcacgaag aactgaaaga ctcggttaga atgtggacga ttgtcgggaa   2400

tacgcagaaa cattcccagc gcgaagtcta tgattcgaga gcttgttgaa aggcgaactc   2460

cattcatctc ttctgtatcg aacacccact cccactctag gcagaggccg cagagaatga   2520

ggtgaaatct tatcgcttga gtaaaattca agccaaagag ggccactcga tgatagttca   2580

actagcgata cctacctacc tacctaccta cctacctacc tacctactca tccagcatcg   2640

tttccatccg taggctgcgg ttcaaaaaga ataaggcact attagacgtc ttcttgtttc   2700

gaaaaaaata ataatagatt ggaatactat ggtaagtgat aggcaagcct tagtattgca   2760

ggaaggtgag cttcgcgatc cacttcgact ccggtagata ggtcttgatt tactcgtgtt   2820

actcagcata gtacctaaac agtactagtt ttttttcttt gtaaattaaa aaggagaggt   2880

tttttcaaag atgatgtgcc acaaacagac taggtcagat cttcagcaga accgtaactt   2940

gattgatgag gaaagaacaa agtccaagtt agacaatctt gcaacaggtc gctacaaatt   3000

aagagtggga aaataca                                                  3017
```

<210> SEQ ID NO 189
<211> LENGTH: 3054
<212> TYPE: DNA
<213> ORGANISM: Aurantiochytrium sp.
<220> FEATURE:
<221> NAME/KEY: misc_feature
<223> OTHER INFORMATION: pSGI-CC-012
<220> FEATURE:
<221> NAME/KEY: misc_feature
<223> OTHER INFORMATION: SG2EUKT123295; Fatty acid synthase alpha
subunit reductase

<400> SEQUENCE: 189

```
ctcaaaatcc ctgcgctgct gctactgctg ctcgtcgccc accactgtgc gcagagagcg     60

agagagagag agagagagag agagaaagag aaagagaaag aactaactaa cgaactatct    120

aactgagcca gtctgctgaa ggatggaaca gcggccgcct gcgtcatcag aggtctgagc    180

cgcatcatcg tcgtacggcc gcactttggt ttgcagggag ggctctgagg cgggccccgc    240

gaagaagacg aggcctcttc tcttctcttc tcttctcttc tcttctctgg agagagacca    300

tgtgtgcgtg gatgcatgga tgcatgaaag agatatggca gacacctgaa tgacaccgag    360

gtgccgcaga aaggtgttat ttattaatta gtatcgcgca atggaccaag agagcggcgc    420

cctccttcgc gggtccaggc ccgtccatag caggaggatt ggccgtaaaa gccgtcccac    480

gcagccggct cagattctcg tttggattgg attagaaaga actcgctcgt tgaaagcaag    540

cgcgtctgtc ctcgaggtta agcagcagca gcgactgaga aagatttgct tcgcgcgagc    600

ggcacggcgt cagagattgc atttatccat ccatccactc atccatctga tcgttgaagc    660

gaagcgacga tctgcagtat ctatctatct atcaatctat caatctatcc atgaatcgct    720

gtacctcttt cccatcatcg tgcatggatc tccctccgtc tgtgtgtgcc acgcattcat    780

tgtgcgaaat gcaggttcct aactagcacg aaggctctgt tggcgatttt gacagagaat    840

tggctgattc atgacacacc caatcttttt ggagcggagc caggccaggc caggccaggc    900
```

```
caagccaagc caatccaagc caagccacgc catgcggcgg cgacgacgac agcaatgcaa    960
tgcaatgcaa tgcaatgcaa tgcaatgcaa tgcaatgcaa tgcaatgcaa tgcaatgcaa   1020
tgaatgtctt gtcttcttca aagccacagc gggtttttac tccagaaact aaaaacactc   1080
ttctttctca atcaaacata aagtaaacga aataaaccac aaactaaata aacagaataa   1140
taagtaaatc ttgagagaga agaaagagaa gaaaggaacc catcgtcatc gaaggcggtg   1200
cttgcgtagt ttgggcgcag aagacgtctg ccgcctgaga acctgaaggc ggccaagcca   1260
cagctcgctc cttgacgcgg cccgactcga gtggacgcgg cagcagcctg tagccagcct   1320
gtagcctgcc cgccagccaa ccaaccagcg agtagctagc tagctggcga gcgagcagac   1380
gaccgctctt cgtgatgacg ccgcgcagag aacacgagca caagcagcgc ctgataagag   1440
cgagcccagt gtcgattgat tcatatgtat gcatagagga atgatggagg agcaaatgat   1500
gtatgtgctt tgtctcttct tctgtttctt tctttttcca gttgaagctt cgaatgaggt   1560
gtgtttttga attgtagttg tttctgtttg ttgagctttg aattttgagt ttttgaagtt   1620
ttatttgttg agttttgaag ttttgaagtt ttgaattttg aattttgaat tttgaacttt   1680
attggtatct ttctacttat gaaaagaatt ggtttgtttg tgaaaagagc agcatttgga   1740
caagggggat cgatcgatcg ccttcccgaa actgctctga catggctgag gagcgcagct   1800
gctgctggag atctctccac tcaggcggag gagagacagg ccgaggcggc agtggaggag   1860
gatctgcgta tccattccat cctcgggatc cggcgctgcg tcgtcattgg cgcctatact   1920
atgtacgtgt gtgttgctct aatcgctgct tctggggttg acgaaaaatt aattaatgtc   1980
attttcatgc ctatttttgc tgtttcattt taagtaagct atttatttaa ttcgttagtt   2040
tattattttc attttcataa aacatcagaa ggtctttttt tttttatta attatttttt   2100
ttaaatttaa aaaaagtgtt ttaaaagtat tcgaatggag aaagtaaaaa agaaaaaaga   2160
aatttggatt tttctcgtcc tcactctctt tgttttggca cctgtttcta ccaggaacct   2220
gaccccttag gttttggggt aggcatgcgc tagtggtgtt tgttagttgg ggattgtttc   2280
gaaaagaggt gctttcaaat gatatgtata tatatataat attcatacat acatgttttg   2340
aaatacctag cacttttgaa aagcgagttg ttagtgaatc gtgtattgtt ggcagaagga   2400
caaggcctga gcagaaagaa gaaggcagca aatccaaatc gaacgggatt tgacggaaag   2460
gagtcgcgca gagctcgcac tccgacgttg cttttcaagg aaacggctgt acgcagcaca   2520
agacacaagt ccagacagcc agacgcagca gacaggactc gctcagcctc ccagaattag   2580
aggcagtcgc accttgtttc gatccctccc tcccctcctc tccccaggga acacatacct   2640
cgtcggtgtg tttctctgta tcatctcttt ctctcctgac cagcttctac ttctacttct   2700
gtagaaagca gcagcactag tgcaatcttc aaaagcacag ctcagctagc gacaagaaga   2760
agaagaagaa gatctcttct tgatcctgct gcctgctgtg gaacgaccgg cacatatata   2820
cataactttt cattcgttcc tttgcacaac ttgccggaat ttgcggactt cactgaccgc   2880
gacaaccaag tctcgcgccg taaatctttc tacgcagctc ctccttcttc attgcaacag   2940
gcggcggctc tcctctgatc cccctagtcc ttgtcgttgt acaaagaaaa catcagaaga   3000
agagtattct acagaagaag aaaagaagat cttcattgtt gaaaaaccat aacc         3054
```

<210> SEQ ID NO 190
<211> LENGTH: 2966
<212> TYPE: DNA
<213> ORGANISM: Aurantiochytrium sp.
<220> FEATURE:

<221> NAME/KEY: misc_feature
<223> OTHER INFORMATION: pSGI-CC-013
<220> FEATURE:
<221> NAME/KEY: misc_feature
<223> OTHER INFORMATION: SG2EUKT121832; NAD(P)-binding Rossmann-fold domains; Nrfp

<400> SEQUENCE: 190

```
cggagaacca ttgcggaatt tgcagcaaaa tccaaaatta aggtgaatgc ctggatatta     60
aggtggttag ccagacccgg caaacggccg aacggtctcc acgatgatcc aaaaggagcg    120
gcttattatg aaacaatgaa tgaatgaatg aatgtttgtt tgcattcttg cctggagcgg    180
agaggaaacc aggtagacag ctatggaatt aaataattat ctgcgtacga tgcaagagcc    240
atccatccat catcagagcc tgtctaaaca tgggtttggc agtcaggttt acttctatct    300
agttttgatt gattctacag acctttccca attgtcagtc taaaatcagg ttgagaccaa    360
tcttttgtaa actacatttc ataaaacgat gatgacaatg aggtgagtac actacaggta    420
tgtatgtatg tatgtatgta tgtatgtatg tatgtatgta tgtatgtatg tattgccttg    480
gatgggaagc ggatctttgc atggagaacc ttattggcca gctctttgaa gaccggggaa    540
gacctcacga gtagccagag aagcctcgtt tctgcgagga ggacctcggc ctgaactggg    600
tttcttcttt gtagctattt tcattcatga tgactgattg cggagaccgc ctcgtcatcg    660
caagttttta tgacgatcac ttacttatag gtagaccctc ggtccttcat tttccaagtt    720
caagtttggt agaattaatg atgtgatgtg gtttagcctc tcaccattcc atgaaatgcc    780
atatctcccg gccttggcta tgttttgttg gcgttgatcg ctttactgcc aagttcaccg    840
tcgttttgaa ggaattgaag atagctttcc gcagatttat tggcatgcac gaggaattga    900
ttactgagtc actttcttaa atacctacct tttatttatt ggtgatgaat aagtgaatta    960
aagatgaaca tacaacttga aacatcaatc taacaactaa aagtgttaga tattgcctgt   1020
catgacttat tatggaaccc ggccatagat aataaggagg aaagacggag caatcttatt   1080
ttcgaagaac tcggaggagg aagaaacatg ggcgacgcag accacggaag gcatcatcat   1140
tgttggtcaa tcaatcaatc aatcaatcaa tcaatcaatc aatcaataag caaatagata   1200
tatagataga tatatacata tatagatata tagattaatc aataaatcaa tcaatcaata   1260
agtaaatata tataaatcga tcaatcaata agtaaataag taaataaata aatcagtgct   1320
tcatcgtcgc tggtttgtcg tacctcctat catttacatc acacttgctg tcagaccatg   1380
gcatgcgatg cgtgcagctt cgaggatcga atctttatat cagtcaattg gtgtgacgat   1440
acatcgattc acatggaccc aatcagtcaa tcgacggcta aacaatcgat caaacccatc   1500
catgactaag tcaagtttcg agatctataa ccaacaactc tattccctct cttttcattt   1560
cttctttctt tctttctttt cttagttttt tcttctttgc tcaaagttct caacctcttc   1620
aagttccgct ctgtaaaatc gcaactaaat tcgcgatcct tgagacgaaa ggtgcccatc   1680
tccctattta cccatccgct tatccgtcca cctgcattgg aaagcaccgc tcgtgtttgc   1740
gtttgccttt ttgtctccaa agattgctct caagttcttc gggttatttt ctctctcgcg   1800
cctcagcatt tttattttat tgttttattg ttttattgtt ttattgtttt attgtttttt   1860
ttttgtttgt ttgtttgttt gtttgtttgt ttgtttgttt gtttgtttgt tcttcagtct   1920
ccttccttcg cctgcttaat cgcagtaagt ttgacgggcg tttttgcagt tccgtgtcgc   1980
tttcggggct ttgatggact gattgattga ttgattgatt gattgattga ttgattgatt   2040
gattgcgtgt ttcccgcgtc tggaggcggc cttttgcttg ggcaacaaaa cgcagacaat   2100
```

gccgcgatga tgaggcggtt tcaaagatgg agcctcggcc cctcaacaag cgagcgaggg 2160
cccttttcac gaaggataca acgacaattg gtttactttc actcgcattt atttgctcac 2220
gactcgtatc aattgccaaa gtatttaatt aaacttttgt gtatttttct tttttaatgt 2280
ttaataatat atgtgagaat taaataaaaa ttgataattg atagtttcat agaaatgaat 2340
tttgtttggc gtcagtaaaa aggaattata aagttgctca tttgtttgtt tgtttgtttg 2400
tttgtttgtt tattgttttg ctaacgatgt ttctgtcctt tcctcggtac tgaaagaact 2460
cctctcaaga aagctcgagt ttgctctatg gatccgctgg cggcggaaga gaccgatggg 2520
ttgacttgag cgagtgattg agtgtcaaaa gcgtctccag taaggatgga ttgaggccct 2580
cttcgctttt caaccagctc atttcaagct tgtccatttc tatcttttaa cttcgtttcg 2640
aagttctttc tctcttgaag ggggaactgg aaagctctgg attaaaatgg ttttctctct 2700
gtcctctgtc tctctctgtc tttatctctg tctctctttc tctccttttt gtttcttccc 2760
ctcagagggg cactatcttc ggaagaaaag aaaagataaa gataaagata aagataaaga 2820
taaaaagaaa agaatagaaa agaatagaat atccgtgaaa gcagcggcgg gtcgaagcaa 2880
tctgagattc cgcttcggca aaccccaaac tcctcgaacc tcgagcccaa atctgcaact 2940
atacagagtc tagtatcttc agcaag 2966

<210> SEQ ID NO 191
<211> LENGTH: 3070
<212> TYPE: DNA
<213> ORGANISM: Aurantiochytrium sp.
<220> FEATURE:
<221> NAME/KEY: misc_feature
<223> OTHER INFORMATION: pSGI-EO-027
<220> FEATURE:
<221> NAME/KEY: misc_feature
<223> OTHER INFORMATION: SG4EUKT151655; Omega-3 polyunsaturated fatty acid synthase subunit A PfaA

<400> SEQUENCE: 191
agaggagagc tcttagtggc ggctactgtg atggactatg agaggggact tcgcaagacc 60
tgtctcggtc gcacgtagct gtgggcagcg agaacccgca gaggactgat tctgattagt 120
gcggatacct tggtcgagga agagcgggga cccgcaggga acccgcatgt gcggagagca 180
gcgacgttgg cacccgacga cgctagggca aagacgcagc atgcgtgcga ggtgcctata 240
agctgcgcaa ttcagagaat taagacagca gcgctgggaa ggaaggagga gatttgaagg 300
ctcggcggga gctgtcgaga tggaggcagg caagcaagca agcaaacgaa agaggcggcc 360
agggctcgcg tcgaagccgc tgatggacga gagaatcgca cgaagaagaa tacggagtgt 420
ttgttttcaa agccaaagaa agccaaagcc aaagccaatt cgttcgttcg tgagttaact 480
cattaattaa tttaattgac atcttcattt actactgttg ttatctatta tttatttatt 540
tatttattta ttgtttatat tttttaaaat taaaaaaatt caaaattcaa aattcaaaat 600
tcacgaataa attgcacttg aaggagatga agcaaagctt tgtttcttct aaaaagagta 660
taaataatac aaagtgatga cggaaagaag catcattctg atggtaagca cttcggcaag 720
atgcacgcac tagcacttgt cgccttgctt gcgatccgcg gaggtaatag tggaggcgaa 780
agaaggagtt cattcctgtt atttcgcgct ggggttacag cagtgccaag atttcgaata 840
tttgaatttt tgaatttttg aatttttgga tcttcgttcc ccttcttcct gaactgttca 900
aacgactcgg aggttgtcga tcggatcact caatctctca ctcactcact caatctctca 960
ctcactcact ttctcagctg cctgatcctt cgcaatgctc gcgaagcgcg agggatatgc 1020

-continued

```
gtgggcgagc acgcaccatc ttctctccac gcgtaaagaa gagcagagcc agaggcaggt   1080
aggtatctcc acccatctca ggctgtgact tctttgtttc tttcttggtt tctttctttc   1140
tttgtgtgtt tgttttctgt tctctctctg tgctctgtcc acacgagaaa gagaaagaga   1200
gagagaaaga accacgggtt tatagagcgc actcgtcctt cctgcttcag cagaaagcac   1260
tgcgtaggag aactacgggg gaggaggaag cacgcacgga ggaggcgtgg aaggaaggag   1320
gagacagaca gagagagaca cagagggaca gagggggaga ggcagaggga gaggcatctg   1380
atgtttgcga gaaaccaata agttttgaaa gtgatttgat ttagctgatt gactgatcta   1440
tggcctgaaa gaaagctttt aaagcggagg gagggagata gatgacgagg gcagctgcga   1500
tggcgtacgg cgcatccgtc tctctctgtg tctctctctc tctctttctc tctcgtcagg   1560
gcgtggagac ctcggaagct gcacgcggcg cggcgaggag gcagggcagc agagggagag   1620
gagagatccc agagtcgaag agcattgatt gattgcagat gatcttgggc aacgcgcgtc   1680
agcttgagcg aggaatgctt tggacttcag gttcttcgct tctgtgtttc attctttctc   1740
gaagaaagaa agaatgaaag aaagagagaa agaaagaaag aaagaaagaa agaaagaatg   1800
aatgaatgaa tgaaagaaag aaagaaagaa tgaatgaatg aatgaatgaa agagagaaag   1860
aaagaacgaa tgaaagaaag aaagagagaa agaatcaaag agaaagcgca ttcgcagttc   1920
ttcttcgtga aagaaaagga aaagagaggc gatggtaggc actgatctca tcatttctgg   1980
tttctctgtt gtacctgtac tctgtgcttg tggccttgcg aaggctgaag acgccatgca   2040
gacaaccacg cctccgcaga gactttgcgg gaaagcagag ggcttctcgc cactctcgaa   2100
gaaacgagct cgccagtttt cgggggtgtt ctcagaattg cgagtgttgg ctttataggg   2160
gatgatggta tggcacttcg tcatcgttac tctcgctcgc ttgcttacga agattttcaa   2220
aagggcgaaa gaagtgctca gcttttaaaa taaagtcaca ccaaagacta ggccgcatag   2280
cagaaagcta aagtaaaccc aatctgtctg aagagagtgt cgtggttaga tacttacgca   2340
agagtttaaa agctgtaaat agtacaggaa caaaaacaaa taaatatata tgtatatata   2400
ttcttttttta ttagtaaaac atgaaaccaa aaaactcctt taaaataaaa taaaataaaa   2460
taaaataaaa taaatttact actatatata catatataca ataaataaaa acaacttttt   2520
cagaccagaa aaagactgag agaaagggaa actaatgact ctcgagcacc gagagcgata   2580
taagagtgga ttagatttgt taggcccacc acgagtgagt cccctaggag gaagcgccct   2640
ctgagacagg agcagaggcg tcgctggtgc tccaaaaagc gacggcgaat ggaaagcaaa   2700
acccttcga gggaggcttg tggccgtgac tattcaaatc tccagcatct cagctccagc   2760
acagcagaag ctacctcgct tctcagctct agctatcaca tcgatcgcag catctagctc   2820
gtagacagct agcgccgcac cttcccccaa atcaacttgg gcaacttaac tctttttca   2880
ccagaactcc tcttttcctt taatcttcga aaagaagacg aataaaagag ataatcctct   2940
gccgcagcac attctaaaag aaaagcggca tactggcgta ggcaagactt tcaagctctt   3000
cctcgcctcc accccgtatt tccctgttca tctttgtgaa acgaggaaac aagaaatttt   3060
ataggacaag                                                          3070
```

<210> SEQ ID NO 192
<211> LENGTH: 3073
<212> TYPE: DNA
<213> ORGANISM: Aurantiochytrium sp.
<220> FEATURE:
<221> NAME/KEY: misc_feature
<223> OTHER INFORMATION: pSGI-EO-003
<220> FEATURE:

<221> NAME/KEY: misc_feature
<223> OTHER INFORMATION: SG4EUKT159530; Heat shock protein 90; hsp90

<400> SEQUENCE: 192
aactagcctc agaacactgc tgccttcgat accaccgctc aagaagctct cggccgcgac 60
ggaaatagct ctggaaacaa gctcgtgacg ggaatgctca actcaagtcg ctatcatcta 120
ctacctaggt aggtacgact tcttagtcta gttctcagac gagcgcaggc actccctcta 180
cttatatcta tctactaaga ctctgtgcaa attgataagg actgcaagat cttctaaacc 240
tgatccacaa cagagtgagg gactcagagc acctcgaggt aggcttgggt aggcgagttc 300
aggccaggct agggatggac cagagcgtaa tgattgctat cacgacgagg tcttctgatc 360
cgtaattata gcagagaaga gatctgtggg tgacctggag cccgagaatg ggttctgtga 420
tgtgctggcg ttacagagac atgaaactac aatattatct ggcccgtact aggtctcgag 480
tagaaataat aaagccctct aaacgctatt gcggccaagc aaaataacct aaagaaggga 540
tctaccgcca cggcgctaga aatgttttga agacgccatg cggatagtag attagtctag 600
cgaagtaaaa gtcgcagtca ttcaatggtg ccatcttggt aaatgcgaaa ggtttctaac 660
tgtttgaggc tgcagtagtt tagctgacgt gtgcatactt aattcccctt gaattgccat 720
gcgatctctt ttctttggaa aggaaagctt attctctttg ggctataaga agatcaccag 780
cctgtcgggc tcaaaatccc aaaaccccga tattgagagt tgctgcgcac gattgcaata 840
gaactcatta gtgccgaccc atggtcccct aacctcatta ttttttttcaa ttattcccag 900 atacaaagat tcgggacaag ttaagcatcc aaaatattac ttctattctc aaacctagaa 960
ctttatttgt atgtccacgt gtcaatgtgg ccatgctaat tcaggtccta tctcatcagc 1020
aaaacattga aaataacata aacttaaaaa aacatgcact atctctacag aagagtactg 1080
ttacccgaca tcacactcat agatccaaaa ttactggcta gtacttcctc ttttggtgtg 1140
tgtgtgtgtg atacgaatga tgtctgaaat taagacgtga tgccatcatt gtcaaaagta 1200
gacagcctgt ttagagacaa aacatcacga tacactatga tgacgacgac gactcaacgc 1260
acggttatcc ctaagcgttg ttttgctttg agacataata ctctccacag catcatcaat 1320
caattcatca ttcacattaa gcaatacgtt ttcaaattaa cctcagcaac tactcccaac 1380
tcgagaggat tcttcgagat cctcctcaag ttctcctcaa gtcggccacc tgctctacct 1440
acctacctac tacttactac ctctcgcttg cgctttctta tactattgtt tccactagca 1500
ccaccttact gatctccttt gcacagcgaa gtcagcccac caggtcatcc ccgccgaagc 1560
acgagttctt cgaagttcgc attgctttcc atcgccacga ccatcatcat catcatcacc 1620
gtcttcgagc agtcagccaa gcaggtgctg ctgctagaac agccctgtgg ccagccaccc 1680
tcgcgagagt cgcgaagaat cgtcgttggc aacgcttagg caataataac tccagtcacc 1740
aacttgctct ggagcacaaa cttttgcaaa attgcacacc cgtgtcagct gttgctattc 1800
acgttgaccc ggaatctact tgagcaccga cacctccatc ggtctgctgc gcttgccgcg 1860
ggagctgcac tgcaccaact gcctgctgct gctgctgcag ccttcaacga cctccagcgc 1920
agagcctcct ccctccaggc ctccctgctg ctcactccac tgggcaccac cacctacctc 1980
tgcgcatgga tggccatagc gccgctctag tcgagcgcgt tgccgttgat ggactcgtac 2040
agagccccta tcattaatat ggaaggcgga cgatccgagc ttcttcggat tctcgaacac 2100
tcgcttgacc cagcgacctc agtacttgac tgcttgcttg cttgcttgct tgcttgcttg 2160
cttgcctgct tgactgtggg ccatccagcc agccagccag gctcgccacg gagcggggcg 2220

-continued

```
cgccgttctc gcctggccgc caacgcccgc ctgagccgtt cccgacttct tcctggcgaa   2280

gagagagaga gagactgaga gcgccgcgtg cgcgaccgtt gacgttgcgg aaccccaatt   2340

tggcctgaaa atgcgttctg gaagaccggc gggttgatag gagtgtgggg agagggggtt   2400

ttcgagaagg atttgcgcct gtttgaaaag aggggagcca gcctggaata ccccttcttc   2460

cttcgagaag gatcggagcg cttcgttggg tgttatttgg gcgatatagg tgcaaatgat   2520

tggggggtag tttgtgagta ggtgagctgg gatggccgag cagcaaattg cggccagagt   2580

tgcggcagac accaaactcg caacggcagg tacgtacttg aggacatata tcttcggccg   2640

cgactattgg cctcgacttc gcttcttctc gctcccatca gtggaggtgt gcttgctttg   2700

tcatctcgca accaactctc gcgcttaact ccgccgagtg cgtcttgcaa ctcggcttgg   2760

tggctcaacg gcggcggctc ggattgtatc ttcttcttac tgttatctat gcacttacta   2820

gtaaatagat agagaggaag tgacaaacgg acggttgcga agcgcagaag ttttgcagcg   2880

caacggagag cttgcgcacg gccttggtgg tacaggagag ggactgagat tgcacagtag   2940

actacttgca tttccatcta caataagtct ttgtgtagga ttgcccgaac acaataaaac   3000

taactgacaa actgttgatt cttttttttg gaaactacag actatttcta gtacagccaa   3060

cccaacaagc aca                                                      3073
```

<210> SEQ ID NO 193
<211> LENGTH: 2942
<212> TYPE: DNA
<213> ORGANISM: Aurantiochytrium sp.
<220> FEATURE:
<221> NAME/KEY: misc_feature
<223> OTHER INFORMATION: pSGI-EO-004
<220> FEATURE:
<221> NAME/KEY: misc_feature
<223> OTHER INFORMATION: SG4EUKT147322; 40S ribosomal protein S8; rps8

<400> SEQUENCE: 193

```
cactgttttg ggagcgaaga tccatgccgc gaggtcttct agccaacctc gccaagcact     60

tgcctcgcaa ggccgcagcg gcgctggccg agcagacctc gagtaaacga gctcaagttc    120

tgctcaacgg gactcaagtc ccgttcactt cgcattatcg acttgtctct agtctttact    180

atcggttata aaccttcaca gtggggtttt ctccattctg cactttatac ccctataggc    240

tatacggttt gctctactgt acatgtctgc acaagtcaat caatcaatcc ttcatcttct    300

tcgtgatttg cgaccggaat gcttcaaggg ctgcgtagaa agcctcaagg atgacgtcct    360

gaggccacct tcgagtcttg ggctgcgggc cacggcgaca tggacgtgca aaagcacagg    420

ttttctatag ggaggacttg tcgtcaaaat taaatagaag tacatcagaa atgtagtact    480

aggtaggtaa gcttaggtat tgcaaagtat catccgacgg ttttttctgg ggaaggacta    540

tttattatgt agtatggtat atatgtactc tattcacggg cgactacaat cagtgaactc    600

aagagcaaca cagaagaagt ccatgaaggc cggggcgtca atctgagcaa gcttttagcg    660

tagtagaatt ataaaccact gatacgacgc agttgggcca ttggccatgc tgaggctgct    720

atgataacct cgtagattac actttgcatg gaaatggcca aataaatatc aaggcccacg    780

gtgacttagt gcggcttaag caggaaacag tgagttgctt atagtgctca aagctttatg    840

tttatgaatg aatgtctcac tgtcgagatt ccttactcgc aaaaatctcg catggtggtt    900

ttttgtcagc gttacgccgt acattttcat agtataccag gacctatcct gcatgataat    960

gtaacttgct cgtgctgtca ctacgttcgt tcgattgtca tagttatcat cgctgctcta   1020

tgacagatga tagagcatgc ctttcgactt ttgcctcttc actcagtact attattcgtt   1080
```

ttgtacaact gccgtagtgc taaattgcag cgtgcaaagg ctctgttagt agttaaatat 1140
cacatgctaa cactgctcac ttctattgga cacagaagat ggtacacact gtctctgttg 1200
acccaagctc tgacccttgc gttgccgcca gatgctttac ccttcgaaaa cgcaaagcca 1260
ctcatgtctg gccatgccat tgttggcttg gcggctttga gctcgtgagg aaatactagc 1320
gaggacccca gctattgtca cgttgggaac tagagtctgc tggttccttg cttttcccag 1380
tttagtaggg agggaagcaa ggaaggacac aaggaactta cttgaactat ggatgaggtt 1440
ggaggggaca aactctgcac aacccatttc caacaatcca ttgtgcgctt gctttctctc 1500
aggatttcat tgatgctttg ccgctcattt aattataaat gctcattgag tctgtcgatg 1560
tgaaggcaat tattgcacct tacatttaca gctcgccaaa ttaatgattg aacagtcaaa 1620
tagtatcaac ttgcaaaaga cgaaatacaa gacacccttg caaacggaat atttatagaa 1680
caaaccttca aattaatatt aggtattgat agcacatgga tgtagttaaa gaaataaatt 1740
ttaaaacaga gacgatggga caggccttgc attcaagatt ttgagaatca agccttttat 1800
cattcaatga tgcaacctat tgctcagtat gagctcgtat ttagaccgtc gaatcaagaa 1860
atccaagtgc atatgaactc aaaacagcct tgactaggac ttctgtgaga tttaattatc 1920
aaaggtgaat gagagggccc ccaaatcctc tcactcactg gattaaagca tgacccagtt 1980
gacagtagtc gctttgatag aagacaccac cattctcagc atctggctgg ctgctcacct 2040
tcgcgtgcga gcacttgagt tcattgccct tgatcccttt tactatctca gtatcgtgtc 2100
aatcaacctt accagttact atggtgtatg aactccagcg cttgcaaatc ctccatacca 2160
tactactcct caggcctgta ggcaggcacc tacctactat ggctcaggtg tgcgaaatcg 2220
ttgagaggtc attgcttcta cctaaccttc aagctcaaga cgatcccgtt tccagagatc 2280
ttccgtgcct tcacctgcac aggcacgata acgaccaccg cactgattcc ctccgtcttc 2340
gtcgcatttg tccattcatt cctcatctct tcaactcgcg ccatttcctt tcctcgctaa 2400
ttcttcgtcg cagtttctgt ccctcattat ccctctctcc ataagtccct caatctcttc 2460
ttcttagcag ctcttcattc ttctcctatc aatcttacat atctttccat tgttatattt 2520
acttttactt attcccttta cattattgtt atatttactt attctcttta cattattgtt 2580
atattcactt atccctttac attattgtta tacttattta ttccctttat attattatag 2640
gcgctcttcc agccgccacc actctcgcgg gttcaccgtc gacaccctag cgggggtccc 2700
tgtcccatat ttcagtaccg cattgggtgg aggagagtgc gcggttaggg taggcaaaac 2760
ttcggcgcaa gtgataggtg tgcgggtata tggttactag tggtaatgga gggaacaaga 2820
ggcaaacttg ggcgcgcacg ggtggtggtg gcagagtgga gaggcgagga gagcagcaga 2880
ggcaatcaat cgagaatcga ctagacgcag cggagcggga gtcgagcgta cgggcaggca 2940
gg 2942

<210> SEQ ID NO 194
<211> LENGTH: 3112
<212> TYPE: DNA
<213> ORGANISM: Aurantiochytrium sp.
<220> FEATURE:
<221> NAME/KEY: misc_feature
<223> OTHER INFORMATION: pSGI-EO-005
<220> FEATURE:
<221> NAME/KEY: misc_feature
<223> OTHER INFORMATION: SG4EUKT158594; Glutamine synthetase root isozyme 1

<400> SEQUENCE: 194

-continued

```
ttagcctcca ctgactttgc agtacctcac ccttcgctag ggtgaactag gggattcgaa     60
cttagaaact gtgtcatgtg gagacagagc tgattggact tgagtggaaa tacctcagag    120
gacctagaga ggaagggctt gaaacccaca ctctgtgggc cgtctatgcg gtctcgttag    180
taggcagcgg gcaaacgcct tgtgagggcg cgagcagtct gagcccagtg gaggcctcga    240
agggggacga gactgaacga aacagtcccc gaacctggaa cctggggaag atgaacgatg    300
atcgcagaaa aagagagagt agtgctaaat gaaaatgaat agatagtctt tttgtttgtt    360
tgtttgtttg tttgtttgtt tgtttgtttg tttgtttgtt gttgagatca agaactcgaa    420
gaacttgaaa gtatcgatca ctgactcgag tgacgatgcc tccgacgaga cagatagata    480
gacaaacaga tagaataacg ctgcgatgcc tccttccctt caacaactat gacaatcgaa    540
gctttgagtg atttcgacaa agaagactcg tgctcgcttt tcaggcacgc aagcaagcaa    600
gcaagcaagc aaggaagcaa atacacagaa gaagaagaag aagggtcgaa gtggagggag    660
ggaatagggg gaagaaagcg aagaaggcgc gtccgtggag gatccatcgt tggcaggcgt    720
cggaaacaac agacagacag agactttttc tctctttctc tctttctctc tctctctctc    780
tctctctctc tcagccgatt ctgttttcgt ggatacataa atgggcgctc aggagatact    840
ttggaacagg agaggatgaa gagaacgctg attcgaccct ttttgcacaa gtctgagctc    900
tgattggtag gaagatgcgc acatagacag aacggtacgg cattgcgcag aaacccctaa    960
ttaacaaata aacaaacaaa caaatcaaac aaacaaataa acaaacaaca actcgagttc   1020
ccccctcct gctcgttgct ctttctttgc atgagtacat acgtgcaaag taaataaaaa   1080
taaaattaga atgaagcact tttccaacct attttaaaag cttaatctaa agagaaaact   1140
tgatgataaa agtaagttct ttggcgaagc actctttctc ctcgaaagat cttcttagaa   1200
aaggaaacac aagtttacta ctaatagtag tcagctaggc tttgaaggaa gcggtcgttg   1260
gtttttagaa aaagaaagga aagagatgtg gatctttccg cgatggcgga attgaggcca   1320
ttcttgaagc aaaaagcaca gaaaagtaat caagaatctt caagttaggc ctcgaacaag   1380
cgagttgaaa gcagagcaga gcagactcat agacagcgac agagacatgg ctgataagct   1440
tgcgccgctg tgccatggct tggcttggct tggcttggct tggcttctcc cgaactggac   1500
agacatagac gctacacgcc cctttctgag cagaggcttt actattcaat tatcaagtca   1560
ttttcttttc ttttctttaa agatatttta tattttataa aaaatggtaa tggtatttaa   1620
ataaataaat gaacaaataa taaaaccttc ttcttcttct tctccctcgc tcaaagcgca   1680
acctttcttt tgaaccttcg gattcctgta aaagactgag tgttttcgct ctttctttcg   1740
cctttcttcc tgagtgtagc gtagttttga tcatcgtaat gagatcagcg ccctttcgct   1800
ctctcttgca caagcagtct ccctgatcta ctaagcagtc agtcaatcaa tcaattggaa   1860
tcacttttc attcctgctt tggactaatc gaagattctt gggttcaagg ggaaaaaaaa    1920
taatctttca ttcattcttt taaaatgtaa cattgattga ttgccgaagc aagattaagc   1980
ccagaattct gaagtcttga gcgcacgggc cgccaggact tgagcgataa gcgtgcttaa   2040
agcccagaaa gcatcgctaa agagtgtgac tcgccccaat cacaccgaga gaaggaaacc   2100
tcccagctac tctgtagaga gggaaagaaa gggattaaag gccaaaacat tttaaagttt   2160
atcattttaa agaggagaaa gagaaaaaga aacaggacta agcacggaag aagaagaaga   2220
aagaaaaatg aaagattgat agatagatag ggatagaaat aaccccgctg gaatctgcgg   2280
cagagtaatt ttggaggaaa agcgcgatgt ctgcgaagga tacacagcac ttggagcgag   2340
```

```
tttggctgac tcttgatggc gtgggagcgc ttaattggtg ggtctctgga cgtaaaaagg   2400

aggtactaga gaagaagaaa ataaggctat agctgcagag cgcagaaaag atatatatta   2460

tatatataaa ttttttaacc attcaacgaa gaaatgaagt tcctcgcatt ccccccttaca  2520

acctttcaag agaaaggaat tcttgaagag aatgttatta ttattatttt tgaagagaag   2580

aagggaaata aagaattgtg aacttaaaag gaaaacgaac tcaggacttt cttcttctcc   2640

tttccgtgtc ttcggagtac tttgtctgat actttctttc cttgaagagg agacattcat   2700

aattgcggtg caaggcaaag caaaggtgca cgccgggaca gcggggtgct ctcagagggg   2760

ccttcatttg gttgctgagt tcattcgagc ggctgctatc gctgctatcg tggatagaga   2820

agttttttct cttgaaacga aataaatgtt ttcttgtttg tttggttttc ttttgattca   2880

gaatcattaa agggaaagtt tttgcactgt aggtaataaa tatcttggta gaaagaatgt   2940

aaagtgagtg aagtaatgta atgcagtgta atgcagtgta atgtaaagtg gcgtcgtcgc   3000

tgctggcaaa agaagcaaag caaagcaaag caaacctgca acctaaagca aaccccaaac   3060

aaagaagcag ccgcagcagc agcagcagtc acagtccgat tcactaagta ag           3112
```

```
<210> SEQ ID NO 195
<211> LENGTH: 3101
<212> TYPE: DNA
<213> ORGANISM: Aurantiochytrium sp.
<220> FEATURE:
<221> NAME/KEY: misc_feature
<223> OTHER INFORMATION: pSGI-EO-006
<220> FEATURE:
<221> NAME/KEY: misc_feature
<223> OTHER INFORMATION: SG4EUKT158417; Actin beta/gamma 1

<400> SEQUENCE: 195

tttgcacctt tcactctctg atttccaaga tggagtgatt tcaaatcgca caccgatttt     60

caagttccat ccgaagtgag tttttgagca actccaatat cagtacgtac tatctactac    120

aacatatcta tgatctcgag cgaggtccag aaatgtgatg ctcttgagca atcaatcaca    180

gagcggggct caagataccc tgaagccaga acccgcctcg gctttccggc ctccactcca    240

ggctgtcaac tagcccagcc agcaatcggg cagccaccga gcttgctgct tcgttctgac    300

caacgtctga ggtgtcagcg gttgtcacag aagtcgcgag gaccatcaga agcagatcgt    360

agctgaagac cgcgatagct cagcgcctta aatgattttc aatcaatcaa aactacagac    420

agagaaacag agagcgaaag aacatggcct tatggcagta ggggacactt acgctccagt    480

gaagaacaaa cggaacggaa cagaccccaa ggcaggcctt gctcctagct tctactatgg    540

taagagttag gaggctgcac ttcgtcctac tggtactgtc tgtaggtagg aatgctagga    600

aactaggtat gaaagaactg aggttgcgga gccaactctg ccgtggctgg tcatttccag    660

ggcggaggca gggatgcagc taggaagagc tgcgccgttg cataggaaat gcctgaaagc    720

tggtctgatc aacgcgaaga gtggttgttt ccctggcccg cccagcttcc aatgcgtttt    780

ccatttctcc aacgagttag ctcttcgtca gcggctgctt cgagtttcca ggtcacccat    840

atctttccag aagcgcataa ataacccact ttacttattt gtttatttgc acgaaaacta    900

aactaaatag atatttttat tattgaactt gttgtagggg ttaacgctaa cgaccatacg    960

tactgagtgt atatatataa tatacatata catacatacg atatgtatgt gtgaacaggg   1020

ttaaagaaag aatagcacag agtggttagc acccgcctgc tactggaaaa gctaaggggg   1080

ccgtaaggtg gttccaaccc accgccgatg cgaaagccgg aggcttcgac tctccggcga   1140

agaagaagtc gaacctgagc ggagagaaca gaccaatcaa cgactcagtc agccagtcag   1200
```

```
tcagtcagta gtcatcagac tgcactgcat cgctcgaatc tgctgcagaa gcgccgcttc   1260
ctcggaatcg agtcggccta aactctcgag agcatgtgct tattgagtgc gaaagcggcc   1320
tttcgtcgcg actttacgtg ttctatgtta taaaagcaaa aggaacagca gcttctgcag   1380
aacatgttat gaaaagtcct tttttctaat ggtatggaaa agaaaaacat acaaactaga   1440
gagatggtac cttacggtac gcactggcgc agctaggtgt acgcgtagca gtgttgtaga   1500
ctttggaaag aatcaaggtt ttttaaatgg agaaaacagc gtctgtgaag gggggtaggt   1560
gtgtaagaag tattgcatta catctcgtcc gtcatacaaa aactgaataa aaacataaag   1620
cttaaggact actgtacttc atcgattgac tgatctgctg atttactcga gtgatgccgc   1680
tgcgtttgtg cggttggaca gctatagcga cttgcccccct tgcgtaccag agagtgagtg   1740
cgcgagtgaa cgcttcgtcg agtaagggtg attgtggatg atggattctc gacggatcga   1800
tggattgttt gctttgtatc cttcgagttt atttttattt ttatttttatt ttttattctt   1860
tcctaaagta aaagtcgatt aatcaatcaa atcactgtga cgtgagatag cagaaacaag   1920
taaataaaca gacaaacaag ggagcaagac agacgggcaa tgtcacactg ccgtcggtgt   1980
gtagcggcgc gacgagtatt gactgccgtg tgtgcacaac cttgattttt agctgattag   2040
ctgttaagcc aggtacacaa aacatccatt catacatcca aagaagatgc aaccataaat   2100
acatacaccc gtgagtgcat aaatagcccg cctccagaca gatcgggcgg cctctgacgc   2160
ggagtgtggg agcaaagagc gcgatttaca catttatcga cagcgaagga tcgctcaatc   2220
cacaaaaaag aaaataaaaa taaaaaatcc taaaatcata cctccacctc cgacagatca   2280
gacttctgaa agaggaattt tgaaagaact tagaaagaaa gaaagaatga acgccaacga   2340
gagactcatt cattctcctc ctcgccttta tctcgaaggg ttcaaaaggg gcgccgctag   2400
ggacaagact agtgatatgg tagagcccag caaagtttta attaaaagct aaagtatata   2460
taacatattg aaaattattc tattgtaaag ctaaaaatta aaagtataat agatgcccta   2520
tattaaacaa tttttatcta actaagaaaa cagaagagta ggtagcgaaa attggaactg   2580
gggtggcaag agagttcaca ctttcttttc gtaagttctt ttggatgagg aagttagtga   2640
gttgtttagt tgagctatcc gtatgtttcc atttgactgt ctgtgtatct atctgtttga   2700
ctcactcact catcttttca caattctcgc aagtgaaggg ggggcatctt gactttctcg   2760
cgattttctt caagacccccc ctcctgcccc actggggtgc tttactgagg cgaaagctct   2820
agtttgatat ggaaaggagg tacagttagg aggaagaggg gtgtgtttgt gagggggaaa   2880
tgaggcagca gtccgggtgc ccctcagagg cagtggtgat gagaggaagt gtgagggggt   2940
gaatttcgaa aggatcctcc ttaagtggag gcattcgaga gagggtgcct gccagctggc   3000
ggtatcgtgg tcgcgacggc tgcgctccag gatcagcaaa cccgcaacct caagctcaag   3060
aagcaacaac acagtagcag aacaagcacc caactagcaa a                       3101
```

<210> SEQ ID NO 196
<211> LENGTH: 3063
<212> TYPE: DNA
<213> ORGANISM: Aurantiochytrium sp.
<220> FEATURE:
<221> NAME/KEY: misc_feature
<223> OTHER INFORMATION: pSGI-EO-007
<220> FEATURE:
<221> NAME/KEY: misc_feature
<223> OTHER INFORMATION: SG4EUKT162250; Heat shock cognate 70; hsp70

<400> SEQUENCE: 196

-continued

```
atgggtgatt gttttggcaa gctaaaagat tttaacttgc tacctctgac tactaagaat     60
gcctcattat ctatggttat tttatcatta ttatcattgt tgctactact gtttcaagta    120
ggtagtagtc gtggcggtct ttatccaggc cttgaaggtt tggaaaggag cctctgactg    180
gtgagagtag cacagagttc cgacgaggac aaatgggtga gctagataga tagatggata    240
gatagataac tctttggccc taatttgaaa gcaaaagagc caaaaggcaa gagaaatcga    300
tgagtcactc gagagagttg aagacctgag agagttgaat tgaagaaggc gcacgcacac    360
tgcgacttgg cgagagaaga ctcagctgac ttgagagcgt tgccccgaag ttctcgaaag    420
ccctccgagg tctgtctctt cctgcggtcg aaaaaaagca agcaacttga agcacgcaac    480
gcacgcaagc aaagaaagaa acaacttgaa cttgaaagaa acacaaataa acggaccaac    540
agacagatca acagagatct acacgagctt ttacaacaag atcagatttt gagacaatcg    600
ccgtggctgt tgacagtggg tgctgatgac ggttggtcct cttgttgaca gtcttgagag    660
tcctcgggag cgttgctcgg cctggaatgc tcgcgaggaa caaacaattg ggtggtaagc    720
tgagagcagt cagacattcc agttgaaggc aatcgaaggc aatcgaaggc aggcagaacc    780
gcacatttca ttcagagaaa ggccttctct aaagctttct cagacttgct tccactttca    840
agaaggtgag taataagaca gctagaagtg gtaatgacca taccaataac ggtaggtaaa    900
tctttttctt tctttaattt aatattattt atttatttta ccaatttttg aagttaaaat    960
agtaacaaat catacaaaag acaggcacct ataccctagc tagtaggcct atctatccta   1020
agcgatgccg gcaggagcac gatgaacgaa accaaacaaa ggtatacgaa gaaagaaaga   1080
aagaaagaaa gaaagaaaga agctacgctc ctactgccct ctaccccccg agcgaactcc   1140
accgatgata gtagtgagct agtcagttag caaccatcta gtcatcacca ccatctctct   1200
ctctctctct ctgtctctgt ctctctctct ctctgtctgt ctgtctgctg tctagctagc   1260
tctccactag gcgcctccta ctgacctccc atgcatgcat gtatgaagcc attccctcct   1320
cactagccag ccagccagcc agccagtcag tcgggtgctc ctctttcgtt ggttgattga   1380
ctccagtggc gaagagactg aatggacgct cgcgctctct gccgagggca cgaagttgag   1440
ggctcctggc tgattgactt tgattttctc ggtggaatgg gagtccgagt cggattcggg   1500
cgtgaggctc cctccgccgc ccgtgtctca caagttgcgg cagagccatc gatgccaatg   1560
gtgctctctc tctccacact ggagaagaga atccgcagag ctcagaaccg tccgctgcga   1620
caacttaaga acatctttcg ctgttttgtg ttacagttcg aagtatcatg acaacaccct   1680
aggacctgct ataggtccag cgagctagaa actagctagc tagctagcca gacacccaaa   1740
cattgtttgc cgtggcacat aacatttgtt tggtgttcaa gttgtttgtc tgtagttgat   1800
tttatgaaga aggcactact gttctatagg caagtgctag gatcaggtat tcaaataaaa   1860
gaactttgtc tctcccttca cgcaaggtgt agaatcacag cataggcaat gattagtgac   1920
tatctgtagg actagcacga gcctagttga acaatttttg gttggagctt cctgcctgct   1980
agctaggtac ctactgagtt gtgtgcatca taagatgatt ctgaagatga ttcgtcatga   2040
atcggcgatg atgctccaaa cttttcaact tgagatgcac caccctctgc aagacgaccc   2100
agagacagca aagaccgcta tcaccgcacc tgaagaggct tcggaagcga tgatgtgaac   2160
acttgattgt actgcgagtc atcgttcatg aggattcatg acttggaatt ctgtgaatct   2220
gatgatagag ttggaagagc atggttttgt aggtacttac caagttgaac tacgtactac   2280
tacttcacta agctttacat gtacaactat actttacccc tcaatttgaa aatttgaatt   2340
ttgaaaaata cagtagtgac tatgccatct gaactttaca agggggctta atagaagtca   2400
```

```
tgccgagtcc gaagcagttc tttgcagttc ttccataaca actgttatga atataccatt   2460

aggaacgttc tggaacgttt acgtatgtgt tctggaacgc tcttaattaa aaaataattc   2520

ttaatatttt aaatgtttta attatttaaa aagcaccttt aaaagttttt aatgtatttc   2580

tagccccggc cgttgaagct aagaaggaaa agccccttat tttggaaggt aagccttata   2640

acagcatact ctttcatgcc cttaataagg tgcaaaagat gatctttcta gaatctttgg   2700

caaagaggat actacccttc gcgaagaccc tcaagaatcc gctagtactc aaatagtgac   2760

tatagtaggg actaagaaca atctggatgg cttagacagt gttcgtgaag gtctctggtt   2820

gcaagttgat agacatacta tgagcgaaaa gtgaatccat gattgcctaa tgagcggagc   2880

tcaataagtt tcaaacagaa aagaatgaag gagagcacaa ccaactaaga gtaagataag   2940

agtaccaagg agtgccagct ggtgaagagc accaagagcc acagacctga agaagcaaac   3000

cccaaaccgc aatcagaagc gaacagtaaa agttacagta gcagaagtaa gacacttagc   3060

aag                                                                  3063
```

<210> SEQ ID NO 197
<211> LENGTH: 3033
<212> TYPE: DNA
<213> ORGANISM: Aurantiochytrium sp.
<220> FEATURE:
<221> NAME/KEY: misc_feature
<223> OTHER INFORMATION: pSGI-EO-008
<220> FEATURE:
<221> NAME/KEY: misc_feature
<223> OTHER INFORMATION: SG4EUKT161511; Voltage-dependent anion-
selective channel protein 3; isoform 1

<400> SEQUENCE: 197

```
gcgctcgttt ctttccaagc cgcttcttcg gcaagaatac gatgataact ctaagtgtac     60

ccacccactt ggtaggaacc ccctttcctc tagctacggt gagatgaaga cagagagaga    120

cagagagaga cagagagagt gaatctcttg caggtacttt agcactgata atcagcgaat    180

gaggcctgcc gttcttctgg atcttttgcc cagagcttca tgctccgggt ccgttgcggt    240

cctcagtggg gatatgtgat gtactatata tggttatgtg ggaattacta ttacaggaat    300

tttaggaatc ttctgtttgt actgatgcaa cattgtactg ctatactgct agtatagcat    360

gaaggccagt gcccattgac gtgtgatctc tgtcccgact gcacgaaaaa atatccattc    420

ctgcttgtta gagggataag tgcgggggga tgtggtgact taaatagact gactgcaatt    480

gatcgataaa tgggaagctg tgggaagtag gtggattaga tcgttctccg ggctgtgggc    540

ctcggcctcg ttatgaaaac aggcggtctc ccagcttttt ccgtaccccc cgcacgaaca    600

cccgcgtctc cactggggaa aactctagtt tatcgagtga tctcctctaa gggcggagag    660

gcagtgttgt acggagaggg tttcaaaaag aggtccgttt cgggaaggtg tctgtctcct    720

ctagcgcttt ctttctttct ttctctcctt ccagcctccg agttgcttgg ccaaaagctc    780

tgcaaagcct gctgtttcct tctcgtttac ggccgttccc gctaaggagg cgcccgcttc    840

cgtcggcctc tgccttttcc tgcctgtcct gagcgtctca ctccccccac tgcctctccc    900

tatctgcttc ctgtttatga tcctggcgag gaaaagagag aaaggctgag aaactgtgct    960

gcatatttgt ttctttcttc tgataattag tagtttttct ctcccagaca atcttttttta   1020

attttttata atttttataa ttttttgttt taaaatttct ctgagtctca aaaggcctcc   1080

gcctcccccc atagtaacct cgtatcagcc tctgcgcagc accggtttcc tttttgccac   1140

aaaactacga tcgttctata ggactcgggt agagacacat aggcgaatct ccctgtctcc   1200
```

ttctttcttt ttcctggata cagacaaaca aacaaacaga cagacagtca tacatattat 1260
ccatatatag gtaggtgtat atagagaggt cgattgattg attgattgat tgatcgaaga 1320
aaggccctgt gtctcttgct ctcttgctcc ctttctcttc cggccgtcgc gaaggcccgt 1380
tccgcctgcc tcaatctggc tccagcgagg cctctgagcg ccttccccgc tgccttctga 1440
gctgccttgg cagctttggc cttctcgcgt ccttctattg cggagctgag tgtcagcgtg 1500
ccctccatcc tgtgttttta ttgacaggca cggaaggacg tctttgatga tttatgtctt 1560
gttgcggagt agtagttagg tagctggcac tagcacgcat ccaatctatt ttgagactaa 1620
tttttcaaat tgaaacatca ctggaggaac agaaggacga tgggtccggt aatgattgca 1680
cgtgatgata caaatattgt agtctgtcag agtacaggtg atcacattaa acgatcaaga 1740
gtagagagga tagatgagac ggtgttaggg gagtcgaaag aatggggctt ttggaatgac 1800
tgtctctttt tttccccttt ctcgaatggc tctctcacca ggcgtagctt tagcagtatg 1860
tgacccatag tagaaatctc tctttgggcc cagtgggggg cactcacata agtcctcctt 1920
ttcggataat ttctcctct gtctccactg gcgcttcgat cgattttcct ctctctgtgt 1980
ggcctcgtta tttcctctga gactcactgc ggaggcgcct gtttgggttt gtatgtgctg 2040
cggcctgttc tgcgccgcaa agagagcgcc aaagagagag cgaaagagaa gagcgaatcc 2100
aaatcattaa cgccgctact cgctcagctc tcgcttctca gacttcgcag gtacgtttac 2160
acagcgctgc gctcggcacg agatggcctc cgtcctggat ggaggacagg ccgggctaca 2220
tacaatgcaa aaggctccat cgcggagccc gcacctcgat tcgcaaggcc atgaagcgtc 2280
gccagttagt tgccttgctg tctgcttgtc tggccatcaa tctttctttg atcagctctg 2340
ttgagtgtca gattggttga ttgatctatt cttttctttg tttggtttgc ttgtttctgt 2400
tggagtattc tctgtttctt agcacaatgt catagtgttg ttgaataaac tgtggaatat 2460
gcgatatgtg tcatatgctg tacaaaatgc caggccgatc tgcttgtgac ctcagcgacg 2520
tggagtacga atctcgaggg ggctgtgtgg attatcagag ctcgcagaga tggaggagta 2580
ctgccaccgc gatggagaca acagcctggc gcaacggagt agaggatgag aagaaatgga 2640
taactcttgg aatcattctt ctcgaataag taaagaatca atgaattggt agatcaacga 2700
gttgaccatc ggttaggttc gaggccatgg ttgaggaccc tgtagatcta cctgtgaaac 2760
agttgatcag aatgtgcggg acgatggtta tctgtagagg cgtcacagac agacaagaca 2820
gagaaacaga acaagacgac acgtaaagga caaatagaca aaagagctga gataccttgt 2880
cccctggatg gatcttaacc cttttctgaa gaatctggct atgttttgtt tgcaattata 2940
tgaaaagaaa taactaacgc tcgtgtaaaa catgtattgc catggattga ataataatta 3000
ttgccattca cagtttaaca cccttttagc aaa 3033

<210> SEQ ID NO 198
<211> LENGTH: 3193
<212> TYPE: DNA
<213> ORGANISM: Aurantiochytrium sp.
<220> FEATURE:
<221> NAME/KEY: misc_feature
<223> OTHER INFORMATION: pSGI-EO-009
<220> FEATURE:
<221> NAME/KEY: misc_feature
<223> OTHER INFORMATION: SG4EUKT159773; Lysophosphatidylcholine
acyltransferase 1

<400> SEQUENCE: 198
attgattgat cggcaggagt gagtgaactc gagttcaagc aagtccggag atctcgaggc 60

```
tcttcttctg gagaaaaaaa attgaataaa ttcaagaaac cttcgccatc gccagcagca    120
gctacgtcac tgagtagatc aggtgcctac gtgcctaagt ggttcatcaa acgagaacaa    180
acggaagaaa acgtgaagaa agcagaaaga aagcagaaag aacctaaagg aagaaaccca    240
aaccagaata ccgtgatcat tcgtattttc atttccactg gcatcatcat aatctttcgt    300
aatcattaaa aaacgtttgt tttttgtttg tttatttttt aaattaaaat attcgtacag    360
gcctatatca tacgatattt atatatatat ttattatttt caataataaa aaatagttgt    420
ttatcgttaa aaagtaattg aagttaatta gacaaaagct ttttcttttc ttttagttta    480
aaaaggtcac ctgcgatgtc ttaatgcgac gcaagaatcc cctccctcct tcaatcacaa    540
aggcggtttg cgagttcttg gttcttgaac ccgagtccgg agtcgagtcg attgatggag    600
cgcgtgagtg agtgttgggt tggtttgcct tcagggtggt tgaccgttat cgttacctga    660
ctaccttccg ctgttcgctc ctggtatcca agcaggcaag aacttcgtcg ccccgtggag    720
atagacggac agatagatga tggatgatgg atgccttggt ttgctcgctt tgggttttct    780
ccgtaggtac tcgctcgcgt cgaggtcagc gaagagacca acgatgcgct cgcagcaggt    840
gcaccaccgc gatcgacctt gacttcaaga gcgccgccat ccagaagtcg ccaagcaaag    900
acgcagcttt ggcatgctct gtagtacctg ttatcattct atgtatccgt tcatttccag    960
cagagtcaaa gacgacgaag cgcctactca cacgagtgcc acatggctgt tcctttcgtg   1020
tagacatctc agagaggctc tgagtcctcc aaagcgaagc cttggcttcg aattcacgct   1080
cgtccaaacc tcgcgtcgcg cacagtttca cgacccacga ccagccagcg agccaattcg   1140
tgagctcaaa gcatcaaatc caagcgagtt caacttcatt ctgcctcggc tcgcgctgtc   1200
ccattctggc ggcgttccgt tcctgcgctg cgttctttct ttcttccctt ctttcttcct   1260
cctgcgacta cgtctcatga acgtatcatt cattgtacaa acactaacct aacctaacct   1320
aacctaacct aacctaacct aacctaggta cctactatgc acgagcgagt ggattaaaga   1380
agagaaaaga aatgaacgcg aagcacactg tatgagaaga caaaggccat ggcgtcgttt   1440
cagtatttcg agagagggtg agcaatggtt gaagcaactg ctcgcctcga accgctgtag   1500
ggtcgtttgg ctcgttggag tttcaagaac cggatgacct tgcggacctc gaggccagag   1560
ccggagactt ggacgcccct ccccttccga agctgcgttc tttcgtttcg tttcaagcga   1620
atgaatgcac tggagtcctt ggacttttgg atttcgtagc agtagacatt cattcacatt   1680
cactttaaaa cagcgttaat cgattgattg actgatcgaa gcgatcaatt gatcgattgg   1740
ttggttggtc tctgttaatt cgcaggtgca tcagcgagtt ggagttcgag ttggagggtt   1800
tccaatcgca gtgaaaggac tttctttctg tagcgcattt cctgatttct ccatcttatt   1860
tcattcttga cttctcctgc ctttaccagg aaccgaaggg cagagagaaa gaggcacagg   1920
aattttattt attgtaaaat taaaatattt tttattcttt aaataataat aaaataaata   1980
aataaatttc aaaggcgtcg tcagcttctt tcgtcgtcgc ctgcgtcgtc aaataagcga   2040
ggaactcaat gctggcggct ctgtacctaa tagatagcta gctagatagc catgtcatgt   2100
catgtcatgt catgtcatgt catgtcatgt catgaagcca tggcggcact cctttcaaga   2160
ctctcgagtt ttggagcgct ttctgtagag acaacggcgg agacaacagc gacgaagcga   2220
gaattgaaaa gaatgaagaa cggcggactc cgcttgaatg acatttaatg gatgagtacg   2280
tagtagacat ttatttacca gtaccaacag tgaaagaaat gacgggtttt tgtaaacctt   2340
tcttccttca agttttgcat ttcatggtag gtaggcgccc gttagacagc agtagcagtt   2400
```

```
ggtttgctat atttattatt attttacttt gacttgctga cttacggtgt tcttcaagaa   2460

gagcttttca atgcgaggaa gatgatggaa ggaggaggcg gagcattacg taggaaacct   2520

ttgcaatggg agagcgaatt agagcaatgg taggcgagag tagaagaggc aaaagagtcg   2580

ccgaaggaaa gtgagagaac tcgtcatcat aacattgagc gacgaaggag gagaactaac   2640

gcatagagtg ccttagctat gaccactttt catgaaagag gactgactga ctgactgact   2700

gactgactga taattctgct catgtcctgc ttgactctaa gctactgcta cctatgtttt   2760

aattttaaga atgttttatt ttattgtatt aaaaaaaatg ttttataaat gttttaaact   2820

caaagttttt atagagaagc cagaaatcgt cgtctcgatc gatcgtcgtc gatcaattct   2880

ggttcacgtt caaccagttc cacatatata catacataca tacatacata catatcaaca   2940

aacgaacgga cgaggggcac tggcctgcac gaacacacat acaaacaaac cccgatcacc   3000

ttgcgccagg tgcccgcgag aggatcgctg gggccgtggg cggaggactt caaggccagg   3060

aattcgcaca atacgacatc aaactacata gattccgtga gcaagcggag gtcaaaacaa   3120

ataagacagc taaagccgga aagagctcgc tgaagaagat actgttgcaa aatagcgatc   3180

ataactagca aga                                                      3193
```

<210> SEQ ID NO 199
<211> LENGTH: 3017
<212> TYPE: DNA
<213> ORGANISM: Aurantiochytrium sp.
<220> FEATURE:
<221> NAME/KEY: misc_feature
<223> OTHER INFORMATION: pSGI-EO-017
<220> FEATURE:
<221> NAME/KEY: misc_feature
<223> OTHER INFORMATION: SG4EUKT160990; P-loop containing nucleoside triphosphate hydrolases; TEF

<400> SEQUENCE: 199

```
agcaggagtg gattcggaag gccccaaatg gatggcacga gcgagctcct tccttcctct     60

cgcgccgcac tctctccctc cctccctcct ctctctcgcg cgcgagtctc gctcactctc    120

ctttgcaaga gcaacaagca gcctcggcag cgaatgaatg agagtcctcc ttcgcttctt    180

tctcgattca actcgaagaa tgaatgattt tcattgctca aataaataaa taaataaata    240

aataaataaa taattattgt tccattcatg gattggcaat tacttggtta gctagctagc    300

tagctagtga gtgagttagt gggttttagt agtgctaacg gatggcggca aagacctcgt    360

caaaaaaaaa tcaagaaagc aagatgaaga agggcctgtg attcaagacc cgcgttctgt    420

ctcgcttact gcgtggagtg cggagctccg acacgcttga aattggccaa aagctgcact    480

tcgcgccacc ctctgcgccc cgaaggtggc tttgggccgg agcaccaagt ttagcgcact    540

gtaaaaaggc gcgaaacttt gttggagaag ccaattaatt aattaattaa ttaattaatc    600

ctttcgacga aaactaaaga agaagaaaga aatcaagttt ccgccctata aaatatccct    660

tcttcacact tccttcattt tgtagttaga tgataggcag cgaaaggact aaaggtgaaa    720

ggcgtaggga ccacataggc gcgctagggc ggagggaaag atacaaatgg cctcagaaag    780

gaagaagaag aggcctcgcg gaggaaggat gctgaagcag gaaagataca gcgaaagaga    840

aatcctgtat cttccacagt ggatggacac cttcgaggcc tgcataagtc cacatcactc    900

gctattcaat cattgaattg gtcatttaat tcaagcattt aattcaatca tgtcttcatg    960

caatccaccg tccaacaaca gagcgcatag aagatgttat ccaggtaagg ctgcaataat   1020

acgcagtttg agttttctat tttaaaagta agtttaaaac ttaaaaattt catacttatg   1080
```

```
catgctattc aaaataagat tgtatcatcc taaagtattc ttcttctcgt tcttcttcta   1140
atcggaacag agacaacttt ggtgggtttg cgggcctttg agagaaagaa aaaaaactct   1200
caaaagaaac caggcttccg aggccgactt gcgcagctct ggattgaggt tccttcgatc   1260
gctcgcttca ccttcctggc ccgcgcatgc ctcgctctgg gtacacagct gagtgagtga   1320
gcgaaagatg agcgaatgaa tgcaatattt ttctattttc tattcattta actgtactta   1380
attaattgat tattgattga ttgattgatt gattgattga ttgattaatg actctcgctt   1440
ctgagaatac atctgttctc atcttcatcg tcacgtcaga atggaaggat gagaaatgaa   1500
aagaattcga tcactttccc gccttcttgc tagctcatgc tcctttcccg ccaaaaagaa   1560
agaagaggaa agcaccccga agaaaagaaa gaaatcaccc aaacaccctc ctccttcctc   1620
gtccacagac agctcagaat aatgaaagct atctttccat cgctcttgac ctaactctct   1680
ttctgctcct gtaaattcat ccaacaaatg tttagtctca gaaacccatc tgcctcatac   1740
tactacttac taccttcctt acttgaaagc aggcaggctc acggccagct tggcagatag   1800
gatagttctc atatctattg ctgatcgttc ccgtttcttt ctcaaagcaa agtcttttct   1860
cttcattcct tttctttttc ttttcttttc aggctctcca cgttttcagg agtagtacat   1920
ttgctactta gtaattagaa agcttagtac tttttgcttt tctggattct gaagacttgg   1980
aaatagaaag aaattaaaaa tctttttctt ctttctttca gcctttgctg gactccctcg   2040
cacgcctcct tcttccccag ccatccatca gcgggcactc cacccgcgct tcaacgctcg   2100
ctcgagtgcg tgcttatttg ccttcaacgc ggcgcggcgg ttaatatagt cccagcactc   2160
cttaaggggg gcatcgcagg gattatcttt ttaaaacctg tcacggagtt acattttccc   2220
tcgcatcaaa gtgttcccgg ccgcgtcgca catctaagtt ttataaccta cacccctcgt   2280
ggggtagggg cgaattctat gtacacagca cctcagaact tgcgcgcgtt ccgtgacaaa   2340
tgaggggtgt ggcggcgcat tcggccgcat cgccacattc agatatctaa catacccccc   2400
cttcgcgatg agtggcaggc gaggcggatt cgctcgcgag aggcgaggtg ccacagcaga   2460
ccagtaacga ggagccaagg taggtgacca ccgacgacta cgaccacgac cacgaccaca   2520
gccacggcgg ctgcagccac gggacgcctc gcatggcagc gcatcagcac cagcaacgac   2580
agctgcgagg agcgcagggc cgatctggac gcgccggagc cgcacgacca atgccgacgc   2640
aacgctgatt cttctggatt acctctacac atgcatatat gtgtagaggt gcggatgaaa   2700
tgccctgcga ataaatgaat ggcttcgagt ttgcctgccg tatgctcgaa agtgcgtgtg   2760
cagacacagg cacgaccgag aggacaacag tctgtgctta cctcaccagc acattcttgc   2820
aacgccatac gaagcacgcg aaatcttgtg gctcagagag gaaggcattc gtgtacggga   2880
acgtggggaa cgctatcaat ttggaattca aaatgagtga accagacaac taactgtgac   2940
ttgaactgtt gctccacgca tcaaaaccaa acccttaaca gaagtagacc agttcgaagc   3000
tactagcacc aaacaaaa                                                  3017
```

<210> SEQ ID NO 200
<211> LENGTH: 2986
<212> TYPE: DNA
<213> ORGANISM: Aurantiochytrium sp.
<220> FEATURE:
<221> NAME/KEY: misc_feature
<223> OTHER INFORMATION: pSGI-EO-011
<220> FEATURE:
<221> NAME/KEY: misc_feature
<223> OTHER INFORMATION: SG4EUKT159831; 40S ribosomal protein S3a; rps3a

<400> SEQUENCE: 200

```
aatgtgagcc aagagggaac taggtaccta ggtactacct aatagcaggt ccaaggtcat     60
acactgtcag agtggaatga ctccgaataa ctgacgaaat gatggtgcct aacacagttt    120
tcgctttgtc ttgatgattg aagtctcctg gctatgtcct gcgtagaaga tatctagatt    180
gtacgtgaat atagatttct agctaggtcg ctaggtattt tcaataaaaa acagaaacaa    240
atcccaagcc tctgctctgt tttcttatgt tttctatcgt ttgatcatca tattcttctt    300
gacatgatct ccaaagcgta gcttcttttt ctgtgcaagc ttatgctggt ccttggaggg    360
ggctgatcga agacaccaga gaaaccaacc tctgccagca atcgcgctac taggtatacc    420
aagctagggt agtatgttaa tggtaatgtt acctggccaa taaggtgtgt cgatgcttca    480
tcacgatgga actaggaagg aagctgttga acttaggttg tacaacagca agcactgatg    540
ataattatca ggttcatcac taattagatg catcacatgg tttgagatcc acacaatccg    600
cacaaagatg ccgcacaacc aaatcatttg attagaggtg gaagatgaac agtcggcctg    660
aagatcttgc gaaaggaatg gtgtttcttt ggatagaaaa gaatgcagaa gcagaagaag    720
aacgtttgaa ttcattctac tatgaaccga cttttgaaaa ccaacaatag tactctaaag    780
atttactcgc caaaaacacc tcttgcaaat ttttgttcat cattgtccaa gtatccggca    840
gagcagattc gtctctattg gcaaatgctg atgatcattt taaaaaatat ttttctgttg    900
tgatcataat tgtgataaca caaatagatc tataaagtga atcgaggtcg atctcaccca    960
ttgcaaccgc tataaacact tgttggtacc aaagtgcatg caattcacta cttcttgccg   1020
tggttctgtt gttccggcca gacccaacag catcgtaccc cgcaaaagac gcgagatctt   1080
gacaatcaac gttcctttta tttgggaaaa aaaggaaaaa aaaagcaccg atacccgcat   1140
tgctgccata gtgtgaagaa ggagatcacc cgtatccatc cttttatttg ggtaataggc   1200
atggcattca tgaagagagc aacattgtac tcctcgacaa tatgcctgtg actagtgctt   1260
aagattcttc aattactggc ttataaccat gaagaagcat gcgttcttag acttggactt   1320
ggactttgac tttccactta ttctttcttt ctttctactt cttacagagc cgcatgttcc   1380
ccgcacgttc atcgctagca acgcaacggg tgtaggagcc atcatgttcg ccttgcccag   1440
aggctacaaa catattaaag atagatgctg acgacaggag acctatctcg agtcggtgaa   1500
cttactgagt ataacgccaa gtgcgagcag tttcgggagc tggcccatgg cgacttgcct   1560
ggcagtcggt tgaggttcaa tgcttagtct acttctggtg actgtcagag caagaagaat   1620
atgtcacgat tggccacaag accattccct ttttgcttct ctgcatattt gcaagaacag   1680
catttcctca aacttcgcaa ctcagagtct tcatggtcat tccaagataa agactaaggg   1740
aaatagtagt aggtattgga aaaatactct tagtacaaga tagggaatga aacacagaga   1800
tgcgccgcat aatctctatc caaagaaaca tttgttcaca tgtagcagtg cctgaccaaa   1860
gctaatctat ccgcttcata aaatgggcca gccgatggtc actctagctc aaataaatat   1920
tgttggcctc cattaccacc atcttctcta caaacagcag cgtagacggt acggcggcgg   1980
ttcgttcttc gaagtactac tttgtagatc ctagctagta cgtaattaat gatgtatagg   2040
ttctacatag aaaaggggag acctcggtag tatacacgta tacactgtca tatgtaaata   2100
gatagcaaat ccagggccac ggggaattat ggcctatgtc ccatgacaac ataacagagt   2160
tcggtataat aggtacaagt aagagatcaa tagggggtat agtagccact agcaagcagc   2220
tcttcaggcg ggcaccgttt gttgcttgct atattgcgct tgtgtcattt gctaaactaa   2280
acgaactgat gatgaggagt gcgcacattt cctcgcgctt tctttgctgt cgcgaacgcc   2340
```

ataatcagcg gtcttgccac cgacctccct ccacatcctt gtttatctaa tgccgcagca 2400
atataggttc tctctaacac ttaaccatgg ccaccagttc ctctcatgaa gcgctttgat 2460
acctgcgcaa cgctttttca gcctggctgc ttccacagaa tctccttaat taccctgtct 2520
aaacctcatt aacctcctta tattttaagg tgagtcaaat ctgcacaact ccttttcagt 2580
ctacttaatc acctccttca tttcccttta cgcagtatct attaaggcgg ttctccccctc 2640 aaactagggt ttaaccctag gcggaacgca gctgaccttc ggcgcagatg cgcgcctaaa 2700
tgagagtgcg gattttgcct ttttgtattt aatatgagct gcggatggcc ttgcaagcag 2760
ggcgtaaatg ggtggaggaa agaaaggagt ggaggggcgc ggccactagc tagaggtatc 2820
tgactcttat gagcgctggg cgagcggcgg ggcatgtagg tgtgttctaa gggtctatta 2880
gaggtaacgc ggggaatggt gcaggggcgg cgaggaagag cagacgggca tccttcaatt 2940
caattcgggt tggttgacgt gcaggacttg cgcgaagtag gcaacc 2986

<210> SEQ ID NO 201
<211> LENGTH: 2956
<212> TYPE: DNA
<213> ORGANISM: Aurantiochytrium sp.
<220> FEATURE:
<221> NAME/KEY: misc_feature
<223> OTHER INFORMATION: pSGI-EO-012
<220> FEATURE:
<221> NAME/KEY: misc_feature
<223> OTHER INFORMATION: SG4EUKT161339; 60S ribosomal protein L8; rpl8

<400> SEQUENCE: 201
gggctcattc gaagtgtttg tgccgacaac aatgatatcc tccatatcag caagcatcat 60
ctcgttgata cgatcctcct cgtcatcaag cggtgataca aagtcttcga gaggggattc 120
aattgcagct tgtttgttgg tctgggcctt gccatttgcg ggtccgcgtt tggtcggggc 180
gcgctcagga agtgcgacgt tctcatcacg atcaattgcc gcgcgaacac gcccaccgag 240
gttgtcgatc ttggcacggg agtcagagtc atcaacaagg atcggaaggc ataaacgacg 300
tcctccgagc ttgccaagaa cgtcgtcaag gcgccagcca gtgcggcaga agagaccctt 360
ttcgtactcg cggctgccaa gagccacgac tgcaaaacga agattagaca ggtagcgagc 420
cttatccaca cgaaagtcca aagccatatc ctcgagccaa gccagcagag gctggccaac 480
ttcaggcgcc tcaccatcag accatgtggg catgacgaag atgacaacct tctcctcctc 540
gagatcgtcc gcaaactcgt agttttcaac ggcgatggcc ttggctccag gaattccggt 600
ggcaacaata tccgcgatgc gccgggcagt tccggtggtc gtggcgtaga taatcttaat 660
cttggctttg cggccttctt ggatggcggc atttgtgtta aagccctcgg catcaaattc 720
gtcgatttcc tcatcatcct cgtcgacgtc tgtgtcatcg ttgttgctgc tgttcttgac 780
agcgtttaca gctgcatttg cggcagagtt tgcagacgca atggctgcac tgagcttgtc 840
atcgacggta ttcttcacat tcgttgcagc atcggccgca gcatgagccc acgagttgag 900
gttttccgcg actcgttccc gagcctcctg gagggcctca gcagtctcgt ctgctagctc 960
caagaagggc ttctcgagag acttgtcaga gtttccacgc gcatctctgt agcgtctgtg 1020
gccggccaca gcagccgcgg ccaacgccac ggcacctgcc gcaaaggcca atgccgtcgc 1080
gcctgagctc tgtgacatcc tggttccgag tttgccacca gtcatcactt ataagatgta 1140
agcagtagga cataatactg tagaataagc aaacctacta taggttataa gcccgtacta 1200
tagtgtatac aaatttacta tagactaaag ccttcagaga agtcatccct aagcctgctc 1260
agttcttagc aagttcctcg cagccgcaaa atacagagac ctgtagatag accatatcct 1320
cctttcgatg tgttttacaa ctcagtcggt atatttgtgc cagcattggg gtgatctctc 1380
ttggcatctt cagaaaacga gacgaactcg agacaacttg tactacaact atcaaaagag 1440
acaacagaag gcatttctct tcttcttctt aatctacact agcctagata ctcctatcta 1500
agcattaggg actcctaata tcctatttta tgcccttaaa gaggccattg tataactaag 1560
cttagtacta cgcctaatat tgccatcacc agttcccagg ttctgagcca gaggcacttt 1620
cgtgtaaaac ggcgatggct cacgctcatg tcagcgcacc attgcagtgg ggatctagtg 1680
ctctcgacct tccgcatccc aggccatttt actctgctcc gctgcaatcc gactgctgag 1740
aaattctcaa tggccaagcg aattctgcag aagaactact gcaaatcggc cctagttcaa 1800
catcgtaggt atctgctagc aggctgcctc gctatctgcc tcatatgcta atccctaaca 1860
gtcccccctt catgctaccc ttaccgtggg cctaccgctc acctaccata tacttgccac 1920
ctaagtaatc cttagccact cttacatggg agtctctgta ctagattccc gtattgccgc 1980
tatgactaac atatgtgtta ctgtaagtac tagcaacacc tgagctccta gtgtggtgct 2040
atgagtatct ggtaggtacg tacctacttc ggtattaaca cacactcacg agtgaagaag 2100
gaattaggaa aacaagtcaa ctcagctcaa ctcgagttga ctattatctg taggtattgc 2160
aaacttactg cgagcactga tagatacgca taggctcgta ccttgatagc aatgggtcat 2220
ccctctcgct ttatcatacg ctataaacac ttctaaacct gagccccaaa gctcaggctg 2280
agcaggagat ggactatcaa tttacatatt tttcatctac tgctactgct agcacatact 2340
taaccactcc tatatgcttg gccttcattt tttcttattc attgattgat tgattgattg 2400
atgcattgat tgattgattg attgattgat tcattcattg actcattgat tgattgattg 2460
attgattgat tgattgactc attcattcat acattcattc attcattaat gtcctataat 2520
gccatcgatc tctatgtgcc cctctatgat aaacagtatc ggtccctatt gctcctctca 2580
tcgagccgtt caaaaccacc cgttctcccg ttctcccgtt ctcccaccac gttccaggaa 2640
ttccttccgt tccacacgtt cctttgcaaa accccttta gttccccgct gccccccctga 2700 agccacaagc aactagggtt agggcacgga attatagtag agagtagctg aattctaggc 2760
gaggcgaagg cggcgcgatg ggggggtagc gtggaagcag cggtggagaa gaagacttgg 2820
cggagcaagg ggcggcaatg agggggaatg cggggaacag ggagggcggc cgaggaatgg 2880
agggcgggag agcagcagac gactttgctc tggctggagg ctccggtttg cttttggcga 2940
agacaaggca gcgaag 2956

<210> SEQ ID NO 202
<211> LENGTH: 2918
<212> TYPE: DNA
<213> ORGANISM: Aurantiochytrium sp.
<220> FEATURE:
<221> NAME/KEY: misc_feature
<223> OTHER INFORMATION: pSGI-EO-013
<220> FEATURE:
<221> NAME/KEY: misc_feature
<223> OTHER INFORMATION: SG4EUKT159881; Actin depolymerizing proteins

<400> SEQUENCE: 202
gtttgcacgg cgatgatgct cctgctcgat ctatctccac ctcatccatc ttataaacta 60
gcaaatcgct ctggtgctgc tggtctgtta tcgattcatc atttcttcaa cttgcgagcc 120
ttcaggacaa agagtgatca caatcaatca attcaagttg gaaacaccaa acaaaatgca 180
caccctctct cctctgcttt cacagcagca gcagcagcag caacaacaaa caacagcagc 240

-continued

```
agcaacacca ccaccactgc tagctagtac ctcgtggcgt gctttatggc gatcgacgcc    300
atgatcctcg ccttctactt cttcttcttc tcaccccacc cttgatgtca aatcaagtct    360
ctctctctcc taaacagctc ttccctcgcc tgctccgcag cttcagcccc tgagcaagct    420
cgcgaatcgc cccaccaaag caccgttctg atctcacatt cttgtgcatc aatgctctcg    480
tcgtgtcgtc taatgcaata aaataaataa gaataaatta taagagctgc tcggcgctcg    540
atcactgcaa aatgtgcgcc agttcccacg agcagcagct cttctcgagg ccgcgcacag    600
ctccgtcgct tcagctttct tagccttcta tgcttcgata atcagtcaat caatcagatc    660
aatcaagatt gcgattgatc ggtcagtcaa gaagagccta gctctgcgtc ttcaagaacc    720
ctcgtccgag cctcgagcgc gatctgcgtc aagagatcgg cgtccaccgc gagcgcgtga    780
atgctctctt tctttctcca cgcggcgccg gtaatcgcgc attcttttat tctgttgtct    840
ttgttttgtt ttgttttgtt ttgttttgct ttgctttctt tttgttttgc tttctttttg    900
tttttgtttt cttttctttt tctgtttgtt ttcttttgtt tcctttttctt agttttccct    960
tgatcttctt gattctctca cactcacagc tatagctacc actacgtaca gctatggcta   1020
catacagcta agcagcacgt tgtacagaca gactgccatc gcgtgaatga atgaatgaag   1080
tgcttttctt ttcagttgcg cagaaaagca cgttttgcga aactcttgat agcgaggagg   1140
atcgaaaacg aatcagcaac aaccaaacga agccgcagac tatctcagcc ctctgtgata   1200
gcgagttgtg cgaggtggca cagtctttct ttgcaaggca gccagccagc cagccaggaa   1260
gagagaaggc ctgccattct gcctattaca atgtatgtat gtgtacgtgc ttgcttgctt   1320
gcttgcttgc aagatagggc taaaagcgaa ggaaaaagaa ctttgcgcta ggggctggtt   1380
aggactcgct tacgtgcggc tagccgttct tatcgcgctg tctatcccag cagttgtaga   1440
gtttccgctt tctccaaatg tgatcctttc ttcttatcac gattgctcta ttcgtctcga   1500
gttctgagcc tctcgatgac gatggtgatc atgacgataa cggcgatgct gttattgctg   1560
ctgctgctgc tgctgatgat gatggtggcg gtgggtccta ggccatctcc agctacgcgt   1620
ttcttgcttc ggtgtatcag ccagctcggc ttctgtcggc gaactgagct gtccttctcg   1680
acgaatcgct atcctccgca aaagttctgc caaaggtttg ttccatttcg aactaaaaac   1740
aatcgatgaa agtaaatgat tttacattta aaataggaaa aagaagtaaa tagacactta   1800
gctaagaaaa acaggcttta aagtaaacat aaaacaaata aaacgatgat tgattgatct   1860
gcgcagacaa aagaaggaaa gactgactga ctgactgcct gctgcaaatt gctgttgacc   1920
tgaatgcaaa tgaatgaatg aatgatctcg tactctacga cacttcggcg gcctctatag   1980
atcgctcgcc tgctccctct ctccctcgct ccgtcccctc tgaacgaagc aaataaagga   2040
gccacaggca aattgtccat ctttctgtgg atagatcaat cgcacacaca ttcgtttgct   2100
acctactttc agtacctgaa attaaaatta gaataggtaa tttgaggtaa tcttgcacat   2160
atacatatat atatttatat aaataatccc aaagacagga gcctcacttt cctacgattg   2220
attttttaat taacttttta aaaactaatt taatttgaga agtaaatgaa aaagaagaaa   2280
agaaacacct cctgctgcta aaagttcctc ttgtgacgag tcttcgtcca taacacaaca   2340
cacataacag attgattgag aaacaaagga aacaagcaga ggaagctcct actagcagcg   2400
gtaaggaact cttacgccgg caagttaggg gaacgtgggg aacacagtct gcacatccgg   2460
aggtggccaa ctcagcgtcc tgcgcctcct ctgtgactgg gtacactgta aaacttttta   2520
ctcacaaagg ggtgtgctct ctgcagtgcg taacttcccg cactctgatt gttaaaaagg   2580
tacttcctca gaggttctac agaaaatact cccgccacag gccaatgttt gttaacatca   2640
```

```
atacaacaga tgaaagtatt tgtccagagt acacagtgat agatagtgag agggagtgag   2700

ggaagctgtg ggagtgagtc tgagaggaga aaggtgggaa agatatagga tatattaata   2760

gacagagtgg ttgagaggag agacgtgggt atctgtgtgg ttctcctctc atcttccact   2820

gggacaaggt cttcctcatg cttcgaagtc gtgcagaccc actactacat ttgaattcta   2880

ctttcgtctc ttcttgacac cacttctatc ttgacacc                           2918


<210> SEQ ID NO 203
<211> LENGTH: 1092
<212> TYPE: DNA
<213> ORGANISM: Aurantiochytrium sp.
<220> FEATURE:
<221> NAME/KEY: misc_feature
<223> OTHER INFORMATION: SG1EUKS224768
<220> FEATURE:
<221> NAME/KEY: misc_feature
<223> OTHER INFORMATION: omega-3 delta 17 desaturase
<220> FEATURE:
<221> NAME/KEY: misc_feature
<223> OTHER INFORMATION: encodes the polypeptide at SEQ ID NO: 204

<400> SEQUENCE: 203

atgtgtcctc ctgctactca tgatgctacc cctatcaagg atggtgctaa tcgtgctgag     60

atcgttgctg agtctaagct tacccttcag gatatccgca aggccattcc tcaagagtgc    120

ttcgagaaga acactgctcg ctctatgctc taccttgttc gcgacctcgc tatttgcgct    180

actgctcctc ttgtttaccc ttacgttgct gcttctggta accctcttgc ttatctcgct    240

tactggaact tctacggctt cttcatgtgg tgcctctttg ttgttggaca cgattgcggc    300

cacactacct tttctcccaa caagaccctt aacgacattt gcggccacat tgctcacgct    360

cctcttatgg tcccttacta cccttgggct atgtctcatc gtcgtcatca catgtaccac    420

aaccaccaaa agaaggacgc ttctcatcct tggttcagca agtcttccct caagaaactt    480

cctgctttta cccgcaactt cctcaagagc cctcttgccc cttttctcgc ttaccctatc    540

tacctcttcg aaggcagctt tgacggttct cacgtgttcc ctctctctaa gctctacaag    600

ggctctcaaa tgcgtgctcg tgttgaatgc gctatttctg cagttaccgt gttcgctttt    660

ggcactgctg cttacatgtt ttgtggcgat gctcgtactc ttgcacttgc ttacggtggt    720

tgctatgctt gcttctcttt ctggctcttc atggtcacct acctccagca ccacgatcat    780

ggcactctcg tttacgacga ctctgattgg acctacctta aaggcgctct tgagactgtt    840

gatcgcaaat acggctttgg cctcgacaac cttcatcaca acattagcga cggtcacgtt    900

gttcaccacc tcttctttac ccaagttcct cattaccacc tcacaaaggc taccgagcag    960

gttgctcctc ttctccgtaa ggctggtgtg tacaagcgtg ttgaccacga caatttcctt   1020

aaggactttt ggcgcacctt tttcacatgc aacttcaccg gctggaaatg ggctaatggc   1080

aaggacaact ga                                                       1092


<210> SEQ ID NO 204
<211> LENGTH: 363
<212> TYPE: PRT
<213> ORGANISM: Aurantiochytrium sp.
<220> FEATURE:
<221> NAME/KEY: misc_feature
<223> OTHER INFORMATION: SG1EUKT1024722
<220> FEATURE:
<221> NAME/KEY: misc_feature
<223> OTHER INFORMATION: omega-3 delta 17 desaturase

<400> SEQUENCE: 204
```

-continued

```
Met Cys Pro Pro Ala Thr His Asp Ala Thr Pro Ile Lys Asp Gly Ala
1               5                   10                  15

Asn Arg Ala Glu Ile Val Ala Glu Ser Lys Leu Thr Leu Gln Asp Ile
            20                  25                  30

Arg Lys Ala Ile Pro Gln Glu Cys Phe Glu Lys Asn Thr Ala Arg Ser
        35                  40                  45

Met Leu Tyr Leu Val Arg Asp Leu Ala Ile Cys Ala Thr Ala Pro Leu
    50                  55                  60

Val Tyr Pro Tyr Val Ala Ala Ser Gly Asn Pro Leu Ala Tyr Leu Ala
65                  70                  75                  80

Tyr Trp Asn Phe Tyr Gly Phe Phe Met Trp Cys Leu Phe Val Val Gly
                85                  90                  95

His Asp Cys Gly His Thr Thr Phe Ser Pro Asn Lys Thr Leu Asn Asp
            100                 105                 110

Ile Cys Gly His Ile Ala His Ala Pro Leu Met Val Pro Tyr Tyr Pro
        115                 120                 125

Trp Ala Met Ser His Arg Arg His His Met Tyr His Asn His Gln Lys
    130                 135                 140

Lys Asp Ala Ser His Pro Trp Phe Ser Lys Ser Ser Leu Lys Lys Leu
145                 150                 155                 160

Pro Ala Phe Thr Arg Asn Phe Leu Lys Ser Pro Leu Ala Pro Phe Leu
                165                 170                 175

Ala Tyr Pro Ile Tyr Leu Phe Glu Gly Ser Phe Asp Gly Ser His Val
            180                 185                 190

Phe Pro Leu Ser Lys Leu Tyr Lys Gly Ser Gln Met Arg Ala Arg Val
        195                 200                 205

Glu Cys Ala Ile Ser Ala Val Thr Val Phe Ala Phe Gly Thr Ala Ala
    210                 215                 220

Tyr Met Phe Cys Gly Asp Ala Arg Thr Leu Ala Leu Ala Tyr Gly Gly
225                 230                 235                 240

Cys Tyr Ala Cys Phe Ser Phe Trp Leu Phe Met Val Thr Tyr Leu Gln
                245                 250                 255

His His Asp His Gly Thr Leu Val Tyr Asp Asp Ser Asp Trp Thr Tyr
            260                 265                 270

Leu Lys Gly Ala Leu Glu Thr Val Asp Arg Lys Tyr Gly Phe Gly Leu
        275                 280                 285

Asp Asn Leu His His Asn Ile Ser Asp Gly His Val Val His His Leu
    290                 295                 300

Phe Phe Thr Gln Val Pro His Tyr His Leu Thr Lys Ala Thr Glu Gln
305                 310                 315                 320

Val Ala Pro Leu Leu Arg Lys Ala Gly Val Tyr Lys Arg Val Asp His
                325                 330                 335

Asp Asn Phe Leu Lys Asp Phe Trp Arg Thr Phe Phe Thr Cys Asn Phe
            340                 345                 350

Thr Gly Trp Lys Trp Ala Asn Gly Lys Asp Asn
        355                 360
```